US011718612B2

(12) United States Patent
Lewis et al.

(10) Patent No.: US 11,718,612 B2
(45) Date of Patent: Aug. 8, 2023

(54) INHIBITORS OF RECEPTOR INTERACTING PROTEIN KINASE I FOR THE TREATMENT OF DISEASE

(71) Applicant: Board of Regents, The University of Texas System, Austin, TX (US)

(72) Inventors: Richard T. Lewis, Missouri City, TX (US); Matthew Hamilton, Missouri City, TX (US); William J. Ray, Houston, TX (US); Fernando Alvarez, Austin, TX (US); Naphtali Reyna, Arlington, TX (US); Jason Cross, Pearland, TX (US); Suyambu Kesava Vijayan Ramaswamy, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 2 days.

(21) Appl. No.: 17/014,184

(22) Filed: Sep. 8, 2020

(65) Prior Publication Data
US 2021/0094951 A1 Apr. 1, 2021

Related U.S. Application Data

(60) Provisional application No. 62/896,786, filed on Sep. 6, 2019.

(51) Int. Cl.
| | | |
|---|---|---|
| C07D 487/04 | (2006.01) |
| C07D 471/04 | (2006.01) |
| A61K 31/4035 | (2006.01) |
| A61K 31/407 | (2006.01) |
| A61K 31/415 | (2006.01) |
| A61K 31/4172 | (2006.01) |
| A61K 31/4196 | (2006.01) |
| A61K 31/4245 | (2006.01) |
| A61K 31/437 | (2006.01) |
| A61K 31/497 | (2006.01) |
| A61K 31/4985 | (2006.01) |
| A61K 31/5383 | (2006.01) |
| A61K 31/551 | (2006.01) |
| A61K 45/06 | (2006.01) |
| C07D 209/44 | (2006.01) |
| C07D 231/44 | (2006.01) |
| C07D 233/90 | (2006.01) |
| C07D 249/14 | (2006.01) |
| C07D 403/06 | (2006.01) |
| C07D 403/12 | (2006.01) |
| C07D 413/12 | (2006.01) |
| C07D 498/04 | (2006.01) |

(52) U.S. Cl.
CPC .......... *C07D 471/04* (2013.01); *A61K 31/407* (2013.01); *A61K 31/4035* (2013.01); *A61K 31/415* (2013.01); *A61K 31/4172* (2013.01); *A61K 31/4196* (2013.01); *A61K 31/4245* (2013.01); *A61K 31/437* (2013.01); *A61K 31/497* (2013.01); *A61K 31/4985* (2013.01); *A61K 31/5383* (2013.01); *A61K 31/551* (2013.01); *A61K 45/06* (2013.01); *C07D 209/44* (2013.01); *C07D 231/44* (2013.01); *C07D 233/90* (2013.01); *C07D 249/14* (2013.01); *C07D 403/06* (2013.01); *C07D 403/12* (2013.01); *C07D 413/12* (2013.01); *C07D 487/04* (2013.01); *C07D 498/04* (2013.01)

(58) Field of Classification Search
CPC ... C07D 231/44; C07D 401/04; C07D 487/04
See application file for complete search history.

(56) References Cited

U.S. PATENT DOCUMENTS

| | | | |
|---|---|---|---|
| 6,291,476 B1 * | 9/2001 | Kordik ................. | C07D 473/34 546/160 |
| 2012/0122889 A1 | 5/2012 | Yuan | |
| 2013/0184287 A1 | 7/2013 | Gray | |
| 2013/0281428 A1 | 10/2013 | Ohki | |
| 2014/0066466 A1 | 3/2014 | Yuan | |
| 2014/0228367 A1 | 8/2014 | Flynn | |
| 2014/0364431 A1 | 12/2014 | Gong | |
| 2015/0353533 A1 | 12/2015 | Bandyopadhyay | |
| 2016/0002255 A1 | 1/2016 | Brockunier | |
| 2016/0075654 A1 | 3/2016 | Bunker | |
| 2016/0221963 A1 | 8/2016 | Beigelman | |
| 2017/0008877 A1 | 1/2017 | Patel | |
| 2017/0226127 A1 | 8/2017 | Estrada | |
| 2017/0266199 A1 | 9/2017 | Berger | |

(Continued)

FOREIGN PATENT DOCUMENTS

| | | | |
|---|---|---|---|
| WO | 2010075561 | 7/2010 | |
| WO | WO-2010122088 A1 * | 10/2010 | ........... C07D 231/14 |

(Continued)

OTHER PUBLICATIONS

Berger, S. et al., "Characterization of GSK'963: A Structurally Distinct, Potent and Selective Inhibitor of RIP1 Kinase", Cell Death Discov., 1:15009, (2015).

(Continued)

*Primary Examiner* — Shawquia Jackson
(74) *Attorney, Agent, or Firm* — Cynthia Hathaway; Lauren L. Stevens; Erik M. Larsen

(57) ABSTRACT

Disclosed herein are compounds which inhibit RIPK1, pharmaceutical compositions, and methods of treatment of RIPK1-mediated diseases, such as neurodegenerative disorders, inflammatory disorders, and cancer.

10 Claims, No Drawings

(56) References Cited

U.S. PATENT DOCUMENTS

| | | |
|---|---|---|
| 2018/0170927 A1 | 6/2018 | Patel |
| 2018/0319819 A1 | 11/2018 | Yogo |
| 2019/0092714 A1 | 3/2019 | Suzuki |
| 2019/0241565 A1 | 8/2019 | Patel |
| 2020/0062735 A1 | 2/2020 | Anbari |
| 2021/0032271 A1 | 2/2021 | Patel |
| 2021/0115010 A1 | 4/2021 | Soth |
| 2021/0154204 A1 | 5/2021 | Lewis |

FOREIGN PATENT DOCUMENTS

| | | |
|---|---|---|
| WO | 2011115725 | 9/2011 |
| WO | 2012125544 | 9/2012 |
| WO | 2014125444 | 8/2014 |
| WO | 2016027253 | 2/2016 |
| WO | 2016044331 | 3/2016 |
| WO | 2016101887 | 6/2016 |
| WO | 2016185423 | 11/2016 |
| WO | 2017069279 | 4/2017 |
| WO | 2017096301 | 6/2017 |
| WO | 2017136727 | 8/2017 |
| WO | 2018100070 | 6/2018 |
| WO | 2018107060 | 6/2018 |
| WO | 2019051038 | 3/2019 |
| WO | 2019110832 | 6/2019 |
| WO | 2019213445 | 11/2019 |
| WO | 2019213447 | 11/2019 |
| WO | 2021046515 | 3/2021 |
| WO | 2021062199 | 3/2021 |
| WO | 2021108198 | 6/2021 |
| WO | 2021173917 | 9/2021 |

OTHER PUBLICATIONS

Choi, S. et al., "Optimization of Tricyclic NEC-3 Necroptosis Inhibitors for In Vitro Liver Microsomal Stability", Bioorg Med Chem. Lett., 22(17):5685-8, (2012).

Harris, P. et al., "Identification of a RIP1 Kinase Inhibitor Clinical Candidate (GSK3145095) for the Treatment of Pancreatic Cancer", ACS Med Chem Lett., 10(6):857-62, (2019).

Jagtap, P. et al., "Structure-Activity Relationship Study of Tricyclic Necroptosis Inhibitors", J Med Chem., 50(8):1886-95, (2007).

Ren, Y. et al., "Discovery of a Highly Potent, Selective, and Metabolically Stable Inhibitor of Receptor-Interacting Protein 1 (RIP1) for the Treatment of Systemic Inflammatory Response Syndrome", J Med Chem., 60(3):972-86, (2017).

U.S. Appl. No. 16/952,422; Application filed, Nov. 19, 2020; 143 pages.

U.S. Appl. No. 17/033,104; Application filed, Sep. 25, 2020; 295 pages.

Yoshikawa, M. et al., "Discovery of 7-Oxo-2,4,5,7-tetrahydro-6 H-pyrazolo[3,4- c]pyridine Derivatives as Potent, Orally Available, and Brain-Penetrating Receptor Interacting Protein 1 (RIP1) Kinase Inhibitors: Analysis of Structure-Kinetic Relationships", J Med Chem., 61(6):2384-409, (2018).

International Application No. PCT/US2020/049667; International Search Report and Written Opinion of the International Searching Authority, dated Feb. 4, 2021; 11 pages.

International Application No. PCT/US2020/052789; International Search Report and Written Opinion of the International Searching Authority, dated Feb. 17, 2021; 10 pages.

International Application No. PCT/US2020/061171; International Search Report and Written Opinion of the International Searching Authority, dated Mar. 17, 2021; 9 pages.

PubChem CID 122183864 Create Date: Oct. 26, 2016 (Oct. 26, 2016), especially p. 2 formula.

PubChem CID 1481295, N-Methyl-4-oxo-1-phenyl-1,4-dihydro-3-pyridazinecarboxamide, create date Jul. 11, 2005.

PubChem CID 58072278, 1-Methyl-4-oxopyridazine-3-carboxamide, create date Aug. 19, 2012.

PubChem CID 891989 Create Date: Jul. 9, 2005 (Jul. 9, 2005), especially p. 2 formula.

PubChem Compound Record for CID 132165444, CN(C(=0)C12CC(C1)(C2)C(=O)O)C, Create Date: Jan. 29, 2018.

PubChem Compound Record for CID 86010391, 3-Methylbicyclo[1,1,1]pentane-1-carboxamide, Create Date: Nov. 3, 2014.

Ameriks, M. et al., "Diazinones as P2 replacements for pyrazole-based cathepsin S inhibitors", Bioorg Med Chem Lett., 20(14):4060-4, (2010).

Chemical Abstracts STN Database, Record for RN 1277246-48-6, "1-(2-Fluorophenyl)-N-(hexahydro-2-oxo-1 H-azepin-3-yl)-1,4-dihydro-6-methyl-4-oxo-3-pyridazinecarboxamide", Entered STN Apr. 11, 2011, (2011).

Chemical Abstracts STN Database, Record for RN 924068-54-2, "N-(3-Chlorophenyl)-1,4-dihydro-6-methyl-4-oxo-1-phenyl-3-pyridazinecarboxamide", Entered STN Mar. 1, 2007, (2007).

Chemical Abstracts STN Registry Database, record for RN 2323881-41-8, "[3-(4-Cyclopropyl-1 H-1,2,3-triazol-1-yl)-1-pyrrolidinyl][3-(trifluoromethyl)bicyclo[1.1.1 ]pent-1-yl]methanone", Entered STN Jun. 4, 2019, (2019).

Chemical Abstracts STN Registry Database, record for RN 2373678-19-2, "3-[[2-(3-Methoxyphenyl)-1-pyrrolidinyl] carbonyl] bicyclo[1.1.1 ]pentane-1-carboxylic acid", Entered STN Sep. 4, 2019, (2019).

Degterev, A. et al., "Targeting RIPK1 for the treatment of human diseases", Proc Natl Acad Sci U S A, 116 (20):9714-22, (2019).

International Application No. PCT/US2020/049667; International Preliminary Report on Patentability, dated Mar. 17, 2022; 8 pages.

International Application No. PCT/US2020/052789; International Preliminary Report on Patentability, dated Apr. 7, 2022; 7 pages.

International Application No. PCT/US2020/061171; International Preliminary Report on Patentability, dated Jun. 9, 2022; 6 pages.

U.S. Appl. No. 16/952,422, Non-Final Office Action, dated Oct. 14, 2022; 36 pages.

U.S. Appl. No. 17/033,104, Non-Final Office Action, dated Oct. 27, 2022; 24 pages.

* cited by examiner

INHIBITORS OF RECEPTOR INTERACTING PROTEIN KINASE I FOR THE TREATMENT OF DISEASE

This application claims the benefit of priority of U.S. Provisional Application No. 62/896,786, filed 6 Sep. 2019, the disclosure of which is hereby incorporated by reference as if written herein in its entirety.

Disclosed herein are new compounds and compositions and their application as pharmaceuticals for the treatment of disease. Methods of inhibition of RIPK1 in a human or animal subject are also provided for the treatment of diseases mediated by RIPK1 such as neurodegenerative disorders, inflammatory disorders, and cancer.

Receptor Interacting Protein Kinase 1 (RIPK1) regulates necroptotic and apoptotic cell death pathways. Furthermore, it coordinates the response to pro-inflammatory signaling in a number of cell types and contexts. RIPK1 consists of an N-terminal kinase domain, a RHIM (RIP homotypic interaction motif) domain, and a death domain, which collectively undergo extensive post-translational modification in response to signaling through various receptors such as tumor necrosis factor α receptors (TNFRs), toll-like receptors, NOD-like receptor, and others. RIPK1 has been most extensively studied in the context of TNFR 1 signaling, which triggers its recruitment to the C-terminal domain of the receptor via the protein TRADD (TNF receptor associated death domain protein). There, RIPK1 is ubiquitinated by the E3 ubiquitin ligases TNF receptor-associated factor 2 (TRAF2) or TRAF5 and the cellular inhibitor of apoptosis proteins (cIAPs) cIAP1 and cIAP2. This molecular assembly is known as complex 1. Cylindromatosis (CYLD) then mediates the deubiquitination of RIPK1 to allow assembly of complex IIb, also known as the necrosome. The necrosome consists of the RIPK1 homolog RIPK3 and the pseudokinase MLKL. The assembly and function of the necrosome is inhibited by caspase 8 such that only when caspase 8 activity is blocked is the necrosome functional. In that context the necrosome causes necroptosis, an inflammatory form of programmed cell death in which membrane lysis by MLKL causes the release of cellular contents into the extracellular space.

RIPK1 can also, in different contexts, regulate apoptosis and inflammation. When cIAPs are inhibited so that RIPK1 ubiquitination does not occur, RIPK1 participates in apoptosis. Ubiquitinated RIPK1 can also recruit NF-KB essential modulator (NEMO) and TAK1 binding protein 2 or 3 (TAB2/3), leading to activation of inhibitor of kappa B (IKB) kinase beta (IKKβ) and transforming growth factor beta (TGFβ)-activated kinase 1 (TAK1), which in turn promote the NF-KB pro-inflammatory or pro-survival gene expression programs. Given its role in cell death and inflammation, RIPK1 has been implicated in many diseases featuring chronic and acute inflammatory signaling, including viral infections, sepsis, retinal degeneration, traumatic brain injury, ischemic stroke, intracerebral hemorrhage, amyotrophic lateral sclerosis, acute kidney injury, myocardial reperfusion injury, Alzheimer's disease, ulcerative colitis, osteoarthritis, and others. In animal models of several of these diseases, RIPK1 kinase inhibitors such as necrostatin-1 have been shown to be effective, leading to the development of such molecules for clinical trials in a number of indications.

DETAILED DESCRIPTION

Provided herein is Embodiment 1, a compound of structural Formula (I):

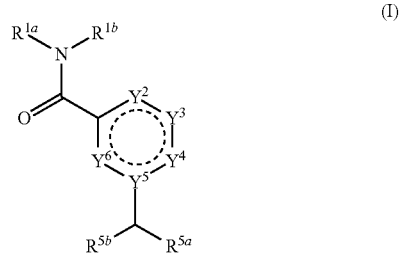

or a salt thereof, wherein:
  $Y^2$ is chosen from $CR^2$, $NR^2$, and N;
  $Y^3$ is chosen from a bond and $CR^3$;
  $Y^4$ is chosen from $CR^4$, $NR^4$, and N;
  $Y^5$ is chosen from C and N;
  $Y^6$ is chosen from $CR^6$, N, and O;
  $Y^2, Y^3, Y^4, Y^5, Y^6$, and the intervening carbon combine to form a 5- or 6-membered heteroaryl;
  $R^{1a}$ is chosen from aryl and heteroaryl, either of which is optionally substituted with one or more $R^7$;
  $R^{1b}$ is chosen from hydrogen and alkyl;
  $R^2$ is chosen from hydrogen, alkyl, and halo;
  or if $R^2$ is present, $R^{1b}$ and $R^2$, together with the intervening atoms, may combine to form a heterocycloalkyl, which is optionally substituted with one or more $R^8$;
  $R^3$ is chosen from hydrogen and alkyl;
  $R^4$ is chosen from hydrogen, alkyl, alkoxy, amino, aminoalkyl, hydroxyalkyl, alkoxyalkyl, cyano, halo, and hydroxy;
  $R^{5a}$ is chosen from hydrogen and alkyl;
  or if $R^4$ is present, $R^4$ and $R^{5a}$, together with the intervening atoms, may combine to form a cycloalkyl or heterocycloalkyl ring, either of which is optionally substituted with one or more $R^9$;
  $R^{5b}$ is chosen from alkyl, cycloalkyl, heterocycloalkyl, aryl and heteroaryl, any of which is optionally substituted with one or more $R^{10}$;
  $R^6$ is chosen from hydrogen, alkyl, alkoxy, cyano, halo, and hydroxy;
  each $R^7$ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or
  two or more $R^7$, together with the intervening atoms, can form a heterocycloalkyl or heteroaryl;
  each $R^8$ is independently chosen from alkyl, cyano, halo, hydroxy, and oxo;
  each $R^9$ is independently chosen from alkyl, cyano, halo, and hydroxy; and
  each $R^{10}$ is independently chosen from alkyl, haloalkyl, alkoxy, haloalkoxy, cyano, halo, and hydroxy.

Certain compounds disclosed herein possess useful RIPK1 inhibiting activity, and may be used in the treatment or prophylaxis of a disease or condition in which RIPK1 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting RIPK1. Other embodiments provide methods for treating a RIPK1-mediated disorder in a patient in need of such treatment, comprising administering to said patient a therapeutically effective amount of a compound or composition as disclosed herein. Also provided is the use of certain compounds disclosed herein for use in the manufacture of a medicament for the treatment of a disease or condition ameliorated by the inhibition of RIPK1.

Provided herein is Embodiment 2, a compound of structural Formula (Ia):

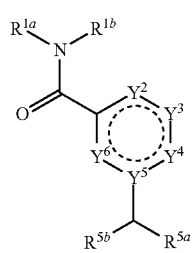

(Ia)

or a salt thereof, wherein:
  $Y^2$ is chosen from $CR^2$, $NR^2$, and N;
  $Y^3$ is chosen from a bond and $CR^3$;
  $Y^4$ is chosen from $CR^4$, $NR^4$, and N;
  $Y^5$ is chosen from C and N;
  $Y^6$ is chosen from N and O;
  $Y^2$, $Y^3$, $Y^4$, $Y^5$, $Y^6$, and the intervening carbon combine to form a 5- or 6-membered heteroaryl;
  $R^{1a}$ is chosen from aryl and heteroaryl, either of which is optionally substituted with one or more $R^7$;
  $R^{1b}$ is chosen from hydrogen and alkyl;
  $R^2$ is chosen from hydrogen, alkyl, and halo;
  or if $R^2$ is present, $R^{1b}$ and $R^2$, together with the intervening atoms, may combine to form a heterocycloalkyl, which is optionally substituted with one or more $R^8$;
  $R^3$ is chosen from hydrogen and alkyl;
  $R^4$ is chosen from hydrogen, alkyl, alkoxy, halo, and hydroxy;
  $R^{5a}$ is chosen from hydrogen and alkyl;
  or if $R^4$ is present, $R^4$ and $R^{5a}$, together with the intervening atoms, may combine to form a cycloalkyl or heterocycloalkyl ring, either of which is optionally substituted with one or more $R^9$;
  $R^{5b}$ is chosen from alkyl, cycloalkyl, heterocycloalkyl, aryl and heteroaryl, any of which is optionally substituted with one or more $R^{10}$;
  each $R^7$ is independently chosen from halo, cyano, hydroxy, alkyl optionally substituted with cyano, alkoxy, haloalkyl, haloalkoxy, heteroaryl optionally substituted with alkyl, and heterocycloalkyl optionally substituted with alkyl, or
  two or more $R^7$, together with the intervening atoms, can form a heterocycloalkyl or heteroaryl;
  each $R^8$ is independently chosen from alkyl, cyano, halo, hydroxy, and oxo;
  each $R^9$ is independently chosen from alkyl, cyano, halo, and hydroxy; and
  each $R^{10}$ is independently chosen from alkyl, haloalkyl, alkoxy, haloalkoxy, cyano, halo, and hydroxy.

In certain embodiments, $R^{1a}$ is chosen from $C_{6-10}$aryl and 5- to 10-membered heteroaryl. In certain embodiments, $R^{1a}$ is chosen from phenyl, pyridyl, pyridazinyl, pyrimidinyl, and pyrazinyl. In certain further embodiments, $R^{1a}$ is aryl. In certain further embodiments, $R^{1a}$ is phenyl. In yet further embodiments, $R^{1a}$ is

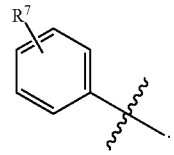

In yet further embodiments, $R^{1a}$ is chosen from

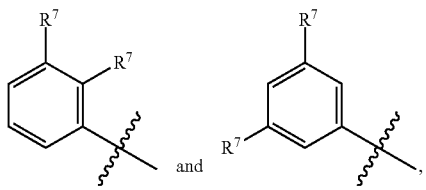

and each $R^7$ is the same or different. In still further embodiments, $R^{1a}$ is

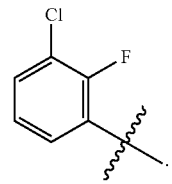 [SMILES: *c1cccc(Cl)c1F]

In certain embodiments, $R^2$ is chosen from hydrogen, $C_{1-6}$alkyl, and halo. In certain embodiments, $R^2$ is chosen from hydrogen and halo. In certain further embodiments, $R^2$ is hydrogen.

In certain embodiments, $R^{1b}$ and $R^2$, together with the intervening atoms, combine to form a heterocycloalkyl, which is optionally substituted with one or more $R^8$. In certain further embodiments, $R^{1b}$ and $R^2$, together with the intervening atoms, combine to form a 6- or 7-membered heterocycloalkyl, which is optionally substituted with one or more $R^8$.

In certain embodiments, $R^3$ is chosen from $C_{1-6}$alkyl and H. In certain further embodiments, wherein $R^3$ is $C_{1-6}$alkyl. In yet further embodiments, $R^3$ is H.

In certain embodiments, $R^4$ is chosen from hydrogen, $C_{1-6}$alkyl, $C_{1-6}$alkoxy, amino, amino$C_{1-6}$alkyl, hydroxy$C_{1-6}$alkyl, $C_{1-6}$alkoxy$C_{1-6}$alkyl, cyano, halo, and hydroxy. In certain further embodiments, $R^4$ is chosen from hydrogen, methyl, methoxy, $NH_2$, $NH_2CH_2$, $HOCH_2$, methoxymethyl, cyano, halo, and hydroxy. In certain further embodiments, $R^4$ is chosen from hydrogen, alkyl, alkoxy, halo, and hydroxy. In certain further embodiments, $R^4$ is chosen from hydrogen, $C_{1-6}$alkyl, $C_{1-6}$alkoxy, halo, and hydroxy. In certain further embodiments, $R^4$ is chosen from hydrogen and halo. In certain further embodiments, $R^4$ is hydrogen.

In certain embodiments, $R^{5a}$ is chosen from hydrogen and $C_{1-6}$alkyl. In certain embodiments, $R^{5a}$ is hydrogen.

In certain embodiments, $R^{5b}$ is chosen from aryl and heteroaryl. In certain embodiments, $R^{5b}$ is chosen from phenyl, pyridinyl, pyridazinyl, pyrimidinyl, and pyrazinyl. In certain embodiments, wherein $R^{5b}$ is chosen from phenyl and pyrazinyl. In certain further embodiments, $R^{5b}$ is chosen from

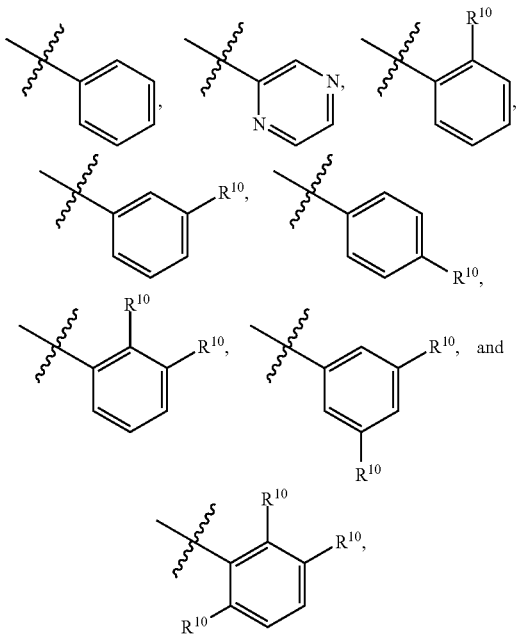

and each $R^{10}$ is the same or different. In yet further embodiments, $R^{5b}$ is chosen from

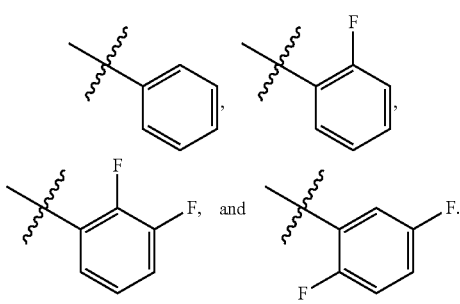

In certain embodiments, $R^4$ and $R^{5a}$, together with the intervening atoms, may combine to form a cycloalkyl or heterocycloalkyl ring, either of which is optionally substituted with one or more $R^9$. In certain embodiments, $R^4$ and $R^{5a}$, together with the intervening atoms, may combine to form a 5- or 6-membered cycloalkyl or 5- or 6-membered heterocycloalkyl ring, either of which is optionally substituted with one or more $R^9$.

In certain embodiments, each $R^7$ is independently chosen from halo, cyano, hydroxy, $C_{1-4}$alkyl, $C_{1-4}$alkoxy, $C_{1-4}$haloalkyl, $C_{1-4}$hydroxyalkyl, cyanoalkyl, $C_{1-4}$alkoxy$C_{1-4}$alkyl, $C_{1-4}$alkoxy$C_{1-4}$alkoxyalkyl, amino$C_{1-4}$alkyl $C_{1-4}$acylamino$C_{1-4}$alkyl, $(C_{1-4}$haloalkyl)amino$C_{1-4}$alkyl, $C_{1-4}$alkylsulfonylamino$C_{1-4}$alkyl, aryl$C_{1-4}$alkyl, heteroaryl$C_{1-4}$alkyl, halo$C_{1-4}$alkoxy, heteroaryl optionally substituted with alkyl, and heterocycloalkyl optionally substituted with alkyl.

In certain embodiments, each $R^7$ is independently chosen from halo, cyano, hydroxy, methyl, methoxy, trifluoromethyl, hydroxymethyl, cyanomethyl, 2-cyanoprop-2-yl, methoxymethyl, (2-(methoxy)ethoxy)methyl, $NH_2CH_2$, $CH_3CONHCH_2$, $CF_3CH_2NHCH_2$, $CH_3SO_2NHCH_2$, aryl$C_{1-4}$alkyl, heteroaryl$C_{1-4}$alkyl, trifluoromethoxy, pyrazolyl, imidazolyl, benzimidazolyl, benzotriazolyl, (methyl)pyrazolyl, (methyl)imidazolyl, (methyl)benzimidazolyl, and (methyl)benzotriazolyl.

In certain embodiments, each $R^7$ is independently chosen from halo, cyano, hydroxy, alkyl, cyanoalkyl, alkoxy, haloalkyl, haloalkoxy, heteroaryl optionally substituted with alkyl, and heterocycloalkyl optionally substituted with alkyl.

In certain embodiments, each $R^7$ is independently chosen from halo, cyano, hydroxy, $C_{1-6}$alkyl, cyano$C_{1-6}$alkyl, $C_{1-6}$alkoxy, $C_{1-6}$haloalkyl, $C_{1-6}$haloalkoxy, 5-10 membered heteroaryl optionally substituted with $C_{1-6}$alkyl, and 5-10 membered heterocycloalkyl optionally substituted with $C_{1-6}$alkyl.

In certain embodiments, each $R^7$ is independently chosen from halo, cyano, hydroxy, methyl, methoxy, trifluoromethyl, hydroxymethyl, cyanomethyl, 2-cyanoprop-2-yl, methoxymethyl, (2-(methoxy)ethoxy)methyl, $NH_2CH_2$, $CH_3CONHCH_2$, $CF_3CH_2NHCH_2$, $CH_3SO_2NHCH_2$, aryl$C_{1-4}$alkyl, heteroaryl$C_{1-4}$alkyl, trifluoromethoxy, pyrazolyl, imidazolyl, benzimidazolyl, benzotriazolyl, (methyl)pyrazolyl, (methyl)imidazolyl, (methyl)benzimidazolyl, and (methyl)benzotriazolyl.

In certain embodiments, each $R^7$ is independently chosen from halo, cyano, hydroxy, alkyl, cyanoalkyl, alkoxy, haloalkyl, haloalkoxy, heteroaryl optionally substituted with alkyl, and heterocycloalkyl optionally substituted with alkyl.

In certain embodiments, each $R^7$ is independently chosen from halo, cyano, hydroxy, $C_{1-6}$alkyl, cyano$C_{1-6}$alkyl, $C_{1-6}$alkoxy, $C_{1-6}$haloalkyl, $C_{1-6}$haloalkoxy, 5-10 membered heteroaryl optionally substituted with $C_{1-6}$alkyl, and 5-10 membered heterocycloalkyl optionally substituted with $C_{1-6}$alkyl.

In certain embodiments, each $R^7$ is independently chosen from halo, cyano, hydroxy, methyl, 2-cyano-2-propyl, methoxy, trifluoromethyl, trifluoromethoxy, and 1-methyl-1H-pyrazol-4-yl.

In certain embodiments, at least one $R^7$ is halo. In certain embodiments, at least one $R^7$ is fluoro. In certain embodiments, at least two $R^7$ are halo.

In certain embodiments, two or more $R^7$, together with the intervening atoms, form a heterocycloalkyl or heteroaryl. In certain embodiments, two or more $R^7$, together with the intervening atoms, form a 5- or 6-membered heterocycloalkyl or heteroaryl.

Also provided herein is Embodiment 3: the compound of Embodiment 1 having structural Formula (II):

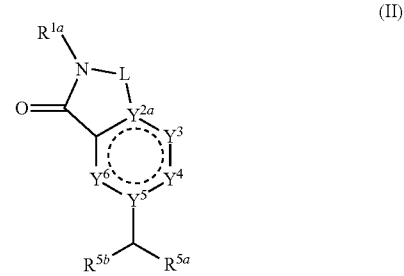

or a salt thereof, wherein:

L is alkylene and is optionally substituted with one or more $R^8$;

$Y^{2a}$ is chosen from C and N;
$Y^3$ is chosen from a bond and $CR^3$;
$Y^4$ is chosen from $CR^4$, $NR^4$, and N;
$Y^5$ is chosen from C and N;
$Y^6$ is chosen from $CR^6$, N, and O;
$Y^{2a}$, $Y^3$, $Y^4$, $Y^5$, $Y^6$, and the intervening carbon combine to form a 5- or 6-membered heteroaryl;
$R^{1a}$ is chosen from aryl and heteroaryl, either of which is optionally substituted with one or more $R^7$;
$R^2$ is chosen from hydrogen, alkyl, and halo;
$R^3$ is chosen from hydrogen and alkyl;
$R^4$ is chosen from hydrogen, alkyl, alkoxy, amino, aminoalkyl, hydroxyalkyl, alkoxyalkyl, cyano, halo, and hydroxy;
$R^{5a}$ is chosen from hydrogen and alkyl;
or if $R^4$ is present, $R^4$ and $R^{5a}$, together with the intervening atoms, may combine to form a cycloalkyl or heterocycloalkyl ring, either of which is optionally substituted with one or more $R^9$;
$R^{5b}$ is chosen from alkyl, cycloalkyl, heterocycloalkyl, aryl and heteroaryl, any of which is optionally substituted with one or more $R^{10}$;
$R^6$ is chosen from hydrogen, alkyl, alkoxy, cyano, halo, and hydroxy;
each $R^7$ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or
two or more $R^7$, together with the intervening atoms, can form a heterocycloalkyl or heteroaryl;
each $R^8$ is independently chosen from alkyl, cyano, halo, hydroxy, and oxo;
each $R^9$ is independently chosen from alkyl, cyano, halo, and hydroxy; and
each $R^{10}$ is independently chosen from alkyl, haloalkyl, amino, aminoalkyl, aminocarbonyl, alkoxy, haloalkoxy, cyano, halo, and hydroxy.

Also provided herein is Embodiment 4: the compound of Embodiment 1 having structural Formula (IIa):

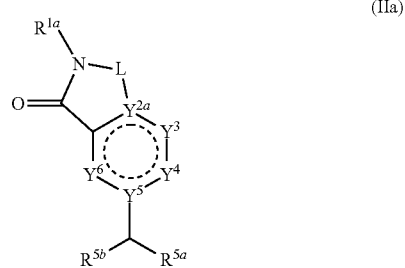

(IIa)

or a salt thereof, wherein:
L is alkylene and is optionally substituted with one or more $R^8$;
$Y^{2a}$ is chosen from C and N;
$Y^3$ is chosen from a bond and $CR^3$;
$Y^4$ is chosen from $CR^4$, $NR^4$, and N;
$Y^5$ is chosen from C and N;
$Y^6$ is chosen from N and O;
$Y^{2a}$, $Y^3$, $Y^4$, $Y^5$, $Y^6$, and the intervening carbon combine to form a 5- or 6-membered heteroaryl;
$R^{1a}$ is chosen from aryl and heteroaryl, either of which is optionally substituted with one or more $R^7$;
$R^2$ is chosen from hydrogen, alkyl, and halo;
$R^3$ is chosen from hydrogen and alkyl;
$R^4$ is chosen from hydrogen, alkyl, alkoxy, halo, and hydroxy;
$R^{5a}$ is chosen from hydrogen and alkyl;
or if $R^4$ is present, $R^4$ and $R^{5a}$, together with the intervening atoms, may combine to form a cycloalkyl or heterocycloalkyl ring, either of which is optionally substituted with one or more $R^9$;
$R^{5b}$ is chosen from alkyl, cycloalkyl, heterocycloalkyl, aryl and heteroaryl, any of which is optionally substituted with one or more $R^{10}$;
each $R^7$ is independently chosen from halo, cyano, hydroxy, alkyl optionally substituted with cyano, alkoxy, haloalkyl, haloalkoxy, heteroaryl optionally substituted with alkyl, and heterocycloalkyl optionally substituted with alkyl, or
two or more $R^7$, together with the intervening atoms, can form a heterocycloalkyl or heteroaryl;
each $R^8$ is independently chosen from alkyl, cyano, halo, hydroxy, and oxo;
each $R^9$ is independently chosen from alkyl, cyano, halo, and hydroxy; and
each $R^{10}$ is independently chosen from alkyl, haloalkyl, alkoxy, haloalkoxy, cyano, halo, and hydroxy.

Also provided are the following embodiments:
Embodiment 5: the compound of Embodiment 1 wherein:
$Y^2$ is chosen from $CR^2$ and $NR^2$; and
$R^{1b}$ and $R^2$, together with the intervening atoms, combine to form a heterocycloalkyl, which is optionally substituted with 1 or 2 $R^8$.

Embodiment 6: the compound of Embodiment 5 wherein $R^{1b}$ and $R^2$, together with the intervening atoms, combine to form a 6- or 7-membered heterocycloalkyl, which is optionally substituted with 1 or 2 $R^8$.

Embodiment 7: the compound of either one of Embodiments 5 and 6 wherein the heterocycloalkyl formed by the combination of $R^{1b}$ and $R^2$, together with the intervening atoms, is optionally substituted with 1 $R^8$.

Embodiment 8: the compound of Embodiment 7 wherein the heterocycloalkyl formed by the combination of $R^{1b}$ and $R^2$, together with the intervening atoms, is substituted with 1 $R^8$.

Embodiment 9: the compound of Embodiment 3 wherein L is optionally substituted with 1 or 2 $R^8$.

Embodiment 10: the compound of Embodiment 9 wherein L is optionally substituted with 1 $R^8$.

Embodiment 11: the compound of Embodiment 10 wherein L is substituted with 1 $R^8$.

Embodiment 12: the compound of any one of Embodiments 3 and 9-11 wherein L is chosen from methylene, ethylene and propylene.

Embodiment 13: the compound of Embodiment 12 wherein L is ethylene.

Embodiment 14: the compound of any one of Embodiments 1-13 wherein each $R^8$ is independently chosen from $C_{1-4}$alkyl, cyano, halo, hydroxy, and oxo.

Embodiment 15: the compound of Embodiment 14 wherein each $R^8$ is independently chosen from methyl, cyano, halo, and hydroxy.

Embodiment 16: the compound of Embodiment 15 wherein each $R^8$ is methyl.

Embodiment 17: the compound of Embodiment 7 wherein the heterocycloalkyl formed by the combination of $R^{1b}$ and $R^2$, together with the intervening atoms, is unsubstituted with an $R^8$.

Embodiment 18: the compound of Embodiment 10 wherein L is unsubstituted with an $R^8$.

Embodiment 19: the compound of Embodiment 18 wherein L is chosen from —$CH_2CH_2$—, —$CH_2CH_2CH_2$—, and —$CH_2CH(CH_3)CH_2$—.

Embodiment 20: the compound of Embodiment 19 wherein L is —$CH_2CH_2$—.

Embodiment 21: the compound of Embodiment 1 wherein:
$R^{1b}$ is chosen from hydrogen and alkyl; and
$R^2$ is chosen from hydrogen, alkyl, and halo.

Embodiment 22: the compound of Embodiment 21 wherein $R^{1b}$ is chosen from hydrogen and $C_{1-6}$alkyl.

Embodiment 23: the compound of Embodiment 22 wherein $R^{1b}$ is hydrogen.

Embodiment 24: the compound of either one of Embodiments 21-23 wherein $R^2$ is chosen from hydrogen, $C_{1-6}$alkyl, and halo.

Embodiment 25: the compound of Embodiment 24 wherein $R^2$ is chosen from hydrogen and halo.

Embodiment 26: the compound of Embodiment 25 wherein $R^2$ is hydrogen.

Embodiment 27: the compound of any one of Embodiments 1-26 wherein two or more $R^7$, together with the intervening atoms, form a heterocycloalkyl or heteroaryl.

Embodiment 28: the compound of Embodiment 27 wherein two or more $R^7$, together with the intervening atoms, form a heterocycloalkyl.

Embodiment 29: the compound of Embodiment 28 wherein two or more $R^7$, together with the intervening atoms, form a 5-membered heterocycloalkyl.

Embodiment 30: the compound of any one of Embodiments 27, 28, and 29 wherein at least one $R^7$ is independently chosen from halo, cyano, hydroxy, alkyl cyanoalkyl, alkoxy, haloalkyl, haloalkoxy, heteroaryl optionally substituted with alkyl, and heterocycloalkyl optionally substituted with alkyl.

Embodiment 31: the compound of any one of Embodiments 30 wherein at least one $R^7$ is independently chosen from halo, cyano, hydroxy, $C_{1-6}$alkyl, $C_{1-6}$alkoxy, $C_{1-6}$haloalkyl, and $C_{1-6}$haloalkoxy.

Embodiment 32: the compound of any one of Embodiments 1-26 wherein each $R^7$ is independently chosen from halo, cyano, hydroxy, $C_{1-4}$alkyl, $C_{1-4}$alkoxy, $C_{1-4}$haloalkyl, $C_{1-4}$hydroxyalkyl, cyanoalkyl, $C_{1-4}$alkoxy$C_{1-4}$alkyl, $C_{1-4}$alkoxy$C_{1-4}$alkoxyalkyl, amino$C_{1-4}$alkyl $C_{1-4}$acylamino$C_{1-4}$alkyl, ($C_{1-4}$haloalkyl)amino$C_{1-4}$alkyl, $C_{1-4}$alkylsulfonylamino$C_{1-4}$alkyl, aryl$C_{1-4}$alkyl, heteroaryl$C_{1-4}$alkyl, halo$C_{1-4}$alkoxy, heteroaryl optionally substituted with alkyl, and heterocycloalkyl optionally substituted with alkyl.

Embodiment 33: the compound of Embodiment 32 wherein each $R^7$ is independently chosen from halo, cyano, hydroxy, methyl, methoxy, trifluoromethyl, hydroxymethyl, cyanomethyl, 2-cyanoprop-2-yl, methoxymethyl, (2-(methoxy)ethoxy)methyl, $NH_2CH_2$, $CH_3CONHCH_2$, $CF_3CH_2NHCH_2$, $CH_3SO_2NHCH_2$, aryl$C_{1-4}$alkyl, heteroaryl$C_{1-4}$alkyl, trifluoromethoxy, pyrazolyl, imidazolyl, benzimidazolyl, benzotriazolyl, (methyl)pyrazolyl, (methyl)imidazolyl, (methyl)benzimidazolyl, and (methyl)benzotriazolyl.

Embodiment 34: the compound of any one of Embodiments 1-26 wherein each $R^7$ is independently chosen from halo, cyano, hydroxy, alkyl, cyanoalkyl, alkoxy, haloalkyl, haloalkoxy, heteroaryl optionally substituted with alkyl, and heterocycloalkyl optionally substituted with alkyl.

Embodiment 35: the compound of Embodiment 34 wherein each $R^7$ is independently chosen from halo, cyano, hydroxy, $C_{1-6}$alkyl, cyano$C_{1-6}$alkyl, $C_{1-6}$alkoxy, $C_{1-6}$haloalkyl, $C_{1-6}$haloalkoxy, 5-10 membered heteroaryl optionally substituted with $C_{1-6}$alkyl, and 5-10 membered heterocycloalkyl optionally substituted with $C_{1-6}$alkyl.

Embodiment 36: the compound of Embodiment 35 wherein each $R^7$ is independently chosen from halo, cyano, hydroxy, $C_{1-4}$alkyl, cyano$C_{1-4}$alkyl, $C_{1-4}$alkoxy, $C_{1-4}$haloalkyl, $C_{1-4}$haloalkoxy, 5-membered heteroaryl optionally substituted with $C_{1-4}$alkyl, and 5-membered heterocycloalkyl optionally substituted with $C_{1-4}$alkyl.

Embodiment 37: the compound of Embodiment 36 wherein each $R^7$ is independently chosen from halo, cyano, hydroxy, methyl, ethyl, 2-cyanoethyl, 2-cyano-2-propyl, methoxy, ethoxy, trifluoromethyl, difluoromethoxy, trifluoromethoxy, methylpyrrolyl, methylpyrazolyl, methylimidazolyl, methyltriazolyl, ethylpyrrolyl, ethylpyrazolyl, ethylimidazolyl, and ethyltriazolyl.

Embodiment 38: the compound of Embodiment 37 wherein each $R^7$ is independently chosen from halo, cyano, hydroxy, methyl, 2-cyano-2-propyl, methoxy, trifluoromethyl, trifluoromethoxy, and 1-methyl-1H-pyrazol-4-yl.

Embodiment 39: the compound of Embodiment 38 wherein each $R^7$ is independently chosen from halo, cyano, and hydroxy.

Embodiment 40: the compound of Embodiment 39 wherein each $R^7$ is independently chosen from halo and cyano.

Embodiment 41: the compound of any one of Embodiments 1-26 and 34-40 wherein $R^{1a}$ is optionally substituted with 1, 2, or 3 $R^7$.

Embodiment 42: the compound of Embodiment 41 wherein $R^{1a}$ is substituted with 1, 2, or 3 $R^7$.

Embodiment 43: the compound of Embodiment 42 wherein $R^{1a}$ is substituted with 1 or 2 $R^7$.

Embodiment 44: the compound of Embodiment 42 wherein $R^{1a}$ is substituted with 2 $R^7$.

Embodiment 45: the compound of Embodiment 42 wherein wherein $R^{1a}$ is substituted with 2 or 3 $R^7$.

Embodiment 46: the compound of Embodiment 42 wherein $R^{1a}$ is substituted with 3 $R^7$.

Embodiment 47: the compound of any one of Embodiments 42-46 wherein at least one $R^7$ is halo.

Embodiment 48: the compound of any one of Embodiments 42-46 wherein at least one $R^7$ is fluoro.

Embodiment 49: the compound of either one of Embodiments 45 and 46 wherein at least two $R^7$ are halo.

Embodiment 50: the compound of either one of Embodiments 45 and 46 wherein at least two $R^7$ are fluoro.

Embodiment 51: the compound of Embodiment 41 wherein $R^{1a}$ is optionally substituted with 1 or 2 $R^7$.

Embodiment 52: the compound of Embodiment 51 wherein $R^{1a}$ is optionally substituted with 1 $R^7$.

Embodiment 53: the compound of Embodiment 51 wherein $R^{1a}$ is substituted with 1 $R^7$.

Embodiment 54: the compound of any one of Embodiments 41-53 wherein each $R^7$ is halo.

Embodiment 55: the compound of Embodiment 54 wherein each $R^7$ is independently chosen from fluoro and chloro.

Embodiment 56: the compound of Embodiment 54 wherein each $R^7$ is fluoro.

Embodiment 57: the compound of any one of Embodiments 1-26 wherein $R^{1a}$ is unsubstituted with an $R^7$.

Embodiment 58: the compound of any one of Embodiments 1-57 wherein $R^{1a}$ is chosen from $C_{6-10}$aryl and 5- to 10-membered heteroaryl.

Embodiment 59: the compound of Embodiment 58 wherein $R^{1a}$ is chosen from phenyl, pyridyl, pyridazinyl, pyrimidinyl, and pyrazinyl.

Embodiment 60: the compound of of any one of Embodiments 1-57 wherein $R^{1a}$ is aryl.

Embodiment 61: the compound of Embodiment 60 wherein $R^{1a}$ is phenyl.

Embodiment 62: the compound of any one of Embodiments 53-56 wherein $R^{1a}$ is

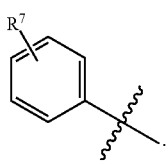

Embodiment 63: the compound of any one of Embodiments 44, 47, and 48, wherein $R^{1a}$ is chosen from

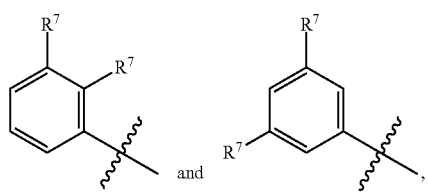

and each $R^7$ is the same or different.

Embodiment 64: the compound of Embodiment 63, wherein $R^{1a}$ is

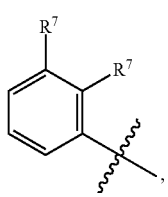

and each $R^7$ is the same or different.

Embodiment 65: the compound of Embodiment 44, wherein $R^7$ is halo.

Embodiment 66: the compound of Embodiment 63 wherein $R^{1a}$ is

Embodiment 67: the compound of any one of Embodiments 46-50 wherein $R^{1a}$ is chosen from

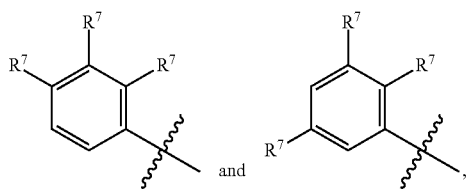

and each $R^7$ is the same or different.

Embodiment 68: the compound of any one of Embodiments 1-67 wherein $Y^3$ is $CR^3$.

Embodiment 69: the compound of Embodiment 68 wherein $R^3$ is chosen from $C_{1-6}$alkyl and H.

Embodiment 70: the compound of Embodiment 69 wherein $R^3$ is $C_{1-6}$alkyl.

Embodiment 71: the compound of Embodiment 69 wherein $R^3$ is H.

Embodiment 72: the compound of any one of Embodiments 1-67 wherein $Y^3$ is a bond.

Embodiment 73: the compound of any one of Embodiments 1-72 wherein:
  $Y^4$ is chosen from $CR^4$ and $NR^4$; and
  $R^4$ and $R^{5a}$, together with the intervening atoms, combine to form a cycloalkyl or heterocycloalkyl ring, either of which is optionally substituted with 1 or 2 $R^9$.

Embodiment 74: the compound of Embodiment 73 wherein $R^4$ and $R^{5a}$, together with the intervening atoms, combine to form a cycloalkyl or heterocycloalkyl ring, either of which is optionally substituted with 1 $R^9$.

Embodiment 75: the compound of Embodiment 74 wherein $R^4$ and $R^{5a}$, together with the intervening atoms, combine to form a cycloalkyl or heterocycloalkyl ring, either of which is substituted with 1 $R^9$.

Embodiment 76: the compound of any one of Embodiments 73-75 wherein each $R^9$ is independently chosen from halo, cyano, and hydroxy.

Embodiment 77: the compound of Embodiment 76 wherein each $R^9$ is independently chosen from halo and cyano.

Embodiment 78: the compound of Embodiment 77 wherein each $R^9$ is halo.

Embodiment 79: the compound of Embodiment 78 wherein each $R^9$ is fluoro.

Embodiment 80: the compound of Embodiment 74 wherein $R^4$ and $R^{5a}$, together with the intervening atoms, combine to form a cycloalkyl or heterocycloalkyl ring, either of which is unsubstituted with an $R^9$.

Embodiment 81: the compound of any one of Embodiments 1-72 wherein $R^4$ is chosen from hydrogen, $C_{1-6}$alkyl, $C_{1-6}$alkoxy, amino, amino$C_{1-6}$alkyl, hydroxy$C_{1-6}$alkyl, $C_{1-6}$alkoxy$C_{1-6}$alkyl, cyano, halo, and hydroxy.

Embodiment 82: the compound of Embodiment 81 wherein $R^4$ is chosen from hydrogen, methyl, methoxy, $NH_2$, $NH_2CH_2$, $HOCH_2$, methoxymethyl, cyano, halo, and hydroxy.

Embodiment 83: the compound of any one of Embodiments 1-72 wherein $R^4$ is chosen from hydrogen, alkyl, alkoxy, halo, and hydroxy.

Embodiment 84: the compound of Embodiment 83 wherein $R^4$ is chosen from hydrogen, $C_{1-6}$alkyl, $C_{1-6}$alkoxy, halo, and hydroxy.

Embodiment 85: the compound of Embodiment 84 wherein $R^4$ is chosen from hydrogen and halo.

Embodiment 86: the compound of Embodiment 85 wherein $R^4$ is hydrogen.

Embodiment 87: the compound of any one of Embodiments 83-86 wherein $R^{5a}$ is chosen from hydrogen and $C_{1-6}$alkyl.

Embodiment 88: the compound of Embodiment 87 wherein $R^{5a}$ is hydrogen.

Also provided herein is Embodiment 89, the compound of Embodiment 1 having structural Formula (III):

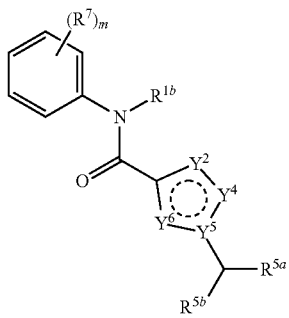

or a salt thereof, wherein:
- $Y^2$ is chosen from $CR^2$, $NR^2$, and N;
- $Y^4$ is chosen from $CR^4$, $NR^4$, and N;
- $Y^5$ is chosen from C and N;
- $Y^6$ is chosen from $CR^6$, N, and O;
- $Y^2$, $Y^4$, $Y^5$, $Y^6$, and the intervening carbon combine to form a 5- or 6-membered heteroaryl;
- $R^{1b}$ is chosen from hydrogen and alkyl;
- $R^2$ is chosen from hydrogen, alkyl, and halo;
- $R^4$ is chosen from hydrogen, alkyl, alkoxy, amino, aminoalkyl, hydroxyalkyl, alkoxyalkyl, cyano, halo, and hydroxy;
- $R^{5a}$ is chosen from hydrogen and alkyl;
- $R^{5b}$ is chosen from alkyl, cycloalkyl, heterocycloalkyl, aryl and heteroaryl, any of which is optionally substituted with one or more $R^{10}$;
- $R^6$ is chosen from hydrogen, alkyl, alkoxy, cyano, halo, and hydroxy; each $R^7$ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or
- two or more $R^7$, together with the intervening atoms, can form a heterocycloalkyl or heteroaryl;
- each $R^{10}$ is independently chosen from alkyl, haloalkyl, amino, aminoalkyl, aminocarbonyl, alkoxy, haloalkoxy, cyano, halo, and hydroxy; and
- m is chosen from 0, 1, 2, and 3.

Embodiment 90: the compound of Embodiment 89 wherein $R^{1b}$ is chosen from hydrogen and $C_{1-6}$alkyl.

Embodiment 91: the compound of Embodiment 90 wherein $R^{1b}$ is hydrogen.

Embodiment 92: the compound of any one of Embodiments 89-91 wherein $R^2$ is chosen from hydrogen, $C_{1-6}$alkyl, and halo.

Embodiment 93: the compound of Embodiment 92 wherein $R^2$ is chosen from hydrogen and halo.

Embodiment 94: the compound of Embodiment 93 wherein $R^2$ is hydrogen.

Embodiment 95: the compound of any one of Embodiments 89-94 wherein $R^4$ is chosen from hydrogen, $C_{1-6}$alkyl, $C_{1-6}$alkoxy, amino, amino$C_{1-6}$alkyl, hydroxy$C_{1-6}$alkyl, $C_{1-6}$alkoxy$C_{1-6}$alkyl, cyano, halo, and hydroxy.

Embodiment 96: the compound of Embodiment 95 wherein $R^4$ is chosen from hydrogen, methyl, methoxy, $NH_2$, $NH_2CH_2$, $HOCH_2$, methoxymethyl, cyano, halo, and hydroxy.

Embodiment 97: the compound of any one of Embodiments 89-94 wherein $R^4$ is chosen from hydrogen, $C_{1-6}$alkyl, $C_{1-6}$alkoxy, halo, and hydroxy.

Embodiment 98: the compound of Embodiment 97 wherein $R^4$ is chosen from hydrogen and halo.

Embodiment 99: the compound of Embodiment 98 wherein $R^4$ is hydrogen.

Embodiment 100: the compound of any one of Embodiments 89-99 wherein $R^{5a}$ is chosen from hydrogen and $C_{1-6}$alkyl.

Embodiment 101: the compound of Embodiment 100 wherein $R^{5a}$ is $C_{1-6}$alkyl.

Embodiment 102: the compound of Embodiment 100 wherein $R^{5a}$ is hydrogen.

Embodiment 103: the compound of any one of Embodiments 89-99 wherein at least one of $Y^2$, $Y^4$, $Y^5$, and $Y^6$ is N.

Embodiment 104: the compound of Embodiment 103 wherein $Y^2$, $Y^4$, $Y^5$, $Y^6$, and the intervening carbon combine to form a 5-membered heteroaryl chosen from 1H-pyrazole, 1H-imidazole, 1,3,4-oxadiazole, and 1H-1,2,4-triazole.

Embodiment 105: the compound of Embodiment 103 wherein exactly two of $Y^2$, $Y^4$, $Y^5$, and $Y^6$ are N.

Embodiment 106: the compound of Embodiment 105 wherein $Y^2$, $Y^4$, $Y^5$, $Y^6$, and the intervening carbon combine to form a 5-membered heteroaryl chosen from 1H-pyrazole, 1H-imidazole, and 1,3,4-oxadiazole.

Embodiment 107: the compound of Embodiment 103 wherein exactly three of $Y^2$, $Y^4$, $Y^5$, and $Y^6$ are N.

Embodiment 108: the compound of Embodiment 107 wherein $Y^2$, $Y^4$, $Y^5$, $Y^6$, and the intervening carbon combine to form 1H-1,2,4-triazole.

Embodiment 109: the compound of any one of Embodiments 1-108 wherein each $R^{10}$ is independently chosen from $C_{1-4}$alkyl, $C_{1-4}$haloalkyl, $NH_2$, $NH_2CH_2$, $NH_2CO$, $C_{1-4}$alkoxy, $C_{1-4}$haloalkoxy, cyano, halo, and hydroxy.

Embodiment 110: the compound of Embodiment 109 wherein each $R^{10}$ is independently chosen from methyl, halomethyl, $NH_2$, $NH_2CH_2$, $NH_2CO$, methoxy, halomethoxy, cyano, halo, and hydroxy.

Embodiment 111: the compound of any one of Embodiments 1-108 wherein each $R^{10}$ is independently chosen from $C_{1-6}$alkyl, $C_{1-6}$haloalkyl, $C_{1-6}$alkoxy, $C_{1-6}$haloalkoxy, cyano, halo, and hydroxy.

Embodiment 112: the compound of Embodiment 111 wherein each $R^{10}$ is independently chosen from methyl, difluoromethyl, trifluoromethyl, difluoromethoxy, trifluoromethoxy, cyano, halo, and hydroxy.

Embodiment 113: the compound of Embodiment 112 wherein each $R^{10}$ is independently chosen from halo, cyano, and hydroxy.

Embodiment 114: the compound of Embodiment 113 wherein each $R^{10}$ is independently chosen from halo and cyano.

Embodiment 115: the compound of any one of Embodiments 1-114 wherein $R^{5b}$ is optionally substituted with 1, 2, or 3 $R^{10}$.

Embodiment 116: the compound of Embodiment 115 wherein $R^{5b}$ is substituted with 1, 2, or 3 $R^{10}$.

Embodiment 117: the compound of Embodiment 116 wherein $R^{5b}$ is substituted with 1 or 2 $R^{10}$.

Embodiment 118: the compound of Embodiment 116 wherein $R^{5b}$ is substituted with 2 $R^{10}$.

Embodiment 119: the compound of Embodiment 116 wherein $R^{5b}$ is substituted with 2 or 3 R10.

Embodiment 120: the compound of Embodiment 116 wherein $R^{5b}$ is substituted with 3 $R^{10}$.

Embodiment 121: the compound of any one of Embodiments 116-120 wherein at least one $R^{10}$ is halo.

Embodiment 122: the compound of any one of Embodiments 116-120 wherein at least one $R^{10}$ is fluoro.

Embodiment 123: the compound of either one of Embodiments 119 and 120 wherein at least two $R^{10}$ are halo.

Embodiment 124: the compound of either one of Embodiments 119 and 120 wherein at least two $R^{10}$ are fluoro.

Embodiment 125: the compound of Embodiment 115 wherein $R^{5b}$ is optionally substituted with 1 or 2 $R^{10}$.

Embodiment 126: the compound of Embodiment 115 wherein $R^{5b}$ is optionally substituted with 1 $R^{10}$.

Embodiment 127: the compound of Embodiment 115 wherein $R^{5b}$ is substituted with 1 $R^{10}$.

Embodiment 128: the compound of any one of Embodiments 115-127 wherein $R^{10}$ is halo.

Embodiment 129: the compound of any one of Embodiments 115-127 wherein $R^{10}$ is fluoro.

Embodiment 130: the compound Embodiment 115 wherein $R^{5b}$ is unsubstituted with an $R^{10}$.

Embodiment 131: the compound any one of Embodiments 115-130 wherein $R^{5b}$ is chosen from aryl and heteroaryl.

Embodiment 132: the compound of Embodiment 131 wherein $R^{5b}$ is chosen from phenyl, pyridinyl, pyridazinyl, pyrimidinyl, and pyrazinyl.

Embodiment 133: the compound of Embodiment 132 wherein $R^{5b}$ is chosen from phenyl and pyrazinyl.

Embodiment 134: the compound of Embodiment 131 wherein $R^{5b}$ is aryl.

Embodiment 135: the compound of Embodiment 134 wherein $R^{5b}$ is phenyl.

Embodiment 136: the compound of Embodiment 115 wherein $R^{5b}$ is chosen from

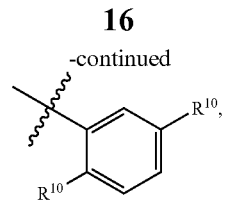

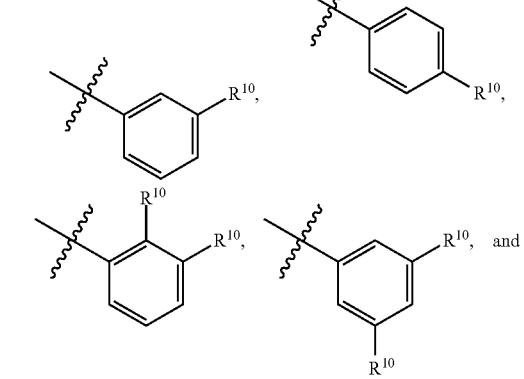

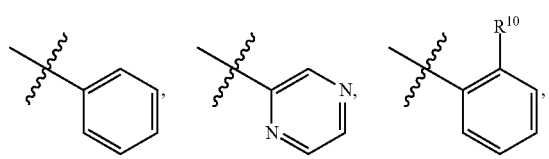

-continued

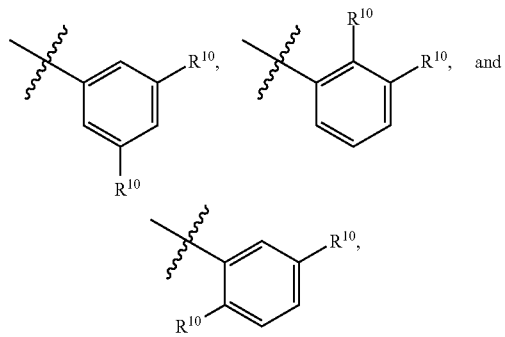

and each $R^{10}$ is the same or different.

Embodiment 137: the compound of Embodiment 115 wherein $R^{5b}$ is chosen from

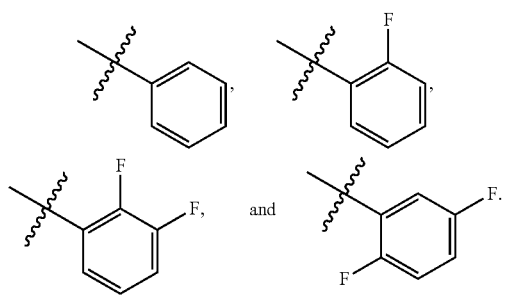

and each $R^{10}$ is the same or different.

Embodiment 138: the compound of either one of Embodiments 136 and 137 wherein each $R^{10}$ is independently chosen from halo and cyano.

Embodiment 139: the compound of Embodiment 138 wherein each $R^{10}$ is fluoro.

Embodiment 140: the compound of Embodiment 136 wherein $R^{5b}$ is chosen from

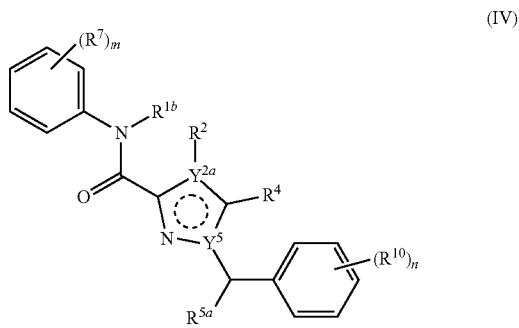

Also provided herein is Embodiment 141, the compound of Embodiment 1 having structural Formula (IV):

(IV)

or a salt thereof, wherein:
- $Y^{2a}$ and $Y^5$ are chosen from C and N;
- exactly one of $Y^{2a}$ and $Y^5$ is N;
- $Y^{2a}$ and $Y^5$ and the intervening nitrogen and carbons combine to form a 5-membered heteroaryl;
- $R^{1b}$ is chosen from hydrogen and alkyl;
- $R^2$ is chosen from hydrogen, alkyl, and halo;
- $R^4$ is chosen from hydrogen, alkyl, alkoxy, amino, aminoalkyl, hydroxyalkyl, alkoxyalkyl, cyano, halo, and hydroxy;
- $R^{5a}$ is chosen from hydrogen and alkyl;
- or $R^4$ and $R^{5a}$, together with the intervening atoms, may combine to form a cycloalkyl or heterocycloalkyl ring, either of which is optionally substituted with one or more $R^9$;
- each $R^7$ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or
- two or more $R^7$, together with the intervening atoms, can form a heterocycloalkyl or heteroaryl;
- each $R^9$ is independently chosen from alkyl, cyano, halo, and hydroxy;
- each $R^{10}$ is independently chosen from alkyl, haloalkyl, amino, aminoalkyl, aminocarbonyl, alkoxy, haloalkoxy, cyano, halo, and hydroxy; and
- m is chosen from 0, 1, 2, and 3; and
- n is chosen from 0, 1, 2, and 3.

Embodiment 142: the compound of Embodiment 141 wherein $Y^{2a}$ is C and $Y^5$ is N.

Embodiment 143: the compound of Embodiment 141 wherein $Y^{2a}$ is N and $Y^5$ is C.

Embodiment 144: the compound of any one of Embodiments 141-143 wherein $R^2$ is chosen from hydrogen, $C_{1-6}$alkyl, and halo.

Embodiment 145: the compound of Embodiment 144 wherein $R^2$ is chosen from hydrogen and halo.

Embodiment 146: the compound of Embodiment 145 wherein $R^2$ is hydrogen.

Also provided herein is Embodiment 147: the compound of Embodiment 1 having structural Formula (V):

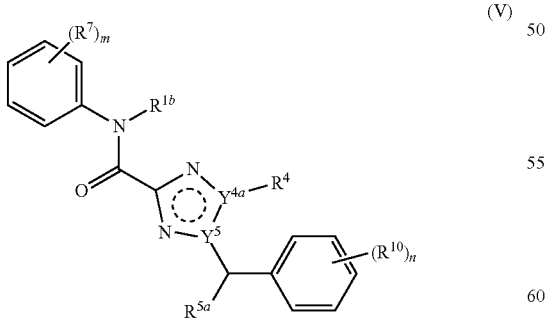

(V)

or a salt thereof, wherein:
- $Y^{4a}$ and $Y^5$ are chosen from C and N; exactly one of $Y^{4a}$ and $Y^5$ is N;
- $Y^{4a}$ and $Y^5$ and the intervening nitrogens and carbon combine to form a 5-membered heteroaryl;
- $R^{1b}$ is chosen from hydrogen and alkyl;
- $R^4$ is chosen from hydrogen, alkyl, alkoxy, amino, aminoalkyl, hydroxyalkyl, alkoxyalkyl, cyano, halo, and hydroxy;
- $R^{5a}$ is chosen from hydrogen and alkyl;
- or $R^4$ and $R^{5a}$, together with the intervening atoms, may combine to form a cycloalkyl or heterocycloalkyl ring, either of which is optionally substituted with one or more $R^9$;
- each $R^7$ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or
- two or more $R^7$, together with the intervening atoms, can form a heterocycloalkyl or heteroaryl;
- each $R^9$ is independently chosen from alkyl, cyano, halo, and hydroxy;
- each $R^{10}$ is independently chosen from alkyl, haloalkyl, amino, aminoalkyl, aminocarbonyl, alkoxy, haloalkoxy, cyano, halo, and hydroxy;
- m is chosen from 0, 1, 2, and 3; and
- n is chosen from 0, 1, 2, and 3.

Embodiment 148: the compound of Embodiment 147 wherein $Y^{4a}$ is C and $Y^5$ is N.

Embodiment 149: the compound of Embodiment 147 wherein $Y^{4a}$ is N and $Y^5$ is C.

Embodiment 150: the compound of any one of Embodiments 141-149 wherein $R^{1b}$ is chosen from hydrogen and $C_{1-6}$alkyl.

Embodiment 151: the compound of Embodiment 150 wherein $R^{1b}$ is hydrogen.

Also provided herein is Embodiment 152: the compound of Embodiment 1 having structural Formula (VI):

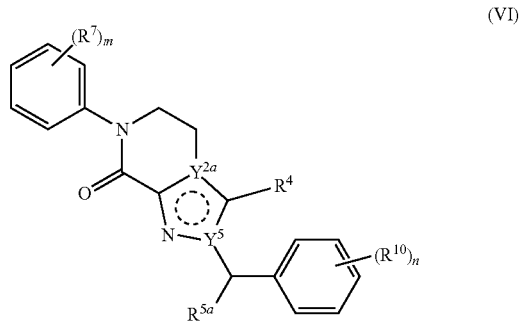

(VI)

or a salt thereof, wherein:
- $Y^{2a}$ and $Y^5$ are chosen from C and N;
- exactly one of $Y^{2a}$ and $Y^5$ is N;
- $Y^{2a}$, $Y^5$ and the intervening nitrogen and carbons combine to form a 5-membered heteroaryl;
- $R^4$ is chosen from hydrogen, alkyl, alkoxy, amino, aminoalkyl, hydroxyalkyl, alkoxyalkyl, cyano, halo, and hydroxy;
- $R^{5a}$ is chosen from hydrogen and alkyl;
- or $R^4$ and $R^{5a}$, together with the intervening atoms, may combine to form a cycloalkyl or heterocycloalkyl ring, either of which is optionally substituted with one or more $R^9$;
- each $R^7$ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or two or more $R^7$, together with the intervening atoms, can form a heterocycloalkyl or heteroaryl;

each $R^9$ is independently chosen from alkyl, cyano, halo, and hydroxy;

each $R^{10}$ is independently chosen from alkyl, haloalkyl, amino, aminoalkyl, aminocarbonyl, alkoxy, haloalkoxy, cyano, halo, and hydroxy;

m is chosen from 0, 1, 2, and 3; and n is chosen from 0, 1, 2, and 3.

Embodiment 153: the compound of Embodiment 152 wherein $Y^{2a}$ is C and $Y^5$ is N.

Embodiment 154: the compound of Embodiment 152 wherein $Y^{2a}$ is N and $Y^5$ is C.

Embodiment 155: the compound of any one of Embodiments 141-154 wherein $R^5$a is chosen from hydrogen and $C_{1-6}$alkyl.

Embodiment 156: the compound of Embodiment 155 wherein $R^{5a}$ is $C_{1-6}$alkyl.

Embodiment 157: the compound of Embodiment 155 wherein $R^{5a}$ is hydrogen.

Embodiment 158: the compound of any one of Embodiments 141-154 wherein $R^4$ and $R^{5a}$, together with the intervening atoms, combine to form a cycloalkyl or heterocycloalkyl ring, either of which is optionally substituted with 1 or 2 $R^9$.

Embodiment 159: the compound of Embodiment 158 wherein wherein $R^4$ and $R^{5a}$, together with the intervening atoms, combine to form a cycloalkyl or heterocycloalkyl ring, either of which is optionally substituted with 1 $R^9$.

Embodiment 160: the compound of Embodiment 159 wherein $R^4$ and $R^{5a}$, together with the intervening atoms, combine to form a cycloalkyl or heterocycloalkyl ring, either of which is substituted with 1 $R^9$.

Embodiment 161: the compound of any one of Embodiments 158-160 wherein each $R^9$ is independently chosen from halo, cyano, and hydroxy.

Embodiment 162: the compound of Embodiment 161 wherein each $R^9$ is independently chosen from halo and cyano.

Embodiment 163: the compound of Embodiment 162 wherein each $R^9$ is halo.

Embodiment 164: the compound of Embodiment 163 wherein each $R^9$ is fluoro.

Embodiment 165: the compound of Embodiment 159 wherein $R^4$ and $R^{5a}$, together with the intervening atoms, combine to form a cycloalkyl or heterocycloalkyl ring, either of which is unsubstituted with an $R^9$.

Embodiment 166: the compound of any one of Embodiments 141-157 wherein $R^4$ is chosen from hydrogen, $C_{1-6}$alkyl, $C_{1-6}$alkoxy, amino, amino$C_{1-6}$alkyl, hydroxy$C_{1-6}$alkyl, $C_{1-6}$alkoxy$C_{1-6}$alkyl, cyano, halo, and hydroxy.

Embodiment 167: the compound of Embodiment 166 wherein $R^4$ is chosen from hydrogen, methyl, methoxy, $NH_2$, $NH_2CH_2$, $HOCH_2$, methoxymethyl, cyano, halo, and hydroxy.

Embodiment 168: the compound of any one of Embodiments 141-157 wherein $R^4$ is chosen from hydrogen, $C_{1-6}$alkyl, $C_{1-6}$alkoxy, halo, and hydroxy.

Embodiment 169: the compound of Embodiment 168 wherein $R^4$ is chosen from hydrogen and halo.

Embodiment 170: the compound of Embodiment 169 wherein $R^4$ is hydrogen.

Embodiment 171: the compound of any one of Embodiments 141-170 wherein each $R^{10}$ is independently chosen from $C_{1-6}$alkyl, $C_{1-6}$haloalkyl, $C_{1-6}$alkoxy, $C_{1-6}$haloalkoxy, cyano, halo, and hydroxy.

Embodiment 172: the compound of Embodiment 171 wherein each $R^{10}$ is independently chosen from methyl, difluoromethyl, trifluoromethyl, difluoromethoxy, trifluoromethoxy, cyano, halo, and hydroxy.

Embodiment 173: the compound of any one of Embodiments 141-170 wherein each $R^{10}$ is independently chosen from $C_{1-6}$alkyl, $C_{1-6}$haloalkyl, $C_{1-6}$alkoxy, $C_{1-6}$haloalkoxy, cyano, halo, and hydroxy.

Embodiment 174: the compound of Embodiment 173 wherein each $R^{10}$ is independently chosen from methyl, difluoromethyl, trifluoromethyl, difluoromethoxy, trifluoromethoxy, cyano, halo, and hydroxy.

Embodiment 175: the compound of Embodiment 174 wherein each $R^{10}$ is independently chosen from halo, cyano, and hydroxy.

Embodiment 176: the compound of Embodiment 175 wherein each $R^{10}$ is independently chosen from halo and cyano.

Embodiment 177: the compound of any one of Embodiments 141-176 wherein n is chosen from 1, 2, and 3.

Embodiment 178: the compound of Embodiment 177 wherein n is chosen from 1 and 2.

Embodiment 179: the compound of Embodiment 177 wherein n is 2.

Embodiment 180: the compound of Embodiment 177 wherein n is chosen from 2 and 3.

Embodiment 181: the compound of Embodiment 177 wherein n is 3.

Embodiment 182: the compound of any one of Embodiments 177-181 wherein at least one $R^{10}$ is halo.

Embodiment 183: the compound of any one of Embodiments 177-181 wherein at least one $R^{10}$ is fluoro.

Embodiment 184: the compound of either one of Embodiments 180 and 181 wherein at least two $R^{10}$ are halo.

Embodiment 185: the compound of either one of Embodiments 180 and 181 wherein at least two $R^{10}$ are fluoro.

Embodiment 186: the compound of any one of Embodiments 141-176 wherein n is chosen from 0, 1, and 2.

Embodiment 187: the compound of any one of Embodiments 186 wherein n is chosen from 0 and 1.

Embodiment 188: the compound of Embodiment 187 wherein n is 1.

Embodiment 189: the compound of any one of Embodiments 141-188 wherein each $R^{10}$ is halo.

Embodiment 190: the compound of any one of Embodiments 141-188 wherein each $R^{10}$ is fluoro.

Embodiment 191: the compound of any one of Embodiments 141-170 wherein n is 0.

Embodiment 192: the compound of any one of Embodiments 89-191 wherein each $R^7$ is independently chosen from halo, cyano, hydroxy, $C_{1-4}$alkyl, $C_{1-4}$alkoxy, $C_{1-4}$haloalkyl, $C_{1-4}$hydroxyalkyl, cyanoalkyl, $C_{1-4}$alkoxy$C_{1-4}$alkyl, $C_{1-4}$alkoxy$C_{1-4}$alkoxyalkyl, amino$C_{1-4}$alkyl, $C_{1-4}$acylamino$C_{1-4}$alkyl, ($C_{1-4}$haloalkyl)amino$C_{1-4}$alkyl, $C_{1-4}$alkylsulfonylamino$C_{1-4}$alkyl, aryl$C_{1-4}$alkyl, heteroaryl$C_{1-4}$alkyl, halo$C_{1-4}$alkoxy, heteroaryl optionally substituted with alkyl, and heterocycloalkyl optionally substituted with alkyl.

Embodiment 193: the compound of Embodiment 192 wherein each $R^7$ is independently chosen from halo, cyano, hydroxy, methyl, methoxy, trifluoromethyl, hydroxymethyl, cyanomethyl, 2-cyanoprop-2-yl, methoxymethyl, (2-

(methoxy)ethoxy)methyl, $NH_2CH_2$, $CH_3CONHCH_2$, $CF_3CH_2NHCH_2$, $CH_3SO_2NHCH_2$, aryl$C_{1-4}$alkyl, heteroaryl$C_{1-4}$alkyl, trifluoromethoxy, pyrazolyl, imidazolyl, benzimidazolyl, benzotriazolyl, (methyl)pyrazolyl, (methyl)imidazolyl, (methyl)benzimidazolyl, and (methyl)benzotriazolyl.

Embodiment 194: the compound of any one of Embodiments 89-191 wherein each $R^7$ is independently chosen from halo, cyano, hydroxy, $C_{1-6}$alkyl, cyano$C_{1-6}$alkyl, $C_{1-6}$alkoxy, $C_{1-6}$haloalkyl, $C_{1-6}$haloalkoxy, 5-10 membered heteroaryl optionally substituted with $C_{1-6}$alkyl, and 5-10 membered heterocycloalkyl optionally substituted with $C_{1-6}$alkyl.

Embodiment 195: the compound of Embodiment 194 wherein each $R^7$ is independently chosen from halo, cyano, hydroxy, $C_{1-4}$alkyl, cyano$C_{1-4}$alkyl, $C_{1-4}$alkoxy, $C_{1-6}$haloalkyl, $C_{1-4}$haloalkoxy, 5-membered heteroaryl optionally substituted with $C_{1-4}$alkyl, and 5-membered heterocycloalkyl optionally substituted with $C_{1-4}$alkyl.

Embodiment 196: the compound of Embodiment 195 wherein each $R^7$ is independently chosen from halo, cyano, hydroxy, methyl, ethyl, 2-cyanoethyl, 2-cyano-2-propyl, methoxy, ethoxy, trifluoromethyl, difluoromethoxy, trifluoromethoxy, methylpyrrolyl, methylpyrazolyl, methylimidazolyl, methyltriazolyl, ethylpyrrolyl, ethylpyrazolyl, ethylimidazolyl, and ethyltriazolyl.

Embodiment 197: the compound of Embodiment 196 wherein each $R^7$ is independently chosen from halo, cyano, hydroxy, methyl, 2-cyano-2-propyl, methoxy, trifluoromethyl, trifluoromethoxy, and 1-methyl-1H-pyrazol-4-yl.

Embodiment 198: the compound of Embodiment 197 wherein each $R^7$ is independently chosen from halo, cyano, and hydroxy.

Embodiment 199: the compound of Embodiment 198 wherein each $R^7$ is independently chosen from halo and cyano.

Embodiment 200: the compound of any one of Embodiments 89-199 wherein m is chosen from 1, 2, and 3.

Embodiment 201: the compound of Embodiment 200 wherein m is chosen from 1 and 2.

Embodiment 202: the compound of Embodiment 200 wherein m is 2.

Embodiment 203: the compound of Embodiment 200 wherein m is chosen from 2 and 3.

Embodiment 204: the compound of Embodiment 200 wherein m is 3.

Embodiment 205: the compound of any one of Embodiment 200-204 wherein at least one $R^7$ is halo.

Embodiment 206: the compound of any one of Embodiment 200-204 wherein at least one $R^7$ is fluoro.

Embodiment 207: the compound of either one of Embodiments 203 and 204 wherein at least two $R^7$ are halo.

Embodiment 208: the compound of either one of Embodiments 203 and 204 wherein at least two $R^7$ are fluoro.

Embodiment 209: the compound of any one of Embodiments 89-199 wherein m is chosen from 0, 1, and 2.

Embodiment 210: the compound of Embodiment 209 wherein m is chosen from 0 and

Embodiment 211: the compound of Embodiment 209 wherein m is 1.

Embodiment 212: the compound of Embodiment 89-211 wherein $R^7$ is halo.

Embodiment 213: the compound of Embodiment 89-211 wherein $R^7$ is fluoro.

Embodiment 214: the compound of any one of Embodiments 89-191 wherein m is 0.

Embodiment 215: The compound of any one of Embodiments 1-214 wherein $R^6$ is chosen from hydrogen, cyano, halo, and hydroxy.

Embodiment 216: The compound of Embodiment 215 wherein $R^6$ is chosen from hydrogen and halo.

Embodiment 217: The compound of Embodiment 216 wherein $R^6$ is chosen from hydrogen and chloro.

Embodiment 218: the compound of Embodiment 1, chosen from:

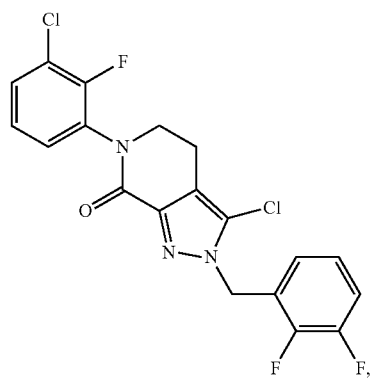

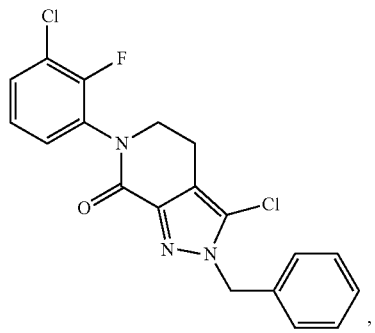

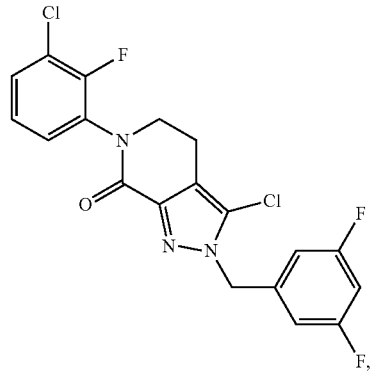

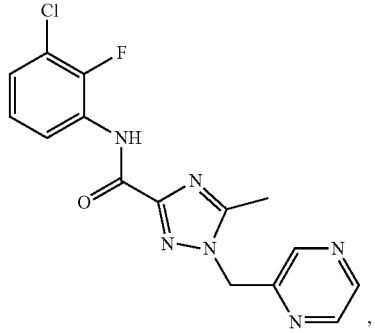

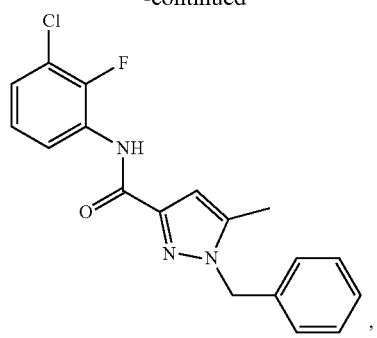,
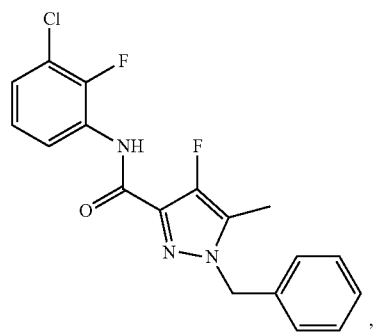,
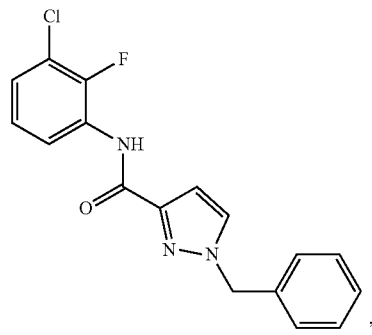,
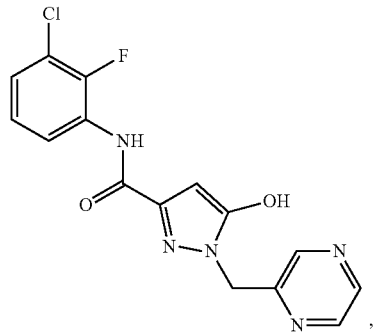,
,
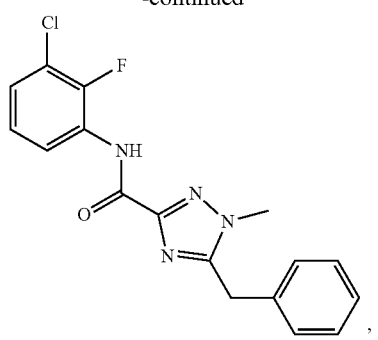,
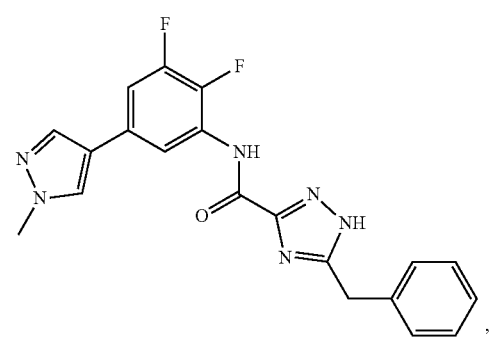,
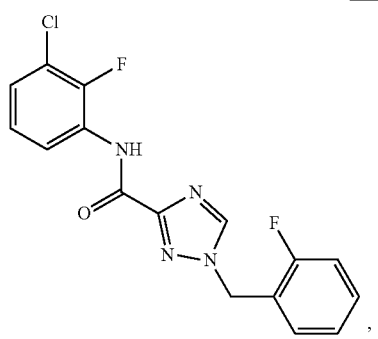,
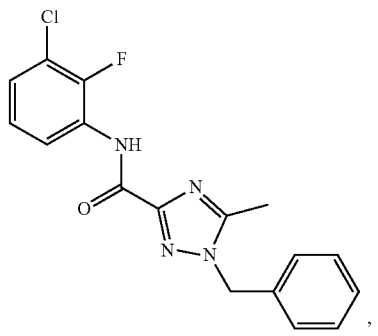,
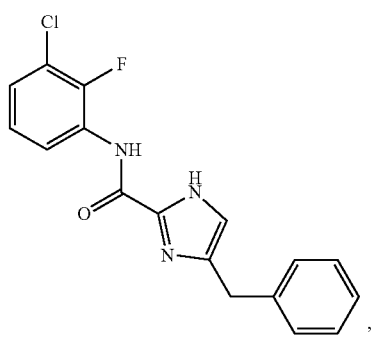,

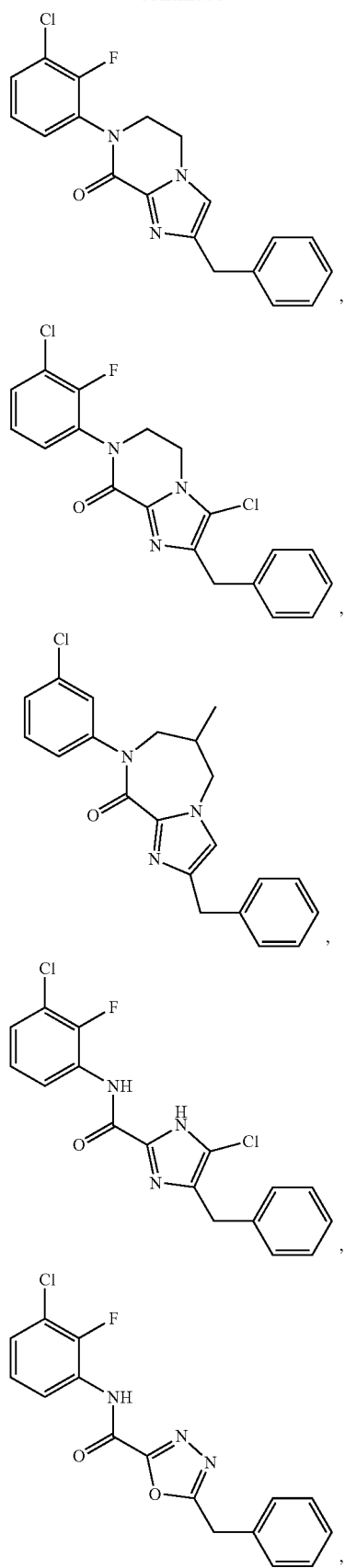
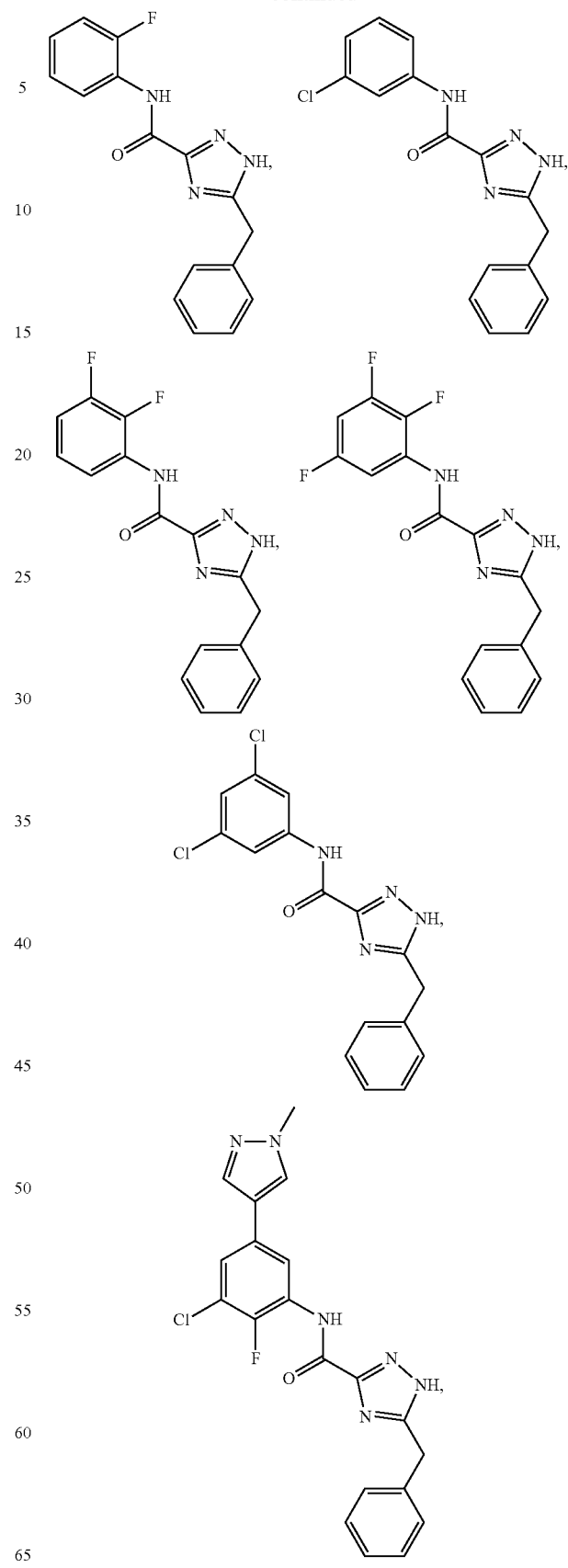

27
-continued
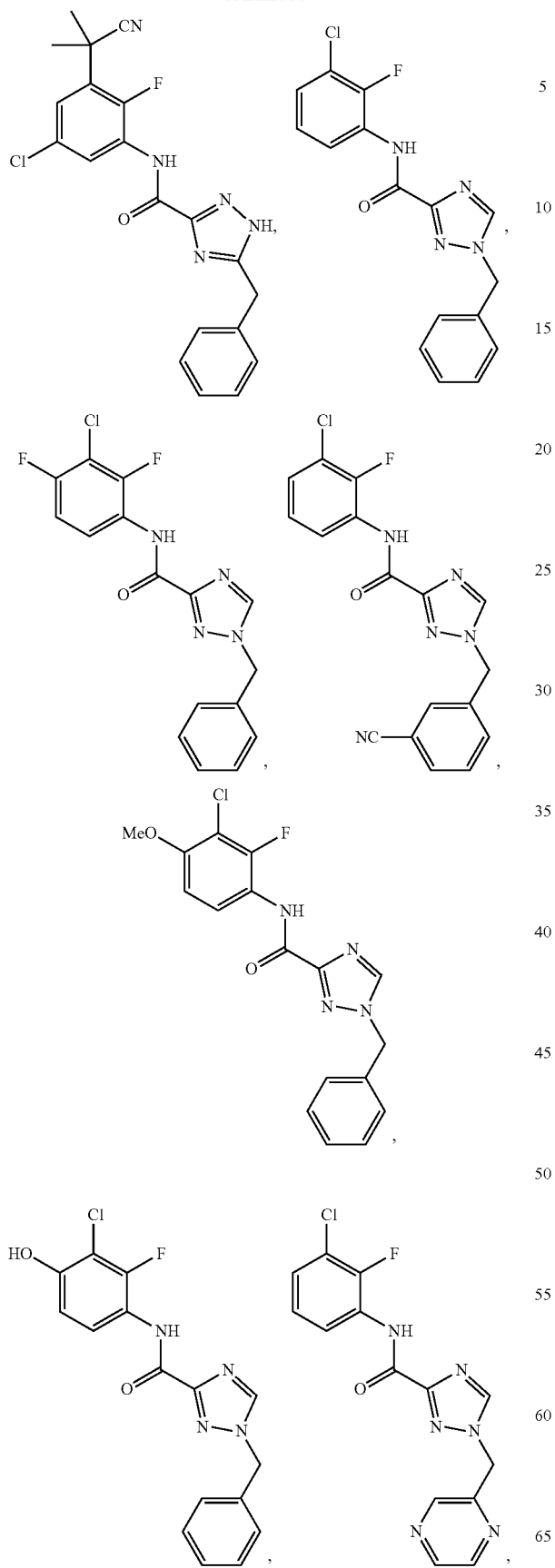
28
-continued
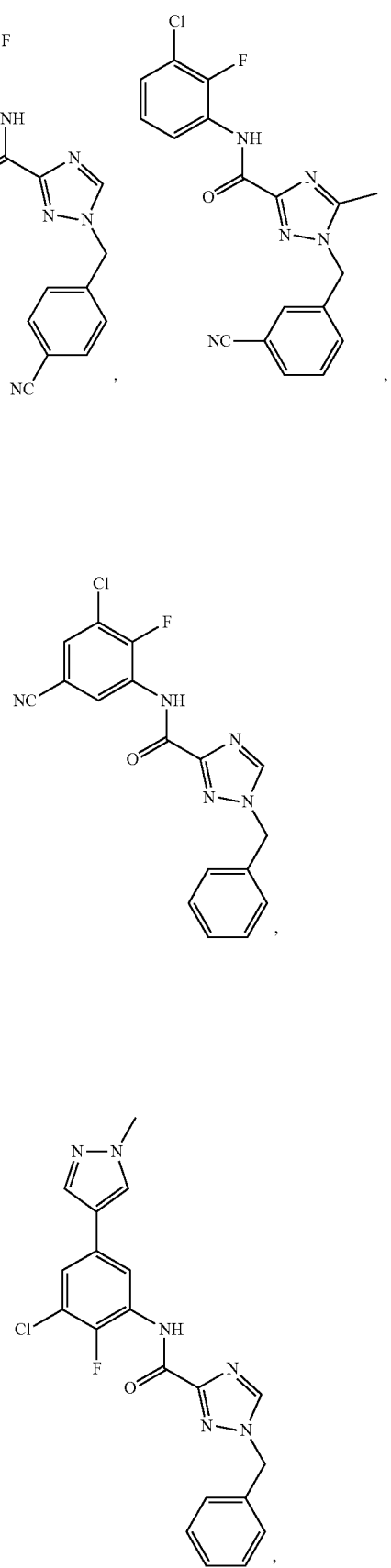

-continued
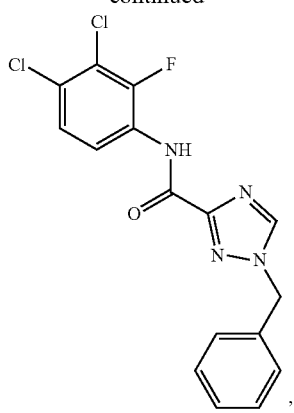
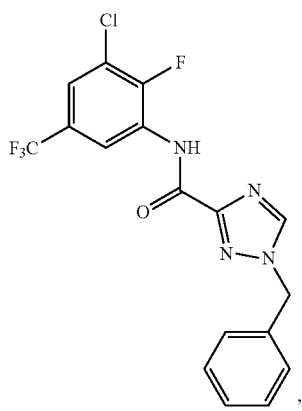
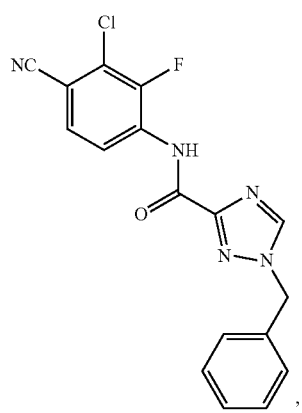
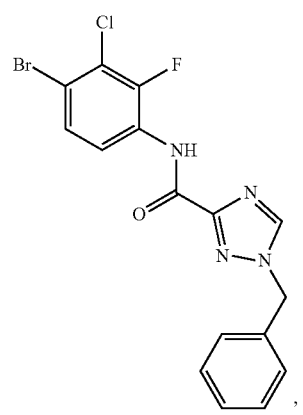
-continued
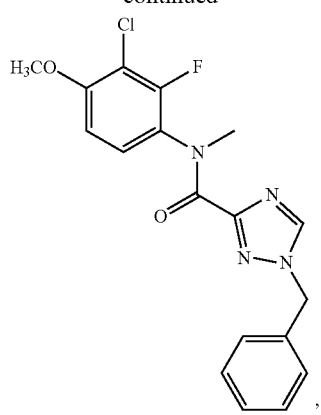
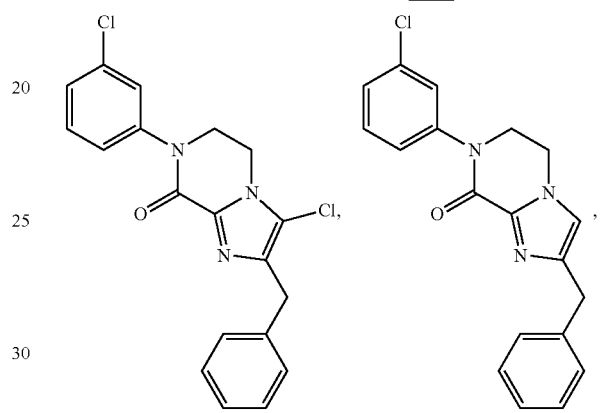

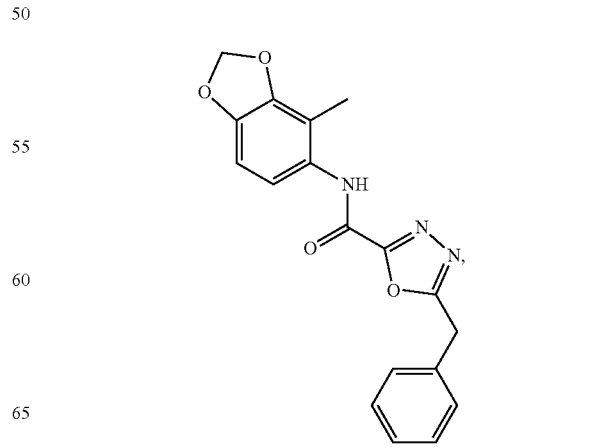

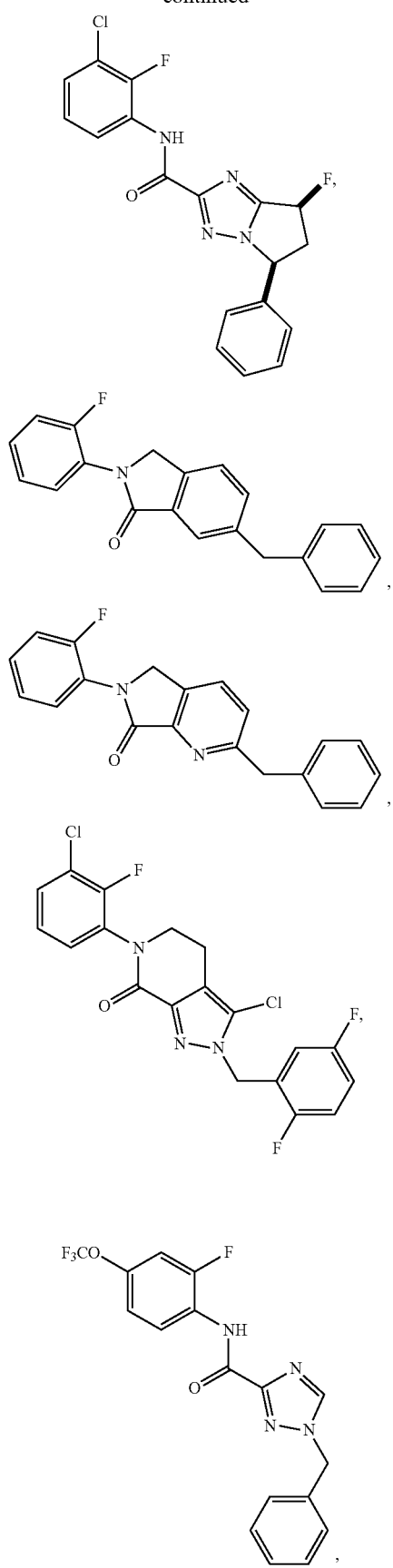
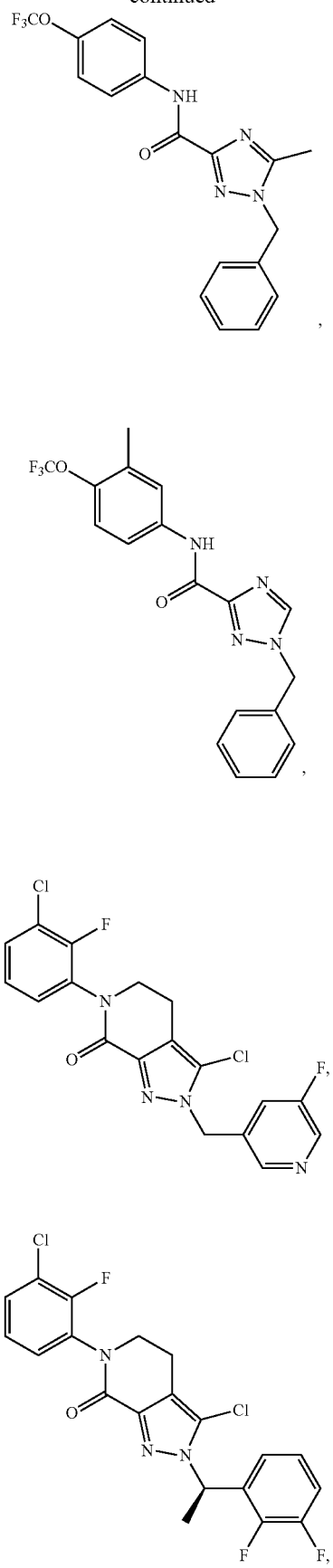

-continued
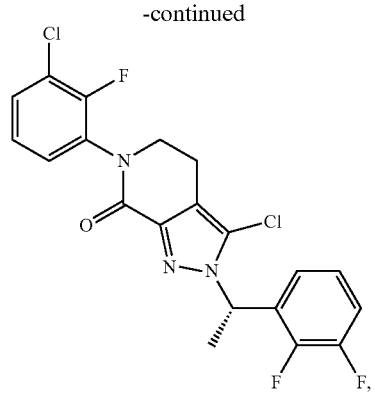
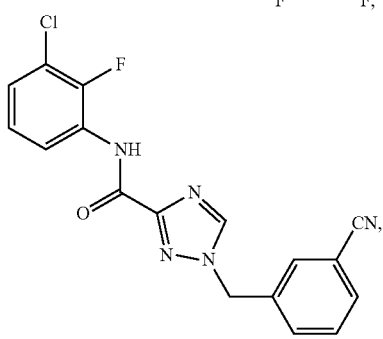
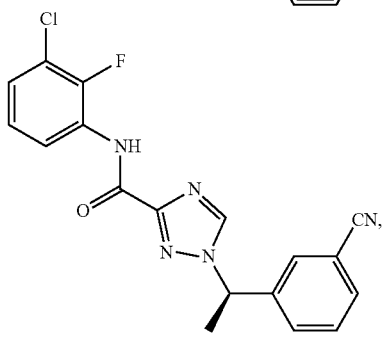
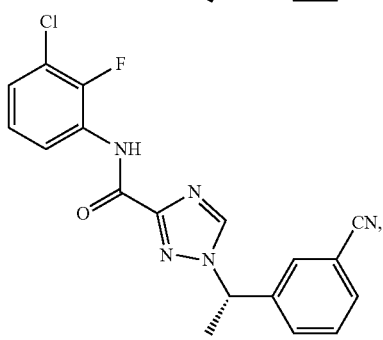
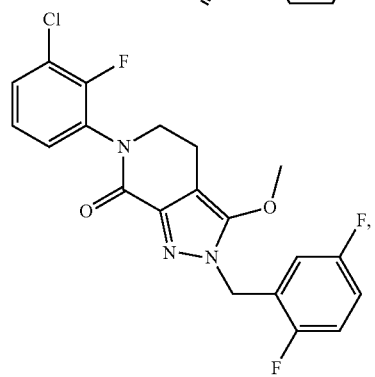
-continued
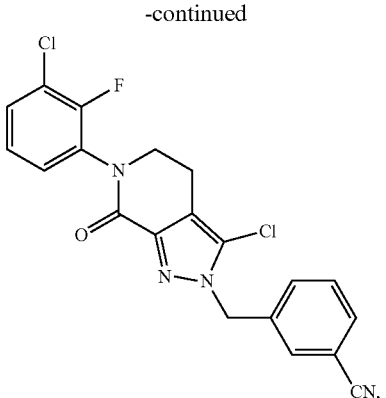
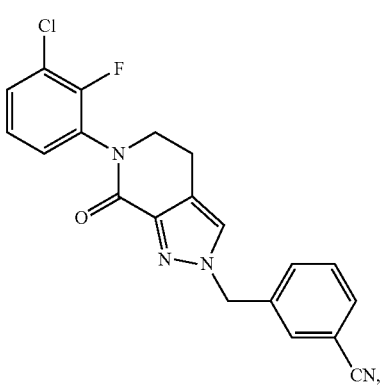
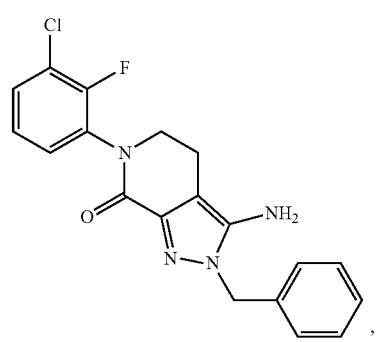
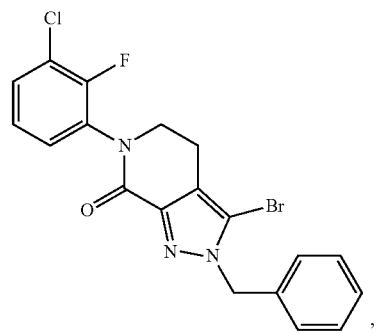

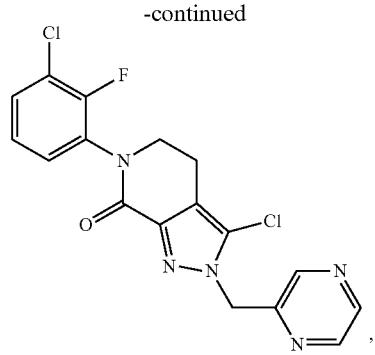
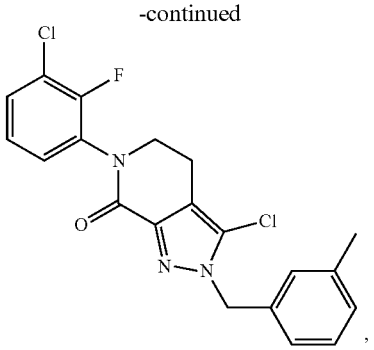

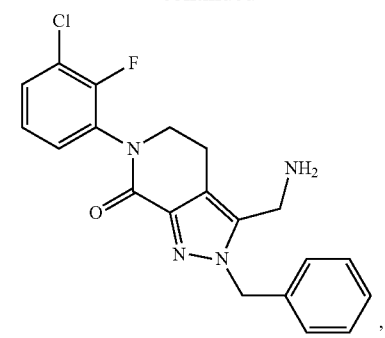
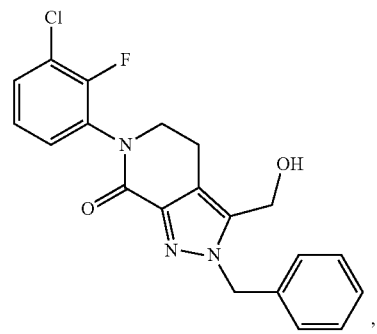
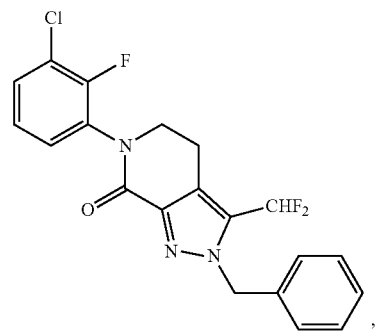
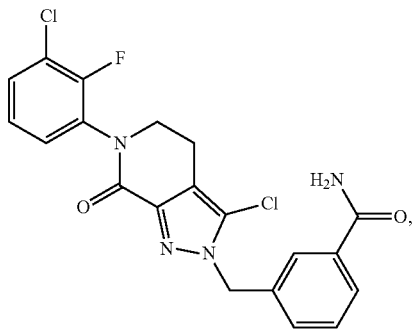
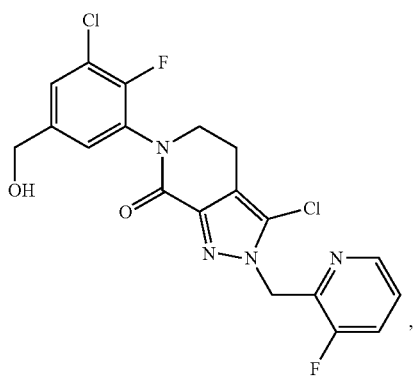
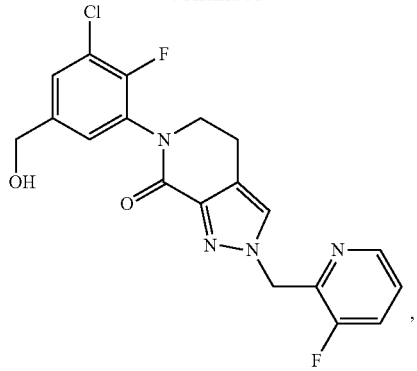
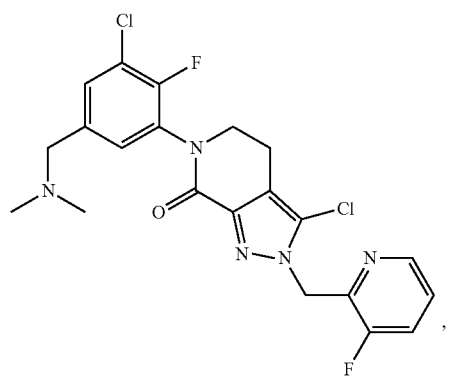
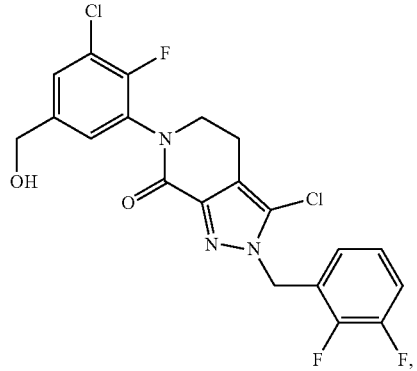
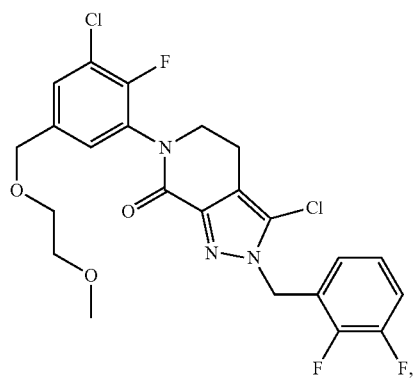

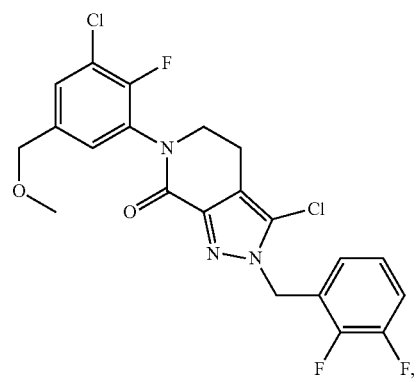
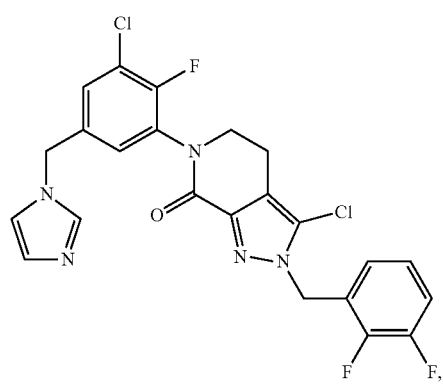
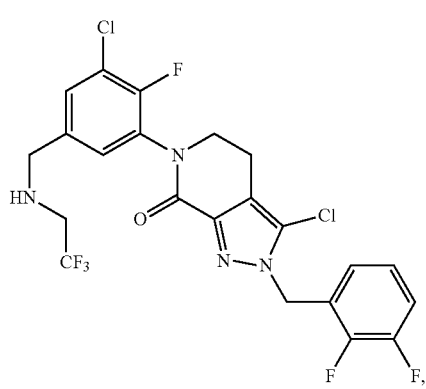
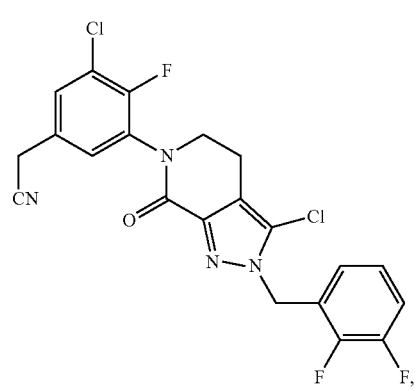
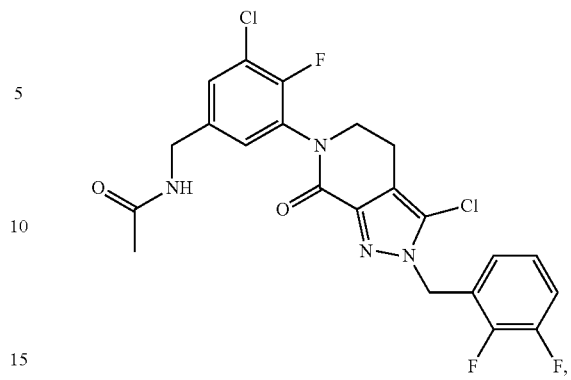
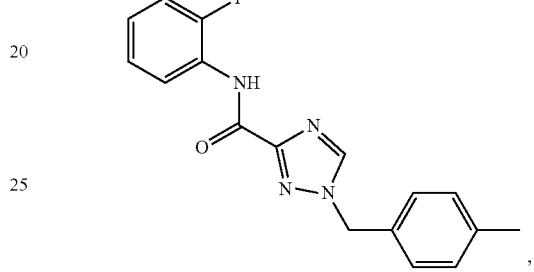
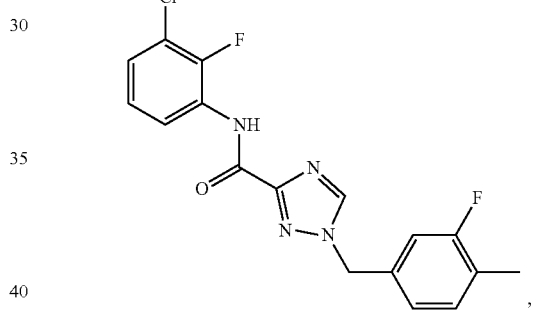
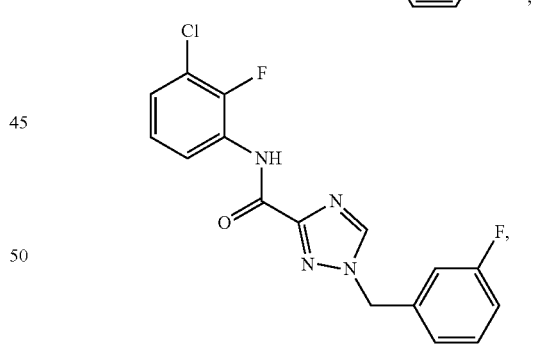
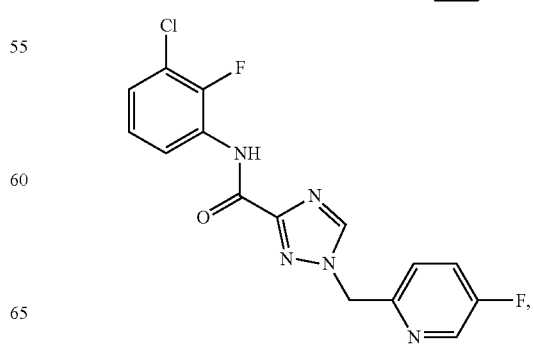

-continued
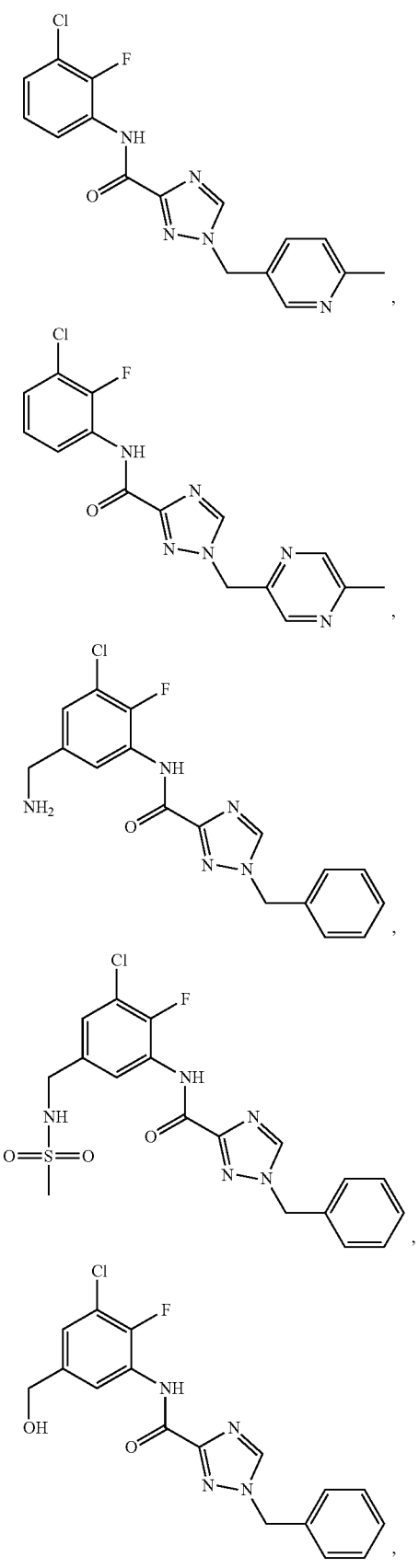 [SMILES: Cc1ccc(Cn2cnc(C(=O)Nc3cccc(Cl)c3F)n2)cn1 ; Cc1cnc(Cn2cnc(C(=O)Nc3cccc(Cl)c3F)n2)cn1 ; NCc1cc(Cl)c(F)c(NC(=O)c2ncn(Cc3ccccc3)n2)c1 ; CS(=O)(=O)NCc1cc(Cl)c(F)c(NC(=O)c2ncn(Cc3ccccc3)n2)c1 ; O=C(Nc1cc(CO)cc(Cl)c1F)c1ncn(Cc2ccccc2)n1]
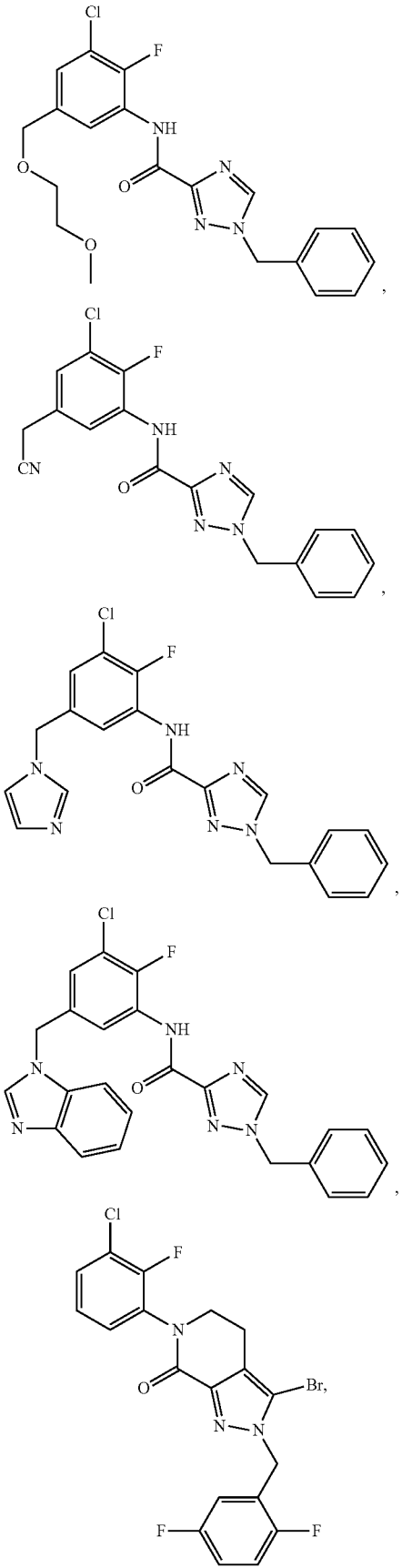

-continued

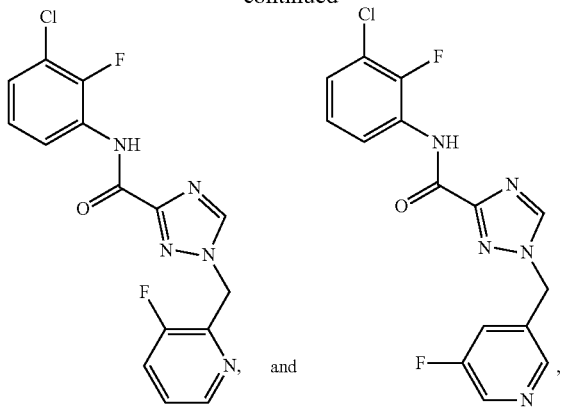

and or a salt thereof.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

Also provided are methods of inhibiting at least one RIPK1 function comprising the step of contacting RIPK1 with a compound as described herein. The cell phenotype, cell proliferation, activity of RIPK1, change in biochemical output produced by active RIPK1, expression of RIPK1, or binding of RIPK1 with a natural binding partner may be monitored. Such methods may be modes of treatment of disease, biological assays, cellular assays, biochemical assays, or the like.

Also provided herein are methods of treatment of a RIPK1-mediated disease comprising the administration of a therapeutically effective amount of a compound as disclosed herein, or a salt thereof, to a patient in need thereof.

In certain embodiments, the disease is chosen from neurodegenerative disorders, inflammatory disorders, and cancer.

In certain embodiments, the disease is cancer. In certain embodiments, the cancer is treated by promoting an appropriate immune response to the tumor. In certain embodiments, the appropriate immune response to the tumor comprises, or results in, one or more of the following:
  an increase in the number or activity, or degree of tumor infiltration, of cytotoxic T-lymphocytes and/or natural killer cells;
  an increase in the number or activity of M1 macrophages in the tumor microenvironment and/or a decrease in the in the number or activity of M2 macrophages in the tumor microenvironment;
  a decrease in the number or activity of regulatory T cells; and
  a decrease in the number or activity of myeloid-derived suppressor cells.

Also provided herein is a compound as disclosed herein for use as a medicament.

Also provided herein is a compound as disclosed herein for use as a medicament for the treatment of a RIPK1-mediated disease.

Also provided is the use of a compound as disclosed herein as a medicament.

Also provided is the use of a compound as disclosed herein as a medicament for the treatment of a RIPK1-mediated disease.

Also provided is a compound as disclosed herein for use in the manufacture of a medicament for the treatment of a RIPK1-mediated disease.

Also provided is the use of a compound as disclosed herein for the treatment of a RIPK1-mediated disease.

Also provided herein is a method of inhibition of RIPK1 comprising contacting RIPK1 with a compound as disclosed herein, or a salt thereof.

Also provided herein is a method for achieving an effect in a patient comprising the administration of a therapeutically effective amount of a compound as disclosed herein, or a salt thereof, to a patient wherein the effect is chosen from cognition enhancement.

Also provided is a method of modulation of a RIPK1-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group.

Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a straight chain saturated or unsaturated hydrocarbon attached at two positions, such as methylene (—CH$_2$—), ethylene (—CH$_2$CH$_2$—), and propylene (—CH$_2$CH$_2$CH$_2$—). "Alkylene" thus consists of units chosen from —CH$_2$— and —CH=CH—.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR' wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, which is optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl,"as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C$_6$H$_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. In certain embodiments, said cycloalkyl will comprise a spirocycle ring system. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and one, two, or three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings wherein heteroaryl rings are fused with other heteroaryl rings wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridinyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member wherein each said heteroatom may be independently chosen from nitrogen, oxygen, and sulfur. In certain embodiments, said heterocycloalkyl will comprise a spirocycle ring system. In certain embodiments, said heterocycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups is optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which is optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR' wherein R and R' are independently chosen from hydrogen and optionally substituted lower alkyl.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)2—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3$CS(O)$_2$NR— group with X is a halogen and R as defined herein.

The term "trihalomethanesulfonyl" refers to a $X_3$CS(O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and R'' where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

A "cognitive disorder," as used herein refers to a mental health disorder in which loss of cognitive function is the primary symptom, and which primarily affects learning, memory, perception, and/or problem solving. Cognitive disorders include amnesia, dementia, and delirium. Causes may include damage to the memory portions of the brain, whether from trauma or chemotherapy.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"RIPK1 binder" is used herein to refer to a compound that exhibits an $K_d$ with respect to RIPK1 of no more than about 100 µM and more typically not more than about 50 µM, as measured in the RIPK1 binding assay described generally herein. The RIPK1 binding assay measures the $K_d$ (dissociation constant) for the binding of a compound with the active site of RIPK1. Certain compounds disclosed herein have been discovered to bind to RIPK1. In certain embodiments, compounds will exhibit an $K_d$ with respect to RIPK1 of no more than about 10 µM; in further embodiments, compounds will exhibit a $K_d$ with respect to RIPK1 of no more than about 1 µM; in yet further embodiments, compounds will exhibit a $K_d$ with respect to RIPK1 of not more than about 0.1 µM; in yet further embodiments, compounds will exhibit a $K_d$ with respect to RIPK1 of not more than about 10 nM, as measured in the RIPK1 assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts and Polymorphs

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

Formulations

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a pre-determined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Administration and Treatment

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with: donepezil, rivastigmine, galantamine, and memantine. Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-glycnacase inhibitors, and other medicines approved for the treatment of Alzheimer's disease. Further examples include metformin, minocycline, tissue plasminogen activator, and other therapies that improve neuronal survival.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating RIPK1-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of RIPK1-mediated disorders.

In a related aspect, certain embodiments provide methods for the treatment of cancer that comprise the coadministration of another therapeutic agent. In some embodiments, the other therapeutic agent is a checkpoint inhibitor. In some embodiments, the other therapeutic agent is chosen from an anti-PD1 inhibitor, an anti-PDL1 inhibitor, an anti-CTLA4 inhibitor, an anti-OX50 inhibitor, an anti-TIM3 inhibitor, and an anti-LAG3 inhibitor.

For use in cancer and neoplastic diseases a RIPK1 inhibitor may be optimally used together with one or more of the following non-limiting examples of anti-cancer agents:
1) inhibitors or modulators of a protein involved in one or more of the DNA damage repair (DDR) pathways such as:
   a. PARP½, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;
2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);

b. PD-L1 inhibitors such as Atezolizumab (TECENTRIQ), Avelumab (Bavencio), Durvalumab (Imfinzi), MPDL3280A (Tecentriq), BMS-936559, and MEDI4736;
c. anti-CTLA-4 antibodies such as ipilimumab (YERVOY) and CP-675,206 (TREMELIMUMAB);
d. inhibitors of T-cell immunoglobulin and mucin domain 3 (Tim-3);
e. inhibitors of V-domain Ig suppressor of T cell activation (Vista);
f. inhibitors of band T lymphocyte attenuator (BTLA);
g. inhibitors of lymphocyte activation gene 3 (LAG3); and
h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptupurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotic, which are often plant alkaloids and terpenoids, or derivatives thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);
8) topoisomerase inhibitors, including, but not limited to: amacrine, camptothecin (CTP), genistein, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;
11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin,
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);
15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide(NILANDRON);
17) tyrosine kinase inhibitors, including, but not limited to: imatinib (GLEEVEC), erlotinib (TARCEVA), lapatininb (TYKERB), sorafenib (NEXAVAR), and axitinib (INLYTA);
18) mTOR inhibitors, including, but not limited to: everolimus, temsirolimus (TORISEL), and sirolimus;
19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
  a. tetracyclines, including, but not limited to: doxycycline;
  b. erythromycins, including, but not limited to: azithromycin;
  c. glycylglycines, including, but not limited to: tigecycline;
  d. antiphrastic, including, but not limited to: pyrvinium pamoate;
  e. beta-lactams, including, but not limited to the penicillins and cephalosporins;
  f. anthracycline antibiotics, including, but not limited to: daunorubicin and doxorubicin;
  g. other antibiotics, including, but not limited to: chloramphenicol, mitomycin C, and actinomycin;
24) antibody therapeutic agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and
25) other agents, such as Bacillus Calmette—Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In certain embodiments, the compounds, compositions, and methods disclosed herein may be useful for the treatment of a disorder associated with an inflammatory component of cellular stress. In certain embodiments, the disorder is chosen from multiple sclerosis, Neimanm-Pick disease, Alzheimers disease, Parkinson's disease, amyotrophic lateral sclerosis, Lewy body dementia, frontotemporal dementia, glutamine expansion diseases such as Huntington's disease, Kennedy's disease, and spinocerebellar ataxia In certain embodiments, the compounds, compositions, and methods disclosed herein may be useful for the treatment of neuropathy. In certain embodiments, the neuropathy is chosen from diabetic neuropathy and chemotherapy induced neuropathy.

In certain embodiments, the compounds, compositions, and methods disclosed herein may be useful for the treatment of a retinal disease. In certain embodiments, the retinal disease is chosen from macular degeneration and retinitis.

In certain embodiments, the compounds, compositions, and methods disclosed herein may be useful for the treatment of an injury to the CNS. In certain embodiments, the injury is chosen from a traumatic brain injury and stroke.

In certain embodiments, the compounds, compositions, and methods disclosed herein may be useful for the treatment of an autoimmune disorder. In certain embodiments, the autoimmune disorder is chosen from ulcerative colitis, rheumatoid arthritis, psoriasis, lupus, inflammatory bowel disease.

In certain embodiments, the compounds, compositions, and methods disclosed herein may be useful for the treatment of viral infections.

In certain embodiments, the compounds, compositions, and methods disclosed herein may be useful for the treatment of sepsis.

In certain embodiments, the compounds, compositions, and methods disclosed herein may be useful for the treatment of retinal degeneration.

In certain embodiments, the compounds, compositions, and methods disclosed herein may be useful for the treatment of ischemic stroke.

In certain embodiments, the compounds, compositions, and methods disclosed herein may be useful for the treatment of intracerebral hemorrhage.

In certain embodiments, the compounds, compositions, and methods disclosed herein may be useful for the treatment of amyotrophic lateral sclerosis.

In certain embodiments, the compounds, compositions, and methods disclosed herein may be useful for the treatment of an acute kidney injury.

In certain embodiments, the compounds, compositions, and methods disclosed herein may be useful for the treatment of a myocardial reperfusion injury.

In certain embodiments, the compounds, compositions, and methods disclosed herein may be useful for the treatment of Alzheimer's disease.

In certain embodiments, the compounds, compositions, and methods disclosed herein may be useful for the treatment of ulcerative colitis.

In certain embodiments, the compounds, compositions, and methods disclosed herein may be useful for the treatment of osteoarthritis.

In certain embodiments, the the compounds, compositions, and methods disclosed herein may be coadministered with another therapeutic agent.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations $Ac_2O$=acetic anhydride; AcCl=acetyl chloride; ACN=MeCN=$CH_3CN$=acetonitrile; AcOH=HOAc=acetic acid; AIBN=azobisisobutyronitrile; aq.=aqueous; BAST=bis(2-methoxyethyl)aminosulfur trifluoride; Bu=butyl; $Bu_3SnH$=tributyltin hydride; $CD_3OD$=deuterated methanol; $CDCl_3$=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCE=1,2-dichloroethane; DCM=dichloromethane; DEAD=diethyl azodicarboxylate; DtBAD=di-t-butyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; dppf=1,1'-bis(diphenylphosphino)ferrocene; EDC.HCl=EDCI.HCl=1-ethyl-3-(3-dimethylaminopropyl)carbodiimide hydrochloride; Et=ethyl; $Et_2O$=diethyl ether; EtOAc=EtOAc; EtOH=ethanol; h=hr=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; iPr=i-Pr=isopropyl=2-propyl; iPrOH=i-PrOH=isopropanol; LAH=lithium aluminiumhydride; LDA=lithium diisopropyl amide; LiHMDS=Lithium bis(trimethylsilyl)amide; MeI=methyl iodide; MeOH=methanol; MP-carbonate resin=macroporous triethylammonium methylpolystyrene carbonate resin; MsCl=mesyl chloride; MTBE=methyl tert-butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; Pd(Ph$_3$)$_4$=tetrakis(triphenylphosphine)-palladium(0); Pd$_2$(dba)$_3$=tris(dibenzylideneacetone)dipalladium(0); PdCl$_2$(PPh$_3$)$_2$32 bis(triphenylphosphine)palladium(II) dichloride; PG=protecting group; Ph=phenyl; prep-HPLC=preparative high-performance liquid chromatography; PMBCl=para-methoxybenzyl; PMBCl=para-methoxybenzyl chloride; PMBOH=para-methoxybenzyl alcohol; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; SELECTFLUOR®=1-(chloromethyl)-4-fluoro-1,4-diazoniabicyclo[2.2.2]octane tetrafluoroborate; tBu=t-Bu=tert-butyl=1,1-dimethylethyl; TBAF=tetrabutylammonium fluoride; TBDPS=t-butyldiphenylsilyl; t-BuOH=tBuOH=tert-butanol; $T_3P$=Propylphosphonic Anhydride; TEA=Et$_3$N=triethylamine; TFA=trifluoroacetic acid; TFAA=trifluoroacetic anhydride; THF=tetrahydrofuran; TIPS=triisopropylsilyl;Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

The following schemes can be used to practice the present invention.

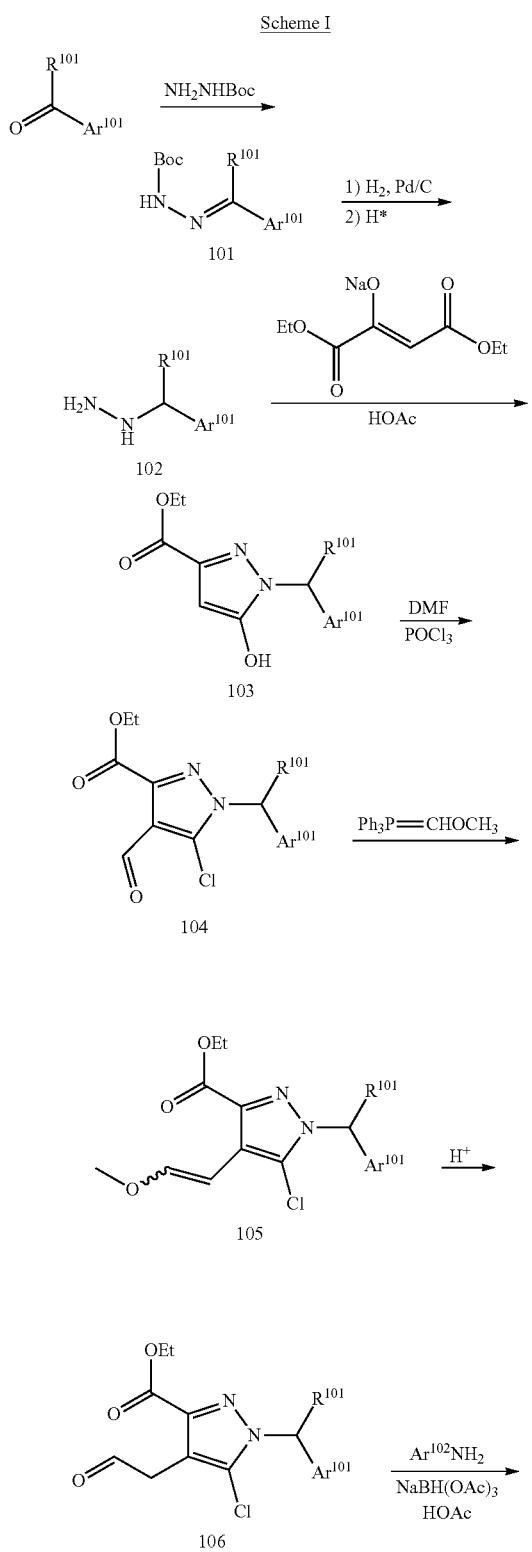

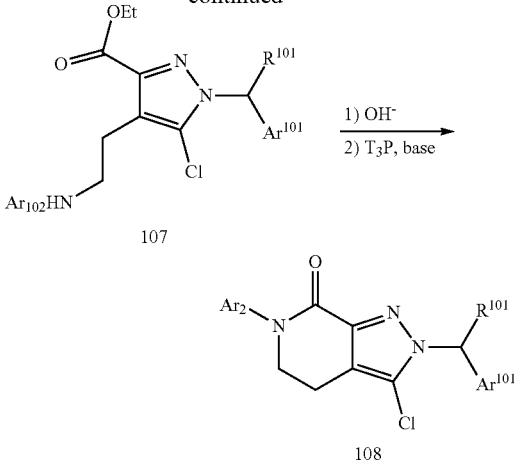

Certain compounds can be prepared with the procedure set forth in Scheme I. A suitable arylcarboxaldehyde ($R^{101}$=H) or acyl arene ($R^{101} \neq$H) is converted to the Boc-protected hydrazone 101, which is catalytically hydrogenated to provide, after removal of the Boc group with acid, the substituted hydrazine 102. Condensation with the sodium salt of diethyl oxosuccinate provides the substituted pyrazole 103. Vilsmeier reaction with DMF and $POCl_3$ introduces the formyl substituent of 104. Wittig reaction, followed by hydrolysis of the Wittig product 105, leads to the homologated aldehyde 106. Reductive amination completes assembly of the (arylamino)ethyl chain of 107. The carboethoxy group is hydrolyzed with hydroxide, and ring closure of the corresponding acid (not shown) is accomplished with a coupling agent such as $T_3P$, to give 108.

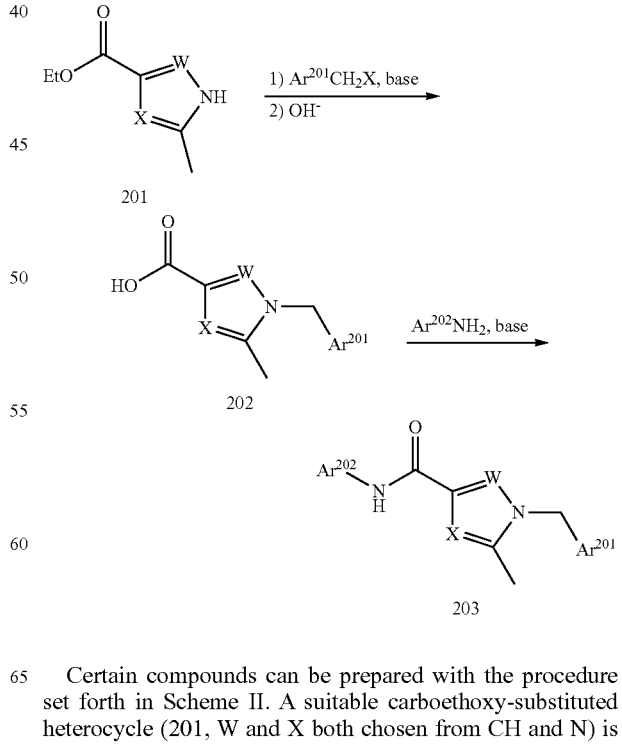

Certain compounds can be prepared with the procedure set forth in Scheme II. A suitable carboethoxy-substituted heterocycle (201, W and X both chosen from CH and N) is reacted with an (aryl)methyl halide to give alkylated product 202. The ester is then hydrolyzed with hydroxide, and amide 203 is synthesized using methods known in the art.

Scheme III

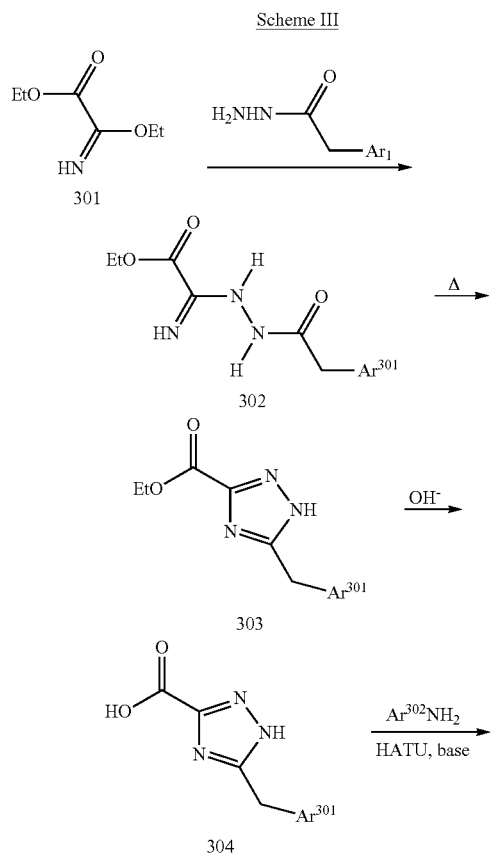

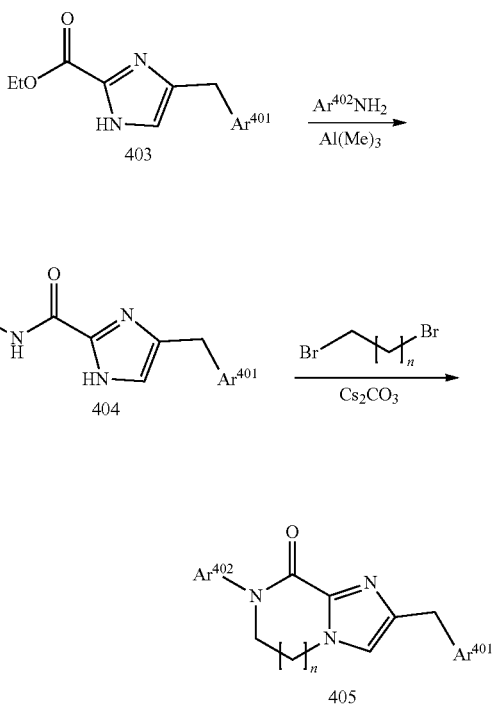

Certain compounds can be prepared with the procedure set forth in Scheme III. The mono(imidate) of oxalic acid ethyl ester 301 is condensed with an acylhydrazone to give the functionalized intermediate 302, which is thermally cyclized to give 1,2,4-triazole 303. The ester functionality is hydrolyzed with hydroxide, and the carboxylic acid 304 is converted to amide 305 using methods known in the art.

Scheme IV

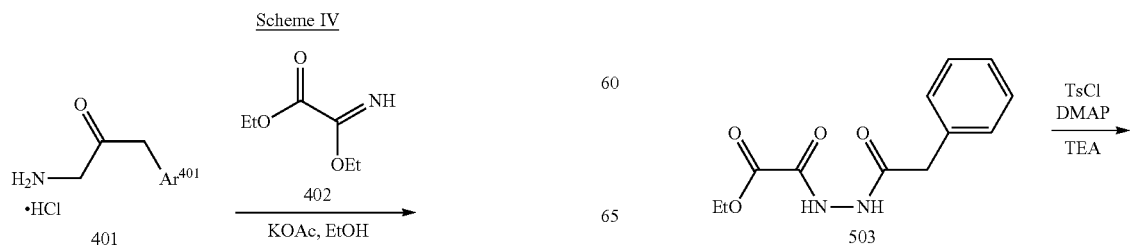

Certain compounds can be prepared with the procedure set forth in Scheme IV. Aryl aminoacetone 401 is condensed with the mono(imidate) of oxalic acid ethyl ester 402 to give imidazole 403. Reaction with an arylamine, in the presence of a Lewis acid, give amide 404. Alkylative cyclization with an a,w-dibromoalkane gives the product 405.

Scheme V

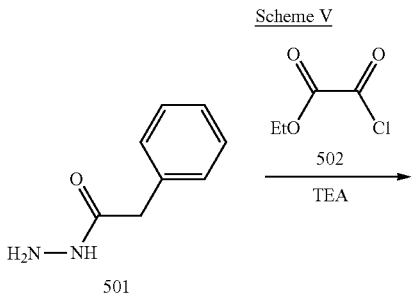

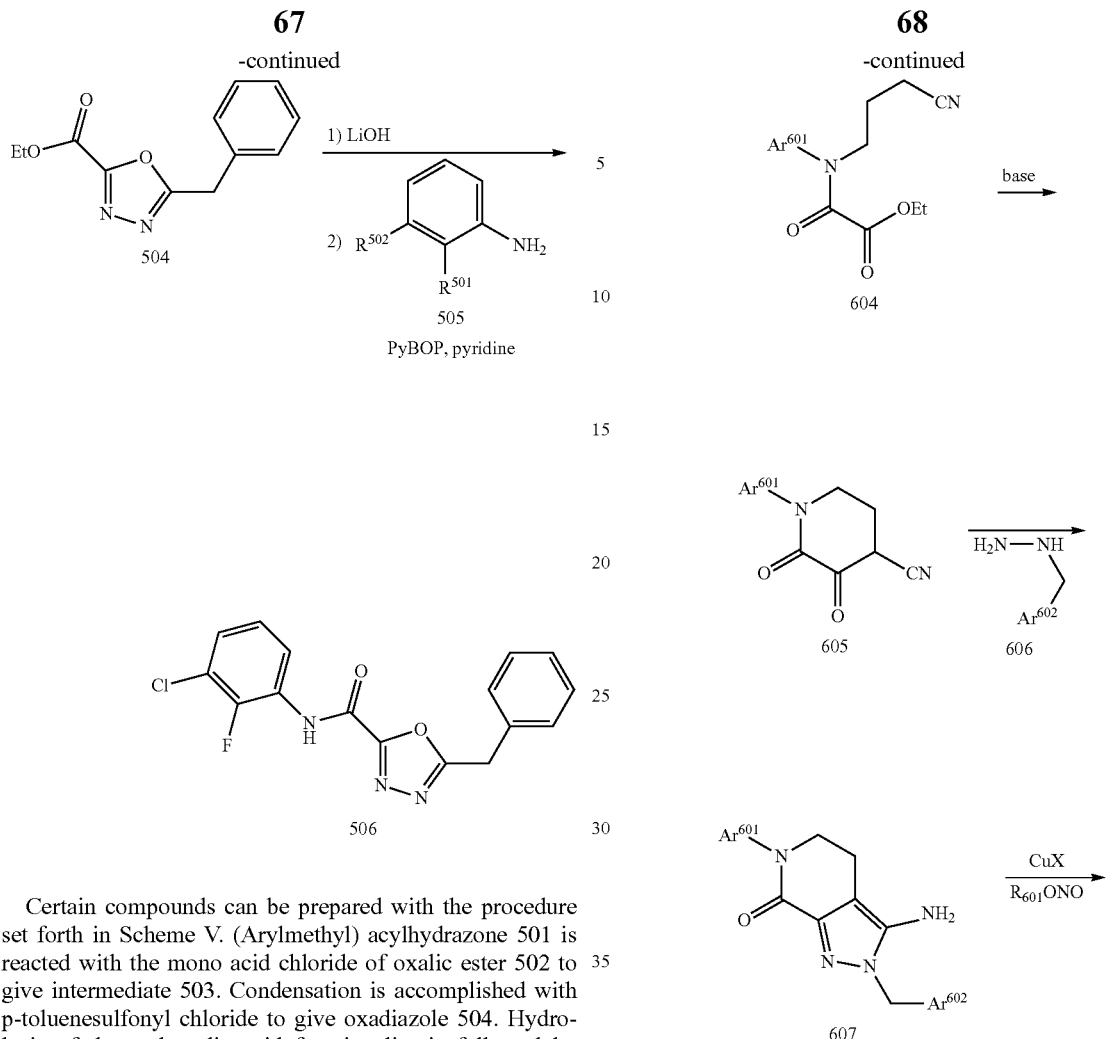

Certain compounds can be prepared with the procedure set forth in Scheme V. (Arylmethyl) acylhydrazone 501 is reacted with the mono acid chloride of oxalic ester 502 to give intermediate 503. Condensation is accomplished with p-toluenesulfonyl chloride to give oxadiazole 504. Hydrolysis of the carboxylic acid functionality is followed by formation of an amide from arylamine 505 (in which substitutents may be chosen, without limitation, from H and halo) to afford product 506.

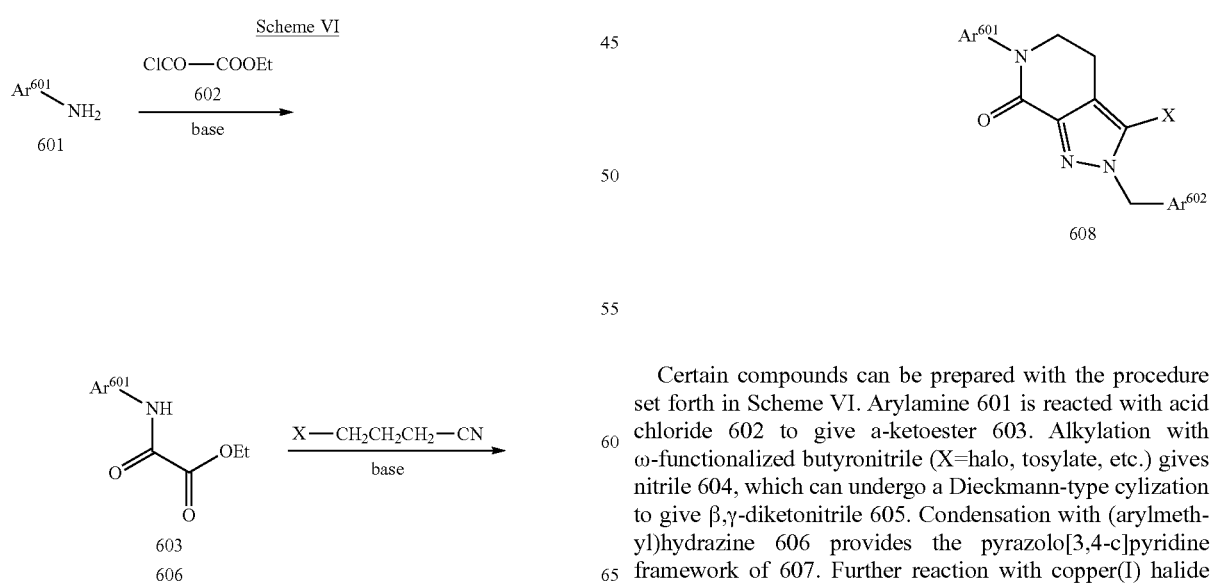

Certain compounds can be prepared with the procedure set forth in Scheme VI. Arylamine 601 is reacted with acid chloride 602 to give a-ketoester 603. Alkylation with ω-functionalized butyronitrile (X=halo, tosylate, etc.) gives nitrile 604, which can undergo a Dieckmann-type cylization to give β,γ-diketonitrile 605. Condensation with (arylmethyl)hydrazine 606 provides the pyrazolo[3,4-c]pyridine framework of 607. Further reaction with copper(I) halide salt in the presence of an alkyl nitrite gives halo compound 608.

Scheme VII

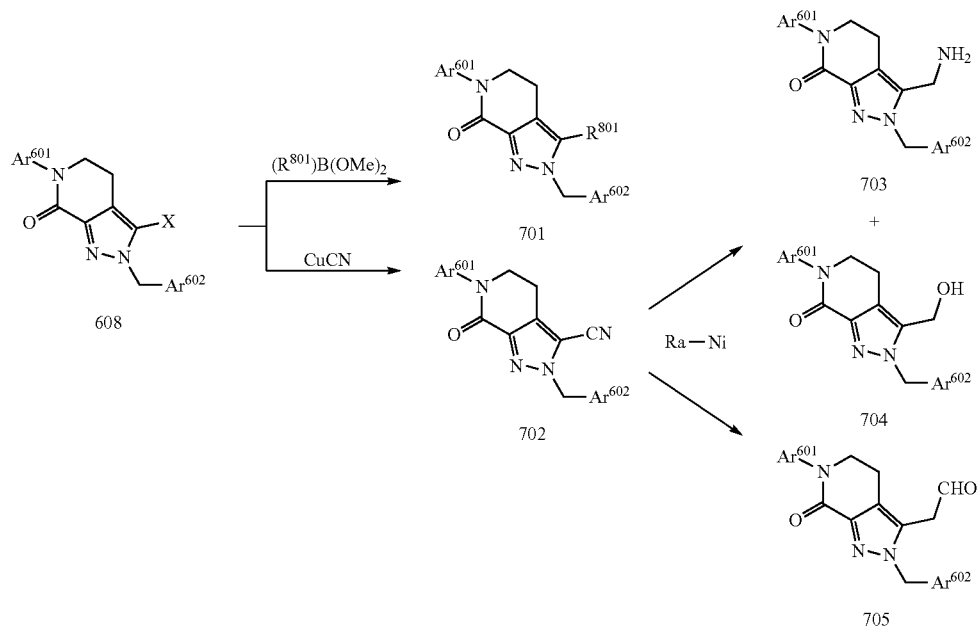

Certain compounds can be prepared with the procedure set forth in Scheme VII. Aryl halide 608 is reacted with Raney nickel to afford, depending on conditions, mixtures of aminomethyl compound 703 and hydroxymethy compound 704, or carboxaldehyde 705. Any of these compounds can be further functionalized using methods known to a person of skill, such as reaction of aldehyde 705 with DAST to give the corresponding difluoromethyl compound (not shown).

Scheme VIII

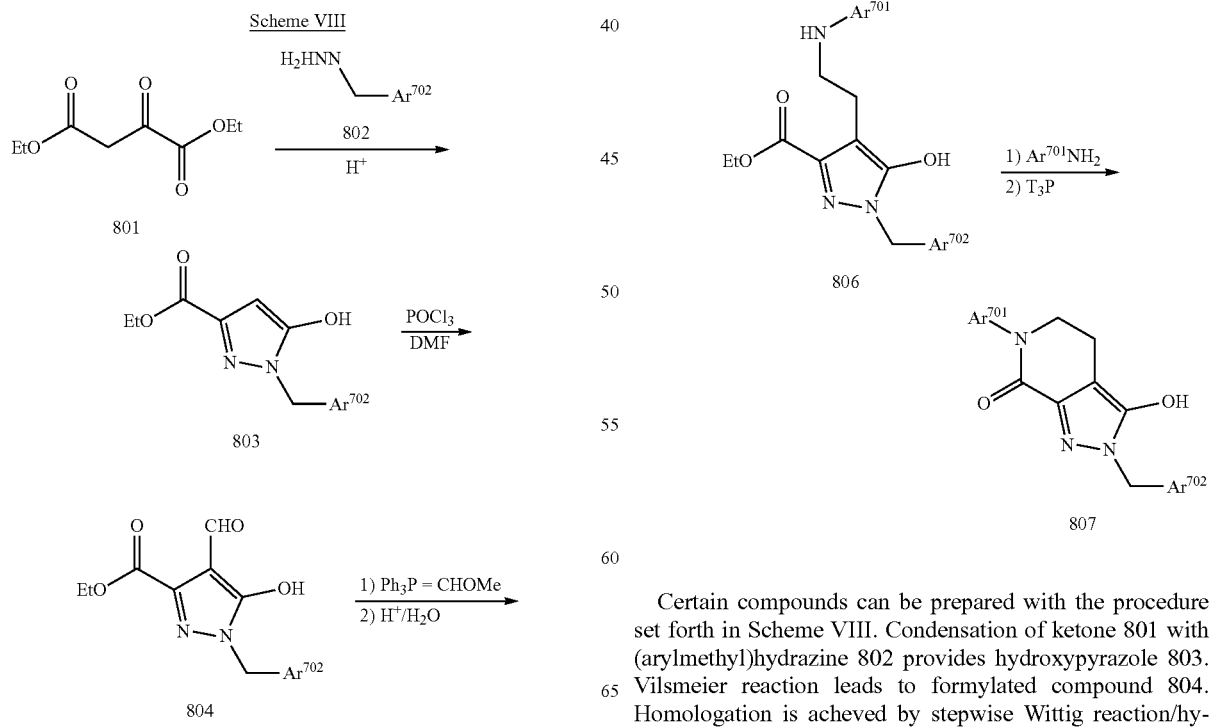

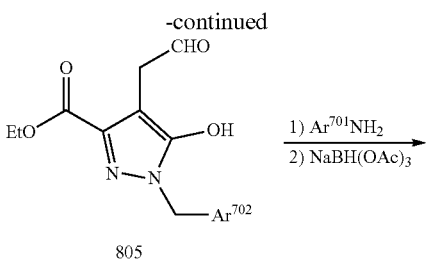

Certain compounds can be prepared with the procedure set forth in Scheme VIII. Condensation of ketone 801 with (arylmethyl)hydrazine 802 provides hydroxypyrazole 803. Vilsmeier reaction leads to formylated compound 804. Homologation is acheved by stepwise Wittig reaction/hydrolysis to give 805. Reductive amination with an arylamine gives amine 806. Finally, stepwise ester hydrolysis/amide coupling provides the pyrazolo[3,4-c]pyridine framework of 807.

The invention is further illustrated by the following examples.

Intermediate A

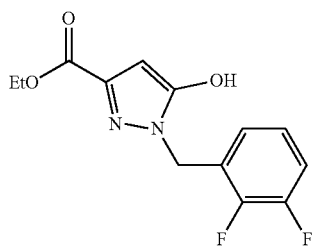 [SMILES: CCOC(=O)c1cc(O)n(Cc2cccc(F)c2F)n1]

Ethyl 1-[(2,3-difluorophenyl)methyl]-5-hydroxy-pyrazole-3-carboxylate

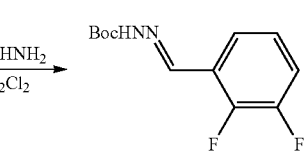

tert-Butyl N-[(E)-(2,3-difluorophenyl)methyleneamino]carbamate A mixture of 2,3-difluorobenzaldehyde (50 g, 351.86 mmol, 38.46 mL, 1 eq) and tert-butyl hydrazinecarboxylate (46.50 g, 351.86 mmol, 1 eq) in CH$_2$Cl$_2$ (400 mL) was stirred at 15° C. for 16 h. The reaction mixture was concentrated under reduced pressure to afford the title compound (90 g, 347.71 mmol, 99% yield) as a white solid, which was used directly in the next step. MS (ES+) C$_{12}$H$_{14}$F$_2$N$_2$O$_2$ requires: 256 found: 201 [M-55]$^+$.

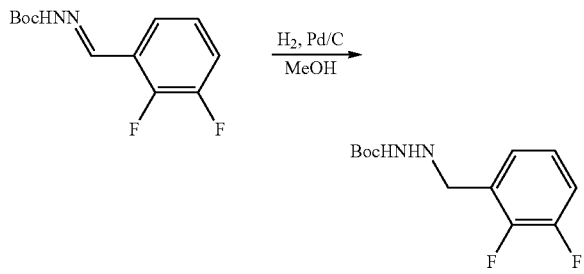

tert-Butyl N-[(2,3-difluorophenyl)methylamino]carbamate To a solution of the product from the previous step (90 g, 351.22 mmol, 1 eq) in MeOH (900 mL) was added 10% Pd/C (35 g). The suspension was degassed under reduced pressure and purged with H$_2$ three times. The mixture was stirred under H$_2$ (50 psi) at 35° C. for 16 h. The H$_2$ was removed by purging with N$_2$. The reaction mixture was then filtered, and the filtrate was concentrated under reduced pressure. The residue was purified by column chromatography (SiO$_2$, petroleum ether/EtOAc=15/1 to 5/1) to afford the title compound (80 g, crude) as a white solid.

$^1$H NMR (400 MHz, CDCl$_3$) δ: 6.98-7.22 (m, 3 H), 6.19 (s, 1 H), 4.10-4.15 (m, 2H), 1.39-1.61 (m, 9 H).

MS (ES+) C$_{12}$H$_{16}$F$_2$N$_2$O$_2$ requires: 258 found: 203 [M-55]$^+$.

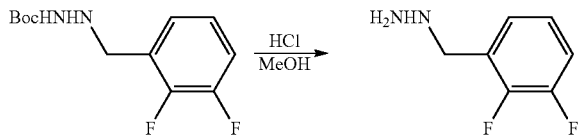

(2,3-difluorophenyl)methylhydrazine To a solution of the product from the previous step (80 g, 309.76 mmol, 1 eq) in MeOH (200 mL) was added HCl/MeOH (4 M, 425.53 mL, 5.49 eq) at 0° C. The mixture was stirred at 15° C. for 16 h. The reaction mixture was concentrated under reduced pressure to afford the title compound (90 g, crude) as a white solid, which was used directly in the next step. MS (ES+) C$_7$H$_8$F$_2$N$_2$ requires: 158 found: 159 [M+1]$^+$.

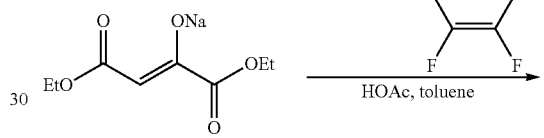

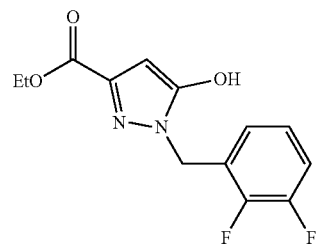

Ethyl 1-[(2,3-difluorophenyl)methyl]-5-hydroxy-pyrazole-3-carboxylate (Intermediate A) To a solution of sodium (Z)-1,4-diethoxy-1,4-dioxobut-2-en-2-olate (46.51 g, 221.31 mmol, 1 eq) in toluene (400 mL) was added HOAc (398.71 g, 6.64 mol, 379.72 mL) and the product from the previous step (35 g, 221.31 mmol, 1 eq). The mixture was stirred at 110° C. for 16 h. The reaction mixture was concentrated under reduced pressure. The residue was triturated with MTBE at 15° C. for 20 min, then filtered. The filter cake was dried under reduced pressure to afford the title compound (15 g, 53.15 mmol, 24% yield) as a white solid.

$^1$H NMR (400 MHz, DMSO-d$_6$) δ: 11.80 (s, 1 H), 7.07-7.61 (m, 2 H), 6.95 (t, J=6.97 Hz, 1 H), 5.87 (s, 1 H), 5.32 (s, 2 H), 4.26 (q, J=7.01 Hz, 2 H), 1.30 (t, J=7.03 Hz, 3 H).

MS (ES+) C$_{13}$H$_{12}$F$_2$N$_2$O$_3$ requires: 282, found: 283 [M+1]$^+$.

Intermediate B

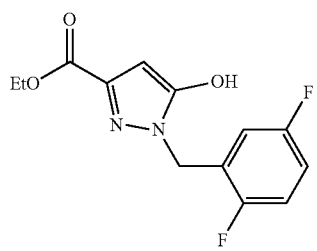 [SMILES: CCOC(=O)c1cc(O)n(Cc2cc(F)ccc2F)n1]

Ethyl 1-(2,5-difluorobenzyl)-5-hydroxy-1H-pyrazole-3-carboxylate

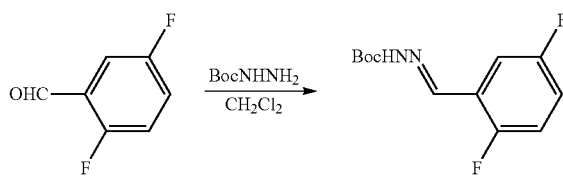

(E)-tert-Butyl 2-(2, 5-difluorobenzylidene)hydrazinecarboxylate To a solution of 2,5-difluorobenzaldehyde (50 g, 351.86 mmol, 38.17 mL, 1 eq) in $CH_2Cl_2$ (200 mL) was added tert-butyl hydrazinecarboxylate (46.50 g, 351.86 mmol, 1 eq). The mixture was stirred at 15° C. for 16 h. The mixture was concentrated to afford the title compound (90 g, crude) as a yellow oil. $^1$H NMR (400 MHz, $CD_3OD$) δ: 8.13 (m, 1H), 7.78 (m, 1H), 7.16-7.11 (m, 2H), 1.55 (s, 9H).

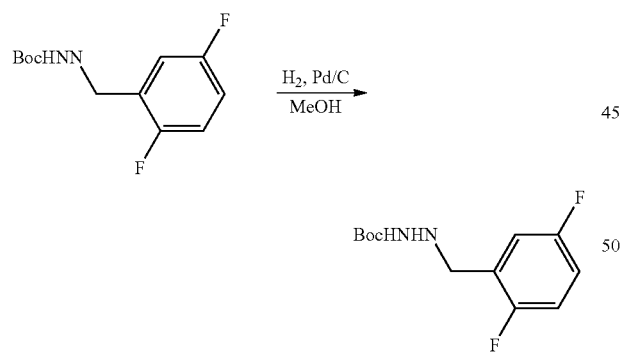

tert-Butyl 2-(2, 5-difluorobenzyl)hydrazinecarboxylate To a solution of the product from the previous step (45 g, 175.61 mmol, 1 eq) in MeOH (200 mL) under $N_2$ was added Pd/C (16 g, 10% w/w). The mixture was purged with $N_2$, then $H_2$, and then stirred at 15° C. under $H_2$ (50 Psi) for 16 hr. The mixture was filtered, and the filtrate was concentrated and purified by column chromatography on silica gel (eluent petroleum ether/EtOAc=20:1) to afford the title compound (33 g, 127.78 mmol, 72% yield) as a colorless oil. $^1$H NMR (400 MHz, $CD_3OD$) δ: 7.26-7.23 (m, 1H), 7.08-7.01 (m, 2H), 3.98 (s, 2H), 1.44 (s, 9H).

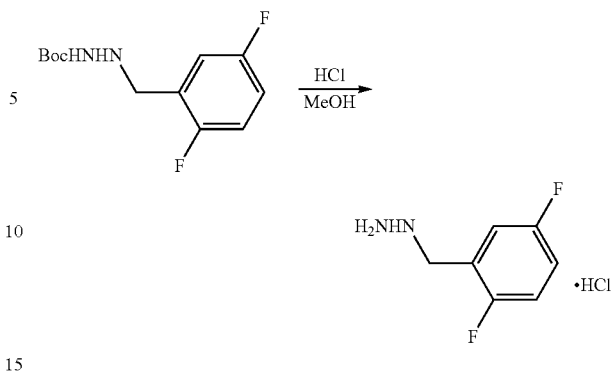

(2, 5-Difluorobenzyl)hydrazine hydrochloride To a solution of HCl in EtOAc (4 M, 100 mL, 3.13 eq) was added the product from the previous step (33 g, 127.78 mmol, 1 eq). The mixture was stirred at 15° C. for 16 hr. The mixture was concentrated to afford the title compound (27 g, 116.85 mmol, 91% yield) as a white solid. $^1$H NMR (400 MHz, $CD_3OD$) δ: 7.38-7.27 (m, 1H), 7.26-7.22 (m, 2H), 4.09 (s, 2H).

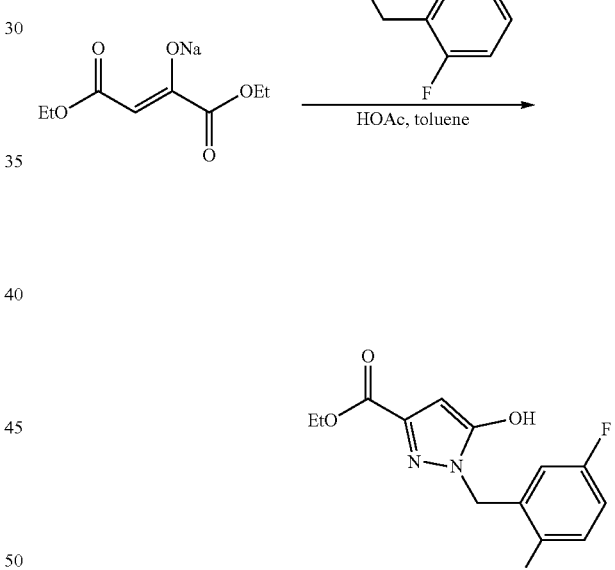

Ethyl 1-(2,5-difluorobenzyl)-5-hydroxy-1H-pyrazole-3-carboxylate (Intermediate B) To a solution of the product from the previous step (26.5 g, 114.68 mmol, 1 eq) in toluene (260 mL) was added sodium (Z)-1,4-diethoxy-1,4-dioxobut-2-en-2-olate (24.10 g, 114.68 mmol, 1 eq) and HOAc (206.60 g, 3.44 mol, 196.76 mL, 30 eq). The mixture was stirred at 110° C. for 16 hr. The mixture was concentrated to afford a yellow solid, which was triturated with MTBE (50 mL) and then filtered. The filter cake was collected and washed with MTBE to afford the title compound (29 g, 102.75 mmol, 89% yield) as a white solid. $^1$H NMR (400 MHz, DMSO-$d_6$) δ: 7.30-7.26 (m, 1H), 7.23-7.21 (m, 1H), 6.85-6.82 (m, 1H) 5.89 (s, 1H), 5.21 (s, 2H), 4.22-4.20 (q, J=7.2 Hz, 2H), 1.27-1.24 (t, J=7.2 Hz, 3H).

Intermediate C

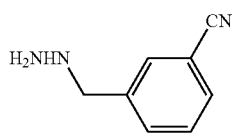

3-(hydrazineylmethyl)benzonitrile

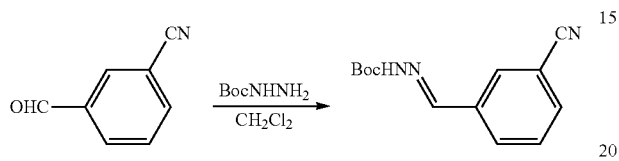

tert-Butyl (Z)-2-(3-cyanobenzylidene)hydrazine-1-carboxylate To a solution of 3-formylbenzonitrile (25 g, 190.6 mmol, 1 eq) in CH$_2$Cl$_2$ (200 mL) was added tert-butyl hydrazinecarboxylate (25.20 g, 190.65 mmol, 1 eq). The mixture was stirred at 25° C. for 16 h, then concentrated under reduced pressure to afford the title compound (41.6 g, 169.6 mmol, 89% yield) as a white solid.

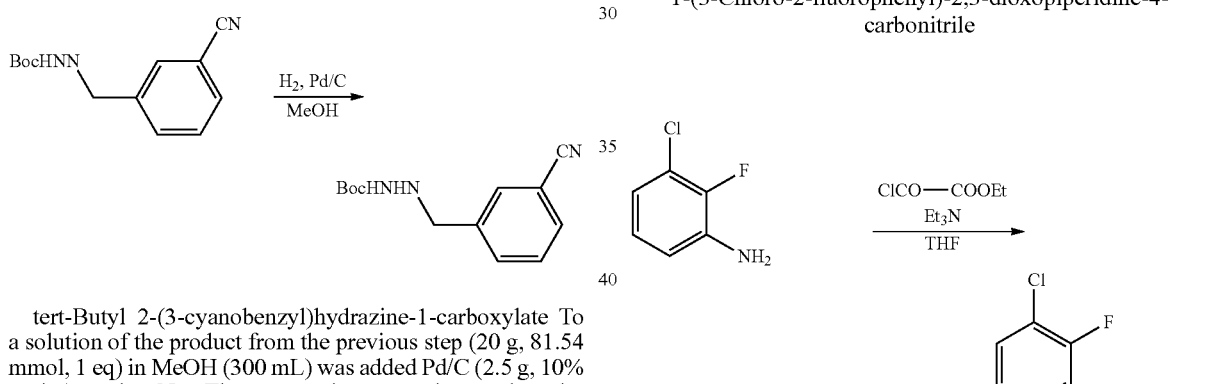

tert-Butyl 2-(3-cyanobenzyl)hydrazine-1-carboxylate To a solution of the product from the previous step (20 g, 81.54 mmol, 1 eq) in MeOH (300 mL) was added Pd/C (2.5 g, 10% purity) under N$_2$. The suspension was degassed under reduced pressure and purged with H$_2$ (5.00 g, 2.48 mol) several times. The mixture was stirred under H$_2$ (15 psi) at 25° C. for 5 h, then filtered through CELITE® and concentrated. The crude product was purified by silica gel chromatography eluted with petroleum ether/EtOAc=3:1 to afford the title compound (12 g, 48.53 mmol, 60% yield) as a colourless oil.

$^1$H NMR (400 MHz, CDCl$_3$) δ=7.67 (s, 1H), 7.62-7.54 (m, 2H), 7.49-7.40 (m, 1H), 6.06 (br s, 1H), 4.30 (br d, J=7.2 Hz, 1H), 4.03 (s, 2H), 1.46 (s, 9H).

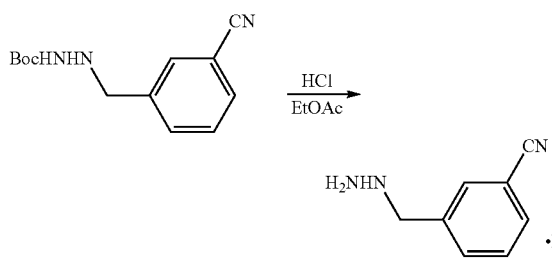

3-(hydrazineylmethyl)benzonitrile (Intermediate C) To a solution of the product from the previous step (6 g, 24.26 mmol, 1 eq) in MeOH (50 mL) was added HCl in EtOAc (2 M, 48.53 mL, 4 eq) at 0° C. The mixture was stirred at 25° C. for 4 h. The resulting solid was removed by filtration to afford the title compound (4.2 g, 22.87 mmol, 94% yield, HCl) as a white solid. The product was carried on to the next step without further purification.

$^1$H NMR (400 MHz, D$_2$O) δ=7.81-7.66 (m, 1H), 7.58-7.40 (m, 2H), 7.35-7.06 (m, 1H), 4.30-4.19 (m, 2H), 4.17-4.10 (m, 1H).

Intermediate D 1-(3-Chloro-2-fluorophenyl)-2,3-dioxopiperidine-4-carbonitrile

Ethyl 2-((3-chloro-2-fluorophenyl)amino)-2-oxoacetate To a cooled 0° C. solution of 3-chloro-2-fluoroaniline (7.6 ml, 69 mmol) in THF (229 ml, 0.2 M) was added Et$_3$N (9.6 ml, 69 mmol) in one portion. Then ethyl 2-chloro-2-oxoacetate (7.7 ml, 69 mmol) was added dropwise while vigorously stirring. The reaction was stirred momentarily at 0° C., then warmed to room temperature and stirred for 1 h. The reaction was then filtered and the filter cake was washed with EtOAc twice. The filtrate was concentrated to give the title compound (16.5 g, 67 mmol, 98% yield) as an off-white fluffy solid.

$^1$H NMR (600 MHz, DMSO-d$_6$) δ 10.75 (s, 1H), 7.59-7.54 (m, 1H), 7.53-7.47 (m, 1H), 7.30-7.24 (m, 1H), 4.33 (q, J=7.1 Hz, 2H), 1.33 (t, J=7.1 Hz, 3H).

LCMS(ES$^+$) C$_{10}$H$_9$ClFNO$_3$ requires: 245, found 246 [M+H]$^+$.

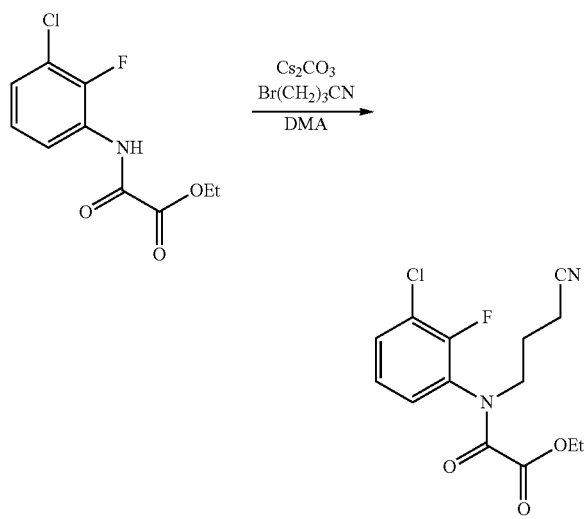

Ethyl 2-((3-chloro-2-fluorophenyl)(3-cyanopropyl)amino)-2-oxoacetate To a solution of the product from the previous step (5 g, 20 mmol) in DMA (41 ml, 0.5 M) was added Cs$_2$CO$_3$ (8.0 g, 24 mmol) and 4-bromobutanenitrile (4.0 ml, 41 mmol) and the reaction was stirred at 80° C. for 2 h. The reaction was then cooled to room temperature. The reaction mixture was diluted with EtOAc, H$_2$O was added, the mixture was stirred, and the layers were separated. The aqueous phase was extracted with EtOAc×3. The combined organic layers were washed with brine×3, dried over Na$_2$SO$_4$, and concentrated under reduced pressure. The residue was purified via silica gel chromatography (0-60% EtOAc in Hexanes) to give the title compound (6.1 g, 19.5 mmol, 96% yield) as a pale yellow oil.

$^1$H NMR (600 MHz, DMSO-d$_6$) δ 7.76-7.70 (m, 1H), 7.54-7.49 (m, 1H), 7.36-7.31 (m, 1H), 4.00-3.94 (m, 2H), 3.92-3.81 (m, 1H), 3.70-3.60 (m, 1H), 2.56-2.52 (m, 2H), 1.82-1.72 (m, 2H), 0.88 (t, J=7.1 Hz, 3H).

LCMS(ES$^+$) C$_{14}$H$_{14}$ClFN$_2$O$_3$ requires: 312, found 313 [M+H]$^+$.

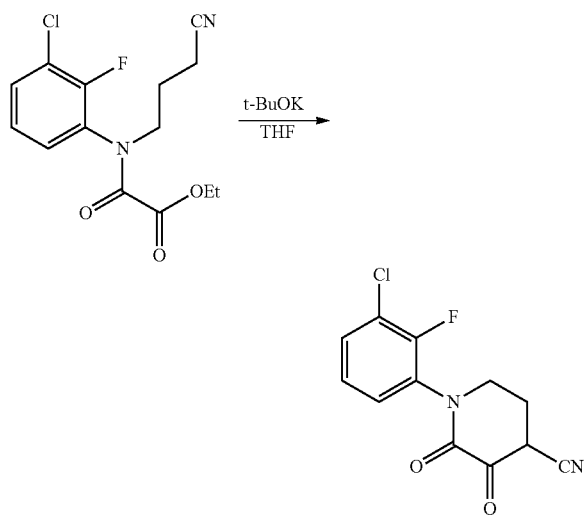

1-(3-Chloro-2-fluorophenyl)-2,3-dioxopiperidine-4-carbonitrile (Intermediate D) To a cooled 0° C. solution of the product from the previous step (5.3 g, 16.8 mmol) in THF (84 ml, 0.2 M) was added t-BuOK (3.8 g, 34 mmol) in one portion and the resulting mixture was stirred at 0° C. for 0.5 h. 1M HCl was added to bring the pH to 4. The reaction mixture was diluted with EtOAc, H$_2$O was added, and the layers were separated. The aqueous phase was acidified to pH 3 with 1M HCl, then extracted with EtOAc×3. The combined organic layers were washed with brine, dried over Na$_2$SO$_4$, and concentrated under reduced pressure. The residue was adsorbed onto silica gel and purified via flash chromatography (0-100% EtOAc in Hexanes) to give the title compound (2.2 g, 8.1 mmol, 48% yield) as a tan solid.

$^1$H NMR (500 MHz, DMSO-d$_6$) δ 11.19 (s, 1H), 7.60 (ddd, J=8.3, 6.8, 1.6 Hz, 1H), 7.47 (ddd, J=8.2, 6.7, 1.7 Hz, 1H), 7.32 (td, J=8.1, 1.3 Hz, 1H), 3.83 (t, J=6.7 Hz, 2H), 2.67 (t, J=6.8 Hz, 2H).

LCMS(ES$^+$) C$_{12}$H$_8$ClFN$_2$O$_2$ requires: 266, found 267 [M+H]$^+$.

Intermediate E

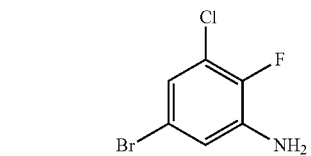

5-bromo-3-chloro-2-fluoroaniline

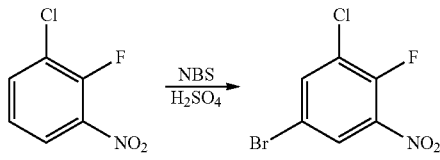

5-Bromo-1-chloro-2-fluoro-3-nitrobenzene To a solution of 1-chloro-2-fluoro-3-nitrobenzene (50 g, 284 mmol, 1 eq) in H$_2$SO$_4$ (279.36 g, 2.85 mol, 151.83 mL, 10 eq) was added NBS (60.83 g, 341.8 mmol, 1.2 eq). The mixture was stirred at 50° C. for 6 h, then poured into ice/H$_2$O (200 mL), and extracted with EtOAc (200 mL×3). The combined organic layers were washed with brine (200 mL×3), dried over Na$_2$SO$_4$, and concentrated under reduced pressure to obtain a residue which was purified by flash silica gel chromatography (ISCO®; 80 g SepaFlash® Silica Flash Column, eluent of 0-20% EtOAc/petroleum ether gradient @ 80 mL/min) to afford the title compound (72 g, 283 mmol, 99% yield) as a brown oil.

$^1$H NMR (400 MHz, CDCl$_3$) δ=8.11-8.09 (m, 1H), 7.87-7.85 (m, 1H).

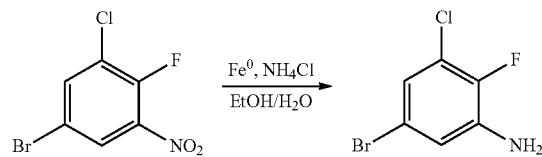 [SMILES: O=[N+]([O-])c1cc(Br)cc(Cl)c1F ; Nc1cc(Br)cc(Cl)c1F]

5-Bromo-3-chloro-2-fluoroaniline (Intermediate E) To a solution of the product from the previous step (72 g, 283 mmol, 1 eq) in EtOH (700 mL) and H$_2$O (140 mL) was added Fe$^0$ (95 g, 1.7 mol, 6 eq) and NH$_4$Cl (91 g, 1.7 mol, 6 eq). The mixture was stirred at 80° C. for 6 h, then poured into H$_2$O (200 mL) and extracted with EtOAc (200 mL×3). The combined organic layers were washed with brine (200 mL×3), dried over Na$_2$SO$_4$, and concentrated under reduced pressure to obtain a residue which was purified by column chromatography (SiO$_2$, petroleum ether/EtOAc=10/1 to 5/1) to afford the title compound (36 g, 160 mmol, 57% yield) as a brown oil.

$^1$H NMR (400 MHz, DMSO-d$_6$) δ=6.95-6.84 (m, 1H), 6.84-6.70 (m, 1H), 5.80 (s, 2H).

Intermediate F

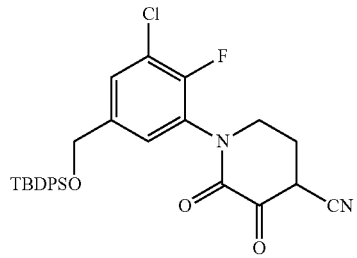

1-(5-(((tert-Butyldiphenylsilyl)oxy)methyl)-3-chloro-2-fluorophenyl)-2,3-dioxopiperidine-4-carbonitrile

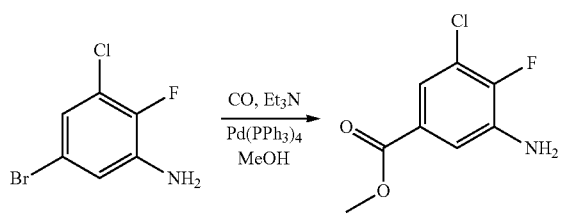

Methyl 3-amino-5-chloro-4-fluorobenzoate To a solution of Intermediate E (18 g, 80 mmol, 1 eq) and Pd(dppf)Cl$_2$ (5.9 g, 8.0 mmol, 0.1 eq) in MeOH (270 mL) was added Et$_3$N (24 g, 241 mmol, 33 mL, 3 eq) at 25° C. The suspension was degassed under reduced pressure and purged with CO several times. The mixture was stirred under CO (50 psi) at 80° C. for 16 h. The mixture was filtered and concentrated under reduced pressure to obtain a residue which was purified by flash silica gel chromatography (ISCO®; 80 g SepaFlash® Silica Flash Column, Eluent of 0-20% EtOAc/petroleum ether gradient @ 80 mL/min) to afford the title compound (6.5 g, 32 mmol, 40% yield) as a white solid.

$^1$H NMR (400 MHz, CDCl$_3$) δ=7.39-7.37 (m, 1H), 7.30-7.28 (m, 1H), 3.83-3.80 (m, 3H).

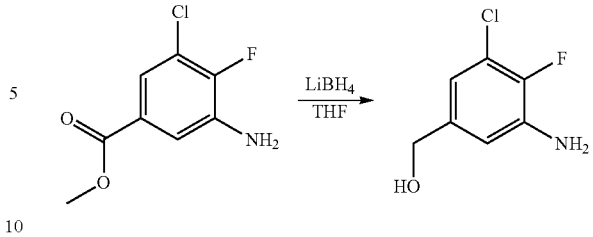

(3-Amino-5-chloro-4-fluoro-phenyl)methanol To a solution of the product from the previous step (4.5 g, 22 mmol, 1 eq) in THF (100 mL) was added LiBH$_4$ (1.9 g, 88 mmol, 4 eq). The mixture was stirred at 50° C. for 2 h. The reaction was quenched with saturated NH$_4$Cl solution (50 mL) and extracted with EtOAc (50 mL×3). The combined organic layers were washed with brine (50 mL×3), dried over Na$_2$SO$_4$, and concentrated under reduced pressure to obtain the title compound (3.3 g, 15 mmol, 69% yield) as a white solid.

LCMS(ES$^+$) C$_7$H$_7$ClFNO requires:175, found 176 [M+H]$^+$.

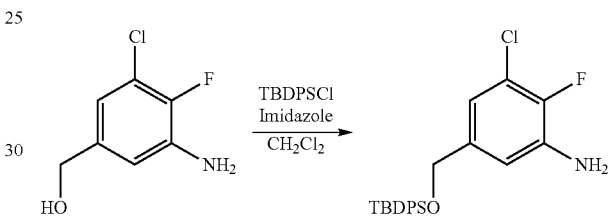

5-(((tert-Butyldiphenylsilyl)oxy)methyl)-3-chloro-2-fluoroaniline To a solution of the product from the previous step (3.2 g, 15 mmol, 1 eq) in CH$_2$Cl$_2$ (65 mL) was added TBDPSCl (8.2 g, 30 mmol, 7.7 mL, 2 eq) and imidazole (3.1 g, 45 mmol, 3 eq). The mixture was stirred at 25° C. for 16 h, then filtered and concentrated under reduced pressure to obtain a residue which was purified by flash silica gel chromatography (ISCO®; 40 g SepaFlash® Silica Flash Column, Eluent of 0~10% EtOAc/petroleum ether gradient @ 40 mL/min) to afford the title compound (9.5 g, 14 mmol, 95% yield) as a red oil.

LCMS(ES$^+$) C$_{23}$H$_{25}$ClFNOSi requires:413, found 414 [M+H]$^+$.

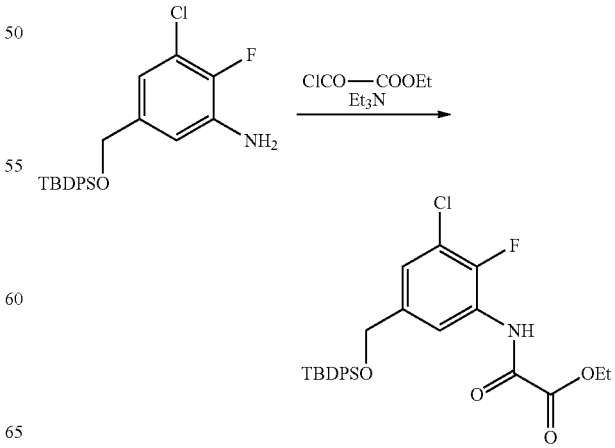

Ethyl 2-((5-(((tert-butyldiphenylsilyl)oxy)methyl)-3-chloro-2-fluorophenyl)-amino)-2-oxoacetate To a solution of the product from the previous step (9.2 g, 14 mmol, 1 eq) in CH$_2$Cl$_2$ (100 mL) was added ethyl 2-chloro-2-oxoacetate (2.3 g, 17 mmol, 1.9 mL, 1.2 eq) and Et$_3$N (4.2 g, 41 mmol, 5.8 mL, 3 eq). The mixture was stirred at 25° C. for 3 h, then poured into H$_2$O (100 mL) and extracted with EtOAc (100 mL×3). The combined organic layers were washed with brine (50 mL×3), dried over Na$_2$SO$_4$, and concentrated under reduced pressure to afford the title compound (9.5 g, 12 mmol, 85% yield) as colourless oil.

LCMS(ES$^+$) C$_{27}$H$_{29}$ClFNO$_4$Si requires:513, found 536 [M+Na]$^+$.

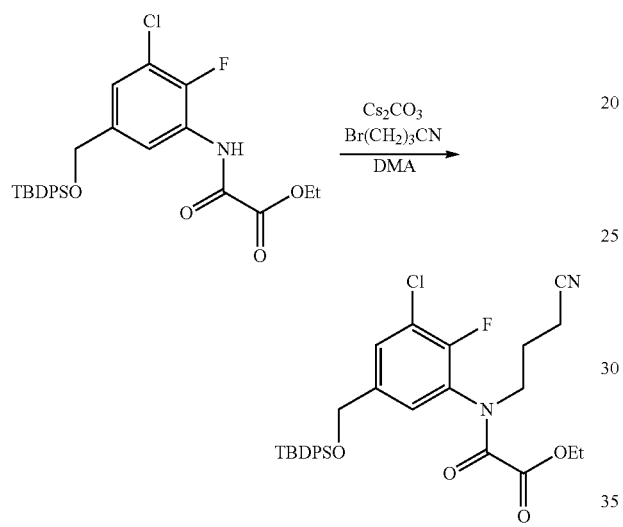

Ethyl 2-((5-(((tert-butyldiphenylsilyl)oxy)methyl)-3-chloro-2-fluorophenyl)(3-cyanopropyl)amino)-2-oxoacetate To a solution of the product from the previous step (9.5 g, 12 mmol, 1 eq) in DMA (25 mL) was added Cs$_2$CO$_3$ (4.6 g, 14.0 mmol, 1.2 eq) and 4-bromo-butanenitrile (3.5 g, 23 mmol, 2 eq). The mixture was stirred at 80° C. for 2 h, then poured into H$_2$O (100 mL) and extracted with EtOAc (100 mL×3). The combined organic layers were washed with brine (50 mL×3), dried over Na$_2$SO$_4$, and concentrated under reduced pressure to obtain a residue which was purified by flash silica gel chromatography (ISCO®; 25 g SepaFlash® Silica Flash Column, Eluent of 0-25% EtOAc/petroleum ether gradient @ 50 mL/min) to afford the title compound (5 g, 7.7 mmol, 67% yield) as a colourless oil.

LCMS(ES$^+$) C$_{31}$H$_{34}$ClFN$_2$O$_4$Si requires: 580, found 581 [M+H]$^+$.

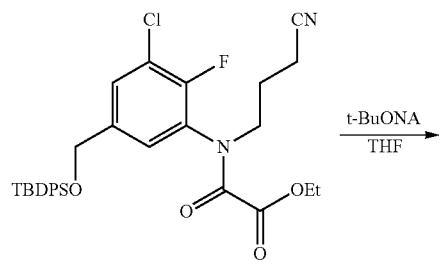

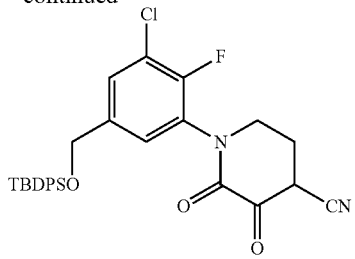

1-(5-(((tert-Butyldiphenylsilyl)oxy)methyl)-3-chloro-2-fluorophenyl)-2,3-dioxopiperidine-4-carbonitrile (Intermediate F) To a solution of the product from the previous step (4.5 g, 7.7 mmol, 1 eq) in THF (60 mL) was added t-BuONa (1.6 g, 17.0 mmol, 2.2 eq). The mixture was stirred at 0° C. for 1 h, then extracted with EtOAc (50 mL×3). The combined organic layers were washed with brine (50 mL×3), dried over Na$_2$SO$_4$, and concentrated under reduced pressure to obtain a residue which was purified by flash silica gel chromatography (ISCO®;40 g SepaFlash® Silica Flash Column, Eluent of 0-100% EtOAc/petroleum ether gradient @ 50 mL/min) to afford the title compound (2.6 g, 3.9 mmol, 50% yield) as a brown oil.

LCMS(ES$^+$) C$_{29}$H$_{28}$ClFN$_2$O$_3$Si requires: 534, found 535 [M+H]$^+$.

Intermediate G

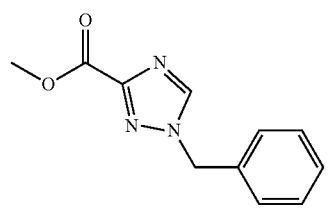 [SMILES: COC(=O)c1ncn(Cc2ccccc2)n1]

Methyl 1-benzyl-1H-1,2,4-triazole-3-carboxylate

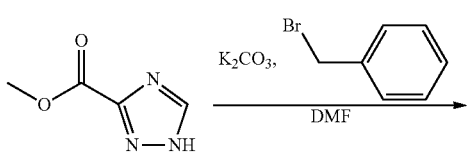

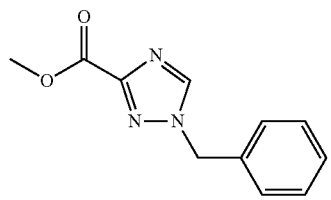

Methyl 1-benzyl-1,2,4-triazole-3-carboxylate (Intermediate G) To a solution of methyl 1H-1,2,4-triazole-3-carboxylate (5 g, 39.34 mmol, 1 eq) in DMF (100 mL) was added K$_2$CO$_3$ (10.87 g, 78.68 mmol, 2 eq) and bromomethylbenzene (8.07 g, 47.21 mmol, 5.61 mL, 1.2 eq) at 25° C. The mixture was stirred at 25° C. for 16 h. To the reaction was added H$_2$O (100 mL), and the mixture was extracted with EtOAc (80 mL×3). The combined organic layers were washed with brine (100 mL×3), dried over Na$_2$SO$_4$, and concentrated under reduced pressure. The residue was purified by column chromatography (SiO$_2$, petroleum ether/EtOAc=10/1 to 0/1) to afford the title compound (2.41 g, 11.0 mmol, 28% yield) as a white solid.

MS(ES+) C$_{11}$H$_{11}$O$_2$N$_3$ requires:217, found 218 [M+H]$^+$.

$^1$H NMR (400 MHz, CDCl$_3$) δ=8.01 (s, 1H), 7.36-7.29 (m, 3H), 7.27-7.22 (m, 2H), 5.35 (s, 2H), 3.94 (s, 3H).

Intermediate H

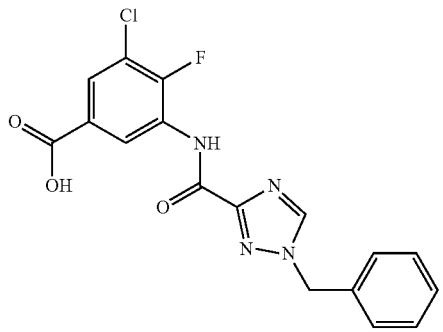 [SMILES: O=C(O)c1cc(Cl)c(F)c(NC(=O)c2ncn(Cc3ccccc3)n2)c1]

3-(1-Benzyl-1H-1,2,4-triazole-3-carboxamido)-5-chloro-4-fluorobenzoic acid

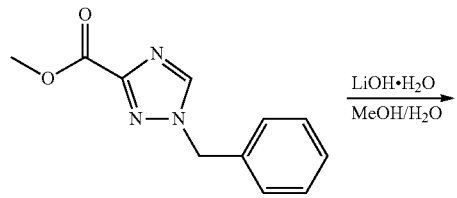

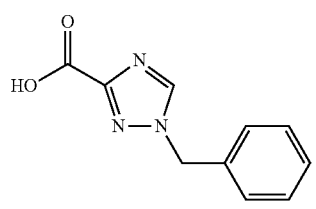

1-Benzyl-1,2,4-triazole-3-carboxylic acid To a solution of Intermediate G (8.73 g, 40.19 mmol, 1 eq) in MeOH (90 mL) and H$_2$O (30 mL) was added LiOH·H$_2$O (2.02 g, 48.23 mmol, 1.2 eq), and the mixture was stirred at 25° C. for 16 h. HCl (1 N) was added to bring the pH to 6. The reaction mixture was concentrated under reduced pressure to afford the title compound (10.6 g, crude) as a white solid.

MS(ES+)C$_{10}$H$_9$N$_3$O$_2$ requires:203, found 204 [M+H]$^+$.

$^1$H NMR (400 MHz, DMSO-d$_6$) δ=8.76 (s, 1H), 7.46-7.26 (m, 5H), 5.42 (s, 2H).

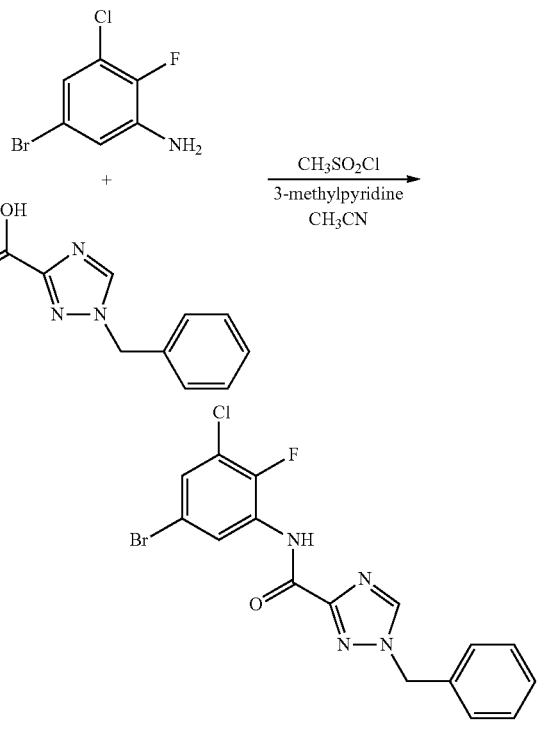

1-Benzyl-N-(5-bromo-3-chloro-2-fluorophenyl)-1H-1,2,4-triazole-3-carboxamide

To a solution of Intermediate E (8 g, 36 mmol, 1 eq) in CH$_3$CN (100 mL) was added the product from the previous step (9.41 g, 46.3 mmol, 1.3 eq), methanesulfonyl chloride (32.66 g, 285.1 mmol, 22.07 mL, 8 eq), and 3-methylpyridine (19.91 g, 213.85 mmol, 20.82 mL, 6 eq), and the mixture was stirred at 25° C. for 16 h. The mixture was diluted with H$_2$O (100 mL) and extracted with EtOAc (100 mL×3). The combined organic layers were washed with brine (100 mL×3), dried over Na$_2$SO$_4$, and concentrated under reduced pressure. The residue was purified by column chromatography (SiO$_2$, petroleum ether/EtOAc=20/1 to 1/1) to afford the title compound (14.9 g, crude) as a yellow solid.

MS(ES+)C$_{16}$H$_{11}$BrClFN$_4$O requires: 410, found 411 [M+H]$^+$.

$^1$H NMR (400 MHz, DMSO-d$_6$) δ=10.29 (s, 1H), 8.93 (s, 1H), 7.92 (dd, J=2.3, 6.1 Hz, 1H), 7.75 (dd, J=2.4, 6.1 Hz, 1H), 7.46-7.28 (m, 5H), 5.54 (s, 2H).

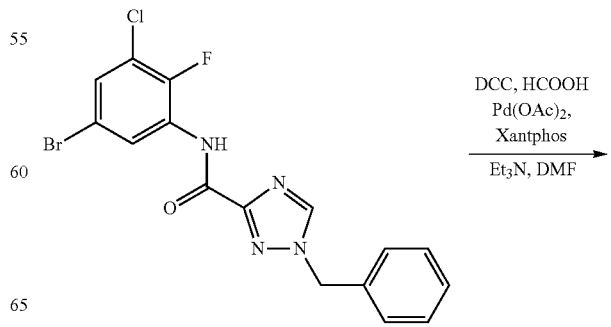

86

3-chloro-6-(3-chloro-2-fluoro-phenyl)-2-[(2, 3-difluorophenyl)methyl]-4,5-dihydropyrazolo[3,4-c]pyridin-7-one

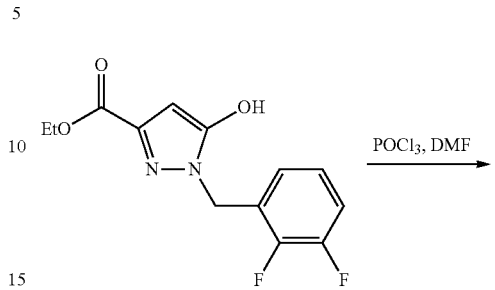

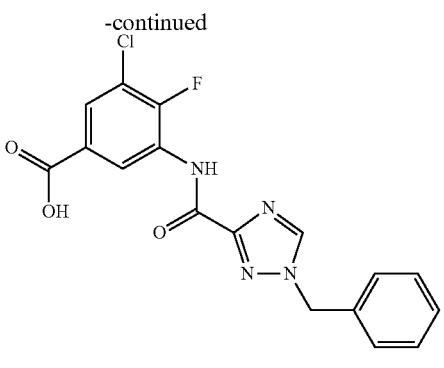

3-(1-benzyl-1H-1,2,4-triazole-3-carboxamido)-5-chloro-4-fluorobenzoic acid (Intermediate H) To a solution of the product from the previous step (853 mg, 2.08 mmol, 1 eq) in DMF (25 mL) was added DCC (859.3 mg, 4.16 mmol, 842 uL, 2 eq), Pd(OAc)$_2$ (46.75 mg, 208.2 μmol, 0.1 eq), HCOOH (700.3 mg, 14.58 mmol, 7 eq), Xantphos (120.49 mg, 208.23 μmol, 0.1 eq) and Et$_3$N (421.4 mg, 4.16 mmol, 579 uL, 2 eq). The mixture was stirred at 80° C. for 16 h. To the mixture was added H$_2$O (40 mL) and extracted with EtOAc (80 mL×3). The combined organic layers were washed with brine (80 mL×3), dried over Na$_2$SO$_4$, and concentrated under reduced pressure. The residue was purified by column chromatography (SiO$_2$, petroleum ether/EtOAc=20/1 to 0/1) to obtain the title compound (570 mg, 1.5 mmol, 73% yield) as a yellow solid.

MS(ES+) C$_{17}$H$_{12}$N$_4$O$_3$FCl requires:374, found 375 [M+H]$^+$.

$^1$H NMR (400 MHz, DMSO-d$_6$) δ=10.3 (s, 1H), 8.94 (s, 1H), 8.24-8.23 (m, 1H), 7.91-7.89 (m, 1H), 7.41-7.36 (m, 5H), 5.55 (s, 2H).

Example 1

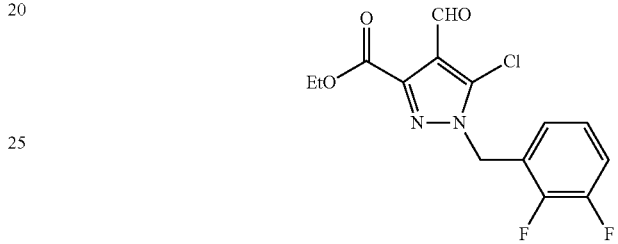

Ethyl 5-chloro-1-[(2,3-difluorophenyl)methyl]-4-formyl-pyrazole-3-carboxylate

A mixture of Intermediate A (15 g, 53.14 mmol, 1 eq), DMF (15.54 g, 212.56 mmol, 16.36 mL, 4 eq) and POCl$_3$ (65.2 g, 425.12 mmol, 39.51 mL, 8 eq) was stirred at 100° C. for 16 h. The reaction mixture was concentrated under reduced pressure, and the residue was dissolved in THF (50 mL), then it was slowly poured into warm H$_2$O (400 mL) while stirring, then extracted with EtOAc (300 mL×3). The combined organic layers were washed with brine (300 mL×2), dried over Na$_2$SO$_4$, concentrated under reduced pressure, and purified by column chromatography (SiO$_2$, petroleum ether/EtOAc=5/1 to 3/1) to afford the title compound (14.3 g, crude) as a white solid.

$^1$H NMR (400 MHz, DMSO-d$_6$) δ: 10.24 (s, 1 H), 7.40-7.52 (m, 1 H), 7.18-7.30 (m, 1 H), 7.06 (t, J=7.09 Hz, 1 H), 5.64 (s, 2 H), 4.36 (q, J=7.09 Hz, 2 H), 1. 31 (t, J=7.09 Hz, 3 H).

MS (ES+) C$_{14}$H$_{11}$ClF$_2$N$_2$O$_3$ requires: 328 found: 329 [M+1]$^+$.

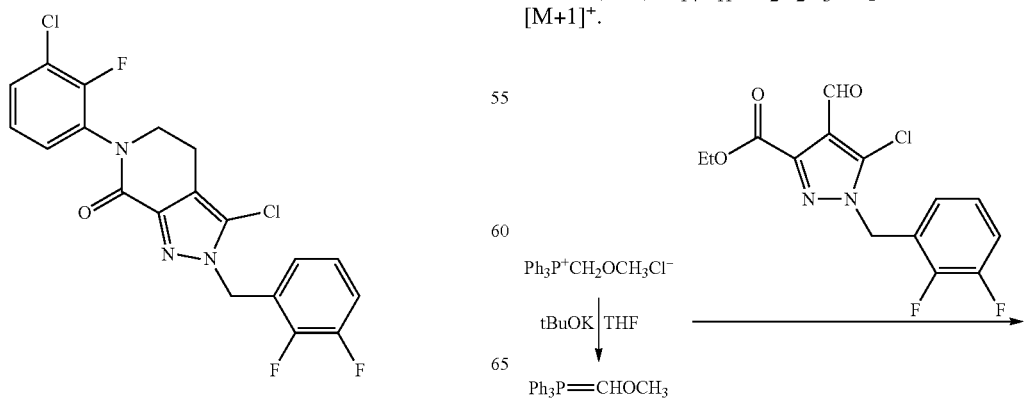

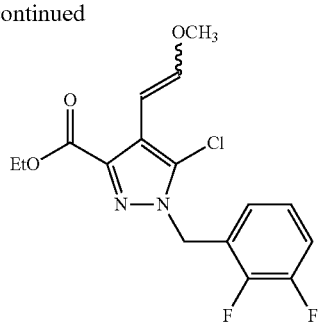

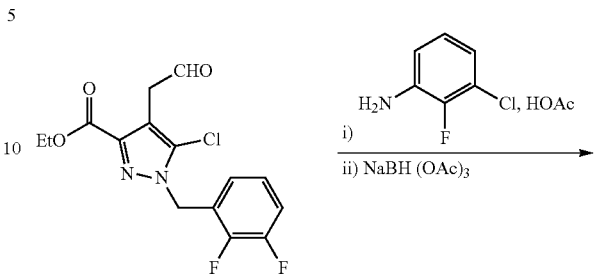

Ethyl 5-chloro-1-[(2,3-difluorophenyl)methyl]-4-[(E)-2-methoxyvinyl]pyrazole-3-carboxylate To a solution of t-BuOK (5.02 g, 44.72 mmol, 1.5 eq) in THF (50 mL) was added methoxymethyl(triphenyl) phosphonium chloride (15.33 g, 44.72 mmol, 1.5 eq) at 0° C. The mixture was stirred at 0° C. for 15 min. A solution of the product from the previous step (10 g, 29.81 mmol, 1 eq) in THF (50 mL) was then added, and the resulting mixture was stirred at 15° C. under $N_2$ for 16 h. The reaction mixture was concentrated under reduced pressure and then diluted with $H_2O$ (60 mL), then extracted with EtOAc (30 mL×3). The combined organic layers were washed with brine (100 mL×2), dried over $Na_2SO_4$, concentrated under reduced pressure and purified by column chromatography ($SiO_2$, petroleum ether/EtOAc=25/1 to 20/1) to afford the title compound (6.5 g, 17.31 mmol, 58% yield, as a mixture of Z and E isomers) as a colorless oil. MS (ES+) $C_{16}H_{15}ClF_2N_2O_3$ requires: 356 found: 357 $[M+1]^+$.

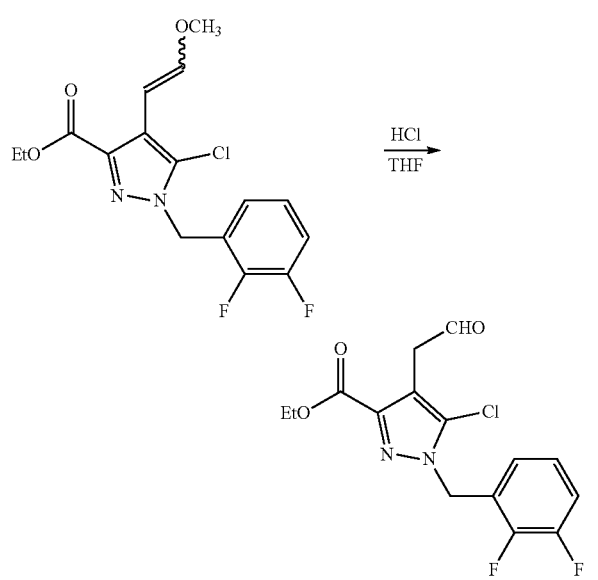

Ethyl 5-chloro-1-[(2,3-difluorophenyl)methyl]-4-(2-oxo-ethyl)pyrazole-3-carboxylate To a solution of the product from the previous step (3.1 g, 8.26 mmol, 1 eq) in THF (100 mL) was added HCl (6 M, 158.22 mL, 115 eq) under $N_2$ atmosphere. The reaction was stirred at 15° C. for 30 minutes. The mixture was concentrated under reduced pressure, diluted with $H_2O$ (50 mL), andextracted with EtOAc (60 mL×3). The combined organic layers were washed with brine (200 mL×2), dried over $Na_2SO_4$, and concentrated under reduced pressure to afford the title compound (3.1 g, 7.52 mmol, 91% yield) as a brown oil, which was used directly in the next step. MS (ES+) $C_{15}H_{13}ClF_2N_2O_3$ requires: 342 found: 343 $[M+1]^+$.

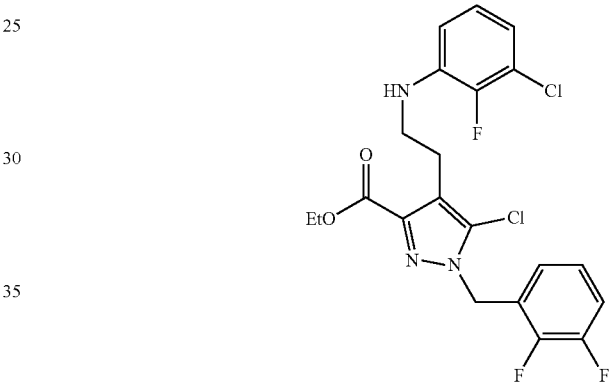

Ethyl 5-chloro-4-[2-(3-chloro-2-fluoro-anilino)ethyl]-1-[(2,3-difluorophenyl)-methyl]pyrazole-3-carboxylate To a solution of the product from the previous step (3.1 g, 7.52 mmol) in DCE (30 mL) was added HOAc (451.67 mg, 7.52 mmol, 1 eq) and 3-chloro-2-fluoroaniline (1.42 g, 9.78 mmol, 1.3 eq). The mixture was stirred at 15° C. for 10 min. To the mixture was then added NaBH(OAc)$_3$ (6.06 g, 28.58 mmol, 3.8 eq) and the mixture was stirred at 15° C. for 16 h. The mixture was concentrated under reduced pressure and diluted with $H_2O$ (20 mL) then extracted with EtOAc (30 mL×3). The combined organic layers were washed with brine (100 mL×2), dried over $Na_2SO_4$, concentrated under reduced pressure, and purified by column chromatography ($SiO_2$, petroleum ether/EtOAc=25/1 to 20/1) to afford the title compound (1.7 g, 3.42 mmol, 45% yield) as a white solid.

$^1$H NMR (400 MHz, CDCl$_3$) δ: 7.07-7.19 (m, 1H), 6.97-7.07 (m, 1H), 6.88 (td, $J_1$=8.13 Hz, $J_2$=1.47 Hz, 1H), 6.72 (t, J=6.97 Hz, 1H), 6.56-6.68 (m, 2H), 5.51 (s, 2H), 4.26-4.54 (m, 3H), 3.41 (t, J=6.66 Hz, 2H), 3.07 (t, J=6.66 Hz, 2H), 1.43 (t, J=7.15 Hz, 3H).

MS (ES+) $C_{21}H_{18}Cl_2F_3N_3O_2$ requires: 471 found: 472 $[M+H]^+$.

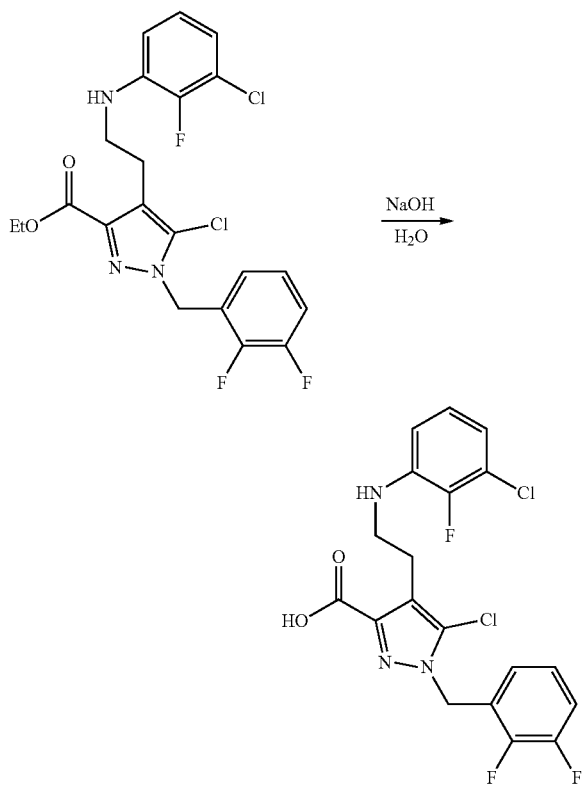

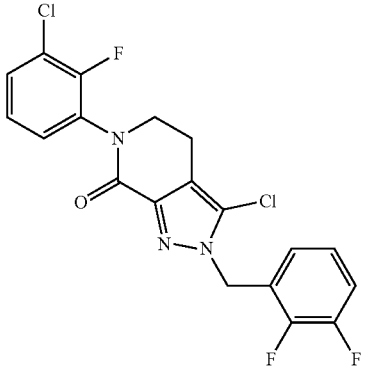 [SMILES: O=C1c2nn(Cc3cccc(F)c3F)c(Cl)c2CCN1c1cccc(Cl)c1F]

3-Chloro-6-(3-chloro-2-fluoro-phenyl)-2-[(2,3-difluoro-pheny)methyl]-4,5-dihydropyrazolo[3,4-c]pyridin-7-one To a solution of the product from the previous step (1.72 g, 3.87 mmol, 1 eq) in DMF (15 mL) was added DIPEA (1.50 g, 11.62 mmol, 2.02 mL, 3 eq) and T$_3$P (5.88 g, 9.23 mmol, 5.49 mL of a 50% solution in EtOAc, 1.5 eq). The mixture was stirred at 15° C. for 16 h. The reaction mixture was purified by prep-HPLC (column: Waters Xbridge C18, 150 mm*50 mm*10 μm; mobile phase: [H$_2$O (0.05% NH$_4$OH)-ACN]; B %: 48%-78%, 11.5 min) and lyophilized to afford the title compound (400.2 mg, 892.01 umol, 23% yield) as a white solid.

$^1$H NMR (400 MHz, CDCl$_3$) δ: 7.42-7.34 (m, 1H), 7.33-7.25 (m, 1H), 7.20-7.10 (m, 2H), 7.10-7.01 (m, 1H), 7.00-6.92 (m, 1H), 5.54 (s, 2H), 3.95 (t, J=6.4 Hz, 2H), 2.94 (t, J=6.5 Hz, 2H).

MS (ES+) C$_{19}$H$_{12}$N$_3$OCl$_2$F$_3$ requires: 425, found: 426 [M+H]$^+$.

5-Chloro-4-[2-(3-chloro-2-fluoro-anilino)ethyl]-1-[(2,3-difluorophenyl)methyl]-pyrazole-3-carboxylic acid To a solution of the product from the previous step (1.7 g, 3.42 mmol, 1 eq) in H$_2$O (15 mL) and MeOH (15 mL) was added NaOH (953.30 mg, 23.83 mmol, 6.97 eq). The mixture was stirred at 60° C. for 12 h. The mixture was quenched by H$_2$O (20 mL), neutralized by addition of 1N HCl, and then extracted with EtOAc (40 mL×3). The combined organic layers were washed with brine (100 mL×2), dried over Na$_2$SO$_4$, and concentrated under reduced pressure to afford the title compound (1.72 g, crude) as a red oil.

$^1$H NMR (400 MHz, CDCl$_3$) δ: 5.97-7.07 (m, 6 H), 5.13 (s, 2 H), 2.31-3.26 (m, 4 H).

MS (ES+) C$_{19}$H$_{14}$Cl$_2$F$_3$N$_3$O$_2$ requires: 443 found: 444 [M+H]$^+$.

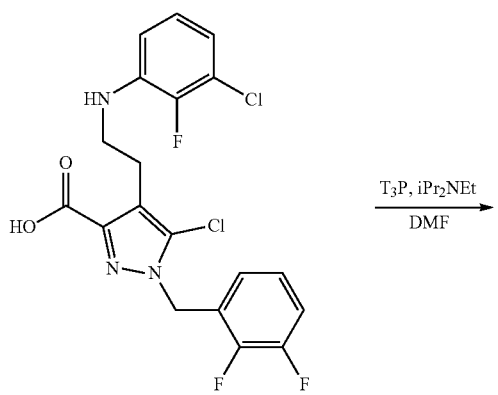

Example 2

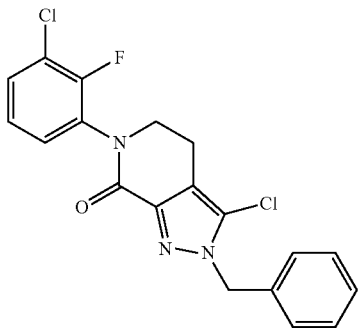 [SMILES: O=C1c2nn(Cc3ccccc3)c(Cl)c2CCN1c1cccc(Cl)c1F]

2-Benzyl-3-chloro-6-(3-chloro-2-fluoro-phenyl)-4,5-dihydropyrazolo[3,4-c]pyridin-7-one

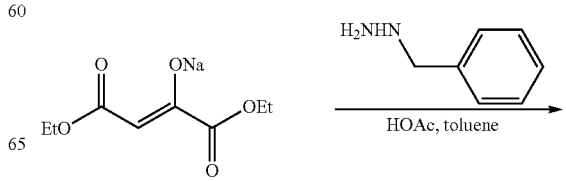

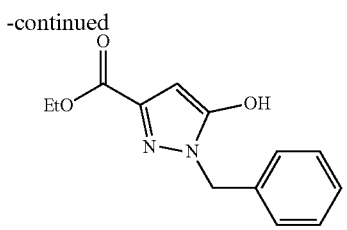

Ethyl 1-benzyl-5-hydroxy-pyrazole-3-carboxylate To a solution of sodium (Z)-1,4-diethoxy-1,4-dioxobut-2-en-2-olate (10 g, 47.58 mmol, 1 eq) in toluene (200 mL) was added HOAc (85.72 g, 1.43 mol, 81.64 mL, 30 eq) and benzylhydrazine (6.98 g, 43.98 mmol, HCl), and the mixture was stirred at 110° C. for 16 hr. The mixture was concentrated under reduced pressure then triturated in MTBE and collected by filtration, to afford the title compound (6.6 g, 24.12 mmol, 50% yield) as a white solid.

MS(ES+)$C_{13}H_{14}N_2O_3$ requires: 246, found: 247 [M+H]+.

$^1$H NMR (400 MHz, DMSO-$d_6$) δ: 7.36-7.27 (m, 3H), 7.19-7.17 (m, 2H), 5.87 (s, 1H), 5.15 (s, 2H), 4.21 (q, J=7.0 Hz, 2H), 1.25 (t, J=7.0 Hz, 3H).

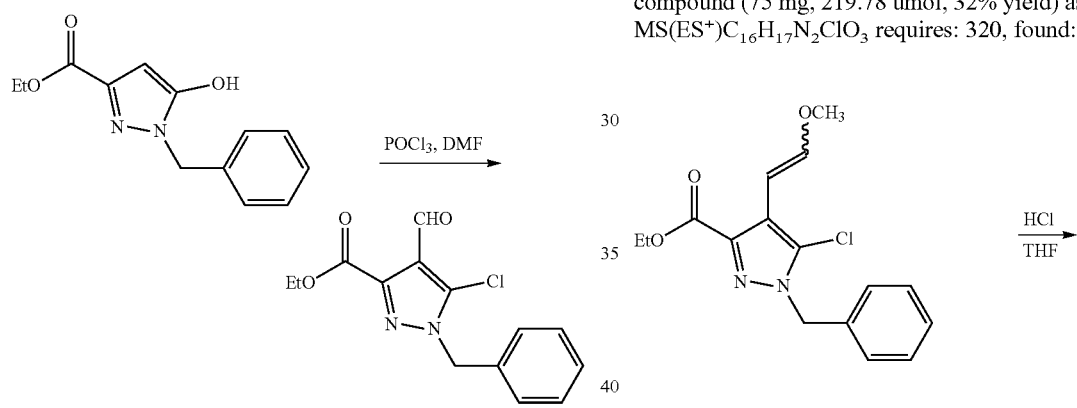

Ethyl 1-benzyl-5-chloro-4-formyl-pyrazole-3-carboxylate

To a solution of the product from the previous step (3 g, 12.18 mmol, 1 eq) in DMF (2.5 mL) was added POCl$_3$ (23.10 g, 150.65 mmol, 14 mL, 12.37 eq), and the mixture was stirred at 120° C. for 7 hr. H$_2$O (50 mL) was then added, the mixture was extracted with EtOAc (50 mL×3), and the combined organic layers were concentrated under reduced pressure to afford the title compound (1.88 g, 6.36 mmol, 52% yield) as a yellow solid.

MS(ES+)$C_{14}H_{13}ClN_2O_3$ requires: 292, found: 293 [M+H]$^+$.

$^1$H NMR (400 MHz, CDCl$_3$) δ: 10.36 (s, 1H), 7.29-7.20 (m, 5H), 5.40 (s, 2H), 4.42 (m, 2H), 1.37 (t, J=7.2 Hz, 3H).

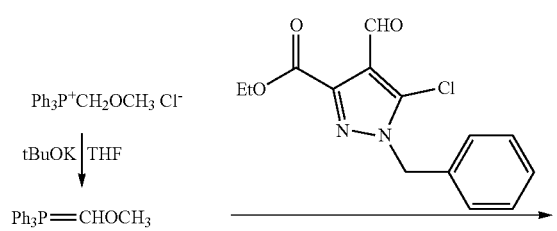

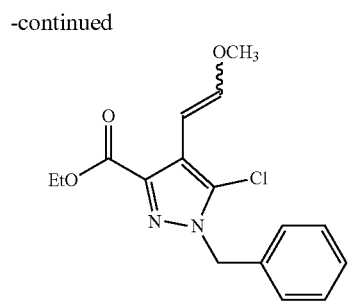

Ethyl 1-benzyl-5-chloro-4-[2-methoxyvinyl]pyrazole-3-carboxylate To a solution of the product from the previous step (200 mg, 683.25 umol, 1 eq) in THF (2 mL) was added t-BuOK (337.34 mg, 3.01 mmol, 4.4 eq) and methoxymethyl(triphenyl) phosphonium chloride (923.98 mg, 3.01 mmol, 4.4 eq) at 0° C. and the mixture was stirred at 25° C. for 16 hr. H$_2$O (10 mL) was added, the mixture was extracted with EtOAc (5 mL×3), the combined organic layers were washed with brine (5 mL×2), dried over Na$_2$SO$_4$, concentrated under reduced pressure, and purified by prep-TLC (petroleum ether/EtOAc=3/1) to afford the title compound (75 mg, 219.78 umol, 32% yield) as a yellow oil.

MS(ES$^+$)$C_{16}H_{17}N_2ClO_3$ requires: 320, found: 321 [M+H]$^+$.

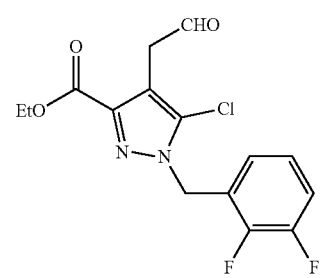

Ethyl 1-benzyl-5-chloro-4-(2-oxoethyl)pyrazole-3-carboxylate A mixture of the product from the previous step (75 mg, 233.81 umol, 1 eq) in HCl (6 M, 4.50 mL, 115.48 eq) and THF (3 mL) was degassed and purged with N$_2$ for 3 times and the mixture was stirred at 25° C. for 0.2 hr. The mixture was concentrated under reduced pressure to afford the title compound (80 mg, 229.51 umol, 98% yield) as a yellow solid.

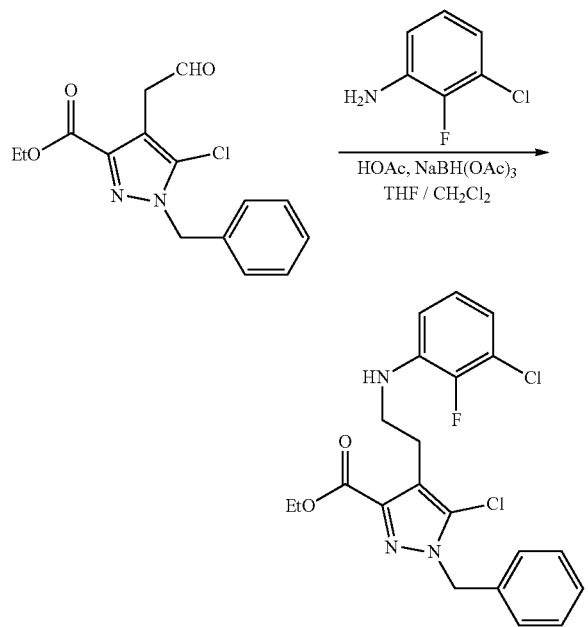

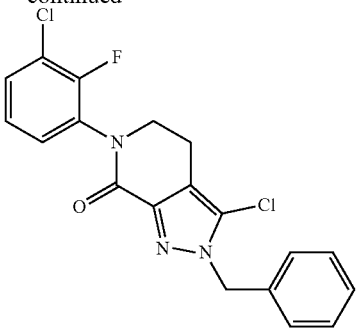

Ethyl 1-benzyl-5-chloro-4-[2-(3-chloro-2-fluoro-anilino)ethyl]pyrazole-3-carboxylate To a solution of the product from the previous step (80 mg, 260.80 umol, 1 eq) in THF (1 mL) and CH₂Cl₂ (1 mL) was added NaBH(OAc)₃ (210.05 mg, 991.06 umol, 3.8 eq), HOAc (15.66 mg, 260.80 umol, 14.92 uL, 1 eq) and 3-chloro-2-fluoroaniline (64.54 mg, 443.37 umol, 1.7 eq), and the mixture was stirred at 25° C. for 16 hr. H₂O (40 mL) was then added, and the mixture was extracted with EtOAc (30 mL×3). The combined organic layers were washed with brine (45 mL×2), dried over Na₂SO₄, and concentrated under reduced pressure and then purified by prep-TLC (petroleum ether/EtOAc=3/1) to afford the title compound (80 mg, 146.69 umol, 56% yield) as a yellow solid.

MS(ES⁺)C₂₁H₂₂FO₂N₃ requires: 435, found: 436 [M+H]⁺.

¹H NMR (400 MHz, CDCl₃) δ: 7.40-7.35 (m, 3H), 6.92-6.62 (m, 5H), 5.46 (s, 2H), 4.50 (q, J=7.2 Hz, 2H), 3.86 (s, 1H), 3.43 (q, J=6.4 Hz, 2H), 3.10 (t, J=6.8 Hz, 2H), 1.47 (t, J=6.0 Hz, 3H).

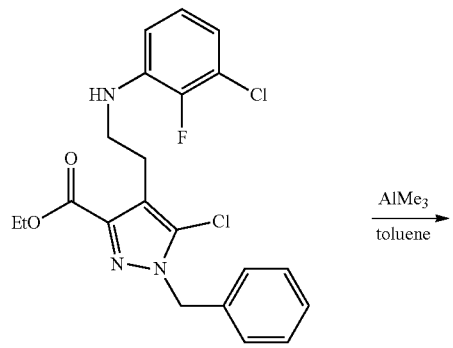

2-Benzyl-3-chloro-6-(3-chloro-2-fluoro-phenyl)-4,5-dihydropyrazolo[3,4-c]-pyridin-7-one To a solution of the product from the previous step (30 mg, 71.04 umol, 1 eq) in toluene (2 mL) was added AlMe₃ (2 M in toluene, 106.56 uL, 3 eq), and the mixture was stirred at 120° C. for 16 hr. H₂O (20 mL) was then added, and the mixture was extracted with EtOAc (8 mL×3). The combined organic layers were washed with brine (8 mL×2), dried over Na₂SO₄, concentrated under reduced pressure, and purified by prep-HPLC (column: Phenomenex Synergi C18 150*25*10 μm; mobile phase: [H₂O (0.1% TFA)-ACN]; B %: 54%-84%,10 min). The eluent was concentrated under reduced pressure to afford the title compound (0.6 mg, 1.43 umol) as a white solid.

MS(ES⁺)C₁₉H₁₄Cl₂FN₃O requires: 389, found: 390 [M+H]⁺.

¹H NMR (400 MHz, CDCl₃) δ: 7.37-7.30 (m, 7H), 7.16-7.12 (m, 1H), 5.45 (s, 2H), 3.93 (t, J=6.4 Hz, 2H), 2.92 (t, J=6.4 Hz, 2H).

Example 3

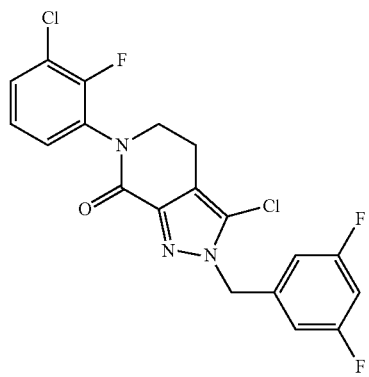 [SMILES: O=C1c2nn(Cc3cc(F)cc(F)c3)c(Cl)c2CCN1c1cccc(Cl)c1F]

3-Chloro-6-(3-chloro-2-fluorophenyl)-2-(3,5-difluorobenzyl)-5,6-dihydro-2H-pyrazolo[3,4-c]pyridin-7(4H)-one

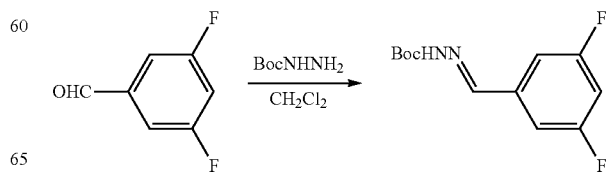

(E)-tert-Butyl 2-(3,5-difluorobenzylidene)hydrazinecarboxylate To a solution of tert-butyl hydrazinecarboxylate (27.90 g, 211.11 mmol, 1 eq) in CH$_2$Cl$_2$ (300 mL) was added 3,5-difluorobenzaldehyde (30 g, 211.11 mmol, 23.08 mL, 1 eq). The mixture was stirred at 15° C. for 16 h. The reaction mixture was concentrated under reduced pressure to obtain the title compound (50 g, 193.17 mmol, 91% yield) as a white solid, which was used directly in the next step.

MS (ES+) C$_{12}$H$_{14}$F$_2$N$_2$O$_2$, requires: 256 found: 201 [M-55]$^+$.

$^1$H NMR (400 MHz, DMSO-d$_6$) δ: 11.13 (br s, 1H), 7.98 (s, 1H), 7.36-7.17 (m, 3H), 1.47 (s, 9H).

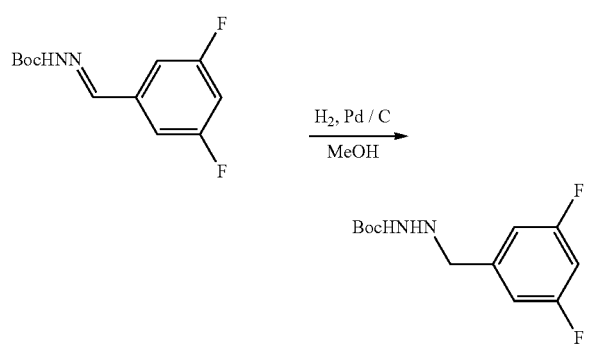

tert-Butyl 2-(3,5-difluorobenzyl)phydrazinecarboxylate To a solution of the product from the previous step (25 g, 96.59 mmol, 1 eq) in MeOH (250 mL) was added 10% Pd/C (10 g) under Ar. The suspension was degassed under reduced pressure and purged with H$_2$ several times. The mixture was stirred under H$_2$ (50 psi) at 35° C. for 16 h. The H$_2$ atmosphere was removed by purging with N$_2$, then the mixture was filtered, and the filtrate was concentrated under reduced pressure and purified by column chromatography (SiO$_2$, petroleum ether/EtOAc=20/1 to 5/1) to afford the title compound (24 g, 93 mmol, 96% yield) as a white solid.

MS (ES+) C$_{12}$H$_{16}$F$_2$N$_2$O$_2$, requires: 258 found: 203 [M-55]$^+$.

$^1$H NMR (400 MHz, DMSO-d$_6$) δ: 8.27 (br s, 1H), 7.11-6.98 (m, 3H), 5.02 (br d, J=3.7 Hz, 1H), 3.90 (br d, J=3.3 Hz, 2H), 1.37 (s, 9H).

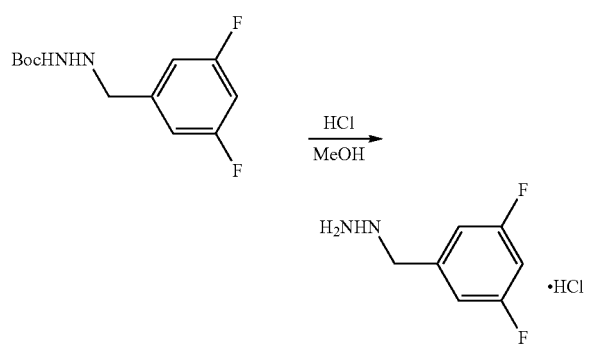

(3,5-Difluorobenzyl)hydrazine hydrochloride To a solution of the product from the previous step (48 g, 185.86 mmol, 1 eq) in MeOH (100 mL) was added HCl/MeOH (4 M, 200 mL) at 15° C. The mixture was stirred at 30° C. for 20 h, then concentrated under reduced pressure to afford the title compound (42 g, 181.76 mmol, 98% yield) as a white solid, which was used in the next step. $^1$H NMR (400 MHz, DMSO-d$_6$) δ: 7.93 (br s, 3H), 7.23-7.08 (m, 3H), 4.07 (s, 2H).

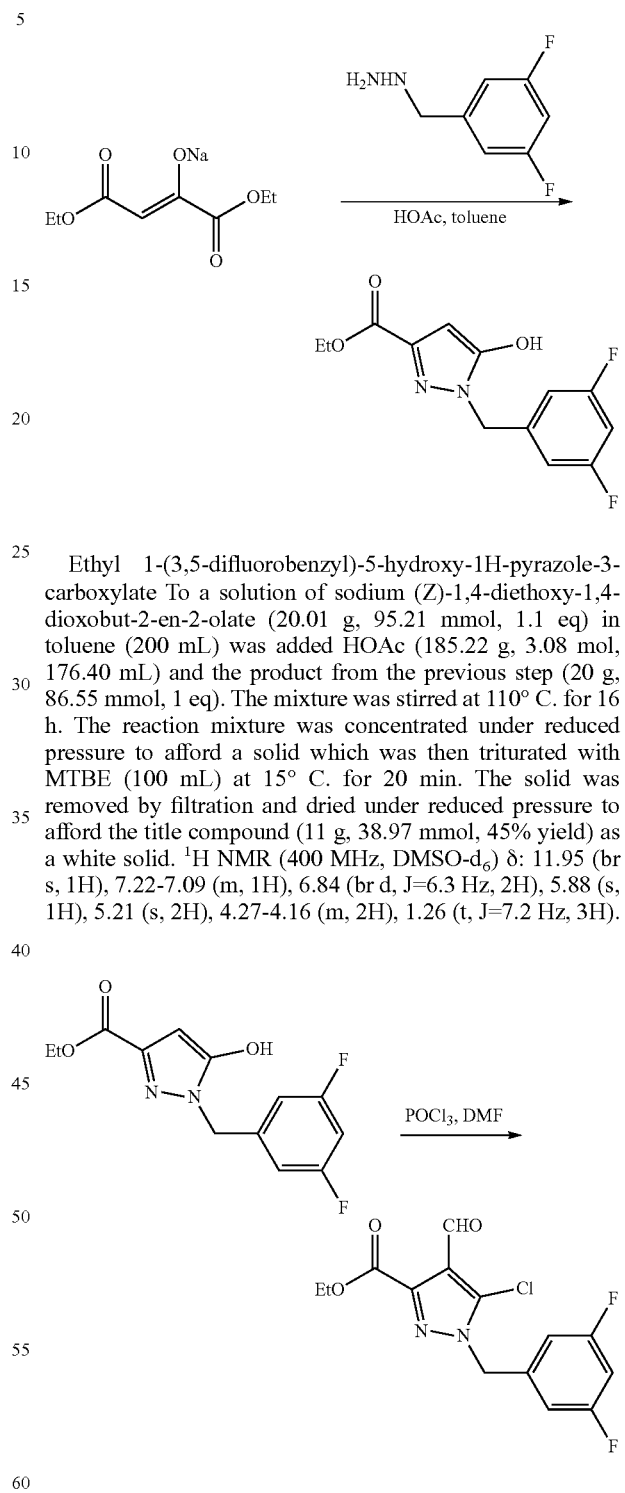

Ethyl 1-(3,5-difluorobenzyl)-5-hydroxy-1H-pyrazole-3-carboxylate To a solution of sodium (Z)-1,4-diethoxy-1,4-dioxobut-2-en-2-olate (20.01 g, 95.21 mmol, 1.1 eq) in toluene (200 mL) was added HOAc (185.22 g, 3.08 mol, 176.40 mL) and the product from the previous step (20 g, 86.55 mmol, 1 eq). The mixture was stirred at 110° C. for 16 h. The reaction mixture was concentrated under reduced pressure to afford a solid which was then triturated with MTBE (100 mL) at 15° C. for 20 min. The solid was removed by filtration and dried under reduced pressure to afford the title compound (11 g, 38.97 mmol, 45% yield) as a white solid. $^1$H NMR (400 MHz, DMSO-d$_6$) δ: 11.95 (br s, 1H), 7.22-7.09 (m, 1H), 6.84 (br d, J=6.3 Hz, 2H), 5.88 (s, 1H), 5.21 (s, 2H), 4.27-4.16 (m, 2H), 1.26 (t, J=7.2 Hz, 3H).

Ethyl 5-chloro-1-(3,5-difluorobenzyl)-4-formyl-1H-pyrazole-3-carboxylate

To a solution of the product from the previous step (11 g, 38.97 mmol, 1 eq) in DMF (11.48 g, 157.06 mmol, 12.08 mL, 4.03 eq) was added POCl$_3$ (51.87 g, 338.29 mmol, 31.44 mL, 8.68 eq). The mixture was stirred at 90° C. for 16 hr. The reaction mixture was concentrated under reduced pressure and the residue was dissolved in THF (50 mL), then slowly poured into warm H₂O (400 mL). The mixture was diluted with EtOAc (500 mL) and extracted with EtOAc (300 mL×3). The combined organic layers were washed with brine (300 mL×2), dried over Na₂SO₄, concentrated under reduced pressure, and purified by column chromatography (SiO₂, petroleum ether/EtOAc=1/0 to 5/1) to afford the title compound (4.5 g, 13.28 mmol, 34% yield) as a yellow solid.

MS (ES+) $C_{14}H_{11}ClF_2N_2O_3$, requires: 328 found: 329 $[M+H]^+$.

$^1$H NMR (400 MHz, CDCl₃) δ: 10.45 (s, 1H), 6.86-6.69 (m, 3H), 5.43 (s, 2H), 4.51 (q, J=7.2 Hz, 2H), 1.46 (t, J=7.2 Hz, 3H).

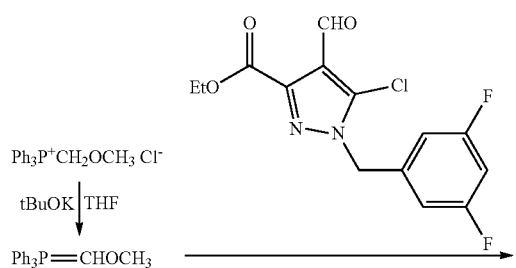

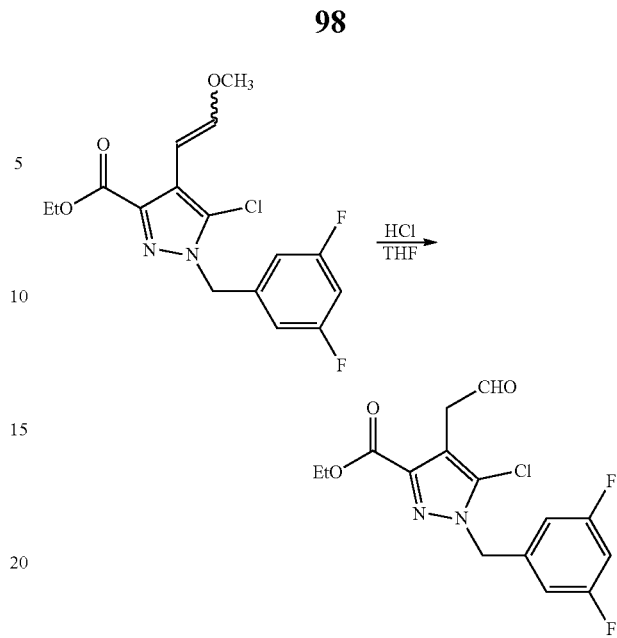

Ethyl 5-chloro-1-(3,5-difluorobenzyl)-4-(2-methoxyvinyl)-1H-pyrazole-3-carboxylate To a solution of t-BuOK (1.49 g, 13.23 mmol, 1.55 eq) in THF (45 mL) was added methoxymethyl(triphenyl) phosphonium chloride (4.40 g, 12.84 mmol, 1.5 eq) at 0° C. under N₂. The mixture was stirred at 0° C. for 10 min. A solution of the product from the previous step (2.9 g, 8.56 mmol, 1 eq) in THF (60 mL) was then added at 0° C. The mixture was stirred at 15° C. for 16 h. To the reaction mixture was added H₂O (100 mL), followed by EtOAc (300 mL). The aqueous layer was extracted with EtOAc (200 mL×2). The combined organic layers were washed with brine (100 mL×2), dried over Na₂SO₄, concentrated under reduced pressure, and purified by column chromatography (SiO₂, petroleum ether/EtOAc=1/0 to 20/1) to afford the title compound (1.5 g, 4.16 mmol, 48% yield) as a white solid. $^1$H NMR (400 MHz, CDCl₃) δ: 7.30 (d, J=13.3 Hz, 1H), 6.81-6.67 (m, 3H), 6.22-6.04 (m, 1H), 5.45-5.37 (m, 2H), 4.50-4.36 (m, 2H), 3.76-3.67 (m, 3H), 1.47-1.35 (m, 3H).

Ethyl 5-chloro-1-(3,5-difluorobenzyl)-4-(2-oxoethyl)-1H-pyrazole-3-carboxylate

To a solution of the product from the previous step (2.9 g, 8.13 mmol, 1 eq) in THF (80 mL) was added HCl (6 M, 155.80 mL) at 15° C. The mixture was stirred at 30° C. for 0.5 h. The reaction mixture was extracted with EtOAc (200 mL×2). The combined organic layers were washed with brine (200 mL×2), dried over Na₂SO₄, and concentrated under reduced pressure to afford the title compound (2.79 g, 7.33 mmol, 90% yield) as a yellow oil, which was used directly in the next step. MS (ES+) $C_{15}H_{13}ClF_2N_2O_3$, requires: 342 found: 343 $[M+H]^+$.

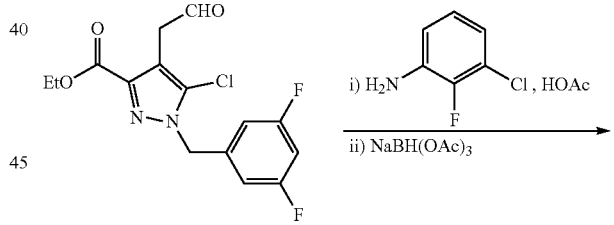

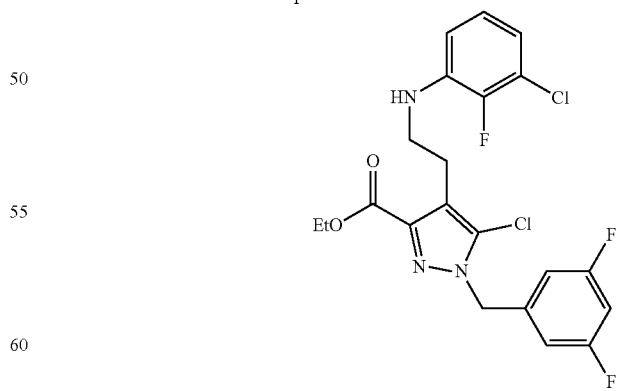

Ethyl 5-chloro-4-(2-((3-chloro-2-fluorophenyl)amino) ethyl)-1-(3,5-difluoro-benzyl)-1H-pyrazole-3-carboxylate
To a solution of the product from the previous step (2.79 g, 7.33 mmol, 1 eq) in DCE (30 mL) was added 3-chloro-2- fluoroaniline (2.51 g, 17.24 mmol, 2.35 eq) and HOAc (439.98 mg, 7.33 mmol, 419.02 uL, 1 eq). The reaction solution was stirred for 10 min, then NaBH(OAc)₃ (7.5 g, 35.39 mmol, 4.83 eq) was added. The mixture was stirred at 30° C. for 3 h. To the reaction mixture was added sat. NaHCO₃ (200 mL) and EtOAc (200 mL). The aqueous layer was extracted with EtOAc (100 mL×2). The combined organic layers were washed with brine (200 mL×2), dried over Na₂SO₄, concentrated under reduced pressure, and purified by column chromatography (SiO₂, petroleum ether/EtOAc=1/0 to 20/1) to give the title compound (3 g, 6.29 mmol, 86% yield) as a yellow solid.

¹H NMR (400 MHz, CDCl₃) δ: 6.88 (dt, J=1.5, 8.2 Hz, 1H), 6.80-6.69 (m, 3H), 6.68-6.57 (m, 2H), 5.38 (s, 2H), 4.53-4.40 (m, 2H), 4.36 (br d, J=2.6 Hz, 1H), 3.40 (q, J=6.6 Hz, 2H), 3.07 (t, J=6.7 Hz, 2H), 1.44 (t, J=7.1 Hz, 3H).

MS (ES+) C₂₁H₁₈Cl₂F₃N₃O₂, requires: 471 found: 472 [M+H]⁺.

¹H NMR (400 MHz, CD₃OD) δ: 6.95-6.87 (m, 1H), 6.87-6.79 (m, 3H), 6.71 (dt, J=1.4, 8.1 Hz, 1H), 6.55 (ddd, J=1.4, 6.5, 8.0 Hz, 1H), 5.43 (s, 2H), 3.41 (t, J=7.0 Hz, 2H), 3.02 (t, J=6.9 Hz, 2H).

MS (ES+) C₁₉H₁₄Cl₂F₃N₃O₂, requires: 443 found: 444 [M+H]⁺.

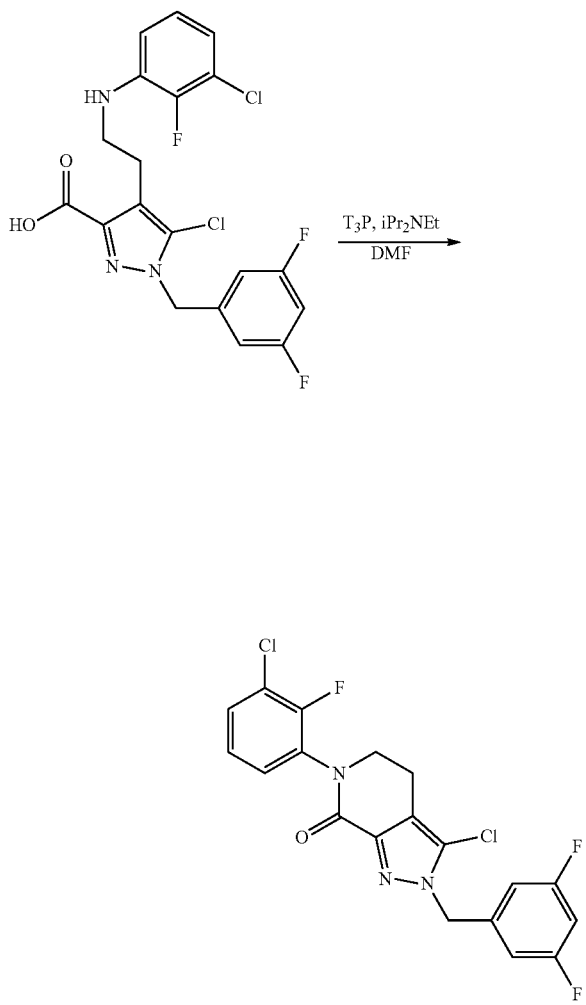

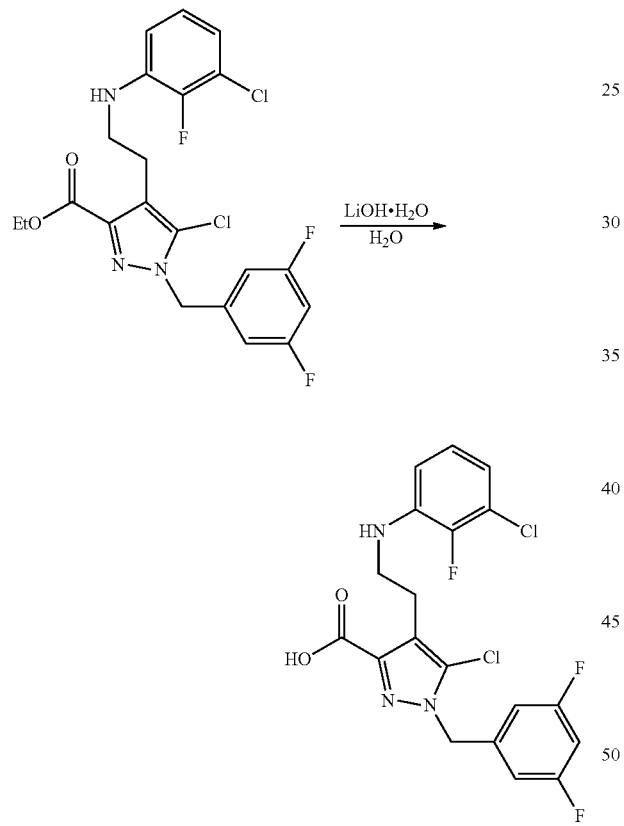

5-Chloro-4-(2-((3-chloro-2-fluorophenyl)amino)ethyl)-1-(3,5-difluorobenzyl)-1H-pyrazole-3-carboxylic acid To a solution of the product from the previous step (3 g, 6.29 mmol, 1 eq) in MeOH (40 mL) was added LiOH·H₂O (650 mg, 15.49 mmol, 2.46 eq) in H₂O (10 mL) at 15° C. The mixture was stirred at 50° C. for 15 h. To the reaction mixture was added aq.1N HCl (50 mL) and was adjusted to pH~1 and then extracted with EtOAc (100 mL×2). The combined organic layers were washed with brine (100 mL×2), dried over Na₂SO₄, and concentrated under reduced pressure to afford the title compound (2.79 g, 6.15 mmol, 98% yield) as a white solid, which was used directly in the next step.

3-Chloro-6-(3-chloro-2-fluorophenyl)-2-(3,5-difluorobenzyl)-5,6-dihydro-2H-pyrazolo[3,4-c]pyridin-7(4H)-one To a solution of the product from the previous step (2.79 g, 6.15 mmol, 1 eq) in DMF (20 mL) was added T₃P (5.88 g, 9.23 mmol, 5.49 mL of a 50% solution in EtOAc, 1.5 eq) and DIPEA (2.39 g, 18.46 mmol, 3.22 mL, 3 eq) at 15° C. The mixture was stirred at 30° C. for 16 h. The reaction mixture was concentrated under reduced pressure. The residue was purified by prep-HPLC (column: Phenomenex Synergi Max-RP 250*50 mm*10 μm; mobile phase: [H₂O (0.225% FA)-ACN]; B %: 45ACN %-75ACN %, 25 min) followed by lyophilization to afford the title compound (2.37 g, 5.51 mmol, 90% yield) as a brown solid.

¹H NMR (400 MHz, CD₃OD) δ: 7.49 (ddd, J=1.6, 6.7, 8.2 Hz, 1H), 7.41 (ddd, J=1.6, 6.7, 8.1 Hz, 1H), 7.30-7.21 (m, 1H), 6.98-6.83 (m, 3H), 5.51 (s, 2H), 4.01 (t, J=6.5 Hz, 2H), 2.98 (t, J=6.5 Hz, 2H).

MS (ES+) C₁₉H₁₂Cl₂F₃N₃O, requires: 425 found: 426 [M+H]⁺.

Example 4

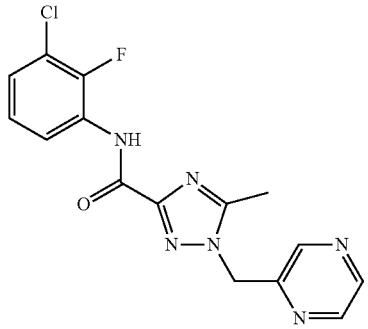 [SMILES: Cc1nc(C(=O)Nc2cccc(Cl)c2F)nn1Cc1cnccn1]

N-(3-Chloro-2-fluoro-phenyl)-5-methyl-1-(pyrazin-2-ylmethyl)-1,2,4-triazole-3-carboxamide

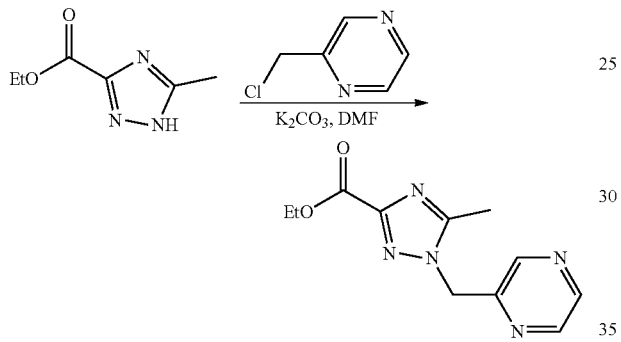

Ethyl 5-methyl-1-(pyrazin-2-ylmethyl)-1,2,4-triazole-3-carboxylate To a solution of ethyl 5-methyl-1H-1,2,4-triazole-3-carboxylate (0.45 g, 2.90 mmol, 1 eq) in DMF (6 mL) was added 2-(chloromethyl)pyrazine (372.87 mg, 2.90 mmol, 1 eq) and K$_2$CO$_3$ (801.69 mg, 5.80 mmol, 2 eq) and the mixture was stirred at 25° C. for 16 hr. H$_2$O (10 mL) was then added, and the mixture was extracted with EtOAc (10 mL×3). The combined organic layers were washed with brine (20 mL×2), dried over Na$_2$SO$_4$, concentrated under reduced pressure, and purified by column chromatography (SiO$_2$, petroleum ether/EtOAc=20/1 to 3/1) to afford the title compound (0.113 g, 457.02 umol, 15% yield) as a yellow oil.

MS(ES+)C$_{11}$H$_{13}$N$_5$O$_2$ requires: 247, found: 248 [M+H]$^+$.

$^1$H NMR (400 MHz, DMSO-d$_6$) δ: 8.73 (d, J=1.3 Hz, 1H), 8.63 (d, J=2.6 Hz, 1H), 8.59 (dd, J=1.6, 2.4 Hz, 1H), 5.68 (s, 2H), 4.27 (q, J=7.1 Hz, 2H), 2.51 (s, 3H), 1.26 (t, J=7.1 Hz, 4H).

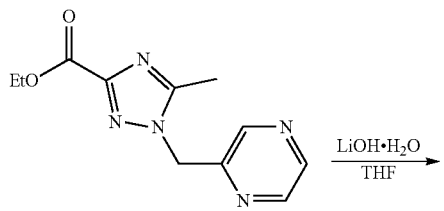

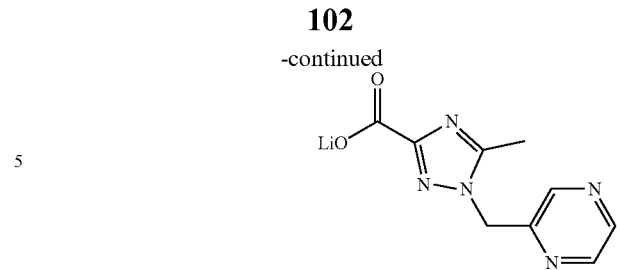

Lithium 5-methyl-1-(pyrazin-2-ylmethyl)-1H-1,2,4-triazole-3-carboxylate To a solution of the product from the previous step (0.15 g, 606.67 umol, 1 eq) in THF (4 mL) and H$_2$O (1 mL) was added LiOH·H$_2$O (30.55 mg, 728.00 umol, 1.2 eq) and the mixture was stirred at 25° C. for 16 hr. The reaction mixture was concentrated under reduced pressure to afford the title compound (0.113 g, 501.93 umol, 82% yield) as a red solid. MS(ES+) The parent acid was detected. C$_9$H$_9$N$_5$O$_2$ requires: 219, found: 220 [M+H]$^+$.

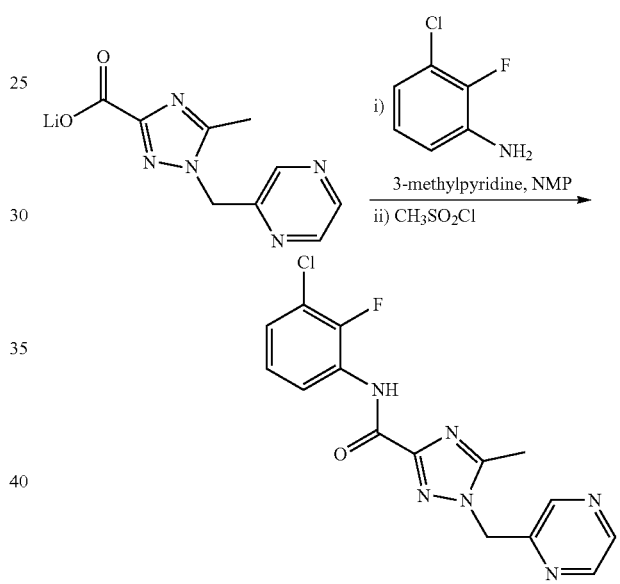

N-(3-chloro-2-fluoro-phenyl)-5-methyl-1-(pyrazin-2-ylmethyl)-1,2,4-triazole-3-carboxamide To a solution of 3-chloro-2-fluoroaniline (35.56 mg, 244.30 umol, 1.1 eq) in NMP (2 mL) was added the product from the previous step (0.05 g, 222.09 umol, 1 eq) and 3-methyl-pyridine (62.05 mg, 666.27 umol, 64.88 uL, 3 eq). To the mixture was added methanesulfonyl chloride (50.88 mg, 444.18 umol, 34.38 uL, 2 eq) at 0° C., and the mixture was stirred at 25° C. for 16 hr. H$_2$O (5 mL) was then added, and the mixture was extracted with EtOAc (5 mL×3). The combined organic layers were washed with brine (10 mL×2), dried over Na$_2$SO$_4$, concentrated under reduced pressure, and purified by prep-HPLC (column: Phenomenex Gemini 150*25 mm*10 μm; mobile phase: [H$_2$O (10 mM NH$_4$HCO$_3$)-ACN]; B %: 30%-52%,8 min). The eluent was concentrated to afford the title compound (0.02 g, 57.68 umol, 25% yield) as a white solid.

MS(ES+)C$_{15}$H$_{12}$N$_6$OFCl requires: 346, found: 347 [M+H]$^+$.

$^1$H NMR (400 MHz, DMSO-d$_6$) δ: 10.16 (s, 1H), 8.77 (d, J=1.3 Hz, 1H), 8.66-8.63 (m, 1H), 8.62 (dd, J=1.5, 2.4 Hz,

1H), 7.75-7.58 (m, 1H), 7.46-7.42 (m, 1H), 7.26-7.22 (m, 1H), 5.72 (s, 2H), 2.58 (s, 3H).

Example 5

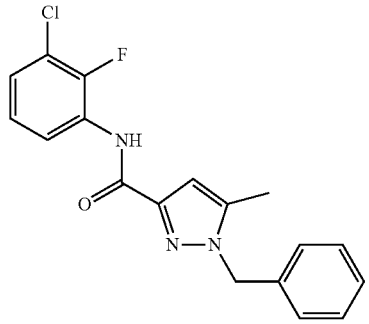 [SMILES: Cc1cc(C(=O)Nc2cccc(Cl)c2F)nn1Cc1ccccc1]

1-benzyl-N-(3-chloro-2-fluoro-phenyl)-5-methyl-pyrazole-3-carboxamide

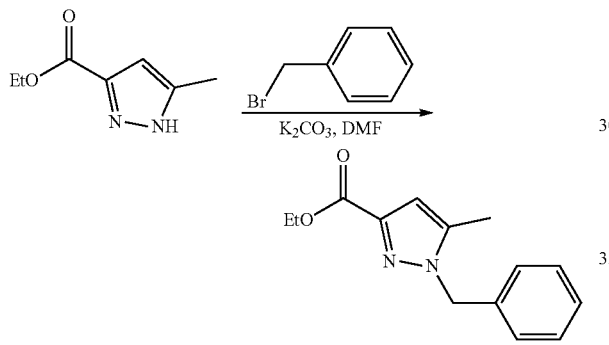

Ethyl 1-benzyl-5-methyl-pyrazole-3-carboxylate To a solution of ethyl 5-methyl-1H-pyrazole-3-carboxylate (1 g, 6.49 mmol, 1 eq) in DMF (40 mL) was added benzyl bromide (1.33 g, 7.78 mmol, 924.51 uL, 1.2 eq), K$_2$CO$_3$ (1.79 g, 12.97 mmol, 2 eq) and the mixture was stirred at 25° C. for 16 hr. H$_2$O (40 mL) was then added, and the mixture was extracted with EtOAc (40 mL×3). The combined organic layers were washed with brine (45 mL×2), dried over Na$_2$SO$_4$, concentrated under reduced pressure, and purified by prep-HPLC (column: Xbridge BEH C18, 250 mm*50 mm*10 μm; mobile phase: [H$_2$O (0.05% NH$_4$OH-ACN]; B %: 40%-65%, 33 min;30% min). The eluent was concentrated to afford the title compound (142 mg, 581.28 umol, 8% yield) as a colorless oil.

MS(ES+)C$_{14}$H$_{16}$N$_2$O$_2$ requires: 244, found: 245 [M+H]$^+$.

$^1$HNMR (400 Hz, MeOD) δ: 7.35-7.28 (m, 3H), 7.17-7.08 (m, 2H), 6.61 (s, 1H), 5.39 (s, 2H), 4.34 (q, J=7.07 Hz, 2H), 2.23 (s, 3H), 1.37 (t, J=7.0 Hz, 3H).

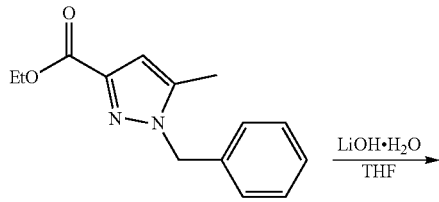

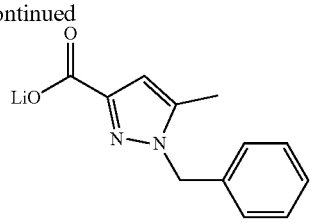

Lithium 1-benzyl-5-methyl-1H-pyrazole-3-carboxylate To a solution of the product from the previous step (0.142 g, 581.28 umol, 1 eq) in THF (2 mL) and H$_2$O (0.5 mL) was added LiOH·H$_2$O (29.27 mg, 697.54 umol, 1.2 eq), and the mixture was stirred at 25° C. for 16 hr. The reaction mixture was concentrated under reduced pressure to afford the title compound (0.125 g, 562.64 umol, 96% yield) as a yellow solid. MS(ES+) The parent acid was detected. C$_{12}$H$_{12}$N$_2$O$_2$ requires: 216, found: 217 [M+H]$^+$.

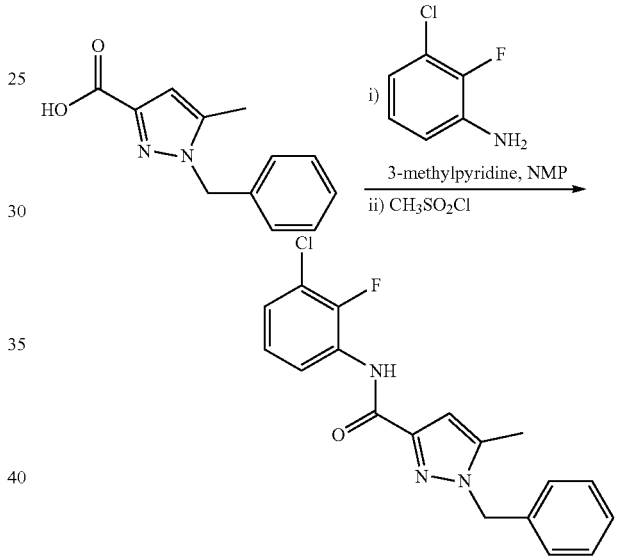

1-Benzyl-N-(3-chloro-2-fluoro-phenyl)-5-methyl-pyrazole-3-carboxamide To a solution of lithium 1-benzyl-5-methyl-pyrazole-3-carboxylate (34.07 mg, 153.5 umol, 1 eq) in NMP (2 mL) was added 3-chloro-2-fluoroaniline (34.40 mg, 236.31 umol, 1.5 eq) and 3-methyl-pyridine (44.01 mg, 472.61 umol, 46.02 uL, 3 eq). To the mixture was added methanesulfonyl chloride (36.09 mg, 315.08 umol, 24.39 uL, 2 eq) at 0° C., and the mixture was stirred at 25° C. for 16 hr. H$_2$O (5 mL) was then added, and the mixture was extracted with EtOAc (5 mL×3). The combined organic layers were washed with brine (10 mL×2), dried over Na$_2$SO$_4$, concentrated under reduced pressure, and purified by prep-HPLC (column: Phenomenex Gemini 150*25 mm*10 μm; mobile phase: [H$_2$O (0.04% NH$_4$OH+10 mM NH$_4$HCO$_3$)-ACN]; B %: 60%-90%,10 min). The eluent was concentrated to afford the title compound (0.02 g, 50.61 umol, 32% yield) as a white solid.

MS(ES+)C$_{18}$H$_{15}$N$_3$OFCl requires: 343, found: 344 [M+H]$^+$.

$^1$H NMR (400 MHz, CD$_3$OD) δ: 8.05-8.01 (m, 1H), 7.43-7.24 (m, 4H), 7.24-7.16 (m, 3H), 6.69 (s, 1H), 5.46 (s, 2H), 2.29 (s, 3H).

Example 6

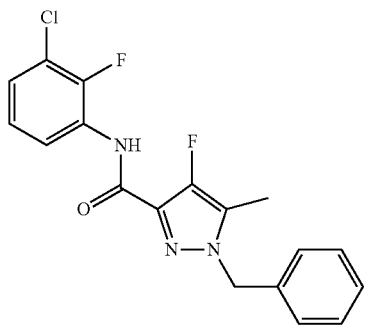 [SMILES: Cc1c(F)c(C(=O)Nc2cccc(Cl)c2F)nn1Cc1ccccc1]

1-Benzyl-N-(3-chloro-2-fluorophenyl)-4-fluoro-5-methyl-1H-pyrazole-3-carboxamide

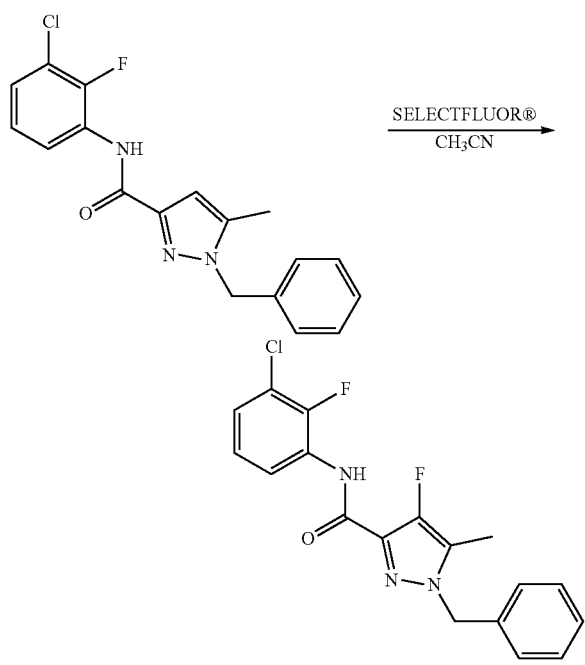

1-Benzyl-N-(3-chloro-2-fluoro-phenyl)-4-fluoro-5-methyl-pyrazole-3-carboxamide To a solution of the Example 5 compound (0.1 g, 290.88 umol, 1 eq) in ACN (3 mL) was added SELECTFLUOR® (206.10 mg, 581.76 umol, 2 eq), and the mixture was stirred at 50° C. for 24 hr. The reaction mixture was concentrated under reduced pressure and then purified by prep-HPLC (column: Phenomenex Synergi C18, 150*25*10 μm; mobile phase: [H$_2$O (0.1% TFA)-ACN]; B %: 60%-80%,10 min). The eluent was concentrated to afford the title compound (0.01 g, 27.64 umol, 9% yield) as a white solid.

MS(ES+)C$_{18}$H$_{14}$N$_3$OF$_2$Cl requires: 361, found: 362 [M+H]$^+$, $^1$H NMR (400 MHz, CD$_3$OD) δ: 8.03-7.99 (m, 1H), 7.43-7.27 (m, 4H), 7.26-7.15 (m, 3H), 5.42 (s, 2H), 2.22 (d, J=1.5 Hz, 3H).

Example 7

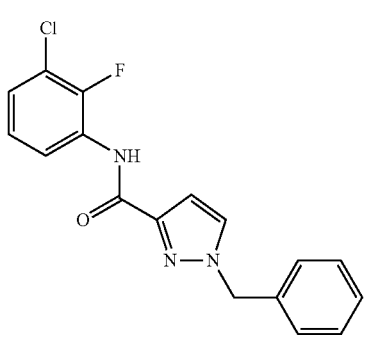 [SMILES: O=C(Nc1cccc(Cl)c1F)c1ccn(Cc2ccccc2)n1]

1-Benzyl-N-(3-chloro-2-fluorophenyl)-1H-pyrazole-3-carboxamide

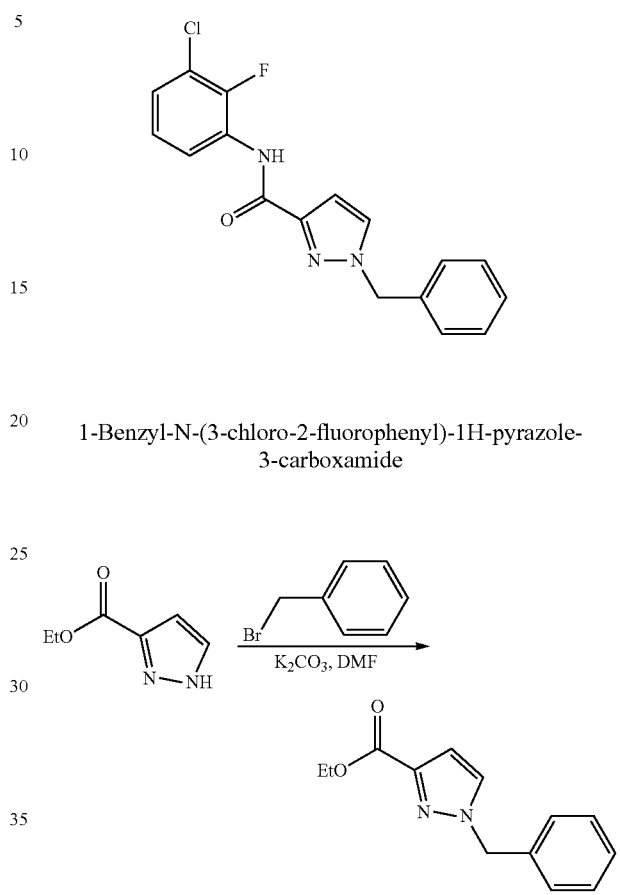

Ethyl 1-benzyl-1H-pyrazole-3-carboxylate To a solution of benzyl bromide (1.28 g, 7.49 mmol, 890 uL, 1.05 eq) in DMSO (20 mL) was added K$_2$CO$_3$ (1.18 g, 8.56 mmol, 1.2 eq) and ethyl 1H-pyrazole-3-carboxylate (1 g, 7.14 mmol, 1 eq) at 0° C. The mixture was stirred at 15° C. for 18 h. The mixture was extracted with EtOAc (100 mL×3). The combined organic layers were washed with H$_2$O (50 mL), dried over Na$_2$SO$_4$, concentrated under reduced pressure, and purified by column chromatography (SiO$_2$, petroleum ether/EtOAc=100:1-5:1) to afford the title compound (840 mg, 3.61 mmol, 50% yield) as a white solid.

MS (ES+) C$_{13}$H$_{14}$N$_2$O$_2$ requires: 230, found: 231 [M+H]$^+$.

$^1$H NMR (400 MHz, CDCl$_3$) δ: 7.42-7.33 (m, 4H), 7.30-7.23 (m, 2H), 6.85 (m, 1H), 5.42 (s, 2H), 4.44 (q, J=7.2 Hz, 2H), 1.43 (t, J=7.2 Hz, 3H).

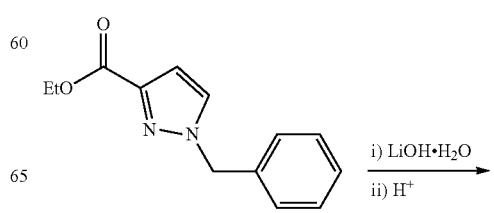

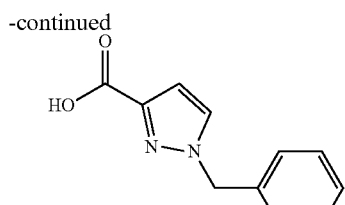

1-Benzyl-1H-pyrazole-3-carboxylic acid To a solution of the product from the previous step (400 mg, 1.74 mmol, 1 eq) in MeOH (6 mL) was added a solution of LiOH (53 mg, 2.21 mmol, 1.27 eq) in H$_2$O (3 mL) at 0° C. The mixture was stirred at 15° C. for 14 h. The mixture was concentrated under reduced pressure. The residue was diluted in H$_2$O (20 mL) and washed with EtOAc (10 mL×3). The aqueous phase was adjusted to pH 4 with citric acid solution. Then the mixture was extracted with EtOAc (30 mL×2), and the combined organic layers were dried over Na$_2$SO$_4$ and concentrated under reduced pressure to afford the title compound (320 mg, 1.58 mmol, 91% yield) as a white solid.

MS (ES+) C$_{11}$H$_{10}$N$_2$O$_2$ requires: 202, found: 203 [M+1]$^+$.

$^1$H NMR (400 MHz, DMSO-d$_6$) δ: 12.59 (s, 1H), 7.94 (d, J=2.4 Hz, 1H), 7.48-7.16 (m, 5H), 6.71 (d, J=2.4 Hz, 1H), 5.40 (s, 2H).

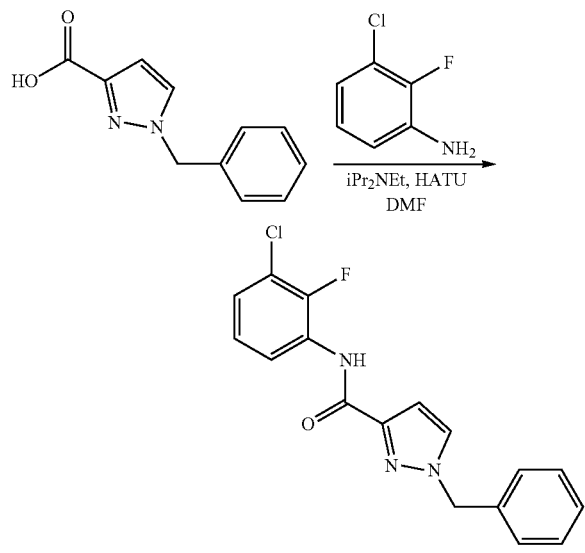

1-benzyl-N-(3-chloro-2-fluorophenyl)-1H-pyrazole-3-carboxamide To a solution the product from the previous step (50 mg, 247.27 umol, 1 eq) and 3-chloro-2-fluoroaniline (43 mg, 295.41 umol, 1.19 eq) in DMF (2 mL) was added DIPEA (96 mg, 742.79 umol, 129.38 uL, 3 eq) and HATU (141 mg, 370.83 umol, 1.5 eq). The mixture was stirred at 40° C. for 14 h, then extracted with EtOAc (20 mL×3). The combined organic layers were washed with H$_2$O (10 mL), dried over Na$_2$SO$_4$, concentrated under reduced pressure, and purified by prep-TLC (petroleum ether/EtOAc=3/1) to afford the title compound (42.1 mg, 118.73 umol, 48% yield, 93% purity) as a yellow solid.

MS (ES+) C$_{17}$H$_{13}$ClFN$_3$O requires: 329, found: 330 [M+H]$^+$.

$^1$H NMR (400 MHz, DMSO-d$_6$) δ: 9.82 (s, 1H), 8.03 (d, J=2.4 Hz, 1H), 7.77-7.63 (m, 1H), 7.43-7.18 (m, 7H), 6.84 (d, J=2.4 Hz, 1H), 5.48 (s, 2H).

Example 8

N-(3-chloro-2-fluoro-phenyl)-5-hydroxy-1-(pyrazin-2-ylmethyl)pyrazole-3-carboxamide

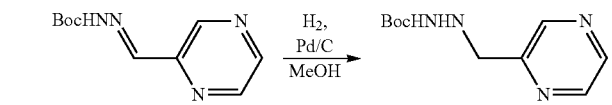

tert-Butyl N-[(E)-pyrazin-2-ylmethyleneamino]carbamate To a solution of tert-butyl hydrazinecarboxylate (11.00 g, 83.26 mmol, 1 eq) in CH$_2$Cl$_2$ (100 mL) was added pyrazine-2-carbaldehyde (9 g, 83.26 mmol, 1 eq), and the mixture was stirred at 20° C. for 16 hr. The reaction mixture was then concentrated under reduced pressure to afford the title compound (18 g, 72.89 mmol, 87% yield) as a yellow solid.

MS(ES+)C$_{10}$H$_{14}$N$_4$O$_2$ requires: 222, found: 223 [M+H]$^+$.

$^1$H NMR (400 MHz, CDCl$_3$) δ: 9.20 (s, 1H), 8.95 (s, 1H), 8.42 (s, 2H), 7.97 (s, 1H), 1.47 (s, 9H).

tert-Butyl N-(pyrazin-2-ylmethylamino)carbamate To a solution of the product from the previous step (18 g, 80.99 mmol, 1 eq) in MeOH (200 mL) was added 10% Pd/C (10 g) under N$_2$. The suspension was degassed under reduced pressure and purged with H$_2$ several times, and the mixture was stirred under H$_2$ (15 psi) at 25° C. for 2 hr. The mixture was filtered, and the filtrate was concentrated under reduced pressure to afford the title compound (18.23 g, 65.03 mmol, 80% yield) as a colorless oil.

MS(ES+)C$_{10}$H$_{16}$N$_4$O$_2$ requires: 224, found: 247 [M+Na]$^+$.

$^1$H NMR (400 MHz, DMSO-d$_6$) δ: 8.72 (s, 1H), 8.54 (dd, J=1.6, 2.4 Hz, 1H), 8.51 (d, J=2.6 Hz, 1H), 8.36 (br s, 1H), 4.02 (d, J=4.2 Hz, 2H), 1.43-1.29 (m, 9H).

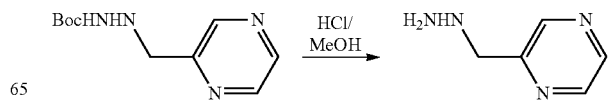

Pyrazin-2-ylmethylhydrazine To a solution of the product from the previous step (9 g, 40.13 mmol, 1 eq) in MeOH (2 mL) was added HCl/MeOH (4 M, 90.00 mL, 8.97 eq) at 0° C., and the mixture was stirred at 25° C. for 2 hr. The reaction mixture was concentrated under reduced pressure to give the title compound (6.27 g, 31.18 mmol, 77% yield) as a yellow solid. ¹H NMR (400 MHz, DMSO-d₆) δ: 8.74 (d, J=1.3 Hz, 1H), 8.68-8.58 (m, 2H), 4.25 (s, 2H).

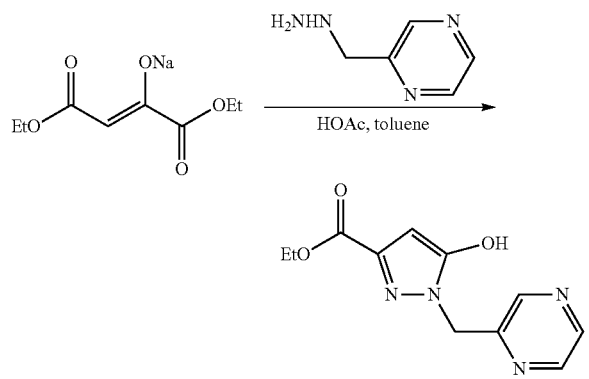

Ethyl 5-hydroxy-1-(pyrazin-2-ylmethyl)pyrazole-3-carboxylate To a solution the product from the previous step (6.27 g, 31.79 mmol, 1 eq) in toluene (5 mL) was added HOAc (68.02 g, 1.13 mol, 64.78 mL, 35.63 eq) and sodium (Z)-1,4-diethoxy-1,4-dioxobut-2-en-2-olate (7.35 g, 34.97 mmol, 1.1 eq), and the mixture was stirred under at 90° C. for 16 hr. The mixture was concentrated under reduced pressure, the residue was triturated with MTBE, and the solid was collected by filtration, washed with MTBE (20 mL×3) and dried under reduced pressure to afford the title compound (7.3 g, 29.41 mmol, 92% yield) as a brown solid.

MS(ES+)C₁₁H₁₂N₄O₃ requires: 248, found: 249 [M+H]⁺.

¹H NMR (400 MHz, DMSO-d₆) δ=8.59 (dd, J=1.9, 6.5 Hz, 2H), 8.44 (d, J=0.7 Hz, 1H), 5.89 (s, 1H), 5.35 (s, 2H), 4.20 (q, J=7.1 Hz, 2H), 1.25 (t, J=7.1 Hz, 3H).

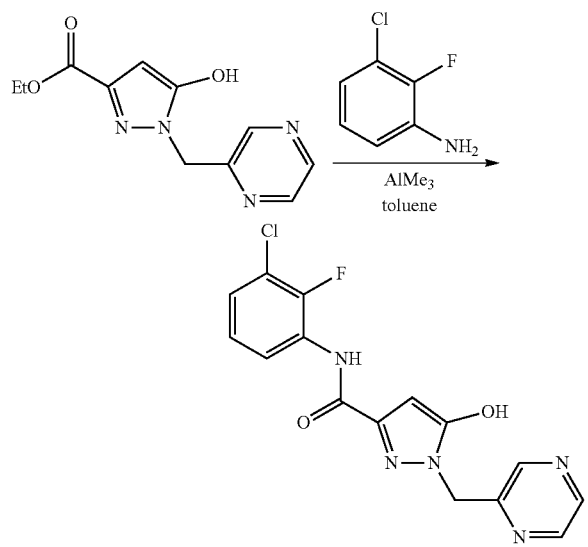

N-(3-chloro-2-fluoro-phenyl)-5-hydroxy-1-(pyrazin-2-ylmethyl)pyrazole-3-carboxamide To a solution of 3-chloro-2-fluoroaniline (140.73 mg, 966.82 umol, 1.2 eq) in toluene (5 mL) was added ethyl 5-hydroxy-1-(pyrazin-2-ylmethyl)pyrazole-3-carboxylate (0.2 g, 805.68 umol, 1 eq) and AlMe₃ (2 M in toluene, 483.41 uL, 1.2 eq) at 0° C., and the mixture was stirred under at 110° C. for 16 hr. The reaction mixture was quenched by the addition of HCl (1 N) at 0° C., the pH was adjusted to 7, then H₂O (3 mL) was added. The phases were separated, and the aqueous layer was extracted with CH₂Cl₂ (5 mL×3). The combined organic layers were dried over Na₂SO₄, concentrated under reduced pressure, and purified by prep-HPLC (column: Phenomenex Luna C18, 150*25 mm*10 μm; mobile phase: [H₂O (0.1% TFA)-ACN]; B %: 30%-60%,10 min). The eluent was concentrated and lyophilized to afford the title compound (0.9 mg, 2.59 umol) as a yellow solid.

MS(ES+) C₁₅H₁₁N₅O₂FCl requires: 347, found: 348 [M+H]⁺.

¹H NMR (400 MHz, CD₃OD) δ=8.65-8.55 (m, 2H), 8.49 (s, 1H), 8.03-7.99 (m, 1H), 7.30-7.26 (m, 1H), 7.21-7.15 (m, 1H), 6.04 (s, 1H), 5.47 (s, 2H).

Example 9

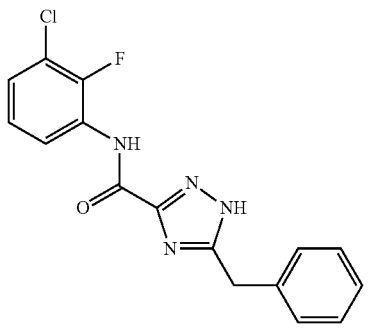 [SMILES: O=C(Nc1cccc(Cl)c1F)c1n[nH]c(Cc2ccccc2)n1]

5-benzyl-N-(3-chloro-2-fluoro-phenyl)-1H-1,2,4-triazole-3-carboxamide

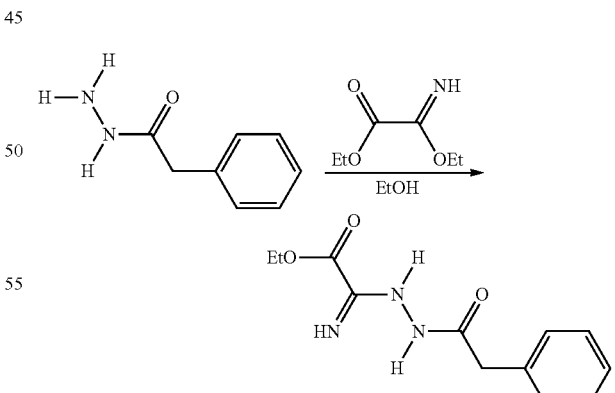

Ethyl 2-imino-2-(2-(2-phenylacetyl)hydrazineyl)acetate To a solution of ethyl 2-ethoxy-2-iminoacetate (5 g, 34.45 mmol, 1 eq) in EtOH (40 mL) was added 2-phenyl-acetohydrazide (5.17 g, 34.45 mmol, 1 eq) at 0° C. The mixture was stirred at 25° C. for 12 hr. The reaction mixture was filtered at 25° C. and the cake was washed with EtOH (40 ml). The filtrate was concentrated to afford the title compound (2 g) as a white solid. (ES+) C₁₂H₁₅N₃O requires: 249, found: 250 [M+H]⁺.

¹H NMR (400 MHz, DMSO-d₆) δ: 9.95 (br d, J=16.24 Hz, 1 H) 7.25-7.38 (m, 5 H) 6.37-6.58 (m, 2 H) 4.15-4.29 (m, 2 H) 3.86 (s, 1 H) 3.43-3.53 (m, 1 H) 1.20-1.35 (m, 1 H) 1.27 (dt, J=17.96, 7.08 Hz, 2 H).

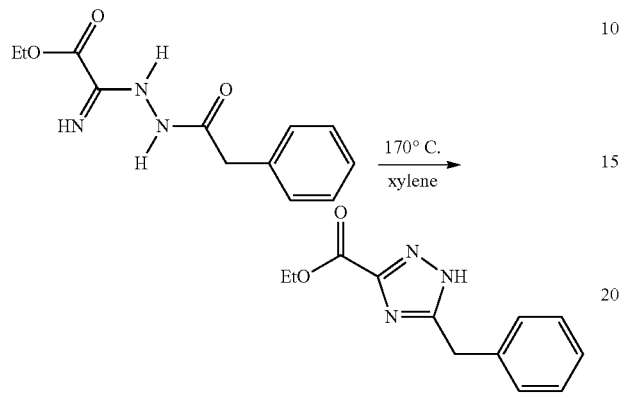

Ethyl 5-benzyl-1H-1,2,4-triazole-3-carboxylate A mixture the product from the previous step (2 g, 8.02 mmol, 1 eq) in xylene (30 mL) was stirred at 170° C. for 6 hr. The reaction mixture was concentrated to afford the title compound (1.8 g, crude) as a light yellow solid. MS (ES+) C₁₂H₁₃N₃O₂ requires: 231, found: 232 [M+H]⁺.

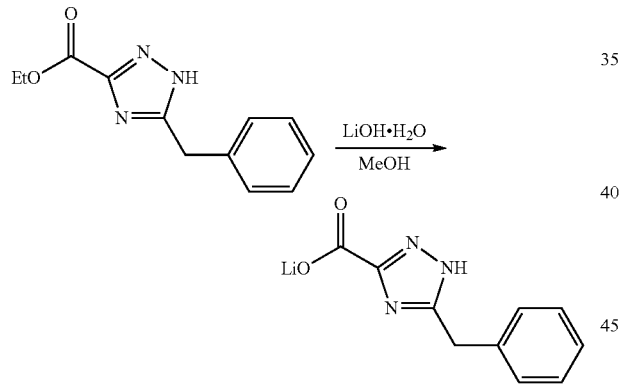

Lithium 5-benzyl-1H-1,2,4-triazole-3-carboxylate To a solution of ethyl 5-benzyl-1H-1,2,4-triazole-3-carboxylate (150 mg, 648.65 umol, 1 eq) in MeOH (1.5 mL) was added LiOH (32 mg, 1.34 mmol, 2.06 eq) in H₂O (1.5 mL) at 0° C. The mixture was stirred at 50° C. for 14 hr. The reaction mixture was concentrated under reduced pressure to afford the title compound (130 mg, 621.62 umol, 96% yield) as a light yellow solid. MS (ES−) C₁₀H₈LiN₃O₂ requires: 203, found: 202 [M−Li]⁻.

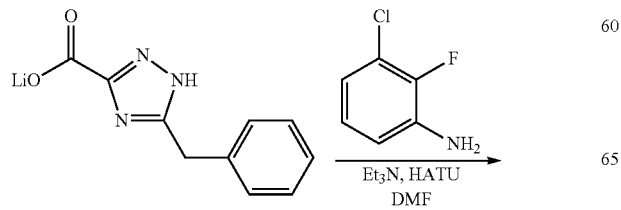

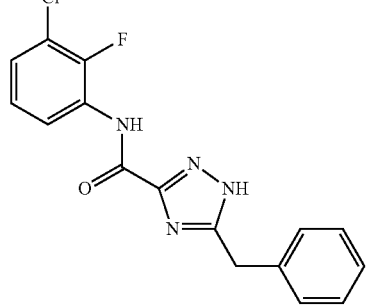

5-Benzyl-N-(3-chloro-2-fluoro-phenyl)-1H-1,2,4-triazole-3-carboxamide To a solution of 3-chloro-2-fluoroaniline (220 mg, 1.51 mmol, 2.43 eq) and the product from the previous step (130 mg, 621.62 umol, 1 eq) in DMF (2 mL) at 0° C. was added HATU (400 mg, 1.05 mmol, 1.69 eq) and TEA (145.40 mg, 1.44 mmol, 200 uL, 2.31 eq). The mixture was stirred at 25° C. for 14 hr. The reaction mixture was filtered, and then H₂O (5 ml) was added to the filtrate. The mixture was extracted with EtOAc (20 ml×3), and the combined organic layers were washed with brine (20 ml×2), dried over anhydrous Na₂SO₄, and filtered. The filtrate was concentrated under reduced pressure, and the residue was purified by prep-HPLC (column: KROMASIL®, 150*25 mm*10 μm; mobile phase: [H₂O (0.1% TFA)-ACN]; B %: 40%-70%, 10 min, Column Temp: 30° C.) to afford the title compound (9.7 mg, 22.88 umol, 3% yield) as a light yellow solid.

MS (ES+) C₁₆H₁₂ClFN₄O requires: 330, found: 331 [M+H]⁺.

¹H NMR (400 MHz, CD₃OD) δ: 7.94-8.11 (m, 1 H) 7.19-7.38 (m, 8 H) 4.24 (s, 2 H).

Example 10

5-Benzyl-N-(3-chloro-2-fluoro-phenyl)-1-methyl-1,2,4-triazole-3-carboxamide

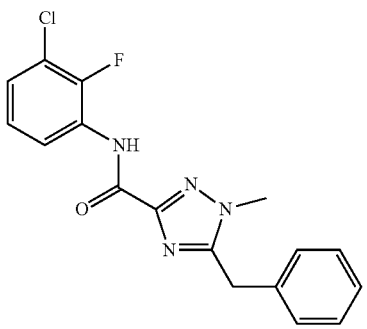 [SMILES: Cn1nc(C(=O)Nc2cccc(Cl)c2F)nc1Cc1ccccc1]

113

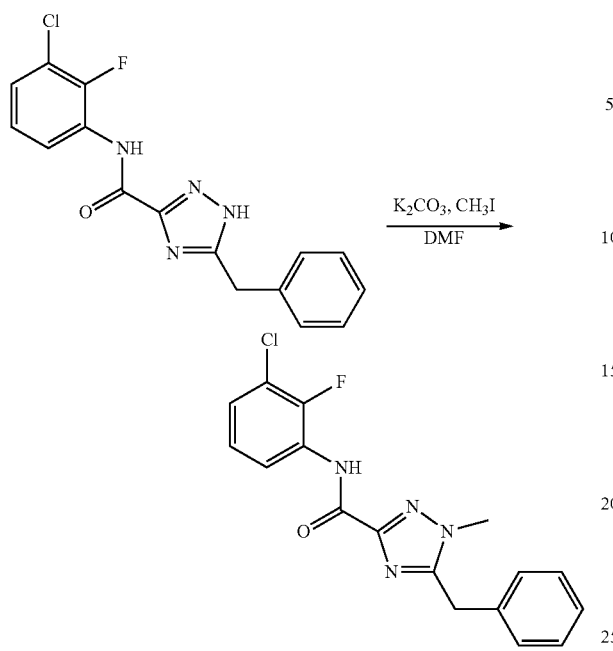

To a solution of the Example 9 compound (60 mg, 181.41 umol, 1 eq) in DMF (1.5 mL) was added MeI (38.62 mg, 272.11 umol, 16.94 uL, 1.5 eq) and K₂CO₃ (37.61 mg, 272.11 umol, 1.5 eq). Then the mixture was stirred at 20° C. for 12 hr. H₂O (10 mL) was then added, and the mixture was then extracted with EtOAc (10 mL×2). The combined organic layers were washed with brine (10 mL×3), dried over Na₂SO₄, concentrated under reduced pressure, and purified by Prep-HPLC (column: Phenomenex Synergi C18, 150*25*10 μm; mobile phase: [H₂O (0.1% TFA)-ACN]; B %: 45%-75%, 10 min). The eluent was concentrated under reduced pressure and lyophilized to afford the title compound (6.8 mg, 19.72 umol, 10.87% yield) as a white solid. (Structure confirmed by HMBC).

MS (ES+) C₁₇H₁₄ClFN₄O requires: 344, found: 345 [M+H]⁺.

¹H NMR (400 MHz, CD₃OD) δ: 10.16 (s, 1H), 7.66-7.60 (m, 1H), 7.44-7.37 (m, 1H), 7.33-7.24 (m, 6H), 4.29 (s, 2H), 3.47 (s, 3H).

5-Benzyl-N-(3-chloro-2-fluoro-phenyl)-2-methyl-1,2,4-triazole-3-carboxamide (3.4 mg, 9.86 umol, 5% yield) was also obtained as a white solid. MS (ES+) C₁₇H₁₄ClFN₄O requires: 344, found: 345 [M+H]⁺.

Example 11

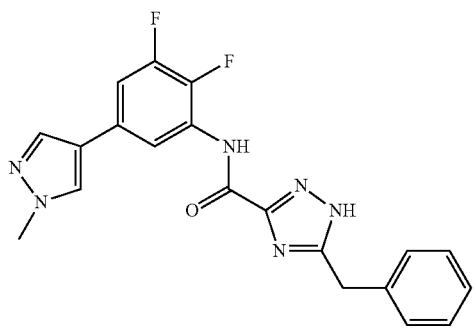 [SMILES: Cn1cc(-c2cc(F)c(F)c(NC(=O)c3n[nH]c(Cc4ccccc4)n3)c2)cn1]

114

5-Benzyl-N-(2,3-difluoro-5-(1-methyl-1H-pyrazol-4-yl)-phenyl)-1H-1,2,4-triazole-3-carboxamide

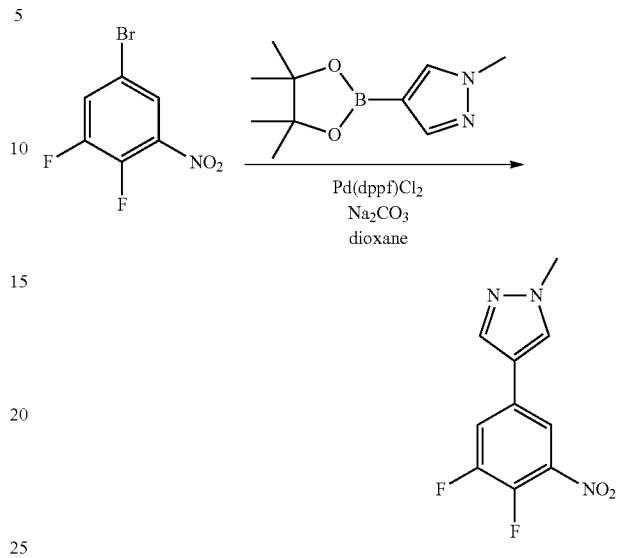

4-(3,4-difluoro-5-nitrophenyl)-1-methyl-1H-pyrazole To a solution of 5-bromo-1,2-difluoro-3-nitrobenzene (0.5 g, 2.10 mmol, 1 eq) in dioxane (2 mL) was added 1-methyl-4-(4,4,5,5-tetramethyl-1,3,2-dioxaborolan-2-yl)pyrazole (525 mg, 2.52 mmol, 1.2 eq), Na₂CO₃ (670 mg, 6.32 mmol, 3.01 eq) and Pd(dppf)Cl₂ (155 mg, 211.83 umol, 0.1 eq) under N₂ at 20° C. The mixture was then stirred at 90° C. for 16 h. The mixture was filtered, and the filtrate was concentrated under reduced pressure and purified by column chromatography (SiO₂, petroleum ether/EtOAc=1:0, 10:1) to afford the title compound (0.6 g, crude) as a yellow solid.

MS (ES+) C₁₀H₇F₂N₃O₂ requires: 239, found: 240 [M+H]⁺.

¹H NMR (400 MHz, CDCl₃) δ 7.89-7.87(m, 1H), 7.74 (s, 1H), 7.66(s, 1H), 7.53-7.51(m, 1H), 3.96 (s, 3H).

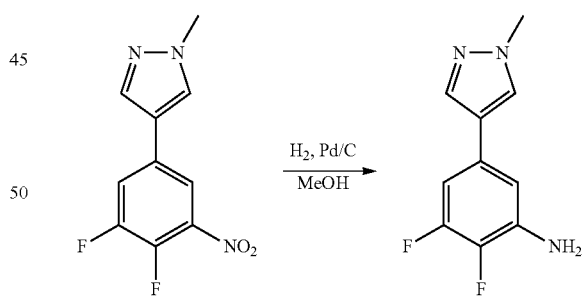

2,3-difluoro-5-(1-methyl-1H-pyrazol-4-yl)aniline To a solution of the product from the previous step (500 mg, 1.76 mmol, 1 eq) in MeOH was added 10% Pd/C (50 mg) at 20° C. under N₂, then purged with H₂ three times and then stirred under H₂ balloon (15 psi) for 3 h. The reaction mixture was filtered, and the filtrate was concentrated under reduced pressure and purified by prep-TLC (SiO₂, petroleum ether/EtOAc=1:1) to afford the title compound (200 mg, 734.24 umol, 41% yield) as a yellow solid.

MS (ES+) C₁₀H₉F₂N₃ requires: 209, found: 210 [M+H]⁺.

¹H NMR (400 MHz, CDCl₃) δ 7.64 (s, 1H), 7.50 (s, 1H), 6.64-6.60 (m, 1H), 3.93 (s, 3H), 3.50 (br, 1H).

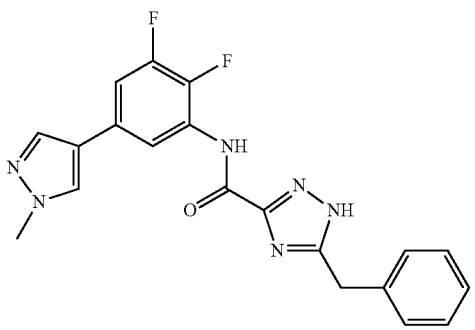 [SMILES: Cn1cc(-c2cc(F)c(F)c(NC(=O)c3n[nH]c(Cc4ccccc4)n3)c2)cn1]

5-Benzyl-N-(2,3-difluoro-5-(1-methyl-1H-pyrazol-4-yl)phenyl)-1H-1,2,4-triazole-3-carboxamide, was prepared from the product of the previous step by the method of Example 9 as a white solid.

MS (ES+) $C_{20}H_{16}F_2N_O$ requires: 394, found: 395 [M+H]$^+$.

$^1$H NMR (400 MHz, DMSO-d$_6$) δ 14.40(br, 1H), 10.20 (br, 1H), 8.15(s, 1H), 7.86(s, 1H), 7.53-7.34(m, 2H), 7.32-7.25(m, 5H), 4.17(s, 2H), 3.85(s, 3H).

Example 12

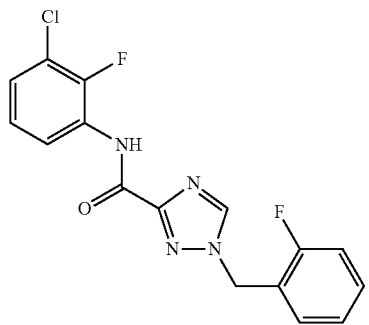 [SMILES: O=C(Nc1cccc(Cl)c1F)c1ncn(Cc2ccccc2F)n1]

N-(3-chloro-2-fluorophenyl)-1-(2-fluorobenzyl)-1H-1,2,4-triazole-3-carboxamide

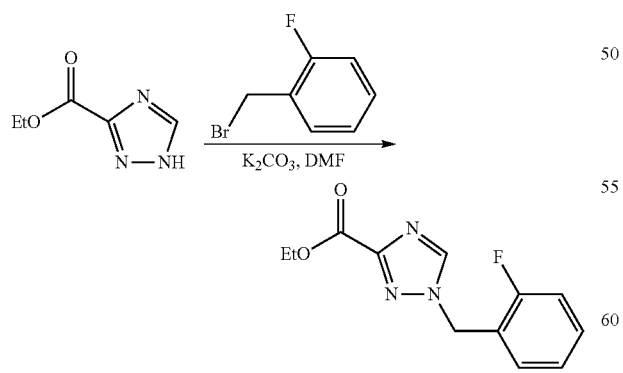

Methyl 1-(2-fluorobenzyl)-1H-1,2,4-triazole-3-carboxylate To a solution of methyl 1H-1,2,4-triazole-3-carboxylate (500 mg, 3.93 mmol, 1 eq) and 1-(bromomethyl)-2-fluorobenzene (817.16 mg, 4.32 mmol, 520.48 uL, 1.1 eq) in DMF (5 mL) was added K$_2$CO$_3$ (1.09 g, 7.86 mmol, 2 eq). Then the mixture was stirred at 40° C. for 12 hr. H$_2$O (15 mL) was then added, and the mixture was extracted with EtOAc (15 mL×2). The combined organic layers were washed with brine (15 mL×3). The organic phase was dried over Na$_2$SO$_4$, concentrated under reduced pressure, and purified by column chromatography (SiO$_2$, petroleum ether/EtOAc=10/1 to 0:1) to afford the title compound (318 mg, 1.28 mmol, 32% yield) as a white solid.

MS (ES+) $C_{11}H_{10}FN_3O_2$ requires: 235 found: 236 [M+H]$^+$.

$^1$H NMR (400 MHz, DMSO-d$_6$) δ: 8.84 (s, 1H), 7.43-7.37 (m, 2H), 7.27-7.22 (m, 2H), 5.56 (s, 2H), 3.81 (s, 3H).

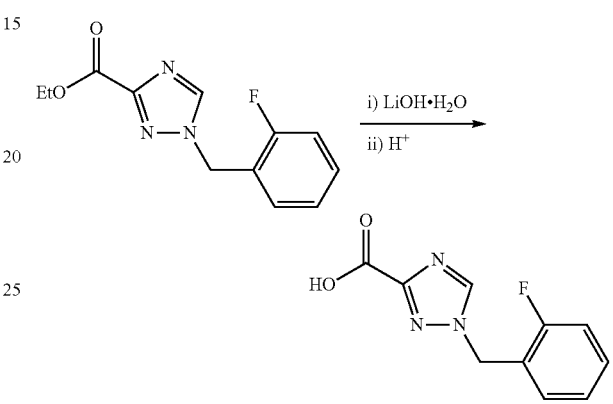

1-(2-Fluorobenzyl)-1H-1,2,4-triazole-3-carboxylic acid To a solution of the product from the previous step (150 mg, 637.72 umol, 1 eq) in THF (1.5 mL) was added a solution of LiOH in H$_2$O (3 M, 425.14 uL, 2 eq). Then the mixture was stirred at 20° C. for 3 hr. To the mixture was added HCl (1M) to adjust the pH to 5. The mixture was then diluted with H$_2$O (10 mL). The solid that had formed was removed by filtration and dried under reduced pressure to afford the title compound (110 mg, 497.32 umol, 77% yield) as a white solid. MS (ES+) $C_{10}H_8FN_3O_2$ requires: 221 found: 222 [M+H]$^+$.

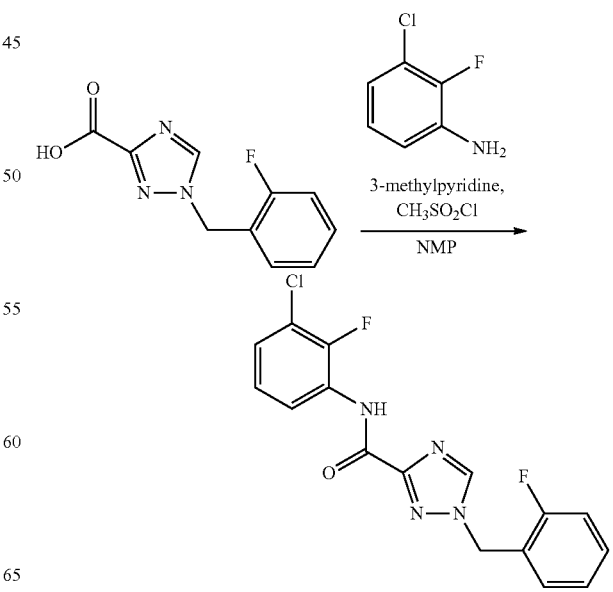

N-(3-chloro-2-fluorophenyl)-1-(2-fluorobenzyl)-1H-1,2,4-triazole-3-carboxamide

To a solution of the product from the previous step (97 mg, 438.54 umol, 1 eq) and 3-methylpyridine (204.21 mg, 2.19 mmol, 213.52 uL, 5 eq) in NMP (1.5 mL) was added methanesulfonyl chloride (100.47 mg, 877.08 umol, 67.88 uL, 2 eq) and 3-chloro-2-fluoroaniline (63.83 mg, 438.54 umol, 1 eq) at 0° C. After addition, the mixture was stirred at 15° C. for 3 hr. LC-MS showed that the reaction was completed. H$_2$O (15 mL) was then added, and the mixture was extracted with EtOAc (15 mL×2). The combined organic layers were washed with HCl (1N, 15 mL) and brine (15 mL×3). The organic phase was dried over Na$_2$SO$_4$, concentrated under reduced pressure, and purified by Prep-HPLC (column: Phenomenex Luna C18, 250*50 mm*10 μm; mobile phase: [H$_2$O (0.1% TFA)-ACN]; B %: 44%-64%,8 min). The eluent was concentrated under reduced pressure then lyophilized to afford the title compound (86 mg, 246.61 umol, 56% yield) as a white solid.

MS (ES+) C$_{16}$H$_{11}$ClF$_2$N$_4$O$_2$ requires: 348 found: 349 [M+H]$^+$.

$^1$H NMR (400 MHz, DMSO-d$_6$) δ 10.20 (s, 1H), 8.90 (s, 1H), 7.44 (t, J=7.6 Hz, 1H), 7.44~7.40 (m, 3H), 7.26~7.23 (m, 3H), 5.60 (s, 2H).

Example 13

1-benzyl-N-(3-chloro-2-fluorophenyl)-5-methyl-1H-1,2,4-triazole-3-carboxamide

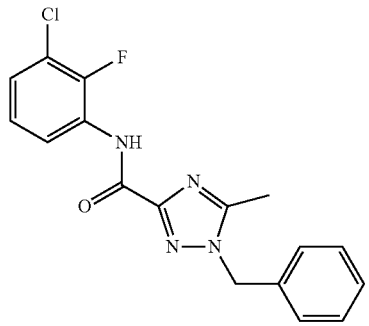 [SMILES: Cc1nc(C(=O)Nc2cccc(Cl)c2F)nn1Cc1ccccc1]

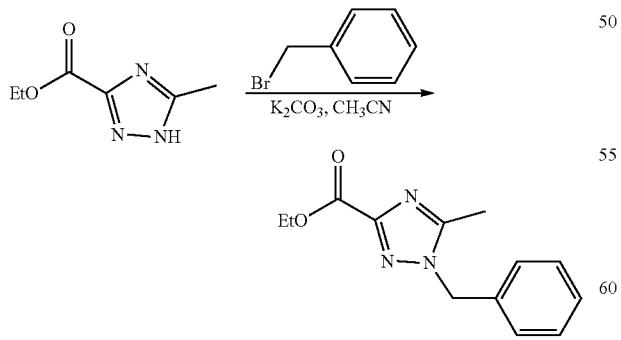

Benzyl-5-methyl-1H-1,2,4-triazole-3-carboxylate To a solution of ethyl 5-methyl-1H-1,2,4-triazole-3-carboxylate (750 mg, 4.83 mmol, 1 eq) in ACN (30 mL) was added benzyl bromide (826.76 mg, 4.83 mmol, 574.14 uL, 1 eq) and K$_2$CO$_3$ (1.34 g, 9.67 mmol, 2 eq). The reaction mixture was stirred at 20° C. for 2 hr. The reaction mixture was concentrated then purified by column chromatography (SiO$_2$, petroleum ether/EtOAc=10/1 to 5/1 to 3/1 to 1/1) to afford the title compound (50 mg, 216.22 umol, 4% yield) as a colorless solid (regioisomer confirmed by HMBC: two additional isomers were obtained).

MS (ES+) C$_{13}$H$_{15}$N$_3$O$_2$ requires: 245, found: 246 [M+H]$^+$.

$^1$H NMR (400 MHz, CDCl$_3$) δ: 7.33 (m, 5H), 5.74 (s, 2H), 4.45 (q, 2H), 2.45 (s, 3H), 1.42 (t, 3H).

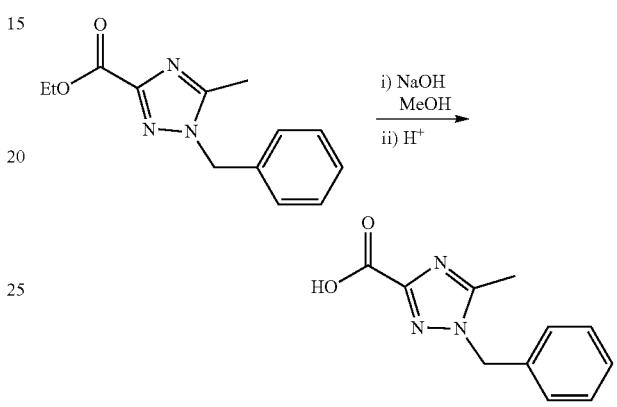

1-Benzyl-5-methyl-1H-1,2,4-triazole-3-carboxylic acid
To a solution of the product from the previous step (150 mg, 611.55 umol, 1 eq) in MeOH (2 mL) was added NaOH (1 M, 1.22 mL, 2 eq), the reaction mixture was stirred at 25° C. for 2 h. The mixture was adjusted to pH 3-5 with HCl (1 N). The aqueous phase was extracted with CH$_2$Cl$_2$ (20 mL×2). The combined organic phases were washed with saturated brine (10 mL×2), and concentrated at reduced pressure to afford the title compound (110 mg) as a white solid. MS (ES+) C$_{13}$H$_{15}$N$_3$O$_2$ requires: 217, found: 216 [M−H]$^-$.

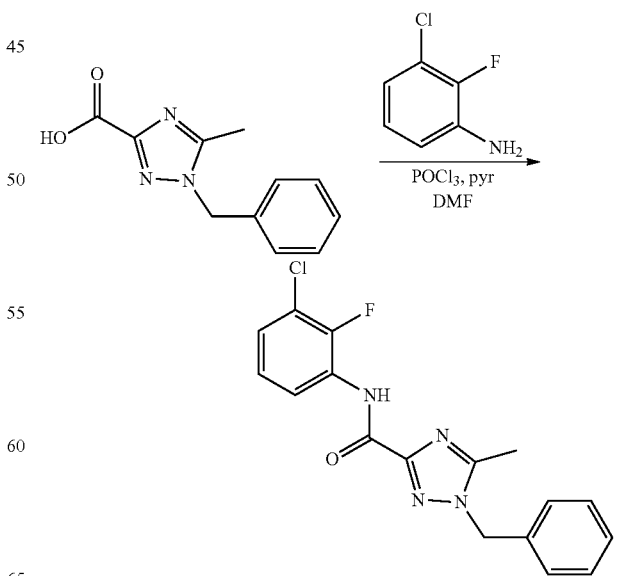

1-benzyl-N-(3-chloro-2-fluorophenyl)-5-methyl-1H-1,2,4-triazole-3-carboxamide

To a solution of the product from the previous step (60 mg, 276.21 umol, 1 eq) in THF (1 mL) was added 3-chloro-2-fluoroaniline (44.23 mg, 303.83 umol, 1.1 eq), pyridine (32.77 mg, 414.32 umol, 33.44 uL, 1.5 eq) and POCl$_3$ (50.82 mg, 331.46 umol, 30.80 uL, 1.2 eq) at 0° C., then the reaction mixture was stirred for 0.5 h. The reaction mixture was concentrated and purified by prep-HPLC (column: Phenomenex Synergi C18, 150*25*10 μm; mobile phase: [H$_2$O (0.1% TFA)-ACN]; B %: 15%-42%,10 min) and lyophilized to afford the title compound (66 mg, 191.24 umol, 69% yield) as a white solid.

MS (ES+) C$_{17}$H$_{14}$ClFN$_4$O requires: 344, found: 345 [M+H]$^+$.

$^1$H NMR (400 MHz, CDCl$_3$) δ: 9.19 (br s, 1H), 8.62-8.40 (m, 1H), 7.43-7.33 (m, 3H), 7.28-7.22 (m, 2H), 7.20-7.10 (m, 2H), 5.41 (s, 2H), 2.47 (s, 3H).

Example 14

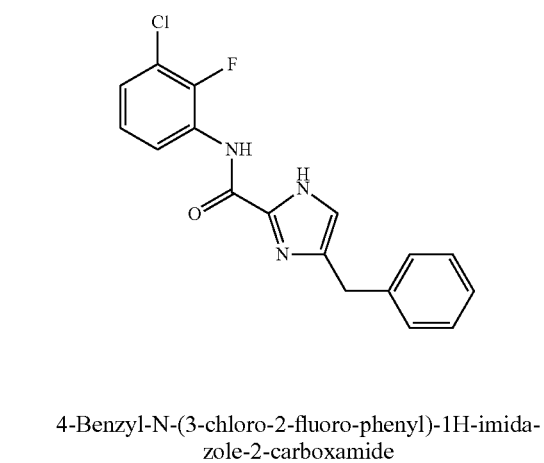

4-Benzyl-N-(3-chloro-2-fluoro-phenyl)-1H-imidazole-2-carboxamide

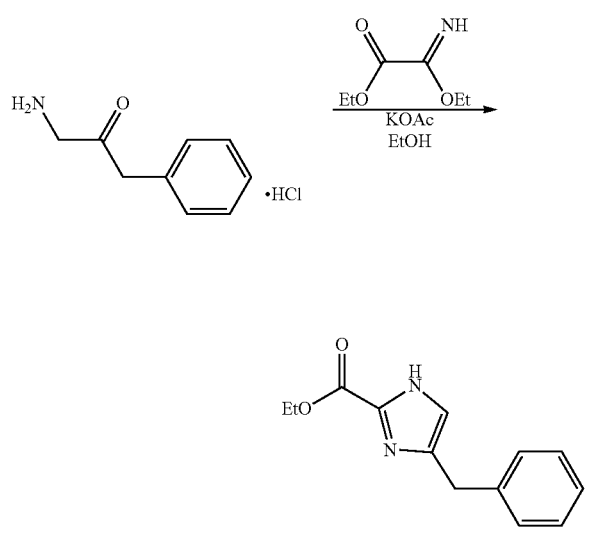

Ethyl 4-benzyl-1H-imidazole-2-carboxylate To a solution of 1-amino-3-phenyl-propan-2-one hydrochloride (400 mg, 2.15 mmol, 1 eq) in EtOH (12 mL) was added ethyl 2-ethoxy-2-imino-acetate (400 mg, 2.20 mmol, 1.02 eq) and KOAc (420 mg, 4.28 mmol, 1.99 eq) at 20° C. The mixture was stirred at 60° C. for 12 hr. The reaction mixture was filtered, and the filtrate was concentrated and purified by prep-HPLC (column: Phenomenex Gemini, 150 mm*25 mm*10 μm; mobile phase: [H$_2$O (10 mM NH$_4$HCO$_3$)-ACN]; B %: 25%-49%, 8 min, Column Temp: 30° C., to afford the title compound (160 mg, 541.99 umol, 25% yield) as a light yellow solid. MS (ES+) C$_{13}$H$_{14}$N$_2$O$_2$ requires: 230, found: 231 [M+H]$^+$.

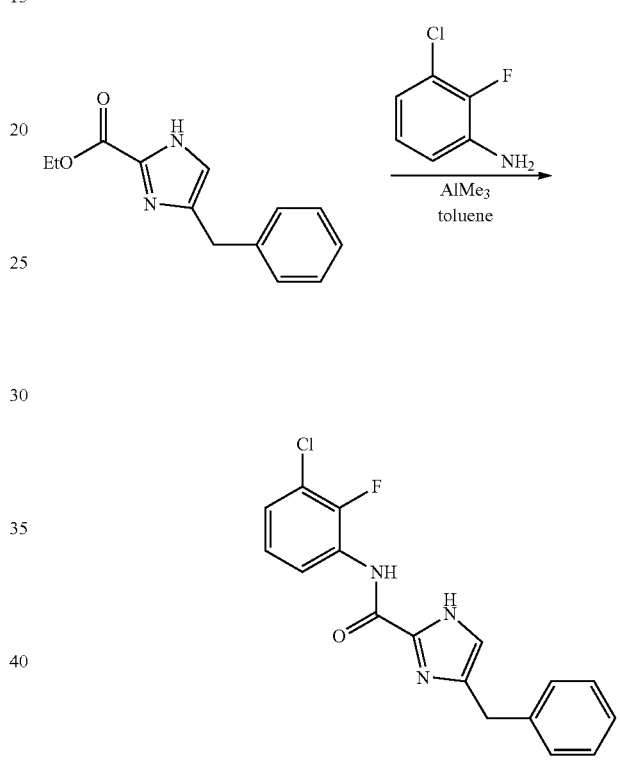

4-Benzyl-N-(3-chloro-2-fluoro-phenyl)-1H-imidazole-2-carboxamide A mixture of the product from the previous step (160 mg, 694.86 umol, 1 eq) and 3-chloro-2-fluoroaniline (300.40 mg, 2.06 mmol, 2.97 eq) in toluene (10 mL) was degassed and purged with N$_2$ for 3 times, then AlMe$_3$ (2 M in toluene, 1.0 mL, 2.88 eq) was added to the mixture dropwise at 25° C. under N$_2$ atmosphere. The mixture was then stirred at 90° C. for 12 hr under N$_2$. To the reaction mixture was added H$_2$O (10 ml) slowly at 0° C., then the mixture was extracted with EtOAc (30 ml×3). The combined organic layers were dried over anhydrous Na$_2$SO$_4$, concentrated under reduced pressure, and purified by prep-HPLC (column: Waters Xbridge, 150 mm*25 mm*5 μm; mobile phase: [H$_2$O (10 mM NH$_4$HCO$_3$)-ACN]; B %: 48%-75%,9 min, Column Temp: 30° C.), affording the title compound (120 mg, 363.91 umol, 52% yield, 100% purity) as a light yellow solid.

MS (ES+): C$_{17}$H$_{13}$ClFN$_3$O requires: 329, found: 330 [M+H]$^+$.

$^1$H NMR (400 MHz, MeOD) δ 8.04-8.15 (m, 1 H) 7.13-7.33 (m, 7 H) 6.98 (s, 1 H) 4.02 (s, 2 H).

Example 15

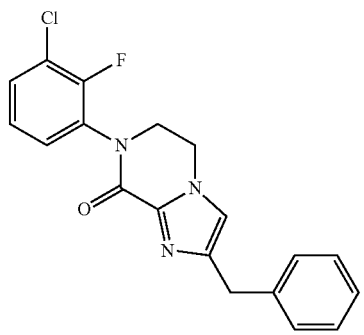 [SMILES: O=C1c2nc(Cc3ccccc3)cn2CCN1c1cccc(Cl)c1F]

2-Benzyl-7-(3-chloro-2-fluoro-phenyl)-5,6-dihydro-imidazo[1,2-a]pyrazin-8-one

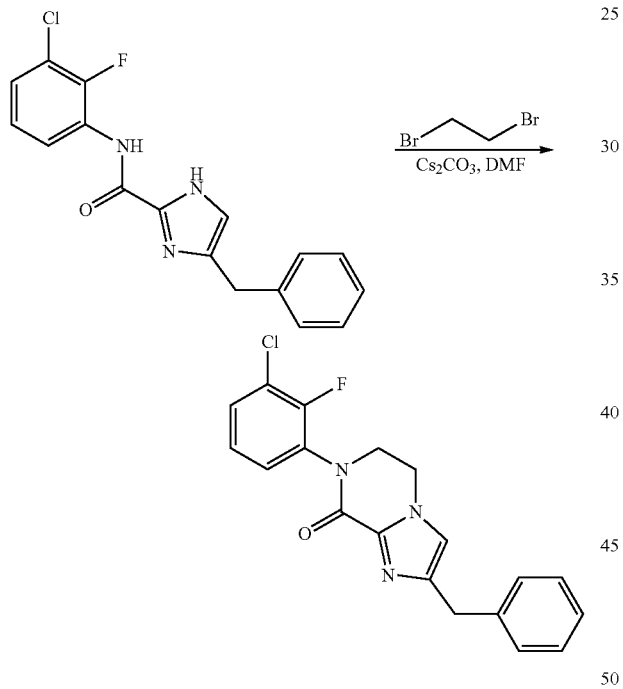

To a solution of the Example 14 compound (40 mg, 121.30 umol, 1 eq) in DMF (2 mL) was added Cs$_2$CO$_3$ (120 mg, 368.30 umol, 3.04 eq) and 1,2-dibromoethane (124.50 mg, 662.72 umol, 50 uL, 5.46 eq). The mixture was stirred at 100° C. for 4 h. The reaction mixture was filtered, and then H$_2$O (8 ml) was added to the filtrate. The mixture was extracted with EtOAc (20 ml×3), then the combined organic layers were washed with brine (20 ml×2), dried over anhydrous Na$_2$SO$_4$, concentrated under reduced pressure, and purified by prep-HPLC (column: Waters Xbridge, 150 mm*25 mm*5 μm; mobile phase: [H$_2$O (10 mM NH$_4$HCO$_3$)-ACN]; B %: 33%-53%,10 min, Column Temp: 30° C.) to afford the title compound (26.4 mg, 70.49 umol, 58% yield) as a white solid.

MS (ES+) C$_{19}$H$_{15}$ClFN$_3$O requires: 355, found: 356 [M+H]$^+$.

$^1$H NMR (400 MHz, MeOD) δ: 7.49-7.55 (m, 1 H) 7.41-7.46 (m, 1 H) 7.23-7.31 (m, 5 H) 7.16-7.23 (m, 1 H) 7.04 (s, 1 H) 4.40-4.46 (m, 2 H) 4.11-4.19 (m, 2 H) 3.97 (s, 2 H).

Example 16

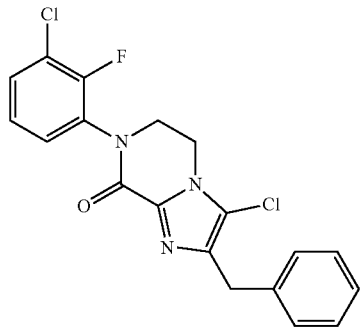 [SMILES: O=C1c2nc(Cc3ccccc3)c(Cl)n2CCN1c1cccc(Cl)c1F]

2-Benzyl-3-chloro-7-(3-chloro-2-fluoro-phenyl)-5,6-dihydroimidazo[1,2-a]pyrazin-8-one To a solution of the Example 15 compound (40 mg, 112.42 umol, 1 eq) in CH$_3$CN (4 mL) was added NCS (18 mg, 134.80 umol, 1.20 eq) at 0° C. The mixture was stirred at 50° C. for 6 hr. The reaction mixture was filtered, and the filtrate was concentrated and purified by prep-HPLC (column: Waters Xbridge, 150 mm*25 mm*5 μm; mobile phase: [H$_2$O (10 mM NH$_4$HCO$_3$)-ACN]; B %: 37%-67%, 10 min, Column Temp: 30° C.), to afford the title compound (8.0 mg, 19.48 umol, 17% yield) as a light yellow solid.

MS (ES+) C$_{19}$H$_{14}$Cl$_2$FN$_3$O requires: 389, found: 390 [M+H]$^+$.

¹H NMR (400 MHz, DMSO-d₆) δ: 7.60 (td, J=7.48, 1.52 Hz, 1 H) 7.49 (td, J=7.42, 1.52 Hz, 1 H) 7.24-7.37 (m, 5 H) 7.17-7.24 (m, 1 H) 4.29-4.40 (m, 2 H) 4.10-4.22 (m, 2 H) 3.91 (s, 2 H).

Example 17

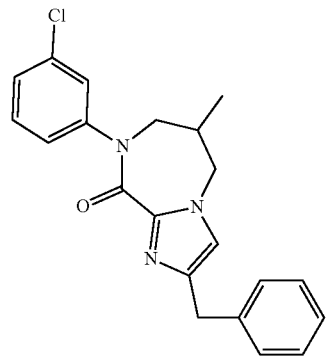 [SMILES: CC1CN(c2cccc(Cl)c2)C(=O)c2nc(Cc3ccccc3)cn2C1]

2-Benzyl-8-(3-chlorophenyl)-6-methylene-5,7-dihydroimidazo[1,2-a][1,4]diazepin-9-one

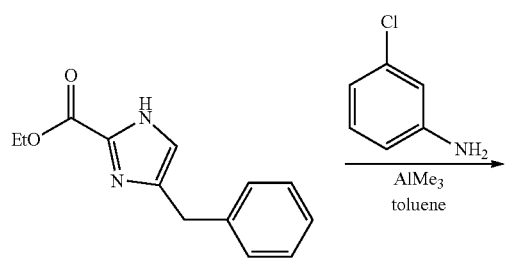

4-Benzyl-N-(3-chlorophenyl)-1H-imidazole-2-carboxamide The title compound was prepared by the method of Example 14 using 3-chloroaniline (460 mg, 1.12 mmol, 42% yield). MS (ES+) $C_{17}H_{13}ClN_3O$ requires: 311, found: 312 [M+H]⁺.

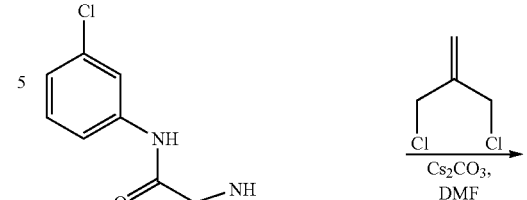

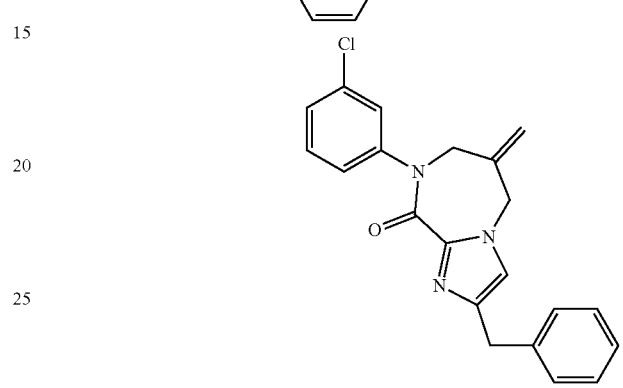

2-Benzyl-8-(3-chlorophenyl)-6-methylene-5,7-dihydroimidazo[1,2-a][1,4]-diazepin-9-one To a solution of the product from the previous step (200 mg, 641.51 umol, 1 eq) in DMF (2 mL) was added $Cs_2CO_3$ (627.05 mg, 1.92 mmol, 3 eq) and 3-chloro-2-(chloromethyl)prop-1-ene (400.93 mg, 3.21 mmol, 371.23 uL, 5 eq). The mixture was stirred at 100° C. for 18 hr. $H_2O$ (5 mL) was then added, and the mixture was extracted with EtOAc (10 mL×3). The combined organic layers were washed with brine (10 mL×2), dried over $Na_2SO_4$, concentrated under reduced pressure, and purified by prep-TLC ($SiO_2$, petroleum ether/EtOAc=3/1) to afford the title compound (70 mg, 150.07 umol, 23% yield) as a yellow solid.

LC-MS MS(ES+)$C_{21}H_{18}N_3OCl$ requires: 363, found: 364 [M+1]⁺.

¹H NMR (400 MHz, CDCl₃) δ: 7.32 (t, J=1.8 Hz, 1H), 7.27-7.22 (m, 5H), 7.28-7.22 (m, 1H), 7.19 (s, 2H), 6.47 (s, 1H), 5.06 (s, 2H), 4.75 (s, 2H), 4.21 (s, 2H), 3.94 (s, 2H).

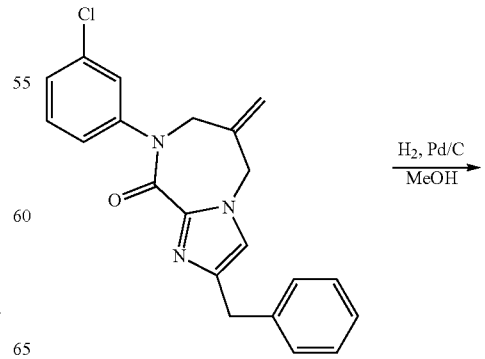

125

-continued

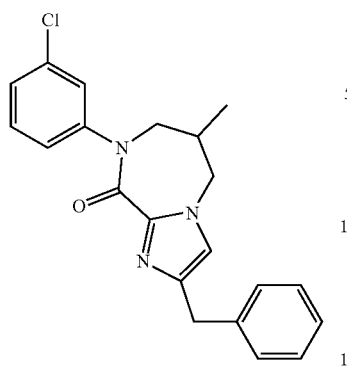

2-Benzyl-8-(3-chlorophenyl)-6-methyl-6,7-dihydro-5H-imidazo[1,2-a][1,4]-diazepin-9-one To a solution of the product from the previous step (30 mg, 82.45 umol, 1 eq) in EtOAc (2 mL) was added Pd/C (31.02 mg, 82.45 umol, 1 eq) and NH₄Cl (4.41 mg, 82.45 umol, 1 eq). The mixture was stirred at under H₂ (15 psi) 25° C. for 0.5 hr. The mixture was filtered to remove insoluble material and concentrated under reduced pressure, then purified by prep-HPLC (column: Waters Xbridge, 150 mm*25 mm*5 μm; mobile phase: [H20-ACN]; B %: 33%-63%,10 min) to afford the title compound (17.3 mg, 36.88 umol, 44% yield) as a yellow solid.

LC-MS MS(ES+)$C_{21}H_{20}N_3OCl$ requires: 365, found: 366 [M+H]⁺.

¹H NMR (400 MHz, CDCl₃) δ: 7.36-7.34 (m, 2H), 7.33-7.32 (m, 4H), 7.29-7.28 (m, 1H), 7.26-7.22 (m, 2H), 6.53 (s, 1H), 4.41-4.27 (dd, J=14, 6.4 Hz, 1H), 4.02-4.01 (m, 2H), 3.85-3.80 (dd, J=14, 4 Hz, 1H), 3.74-3.69 (dd, J=15, 5.8 Hz, 1H), 3.46-3.40 (dd, J=15.2, 8.4 Hz, 1H), 2.64-2.60 (m, 1H), 0.99 (d, J=6.4 Hz, 3H).

Example 18

4-Benzyl-5-chloro-N-(3-chloro-2-fluoro-phenyl)-1H-imidazole-2-carboxamide

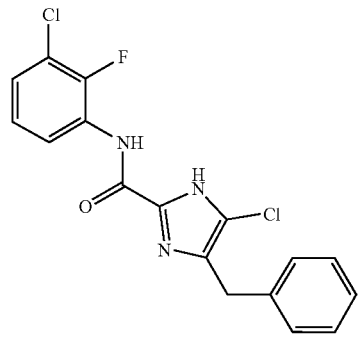 [SMILES: O=C(Nc1cccc(Cl)c1F)c1nc(Cc2ccccc2)c(Cl)[nH]1]

126

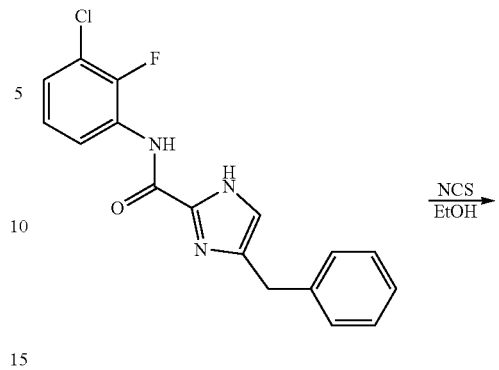

4-Benzyl-5-chloro-N-(3-chloro-2-fluoro-phenyl)-1H-imidazole-2-carboxamide

To a solution of the Example 14 compound (50 mg, 151.63 umol, 1 eq) in EtOH (3 mL) was added NCS (22.50 mg, 168.50 umol, 1.11 eq) at 25° C. The mixture was stirred at 50° C. for 6 hr. The reaction mixture was filtered, the filtrate was concentrated, and the residue was purified by prep-HPLC (column: Waters Xbridge, 150 mm*25 mm*5 μm; mobile phase: [H₂O (10 mM NH₄HCO₃)-ACN]; B %: 50%-80%, 10 min, Column Temp: 30° C.) to afford the title compound (19.7 mg, 52.47 umol, 34% yield) as a light yellow solid.

MS (ES+) $C_{17}H_{12}C_{12}FN_3O$ requires: 363, found: 364 [M+H]⁺.

¹H NMR (400 MHz, CD₃OD) δ 8.04 (m, 1 H) 7.13-7.34 (m, 7 H) 4.02 (s, 2 H).

Example 19

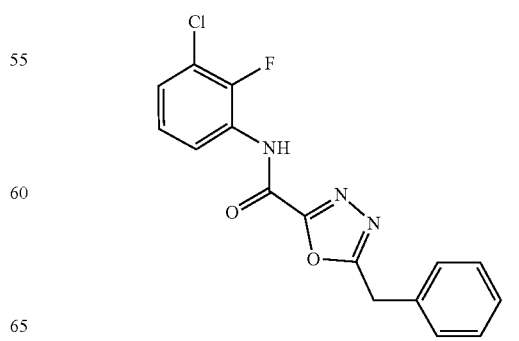

5-Benzyl-N-(3-chloro-2-fluorophenyl)-1,3,4-oxadiazole-2-carboxamide

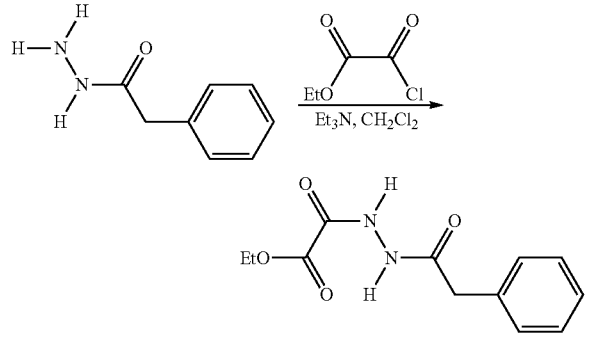

Ethyl 2-oxo-2-(2-(2-phenylacetyl)hydrazinyl)acetate To a solution of 2-phenylacetohydrazide (10 g, 66.59 mmol, 1 eq) in CH$_2$Cl$_2$ (50 mL) was added Et$_3$N (20.21 g, 199.76 mmol, 27.80 mL, 3 eq) and ethyl 2-chloro-2-oxo-acetate (8.18 g, 59.93 mmol, 6.71 mL, 0.9 eq) at −20° C. dropwise slowly. The mixture was stirred at 25° C. for 1 hr. The reaction mixture was concentrated under reduced pressure and purified by column chromatography (SiO$_2$, PE/EtOAc=10/1 to 3/1) to afford the title compound (5.92 g, 18.93 mmol, 28% yield) as a white solid. $^1$H NMR (400 MHz, CDCl$_3$) δ: 10.80 (s, 1H), 10.29 (s, 1H), 7.39-7.18 (m, 4H), 4.29-4.23 (m, 2H), 3.51 (s, 2H), 1.27 (t, J=7.1 Hz, 3H).

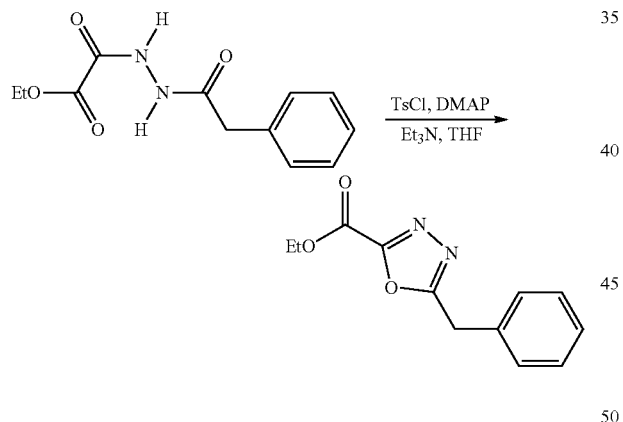

Ethyl 5-benzyl-1,3,4-oxadiazole-2-carboxylate To a solution of the product from the previous step (4.90 g, 15.66 mmol, 1.5 eq) in THF (16 mL) was added p-toluene-sulfonyl chloride (3.98 g, 20.89 mmol, 2 eq), DMAP (255.16 mg, 2.09 mmol, 0.2 eq) and Et$_3$N (2.11 g, 20.89 mmol, 2.91 mL, 2 eq), and the mixture was then stirred at reflux in an oil bath heated to 78° C. for 48 hr. H$_2$O (20 mL) was then added, and the mixture was extracted with EtOAc (25 mL×3). The combined organic layers were washed with brine (30 mL×2), dried over Na$_2$SO$_4$, concentrated under reduced pressure, and purified by column chromatography (SiO$_2$, petroleum ether/EtOAc=5/1 to 3/1) to afford the title compound (2.5 g, 10.44 mmol, 99% yield) as a yellow oil.

MS(ES+)C$_{12}$H$_{12}$N$_2$O$_3$ requires: 232, found: 233 [M+H]$^+$.

$^1$H NMR (400 MHz, CD$_3$OD) δ: 7.40-7.23 (m, 4H), 4.48-4.42 (m, 2H), 4.33 (s, 2H), 1.39 (t, J=7.1 Hz, 3H).

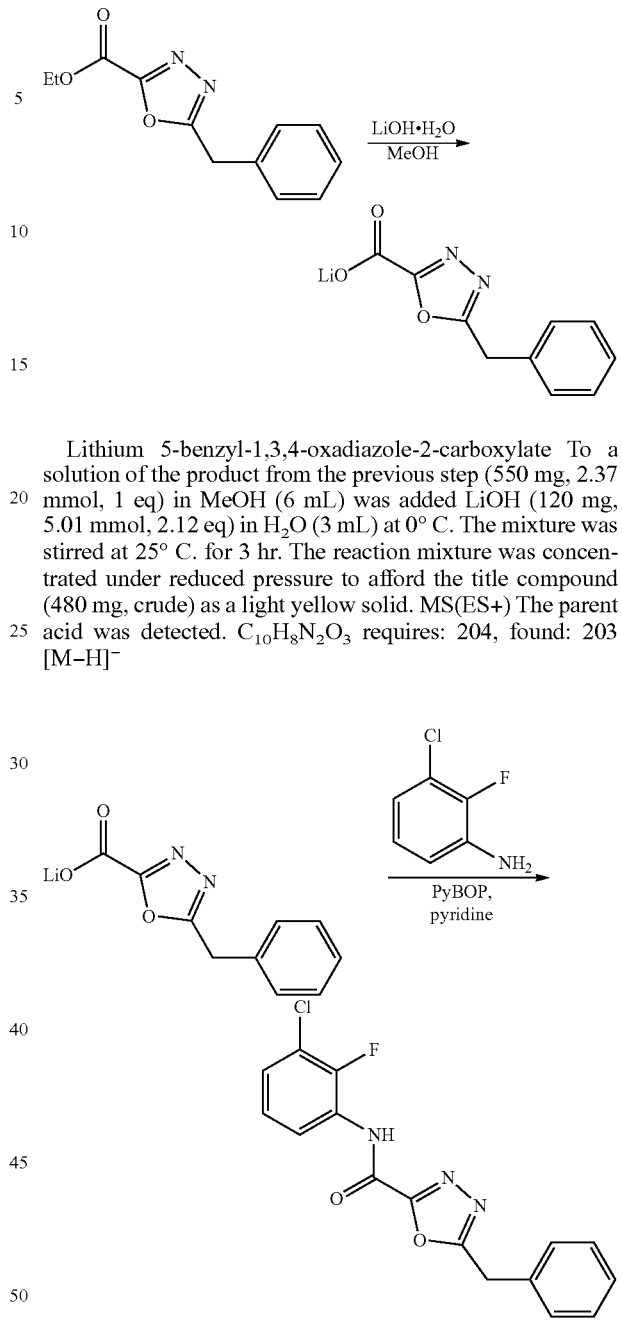

Lithium 5-benzyl-1,3,4-oxadiazole-2-carboxylate To a solution of the product from the previous step (550 mg, 2.37 mmol, 1 eq) in MeOH (6 mL) was added LiOH (120 mg, 5.01 mmol, 2.12 eq) in H$_2$O (3 mL) at 0° C. The mixture was stirred at 25° C. for 3 hr. The reaction mixture was concentrated under reduced pressure to afford the title compound (480 mg, crude) as a light yellow solid. MS(ES+) The parent acid was detected. C$_{10}$H$_8$N$_2$O$_3$ requires: 204, found: 203 [M−H]$^-$ 5-Benzyl-N-(3-chloro-2-fluorophenyl)-1,3,4-oxadiazole-2-carboxamide To a solution of the product from the previous step (70 mg, 333.15 umol, 1 eq) in pyridine (2 mL) was added 3-chloro-2-fluoroaniline (72.74 mg, 499.73 umol, 1.5 eq) and PyBOP (260.05 mg, 499.73 umol, 1.5 eq). The mixture was stirred at 20° C. for 1 hr. The residue was diluted with H$_2$O (20 mL) and extracted with EtOAc (20 mL×2). The combined organic layers were concentrated and purified by prep-HPLC (column: Phenomenex Synergi C18, 150 mm*25 mm*10 μm; mobile phase: [H$_2$O (0.1% TFA)-ACN]; B %: 46%-70%,10 min) and lyophilized to afford the title compound (3.0 mg, 8.41 umol, 2% yield) as a white solid.

MS (ES+) C$_{16}$H$_{11}$N$_3$O$_2$FCl requires: 331 and 333, found: 332 and 334 [M+H]$^+$.

¹H NMR (400 MHz, CD₃OD) δ: 7.82-7.73 (m, 1H), 7.45-7.29 (m, 6H), 7.23 (dt, J=1.6, 8.2 Hz, 1H), 4.39 (s, 2H). Examples 20-46 and 51-53 are provided in Table 1, below.

Example 47

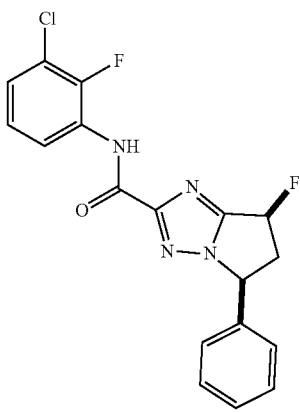 [SMILES: O=C(Nc1cccc(Cl)c1F)c1nc2n(n1)[C@H](c1ccccc1)C[C@@H]2F]

(5S,7S)—N-(3-chloro-2-fluorophenyl)-7-fluoro-5-phenyl-6,7-dihydro-5H-pyrrolo[1,2-b][1,2,4]triazole-2-carboxamide

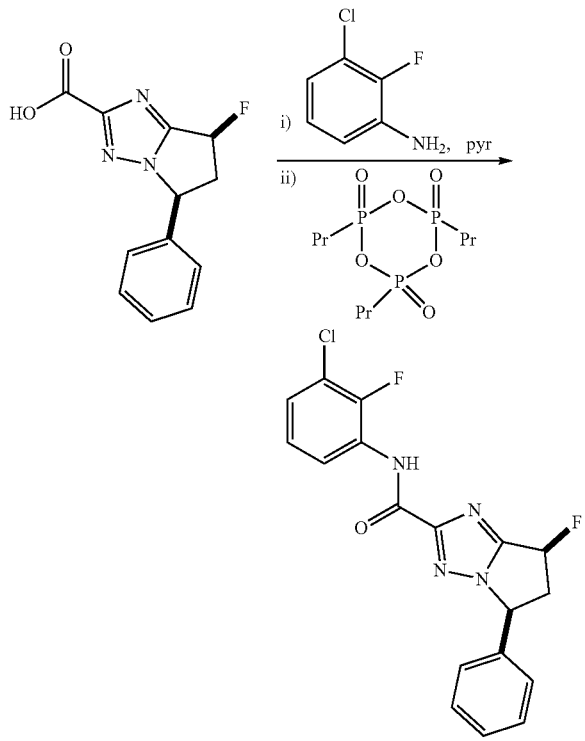

(5S,7S)—N-(3-chloro-2-fluorophenyl)-7-fluoro-5-phenyl-6,7-dihydro-5H-pyrrolo-[1,2]-[1,2,4]triazole-2-carboxamide To cooled flask containing (5S,7S)-7-fluoro-5-phenyl-6,7-dihydro-5H-pyrrolo[1,2-b][1,2,4]triazole-2-carboxylic acid (150 mg, 0.607 mmol) in THF (2.2 ml) was added 3-chloro-2-fluoroaniline (80 mg, 0.552 mmol) and pyridine (0.133 ml, 1.655 mmol). The resulting mixture was stirred at 0° C. for 5 min. To the vessel was charged 2,4,6-tripropyl-1,3,5,2,4,6-trioxatriphosphinane 2,4,6-trioxide (0.985 ml, 1.655 mmol), and the reaction was stirred at room temperature overnight. The reaction was concentrated and the residue was diluted with EtOAc, then washed with H₂O, then brine, and then the organic layer was dried, concentrated under reduced pressure, and purified via silica gel chromatography (10-90%) EtOAc in hexanes to give the title compound (150 mg, 0.400 mmol, 72% yield) as a white crystalline solid.

MS (ES+) $C_{18}H_{13}ClF_2N_4O$ requires: 374 and 376, found: 375 and 377 [M+H]⁺.

¹H NMR (600 MHz, DMSO-d₆) δ 10.44 (s, 1H), 7.66-7.55 (m, 1H), 7.52-7.35 (m, 4H), 7.35-7.17 (m, 3H), 6.36-6.17 (m, 1H), 5.80-5.68 (m, 1H), 3.86-3.66 (m, 1H), 2.74 (ddd, J=27.1, 15.1, 2.9 Hz, 1H).

Example 48

6-Benzyl-2-(2-fluorophenyl)isoindolin-1-one

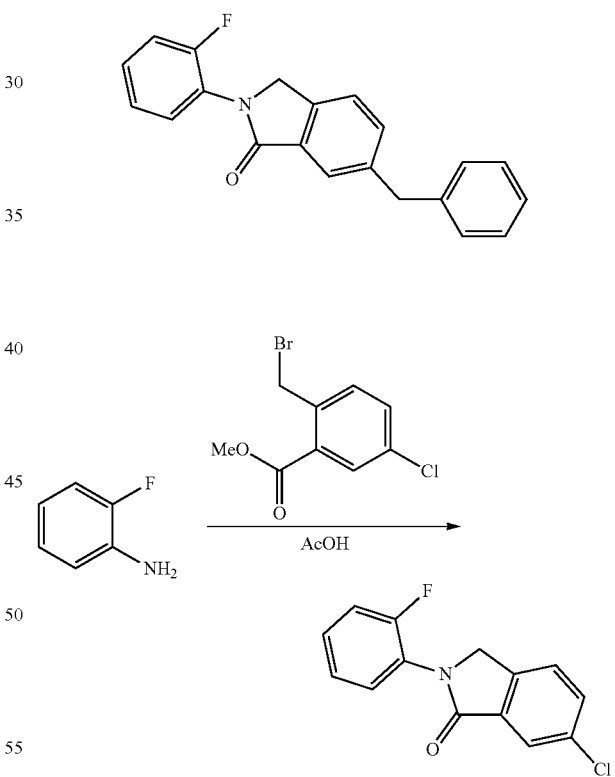

6-Chloro-2-(2-fluorophenyl)isoindolin-1-one To a solution of 2-fluoroaniline (62 mg, 0.558 mmol) in HOAc (2 ml) were added methyl 2-(bromomethyl)-5-chlorobenzoate (100 mg, 0.379 mmol) and the resulting mixture was stirred at 115° C. overnight. The reaction was concentrated, diluted in EtOAc, liquid extracted, and purified by flash chromatography to give the title compound (58 mg, 0.22 mmol, 58% yield) as an off white solid. MS (ES⁺) $C_{14}H_9ClFNO$ requires: 261, found: 262 [M+H]⁺.

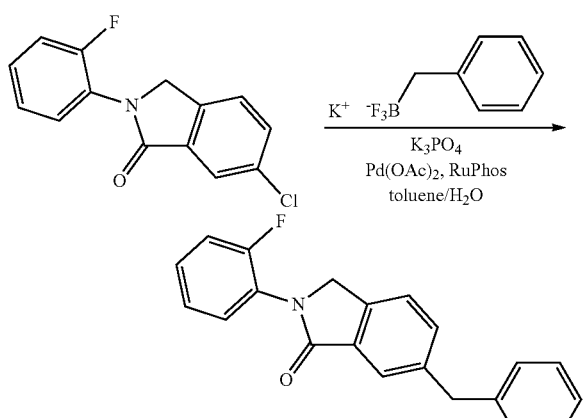

6-Benzyl-2-(2-fluorophenyl)isoindolin-1-one To a vial containing the product from the previous step (55 mg, 0.21 mmol), potassium benzyltrifluoroborate (62 mg, 0.32 mmol), and K$_3$PO$_4$ (0.13 mg, 0.63 mmol) was added toluene (0.88 ml) and H$_2$O (0.18 ml) and the mixture purged with N$_2$. To this was added Pd(OAc)$_2$ (3.5 mg, 0.016 mmol) and RuPhos (15 mg, 0.032 mmol), the vial was purged with N$_2$, sealed, and the resulting mixture was stirred at 115° C. for 1 hr. The reaction was diluted with CH$_2$Cl$_2$ and filtered. The filtrate was concentrated and purified by flash chromatography (0 to 30% EtOAc in hexanes) to give the title compound (5.3 mg, 0.017 mmol, 7% yield) as a white solid.

MS (ES$^+$) C$_{21}$H$_{16}$FNO requires: 317, found: 318 [M+H]$^+$.

$^1$H NMR (600 MHz, CDCl$_3$) δ ppm 7.78-7.83 (m, 1 H), 7.58-7.65 (m, 1 H), 7.40-7.47 (m, 2 H), 7.27-7.32 (m, 3 H), 7.18-7.25 (m, 5 H), 4.78-4.85 (m, 2 H), 4.06-4.12 (m, 2 H).

Example 49

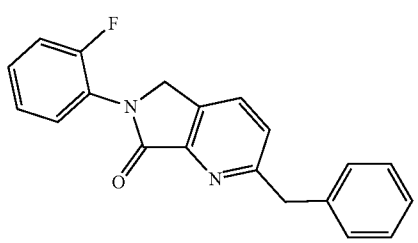 [SMILES: O=C1c2nc(Cc3ccccc3)ccc2CN1c1ccccc1F]

2-Benzyl-6-(2-fluorophenyl)-5,6-dihydro-7H-pyrrolo[3,4-b]pyridin-7-one

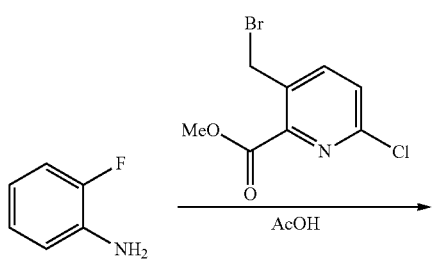

2-Chloro-6-(2-fluorophenyl)-5,6-dihydro-7H-pyrrolo[3,4-b]pyridin-7-one To a solution of methyl 3-(bromomethyl)-6-chloropicolinate (30 mg, 0.11 mmol) in HOAc (0.38 ml) was added 2-fluoroaniline (15 mg, 0.14 mmol), and the resulting mixture was stirred at 120° C. for 12 h. The reaction was diluted with MeOH and concentrated. The crude product (dark blue) was taken to the next step. MS (ES$^+$) C$_{13}$H$_8$ClFN$_2$O requires: 262, found: 263 [M+H]$^+$.

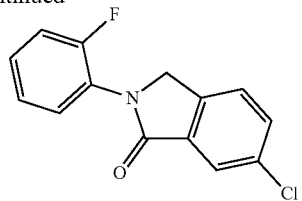

2-Benzyl-6-(2-fluorophenyl)-5,6-dihydro-7H-pyrrolo[3,4-b]pyridin-7-one To a vial containing the product from the previous step (29 mg, 0.11 mmol), potassium benzyltrifluoroborate (34 mg, 0.17 mmol), and K$_3$PO$_4$ (72 mg, 0.34 mmol) was added toluene (0.47 ml) and H$_2$O (95 µl) and the mixture was purged with N$_2$. To this was added Pd(OAc)$_2$ (1.9 mg, 8.5 µmol) and RuPhos (7.9 mg, 0.017 mmol), the vial purged with N$_2$, sealed, and the resulting mixture was stirred at 115° C. overnight. The reaction was diluted with saturated NH$_4$Cl and EtOAc, and the phases were separated. The aqueous layer was extracted with EtOAc. The organic layers were combined, washed with saturated NaCl, dried over MgSO$_4$, concentrated under reduced pressure, and purified by flash chromatography to give the title compound (3.8 mg, 0.012 mmol, 10% yield) as a white solid.

MS (ES$^+$) C$_{20}$H$_{15}$FN$_2$O requires: 318, found: 319 [M+H]$^+$.

$^1$H NMR (DMSO-d$_6$) δ: 8.03-8.09 (m, 1H), 7.63-7.70 (m, 1H), 7.55-7.60 (m, 1H), 7.36-7.48 (m, 2H), 7.26-7.35 (m, 5H), 7.16-7.25 (m, 1H), 4.83-5.02 (m, 2H), 4.12-4.35 (m, 2H).

Example 50

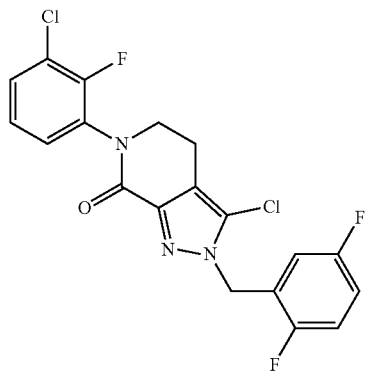 [SMILES: O=C1c2nn(Cc3cc(F)ccc3F)c(Cl)c2CCN1c1cccc(Cl)c1F]

3-Chloro-6-(3-chloro-2-fluorophenyl)-2-(2,5-difluorobenzyl)-5,6-dihydro-2H-pyrazolo[3,4-c]pyridin-7(4H)-one

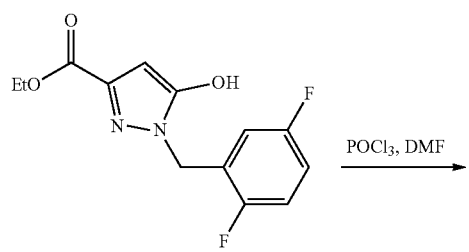

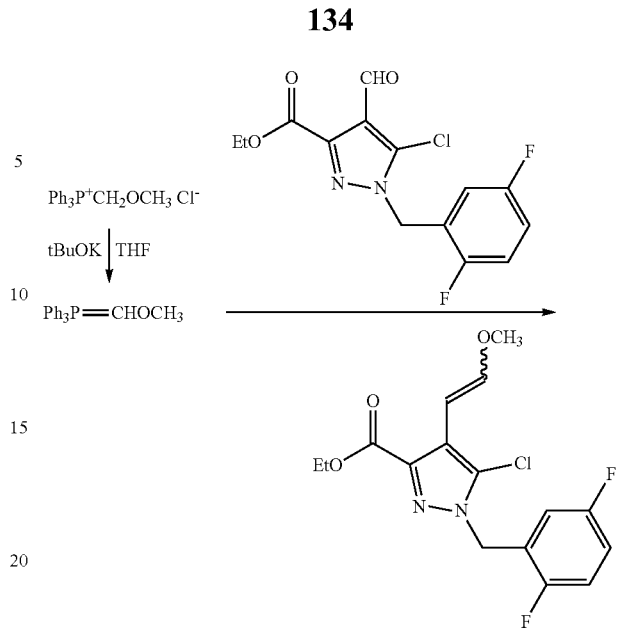

Ethyl 5-chloro-1-(2,5-difluorobenzyl)-4-(2-methoxyvinyl)-1H-pyrazole-3-carboxylate To a solution of t-BuOK (7.94 g, 70.73 mmol, 1.5 eq) in THF (150 mL) was added methoxymethyl(triphenyl) phosphonium chloride (24.25 g, 70.73 mmol, 1.5 eq) at 0° C. The mixture was stirred at 0° C. for 15 min. To the mixture was added the product from the previous step (15.5 g, 47.16 mmol, 1 eq), and the mixture was stirred at 15° C. for 16 hr. The mixture was concentrated and then purified by column chromatography on silica gel (eluent petroleum ether/EtOAc=5:1) to afford the title compound (11 g, 30.83 mmol, 65% yield) as a white solid. $^1$H NMR showed it is a mixture of Z & E geometrical isomers.

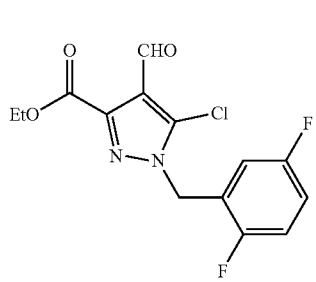

Ethyl 5-chloro-1-(2,5-difluorobenzyl)-4-formyl-1H-pyrazole-3-carboxylate

To a solution of Intermediate B (12.00 g, 42.52 mmol, 1 eq) in DMF (12.43 g, 170.07 mmol, 13.09 mL, 4 eq) was slowly added POCl$_3$ (52.15 g, 340.13 mmol, 31.61 mL, 8 eq). The mixture was stirred at 90° C. for 7 hr. The mixture was concentrated under reduced pressure, and the residue was diluted with H$_2$O (200 mL, 40° C.). The mixture was extracted with EtOAc (200 mL×2), washed with H$_2$O (50 mL), dried over Na$_2$SO$_4$, concentrated under reduced pressure, and purified by column chromatography on silica gel (eluent petroleum ether/EtOAc=10:1) to afford the title compound (9 g, 26.83 mmol, 63% yield) as a yellow solid. $^1$H NMR (400 MHz, CD$_3$OD) δ: 10.34 (s, 1H), 7.21-7.17 (m, 2H), 7.16-7.06 (m, 1H) 5.56 (s, 2H), 4.47-4.42 (q, J=6.8 Hz, 2H), 1.43-1.39 (t, J=6.8 Hz, 3H).

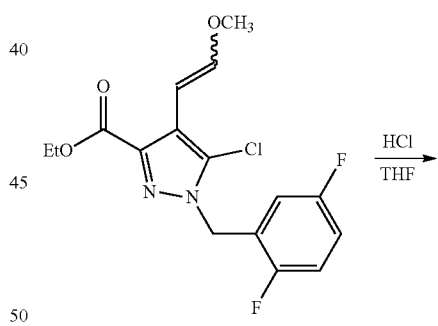

Ethyl 5-chloro-1-(2, 5-difluorobenzyl)-4-(2-oxoethyl)-1H-pyrazole-3-carboxylate

To a solution of the product from the previous step (4 g, 11.21 mmol, 1 eq) in THF (143 mL) was added aqueous HCl (6 M, 214.90 mL, 115 eq). The mixture was stirred at 15° C. for 0.2 h. The mixture was concentrated, and then diluted with H₂O (50 mL) and extracted with EtOAc (50 mL×2). The combined organic layers were washed with H₂O (30 mL), dried over Na₂SO₄, and concentrated under reduced pressure to afford the title compound (4.5 g, crude) as a yellow oil.

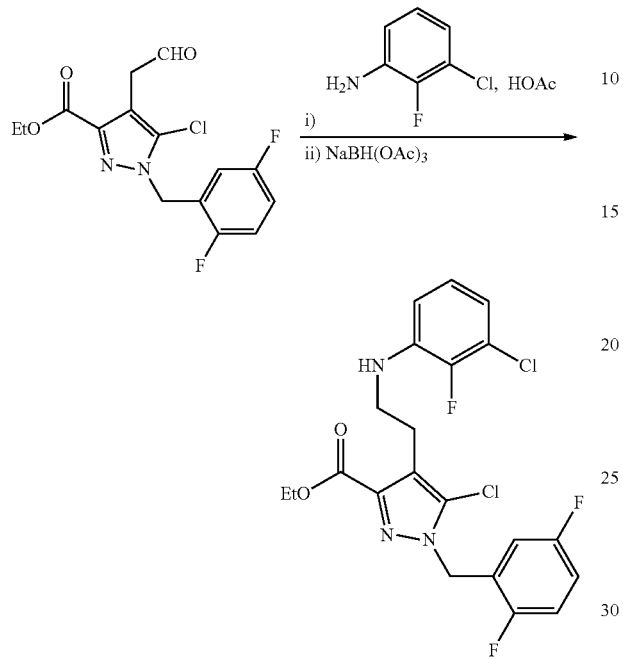

Ethyl 5-chloro-4-(2-((3-chloro-2-fluorophenyl)amino)ethyl)-1-(2,5-difluorobenzyl)-1H-pyrazole-3-carboxylate To a solution of the product from the previous step (4.5 g, 13.13 mmol, 1 eq) in THF (40 mL) and CH₂Cl₂ (40 mL) was added HOAc (788.46 mg, 13.13 mmol, 750.92 uL, 1 eq) and 3-chloro-2-fluoroaniline (3.25 g, 22.32 mmol, 1.7 eq). The mixture was stirred at 15° C. for 10 min. To the mixture was then added NaBH(OAc)₃ (10.57 g, 49.89 mmol, 3.8 eq), and the mixture was stirred at 15° C. for 16 hr. The mixture was concentrated and diluted with H₂O (20 mL) and extracted with EtOAc (20 mL×2). The combined organic layers were washed with H₂O (10 mL), dried over Na₂SO₄, concentrated under reduced pressure, and purified by column chromatography on silica gel (eluent petroleum ether/EtOAc=5:1) to afford the title compound (5 g, 4.55 mmol, 34% yield) as a yellow oil. MS (ES⁺) C₂₁H₁₈C₁₂F₃N₃O₂ requires: 471, found: 472 [M+H]⁺.

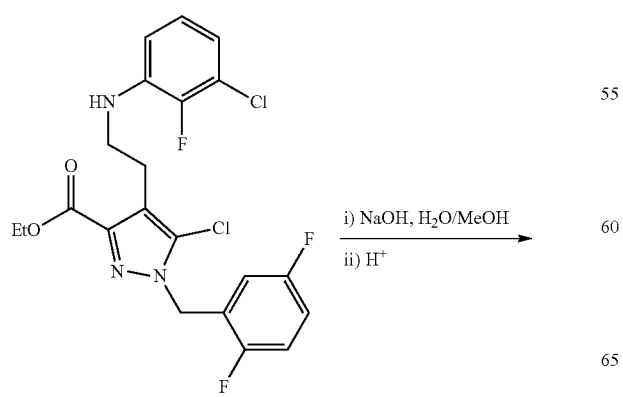

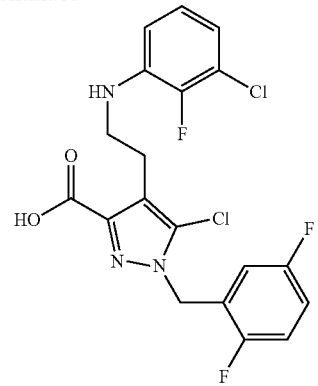

5-Chloro-4-(2-((3-chloro-2-fluorophenyl)amino)ethyl)-1-(2,5-difluorobenzyl)-1H-pyrazole-3-carboxylic acid To a solution of the product from the previous step (5 g, 4.55 mmol, 1 eq) in H₂O (20 mL) and MeOH (20 mL) was added NaOH (1.27 g, 31.75 mmol, 6.97 eq). The mixture was stirred at 60° C. for 3 hr. The mixture was diluted with H₂O (20 mL), acidified by addition of 1N HCl, and then extracted with EtOAc (20 mL×2), washed with H₂O (10 mL), dried over Na₂SO₄, and concentrated under reduced pressure. The residue was purified by column chromatography on silica gel (eluent EtOAc/MeOH=10:1) to afford the title compound (2 g, 4.23 mmol, 93% yield) as a yellow solid.

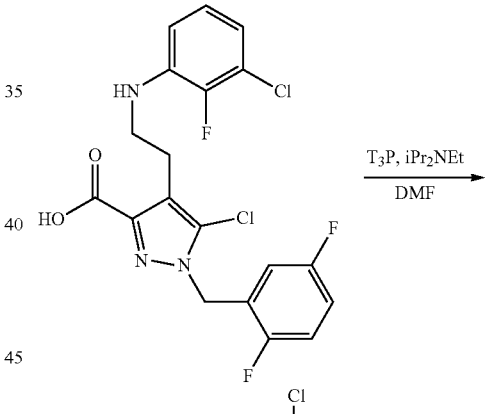

3-Chloro-6-(3-chloro-2-fluorophenyl)-2-(2,5-difluorobenzyl)-5,6-dihydro-2H-pyrazolo[3,4-c]pyridin-7(4H)-one To a solution of the product from the previous step (2 g, 4.50 mmol, 1 eq) in DMF (20 mL) was added DIPEA (1.75 g, 13.51 mmol, 2.35 mL, 3 eq) and T₃P (4.30 g, 6.75 mmol, 4.02 mL, 50 wt %, 1.5 eq). The mixture was stirred at 15°

C. for 16 hr. The mixture was diluted with H₂O (50 mL) and extracted with EtOAc (50 mL×2), washed with H₂O (20 mL), dried over Na₂SO₄, concentrated under reduced pressure, and purified by column chromatography on silica gel (eluent petroleum ether/EtOAc=3:2) to afford the title compound (606.4 mg, 1.42 mmol, 31% yield) as a white solid.

MS (ES⁺) $C_{19}H_{12}N_3OCl_2F_3$ requires: 425, found: 426, [M+H]⁺.

¹H NMR (400 MHz, CD₃OD) δ: 7.50 (td, J=7.4 Hz, 1.6 Hz, 1H), 7.41 (td, J=7.4 Hz, 1.6 Hz, 1H), 7.31-7.08 (m, 3H), 6.97 (m, 1H), 5.55 (s, 2H), 4.02 (t, J=6.4 Hz, 2H), 3.00 (t, J=6.6 Hz, 2H).

Example 54

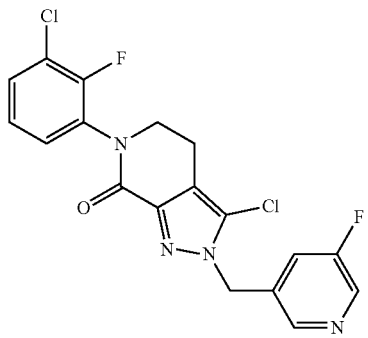 [SMILES: O=C1c2nn(Cc3cncc(F)c3)c(Cl)c2CCN1c1cccc(Cl)c1F]

3-Chloro-6-(3-chloro-2-fluorophenyl)-2-((5-fluoropyridin-3-yl)methyl)-5,6-dihydro-2H-pyrazolo[3,4-c]pyridin-7(4H)-one

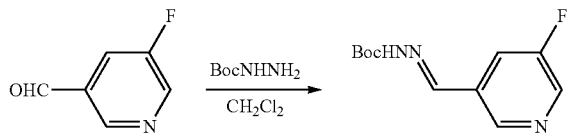

tert-Butyl 2-((5-fluoropyridin-3-yl)methylene)hydrazinecarboxylate To a solution of tert-butyl hydrazinecarboxylate (16 g, 121.06 mmol, 1.06 eq) in DCM (140 mL) was added 5-fluoronicotinaldehyde (14.3 g, 114.31 mmol, 1 eq), and the mixture was stirred at 25° C. for 14 h. The mixture was concentrated under reduced pressure to afford the title compound (30 g, crude) as a white solid. ¹H NMR (400 MHz, DMSO) 11.21 (s, 1H), 8.64 (m, 1H), 8.56 (m, 1H), 8.06 (m, 1H), 7.91-7.79 (m, 1H), 1.47 (s, 9H).

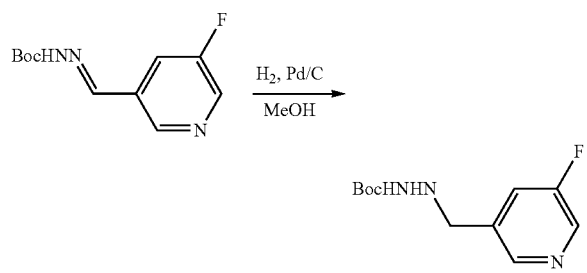

tert-Butyl 2-((5-fluoropyridin-3-yl)methyl)hydrazinecarboxylate To a solution of the product from the previous step (30 g, 125.39 mmol, 1 eq) in MeOH (200 mL) under N₂ was added Pd/C (10 g, 10% w/w). The N₂ atmosphere was replaced with H₂ and the mixture was stirred at 25° C. under H₂ (45 Psi) for 4 h. The H₂ was purged and the mixture was filtered. The filtrate was concentrated under reduced pressure to afford the title compound (30 g, 118.13 mmol, 94% yield) as a yellow oil.

MS (ES⁺) $C_{11}H_{16}N_3FO_2$ requires: 241, found: 242 [M+H]⁺.

¹H NMR (400 MHz, DMSO-d₆) δ: 8.47-8.42 (m, 1H), 8.37 (m, 1H), 7.72-7.61 (m, 1H), 3.94 (s, 2H), 1.36 (s, 9H).

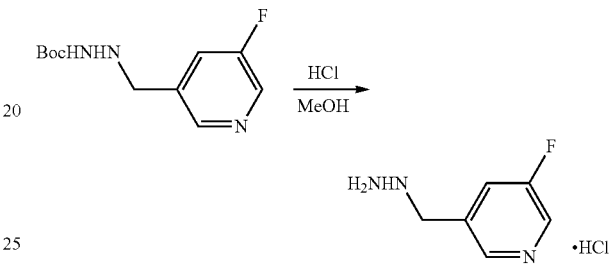

3-Fluoro-5-(hydrazinylmethyl)pyridine To a solution of the product from the previous step (30 g, 124.35 mmol, 1 eq) in MeOH (200 mL) was added HCl/MeOH (4 M, 250 mL) at 0° C. The mixture was stirred at 25° C. for 14 h. The mixture was concentrated under reduced pressure to afford the title compound (26 g, crude, HCl salt) as a yellow solid. MS (ES⁺) $C_6H_8FN_3$ requires: 141, found: 142 [M+H]⁺.

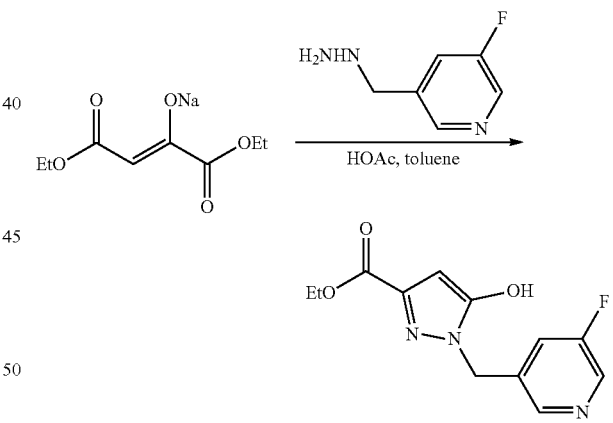

Ethyl 1-((5-fluoropyridin-3-yl)methyl)-5-hydroxy-1H-pyrazole-3-carboxylate

To a solution of the product from the previous step (15 g, 70.07 mmol, 1 eq, 2 HCl) in toluene (150 mL) was added sodium (Z)-1,4-diethoxy-1,4-dioxobut-2-en-2-olate (14.73 g, 70.09 mmol, 1 eq) and HOAc (126.22 g, 2.10 mol, 120.21 mL, 30 eq). The mixture was stirred at 110° C. for 14 h. The mixture was concentrated under reduced pressure, then diluted with H₂O (200 mL) and adjusted to pH=7 with NaOH (solid) at 0° C. The mixture was extracted with EtOAc (100 mL×2), and the combined organic layers were washed with H₂O (100 mL), dried over Na₂SO₄, and concentrated under reduced pressure. The residue was diluted with petroleum ether/EtOAc=5/1 (100 mL) and the mixture was stirred for 30 min. The mixture was then filtered, and the filter cake was washed with petroleum ether: EtOAc=5/1 (50 mL). The filter cake was collected and dried under reduced pressure to afford the title compound (7.65 g, 27.98 mmol, 40% yield) as a yellow solid.

MS (ES$^+$) $C_{12}H_{12}FN_3O_3$ requires: 265, found: 266 [M+H]$^+$.

$^1$H NMR (400 MHz, DMSO-d$_6$) δ: 11.80 (m, 1H), 8.53 (d, J=2.8 Hz, 1H), 8.32 (m, 1H), 7.51 (m, 1H), 5.80 (s, 1H), 5.28 (s, 2H), 4.22 (q, J=7.2 Hz, 2H), 1.25 (t, J=7.2 Hz, 3H).

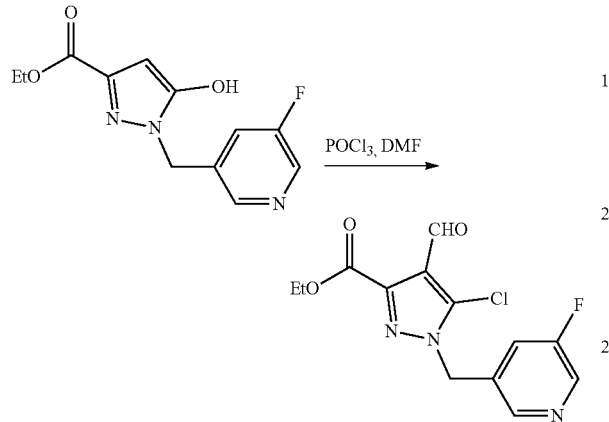

Ethyl 5-chloro-1-((5-fluoropyridin-3-yl)methyl)-4-formyl-1H-pyrazole-3-carboxylate To a solution of the product from the previous step (7.65 g, 28.84 mmol, 1 eq) in DMF (8.46 g, 115.67 mmol, 8.9 mL, 4.01 eq) was slowly added POCl$_3$ (35.47 g, 231.36 mmol, 21.5 mL, 8.02 eq) at 0° C. The mixture was stirred at 90° C. for 14 h. The mixture was quenched with H$_2$O (500 mL, 40° C.) and stirred for 30 min. The mixture was adjusted to pH=7 with NaOH (solid) at 0° C. The mixture was extracted with EtOAc (200 mL×3), and the combined organic layers were washed with H$_2$O (100 mL), dried over Na$_2$SO$_4$, and concentrated under reduced pressure to afford the title compound (7.4 g, 23.03 mmol, 80% yield) as a yellow solid. MS (ES$^+$) $C_{13}H_{11}ClFN_3O_3$ requires: 311, found: 312 [M+H]$^+$.

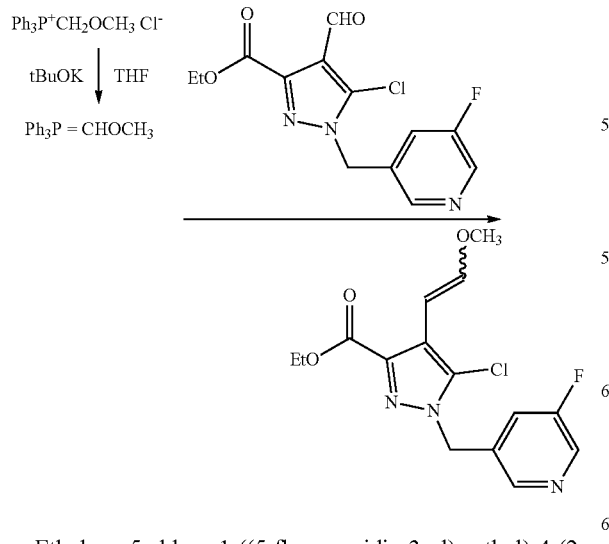

Ethyl 5-chloro-1-((5-fluoropyridin-3-yl)methyl)-4-(2-methoxyvinyl)-1H-pyrazole-3-carboxylate To a solution of t-BuOK (1 M, 24.00 mL, 1.5 eq) in THF (40 mL) was added methoxymethyl(triphenyl) phosphonium chloride (8.30 g, 24.21 mmol, 1.51 eq) at 0° C. The mixture was stirred at 0° C. for 15 min. To the mixture was added a solution of the product from the previous step (5 g, 16.04 mmol, 1 eq) in THF (35 mL), and the mixture was stirred at 25° C. for 14 h. The mixture was concentrated under reduced pressure and then purified by flash silica gel chromatography (ISCO®; 40 g SepaFlash® Silica Flash Column, Eluent of 10~40% EtOAc/petroleum ether gradient @ 50 mL/min) to afford the title compound (3.1 g, 9.12 mmol, 57% yield) as a yellow oil. MS (ES$^+$) $C_{15}H_{15}ClFN_3O_3$ requires: 339, found: 340 [M+H]$^+$.

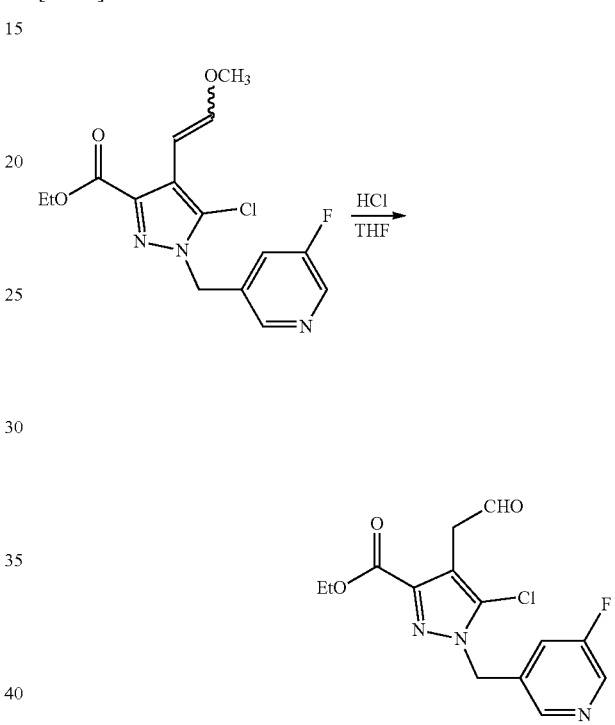

Ethyl 5-chloro-1-((5-fluoropyridin-3-yl)methyl)-4-(2-oxoethyl)-1H-pyrazole-3-carboxylate To a solution of the product from the previous step (3.1 g, 9.12 mmol, 1 eq) in THF (31 mL) was added HCl (6 M, 174.88 mL, 115 eq) at 0° C. The mixture was stirred at 0° C. for 10 min. The mixture was adjusted the pH=7 with NaOH (sat.aq). The mixture was extracted with EtOAc (50 mL×3), and the combined organic layers were washed with H$_2$O (50 mL), dried over Na$_2$SO$_4$, concentrated under reduced pressure, and purified by column chromatography (SiO$_2$, petroleum ether: EtOAc=5/1 to 2/1) to afford the title compound (2.3 g) as a yellow oil. MS (ES$^+$) $C_{14}H_{13}ClFN_3O_3$ requires: 325, found: 326 [M+H]$^+$.

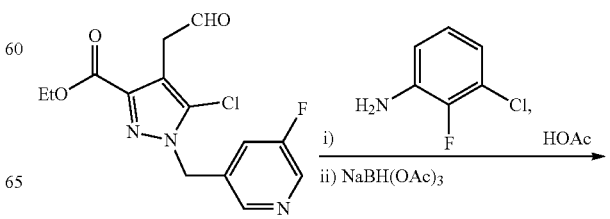

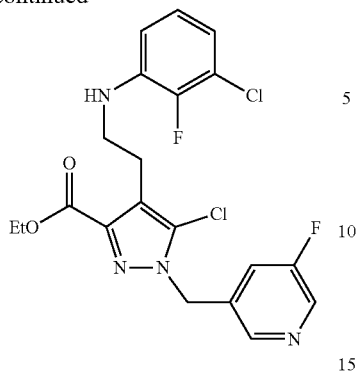

Ethyl 5-chloro-4-(2-((3-chloro-2-fluorophenyl)amino)ethyl)-1-((5-fluoropyridin-3-yl) methyl)-1H-pyrazole-3-carboxylate To a solution of the product from the previous step (2.3 g, 7.06 mmol, 1 eq) and 3-chloro-2-fluoroaniline (1.23 g, 8.48 mmol, 1.2 eq) in CH$_2$Cl$_2$ (40 mL) was added HOAc (294.00 mg, 4.90 mmol, 280 uL, 0.69 eq) at 0° C. and the mixture was stirred at 0° C. for 15 min. NaBH(OAc)$_3$ (7.18 g, 33.89 mmol, 4.8 eq) was added and the mixture was stirred at 25° C. for 14 h. The mixture was quenched with H$_2$O (30 mL) and stirred for 30 min. The mixture was extracted with DCM (30 mL×3), washed with H$_2$O (20 mL), dried over Na$_2$SO$_4$, concentrated under reduced pressure, and purified by flash silica gel chromatography (ISCO®; 45 g SepaFlash® Silica Flash Column, Eluent of 0-100% EtOAc/petroleum ether gradient @ 50 mL/min) to afford the title compound (580 mg, 1.22 mmol, 17% yield) as a yellow oil. MS (ES$^+$) C$_{20}$H$_{18}$Cl$_2$F$_2$N$_4$O$_2$ requires: 454, found: 455 [M+H]$^+$.

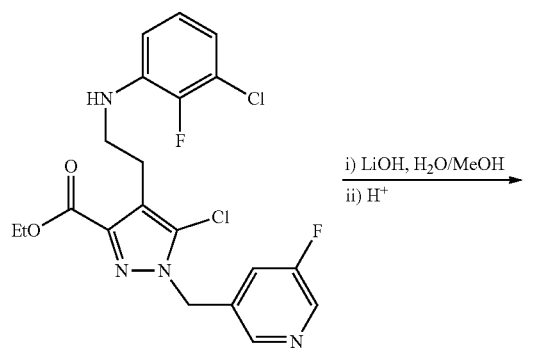

5-Chloro-4-(2-((3-chloro-2-fluorophenyl)amino)ethyl)-1-((5-fluoropyridin-3-yl)methyl)-1H-pyrazole-3-carboxylic acid To a solution of the product from the previous step (580 mg, 1.27 mmol, 1 eq) in MeOH (10 mL) was added a solution of LiOH·H$_2$O (134 mg, 3.19 mmol, 2.51 eq) in H$_2$O (2.5 mL) at 0° C. The mixture was stirred at 60° C. for 1.5 h. The mixture was concentrated under reduced pressure and then diluted with H$_2$O (10 mL) and adjusted to pH=4 with 1 N HCl. The mixture was extracted with EtOAc (10 mL×3), washed with H$_2$O (20 mL), dried over Na$_2$SO$_4$, and concentrated under reduced pressure to afford the title compound (550 mg, 1.20 mmol, 94% yield) as a yellow oil. MS (ES$^+$) C$_{18}$H$_{14}$Cl$_2$F$_2$N$_4$O$_2$ requires: 426, found: 427 [M+H]$^+$.

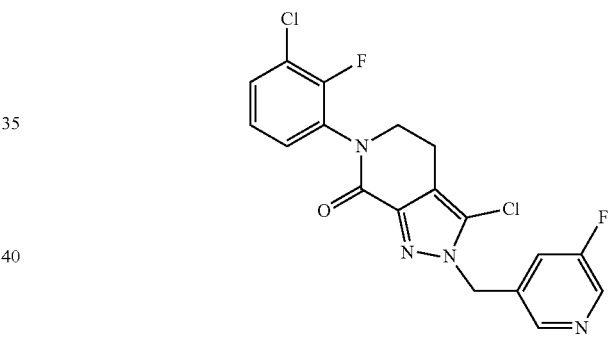

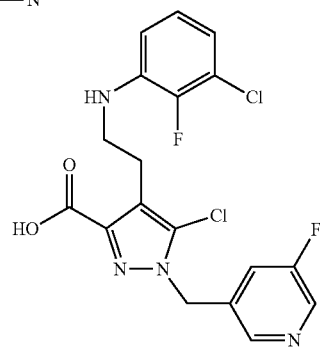

3-Chloro-6-(3-chloro-2-fluorophenyl)-2-((5-fluoropyridin-3-yl)methyl)-5,6-dihydro-2H-pyrazolo[3,4-c]pyridin-7(4H)-one To a solution of the product from the previous step (550 mg, 1.29 mmol, 1 eq) in DMF (10 mL) was added DIPEA (519.40 mg, 4.02 mmol, 0.7 mL, 3.12 eq) and T$_3$P (1.23 g, 1.93 mmol, 1.15 mL of a 50% solution in EtOAc, 1.5 eq) at 0° C. The mixture was stirred at 25° C. for 14 h. The mixture was diluted with H$_2$O (10 mL) and adjusted to pH=6 with 1 N HCl. The mixture was extracted with EtOAc (10 mL×3), and the combined organic extracts were washed with H$_2$O (10 mL), dried over Na$_2$SO$_4$, and concentrated under reduced pressure. The residue was purified by column chromatography (SiO$_2$, petroleum ether/EtOAc=10/1 to 2/1) to afford the title compound (250.3 mg, 605.54 umol, 47% yield) as a white solid.

MS (ES$^+$) C$_{18}$H$_{12}$Cl$_2$F$_2$N$_4$O requires: 408, found: 409 [M+H]$^+$.

$^1$H NMR (400 MHz, DMSO-d$_6$) δ: 8.58 (d, J=2.8 Hz, 1H), 8.41 (m, 1H), 7.63 (m, 1H), 7.58 (m, 1H), 7.47 (m, 1H), 7.31 (dt, J=1.2, 8.0 Hz, 1H), 5.61 (s, 2H), 3.96 (t, J=6.4 Hz, 2H), 2.89 (t, J=6.4 Hz, 2H).

Example 55

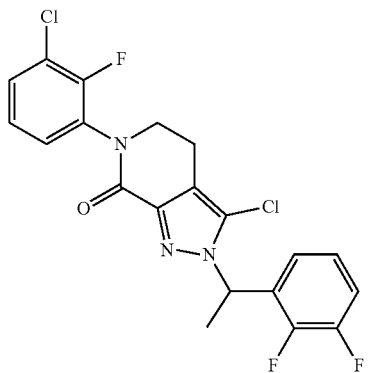

3-chloro-6-(3-chloro-2-fluorophenyl)-2-(1-(2,3-difluorophenyl)ethyl)-2,4,5,6-tetrahydro-7H-pyrazolo[3,4-c]pyridin-7-one

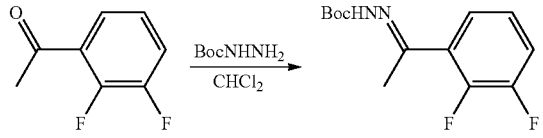

tert-Butyl (Z)-2-(1-(2,3-difluorophenypethylidene)hydrazine-1-carboxylate

To a solution of 1-(2,3-difluorophenyl)ethanone (10 g, 64.05 mmol, 1 eq) in DCM (100 mL) was added tert-butyl hydrazinecarboxylate (8.46 g, 64.05 mmol, 1 eq) and AcOH (3.85 g, 64.05 mmol, 3.66 mL, 1 eq). The mixture was stirred at 40° C. for 18 hr. The mixture was diluted with DCM (50 mL), washed with brine (50 mL×3), dried over Na$_2$SO$_4$, and concentrated under reduced pressure to afford the title compound (17.55 g, 55.19 mmol, 86% yield) as a white solid.

MS(ES+)C$_{13}$H$_{16}$N$_2$O$_2$F$_2$ requires: 270, found 271 [M+H]$^+$.

$^1$H NMR (400 MHz, CDCl$_3$) δ=7.81 (s, 1H), 7.42-7.33 (m, 1H), 7.10-7.04 (m, 1H), 7.02-6.95 (m, 1H), 2.15 (d, J=2.9 Hz, 3H), 1.47 (s, 9H).

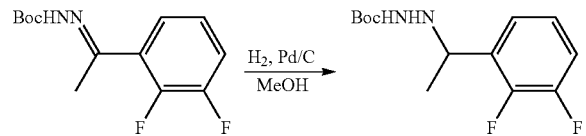

tert-Butyl N-[(E)-1-(2,3-difluorophenyl)ethylideneamino]carbamate To a solution of the product from the previous step (15.55 g, 57.53 mmol, 1 eq) in MeOH (100 mL) was added Pd/C (1 g, 10% w/w) under N$_2$. The suspension was degassed under reduced pressure and purged with H$_2$ several times. The mixture was stirred under H$_2$ (50 psi) at 40° C. for 16 hr. The mixture was then purged with N$_2$ and concentrated under reduced pressure to afford the title compound (12.5 g, 45.45 mmol, 78% yield) as a white solid.

MS(ES+)C$_{13}$H$_{18}$N$_2$O$_2$F$_2$ requires: 272, found 273 [M+H]$^+$.

$^1$H NMR (400 MHz, CDCl$_3$) δ=7.26-7.18 (m, 1H), 7.11-6.98 (m, 2H), 6.11 (br s, 1H), 4.55 (q, J=6.4 Hz, 1H), 4.29-4.12 (m, 1H), 1.43 (s, 9H), 1.33 (d, J=6.7 Hz, 3H).

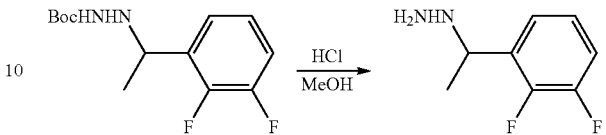

1-(2,3-Difluorophenyl)ethylhydrazine To a solution of the product from the previous step (12.5 g, 45.91 mmol, 1 eq) in EtOAc (50 mL) was added HCl/EtOAc (4 M, 100 mL, 8.71 eq) at 0° C., the mixture was stirred at 25° C. for 0.5 hr. The mixture was filtered, and the filter cake was washed with EtOAc (20 mL×3) and dried under reduced pressure to afford the title compound (11.2 g, 45.70 mmol, 99% yield, HCl salt) as a white solid. $^1$H NMR (400 MHz, DMSO-d$_6$) δ=9.92-8.77 (m, 2H), 7.42-7.39 (m, 2H), 7.31-7.21 (m, 1H), 6.54-5.27 (m, 1H), 4.53-4.48 (m, 1H), 1.39 (s, 3H).

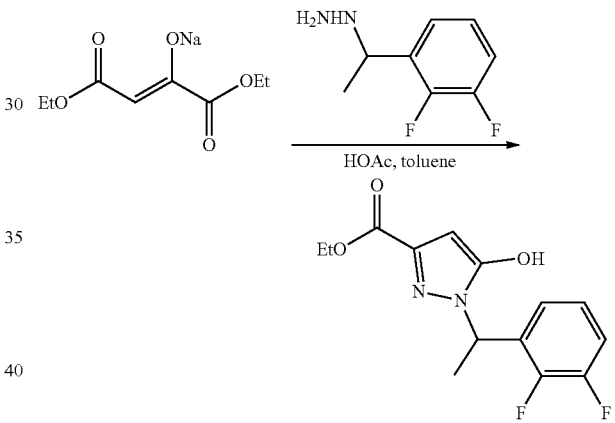

Ethyl 1-[1-(2,3-difluorophenyDethyl]-5-hydroxy-pyrazole-3-carboxylate To a solution of the product from the previous step (9.4 g, 38.35 mmol, 1 eq, HCl salt) in toluene (20 mL) was added AcOH (82.06 g, 1.37 mol, 78.15 mL, 35.63 eq) and sodium (Z)-1,4-diethoxy-1,4-dioxobut-2-en-2-olate (8.87 g, 42.19 mmol, 1.1 eq). The mixture was stirred under at 110° C. for 16 hr. The mixture was concentrated under reduced pressure and the residue was diluted with H$_2$O (200 mL) and adjusted to pH=7 with NaOH (solid) at 0° C. The mixture was extracted with EtOAc (100 mL×2), washed with H$_2$O (100 mL), dried over Na$_2$SO$_4$, and concentrated under reduced pressure. The residue was diluted with petroleum ether/EtOAc=5/1 (100 mL), and the mixture was stirred for 30 min. The mixture was then filtered, and the filter cake was washed with petroleum ether (30 mL×3) and MTBE (5 mL×2). The solid was dried under reduced pressure to afford the title compound (12.1 g, 36.76 mmol, 95% yield) as a white solid.

MS(ES+)C$_{14}$H$_{14}$N$_2$F$_2$O$_3$ requires: 296, found 297 [M+H]$^+$.

$^1$H NMR (400 MHz, DMSO-d$_6$) δ=11.92 (s, 1H), 7.45-7.27 (m, 1H), 7.25-7.08 (m, 1H), 6.95 (t, J=7.1 Hz, 1H), 5.92-5.74 (m, 2H), 4.35-4.12 (m, 2H), 1.74 (d, J=7.0 Hz, 3H), 1.27 (t, J=7.1 Hz, 3H).

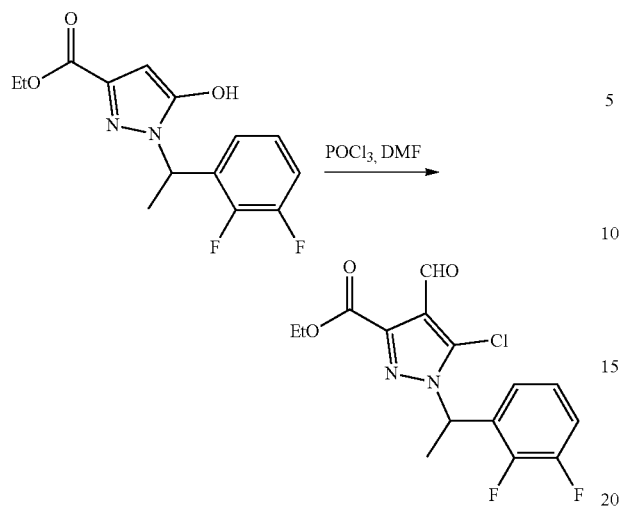

Ethyl 5-chloro-1-[1-(2,3-difluorophenyl)ethyl]-4-formyl-pyrazole-3-carboxylate To a mixture of the product from the previous step (7 g, 23.63 mmol, 1 eq), and DMF (6.91 g, 94.51 mmol, 7.27 mL, 4 eq) was added POCl₃ (31.45 g, 205.08 mmol, 19.06 mL, 8.68 eq) at 0° C. The mixture was then stirred at 90° C. for 16 hr. To the mixture was added THF (50 mL) and the reaction was quenched by slow addition into H₂O (100 mL) dropwise at 40° C., then extracted with EtOAc (100 mL×3). The combined organic layers were dried over Na₂SO₄ and concentrated under reduced pressure to afford a residue which was purified by column chromatography (SiO₂, petroleum ether/EtOAc=50/1 to 20/1) to afford the title compound (2.6 g, 7.59 mmol, 32% yield) as a white solid.

MS(ES+)$C_{15}H_{13}N_2O_2F_2Cl$ requires:342, found 343 [M+H]⁺.

¹H NMR (400 MHz, DMSO-d₆) δ=10.23 (s, 1H), 7.48-7.42 (m, 1H), 7.34-7.19 (m, 1H), 7.16-7.00 (m, 1H), 6.20 (q, J=6.8 Hz, 1H), 4.45-4.29 (m, 2H), 1.86 (d, J=7.0 Hz, 3H), 1.33 (t, J=7.1 Hz, 3H).

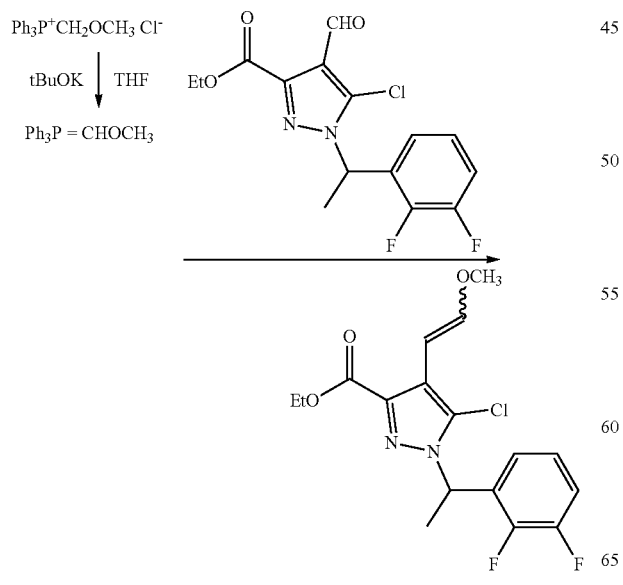

Ethyl 5-chloro-1-[1-(2,3-difluorophenyl)ethyl]-4-[(E)-2-methoxyvinyl]pyrazole-3-carboxylate To a solution of methoxymethyl(triphenyl) phosphonium chloride (2.25 g, 6.57 mmol, 1.5 eq), in THF (20 mL) was added t-BuOK (1 M, 8.75 mL, 2 eq) at 0° C. The mixture was stirred at 0° C. for 0.5 hr. To the mixture was added the product from the previous step (1.5 g, 4.38 mmol, 1 eq) in THF (10 mL), and the mixture was stirred at 25° C. for 16 hr. H₂O (20 mL) was then added, and the mixture was extracted with EtOAc (20 mL×3). The combined organic layers were dried over Na₂SO₄, concentrated under reduced pressure, and purified by column chromatography (SiO₂, petroleum ether/EtOAc=50/1 to 10/1) to afford the title compound (1.27 g, 3.29 mmol, 75% yield) as a white solid. MS(ES+) $C_{17}H_{17}O_3N_2ClF_2$ requires:370, found 371 [M+H]⁺,

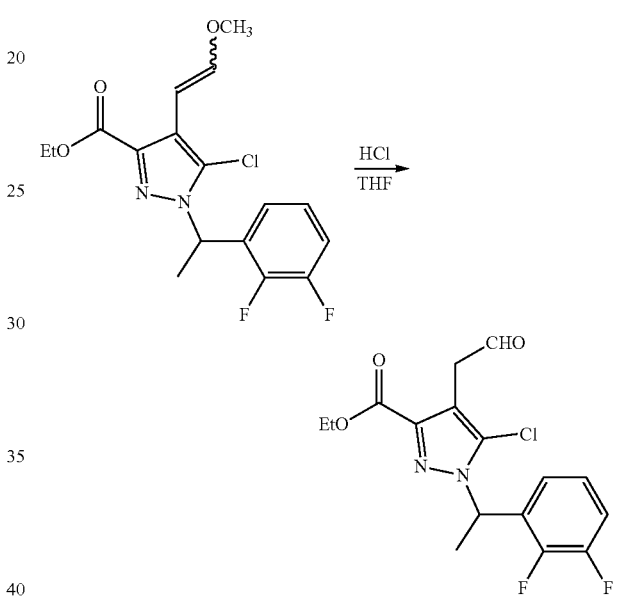

Ethyl 5-chloro-1-[1-(2,3-difluorophenyl)ethyl]-4-(2-oxo-ethyl)pyrazole-3-carboxylate To a solution of the product from the previous step (1.27 g, 3.43 mmol, 1 eq) in THF (32 mL) was added HCl (6 M, 65.65 mL, 115 eq). The mixture was stirred at 25° C. for 0.5 hr. H₂O (20 mL) was then added, and the mixture was extracted with EtOAc(30 mL×3). The combined organic layers were washed with brine (40 mL×3), dried over Na₂SO₄, and concentrated under reduced pressure to afford the title compound (1.13 g, 3.17 mmol, 92% yield) as a colorless oil, which was used directly in next step.

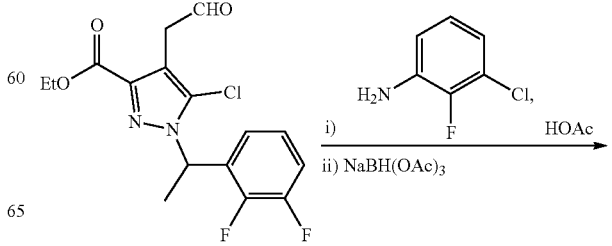

-continued

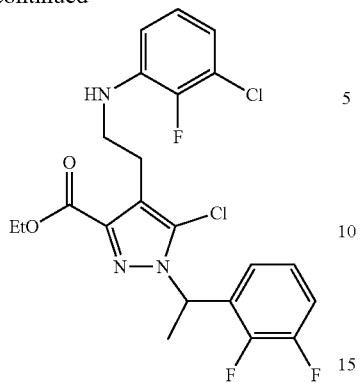

Ethyl 5-chloro-4-[2-(3-chloro-2-fluoro-anilino)ethyl]-1-[1-(2,3-difluorophenyl)-ethyl]pyrazole-3-carboxylate To a solution of the product from the previous step (1.13 g, 3.17 mmol, 1 eq) and 3-chloro-2-fluoroaniline (600.44 mg, 4.13 mmol, 1.3 eq) in DCE (20 mL) was added AcOH (190.55 mg, 3.17 mmol, 181.48 uL, 1 eq). The mixture was stirred at 25° C. for 0.5 hr. To the mixture was added NaBH(OAc)$_3$ (3.25 g, 15.33 mmol, 4.83 eq), and the mixture was stirred at 25° C. for 16 hr. H$_2$O (20 mL) was then added, and the mixture was extracted with DCM (20 mL×3). The combined organic layers were washed with brine (30 mL×3), dried over Na$_2$SO$_4$, concentrated under reduced pressure, and purified by prep-HPLC (column: Phenomenex Synergi C18, 150 mm*25 mm*10 μm; mobile phase: [H$_2$O (0.1% TFA)-ACN]; B %: 28%-42%,10 min). The eluent was concentrated and lyophilized to afford the title compound (0.7 g, 1.44 mmol, 45% yield) as a colorless oil. MS(ES+) C$_{22}$H$_{20}$O$_2$N$_3$Cl$_2$F$_3$ requires:485, found 486 [M+H]$^+$.

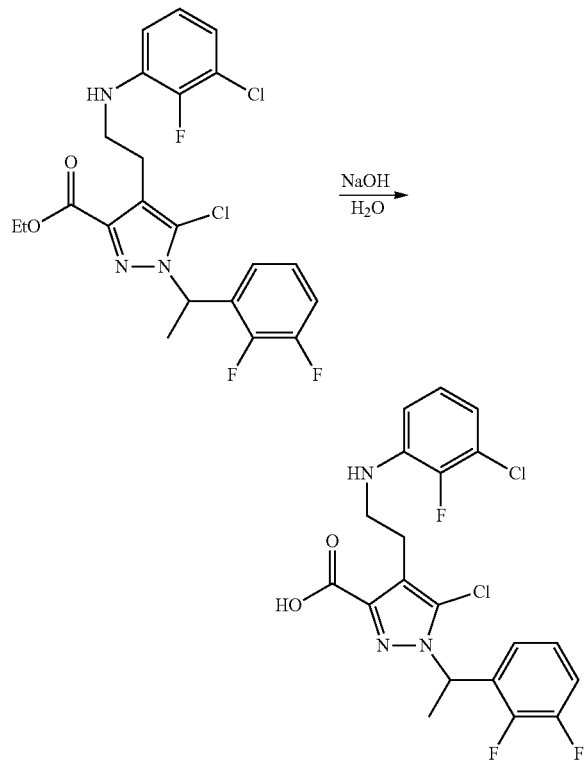

5-Chloro-4-[2-(3-chloro-2-fluoro-anilino)ethyl]-1-[1-(2,3-difluorophenyl)ethyl]-pyrazole-3-carboxylic acid To a solution of the product from the previous step (0.7 g, 1.44 mmol, 1 eq) in MeOH (5 mL) was added LiOH·H$_2$O (1.5 M, 2.40 mL, 2.5 eq), and the mixture was stirred at 60° C. for 2 hr. H$_2$O (20 mL) was then added, and the pH was adjusted to 4 by addition of HCl (1 N). The mixture was then extracted with DCM (20 mL×3). The combined organic layers were washed with brine (30 mL×3), dried over Na$_2$SO$_4$, and concentrated under reduced pressure to give the title compound (0.66 g, 1.43 mmol, 99% yield). MS(ES+) C$_{22}$H$_{16}$O$_2$N$_3$Cl$_2$F$_3$ requires:457, found 458 [M+H]$^+$,

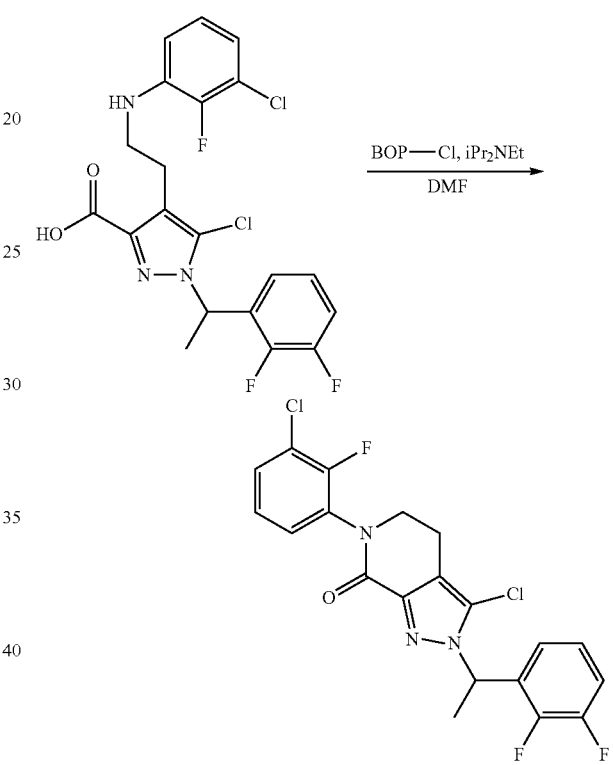

3-Chloro-6-(3-chloro-2-fluoro-phenyl)-2-[1-(2,3-difluorophenyl)ethyl]-4,5-dihydropyrazolo[3,4-c]pyridin-7-one To a solution of the product from the previous step (0.33 g, 720.11 umol, 1 eq) in DCM (5 mL) was added BOP-Cl (274.97 mg, 1.08 mmol, 1.5 eq) and DIPEA (279.21 mg, 2.16 mmol, 376.29 uL, 3 eq), and the mixture was stirred at 25° C. for 16 hr. H$_2$O (10 mL) was then added, and the mixture was extracted with DCM (10 mL×3). The combined organic layers were washed with brine (20 mL×3), dried over Na$_2$SO$_4$, concentrated under reduced pressure, and purified by prep-HPLC (column: Phenomenex Luna C18, 150 mm*40 mm*15 μm; mobile phase: [H$_2$O (0.1% TFA)-ACN]; B %: 52%-82%,11 min). The eluent was concentrated and lyophilized to afford the title compound (320 mg, 712.33 umol, 98% yield) as a white solid.

MS(ES+)C$_{20}$H$_{14}$Cl$_2$F$_3$N$_3$O requires:440, found 441 [M+H]$^+$.

$^1$H NMR (400 MHz, CDCl$_3$) δ=7.42-7.38 (m, 1H), 7.34-7.29 (m, 1H), 7.20-7.04 (m, 4H), 6.13-6.08 (m, 1H), 3.98-3.94 (m, 2H), 2.99-2.89 (m, 2H), 1.99 (d, J=7.0 Hz, 3H).

Examples 55a and 55b

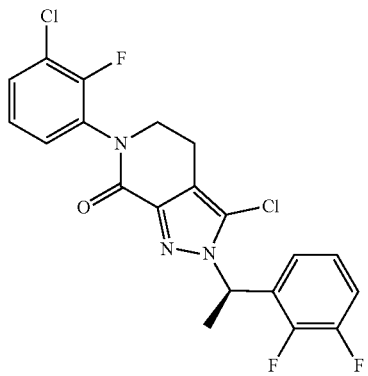 [SMILES: C[C@H](c1cccc(F)c1F)n1nc2c(c1Cl)CCN(c1cccc(Cl)c1F)C2=O]

(R)-3-chloro-6-(3-chloro-2-fluorophenyl)-2-(1-(2,3-difluorophenyl)ethyl)-2,4,5,6-tetrahydro-7H-pyrazolo[3,4-c]pyridin-7-one and

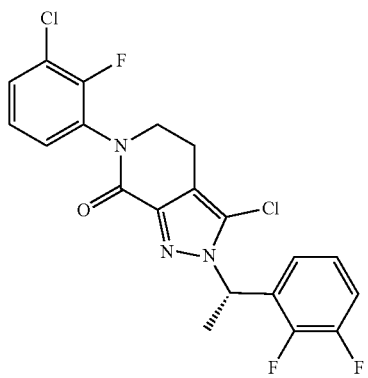 [SMILES: C[C@@H](c1cccc(F)c1F)n1nc2c(c1Cl)CCN(c1cccc(Cl)c1F)C2=O]

(S)-3-chloro-6-(3-chloro-2-fluorophenyl)-2-(1-(2,3-difluorophenyl)ethyl)-2,4,5,6-tetrahydro-7H-pyrazolo[3,4-c]pyridin-7-one

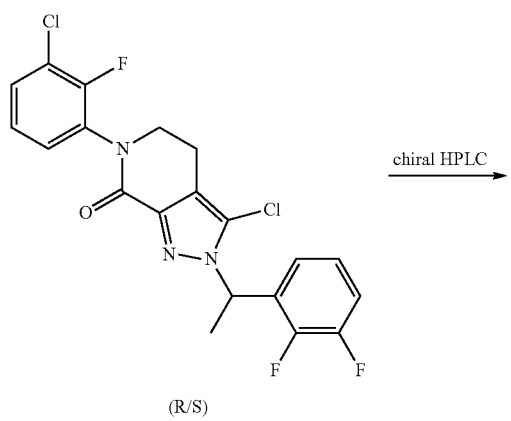

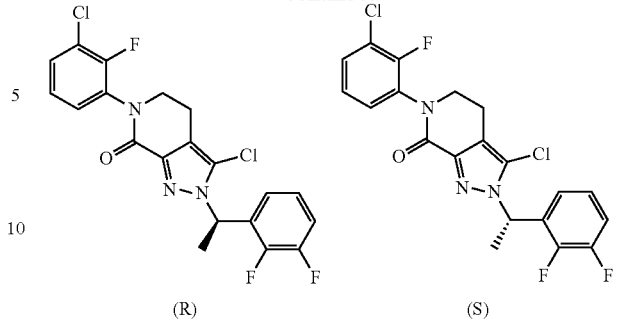

(R)-3-chloro-6-(3-chloro-2-fluoro-phenyl)-2-[1-(2,3-difluorophenyl)ethyl]-4,5-dihydropyrazolo[3,4-c]pyridin-7-one and (S)-3-chloro-6-(3-chloro-2-fluoro-phenyl)-2-[1-(2,3-difluorophenyl)ethyl]-4,5-dihydropyrazolo[3,4-c]pyridin-7-one The Example 55 material (0.3 g, 681.44 umol, 1 eq) was separated into its constituent enantiomers by SFC (column: Daicel CHIRALCEL® OJ, 250 mm*30 mm*10 μm; mobile phase: [0.1% NH$_4$OH/H$_2$O MeOH]; B %: 25%-25%, 2.8 min; 85 min) to afford two enantiomers of undetermined absolute stereochemistry.

Example 55a: white solid (84.8 mg, 190.69 umol, 27% yield, 99% purity), MS(ES+)C$_{20}$H$_{14}$Cl$_2$F$_3$N$_3$O requires:440, found 441 [M+H]$^+$. $^1$H NMR (400 MHz, CDCl$_3$) δ=7.41-7.37 (m, 1H), 7.35-7.30 (m, 1H), 7.20-7.01 (m, 4H), 6.13-6.09 (m, 1H), 3.96-3.93 (m, 2H), 3.03-2.83 (m, 2H), 2.00 (d, J=7.0 Hz, 3H).

Example 55b: white solid (97.4 mg, 219.03 umol, 32% yield, 99% purity), MS(ES+)C$_{20}$H$_{14}$Cl$_2$F$_3$N$_3$O requires:440, found 441 [M+H]$^+$.$^1$H NMR (400 MHz, CDCl$_3$) δ=7.41-7.37 (m, 1H), 7.33-7.29 (m, 1H), 7.19-7.02 (m, 4H), 6.13-6.08 (m, 1H), 3.96-3.93 (m, 2H), 2.96-2.91 (m, 2H), 2.00 (d, J=7.0 Hz, 3H).

Example 56

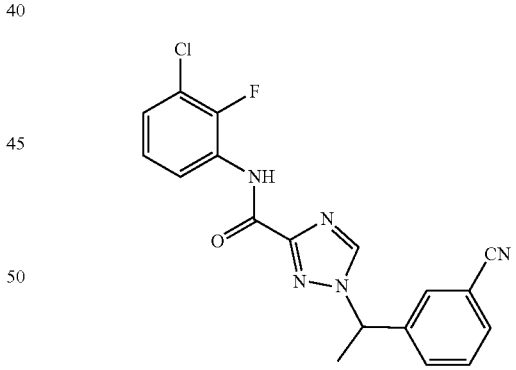

N-(3-chloro-2-fluorophenyl)-1-(1-(3-cyanophenyl)ethyl)-1H-1,2,4-triazole-3-carboxamide

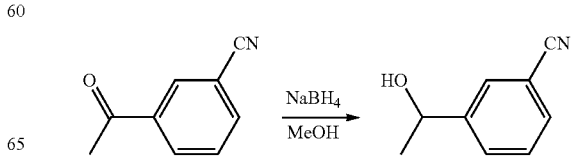

3-(1-Hydroxyethyl)benzonitrile To a solution of 3-acetylbenzonitrile (1 g, 7 mmol, 1 eq) in MeOH (10 mL) was added NaBH₄ (521.23 mg, 13.78 mmol, 2 eq), and the mixture was stirred at 25° C. for 10 mins. The mixture was filtered and concentrated under reduced pressure to give the title compound (1 g, 6.52 mmol, 95% yield) as a yellow oil.

¹H NMR (400 MHz, CDCl₃) δ=7.61 (s, 1H), 7.54 (d, J=7.8 Hz, 1H), 7.51-7.45 (m, 1H), 7.41-7.34 (m, 1H), 4.89-4.84 (m, 1H), 2.19 (s, 1H), 1.42 (d, J=6.5 Hz, 3H).

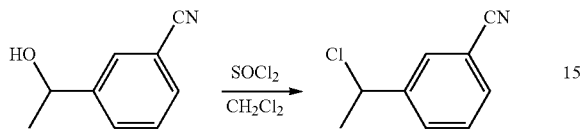

3-(1-Chloroethyl)benzonitrile To a solution of the product from the previous step (0.8 g, 5 mmol, 1 eq) in CH₂Cl₂ (10 mL) was added SOCl₂ (8 mL) at 0° C., and the mixture was stirred at 25° C. for 30 minutes. The mixture was concentrated under reduced pressure to give the title compound (0.9 g, 5 mmol, 99% yield) as a yellow oil.

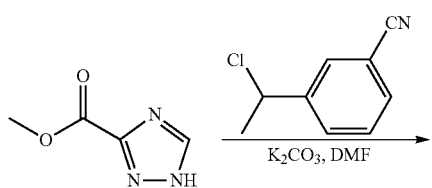

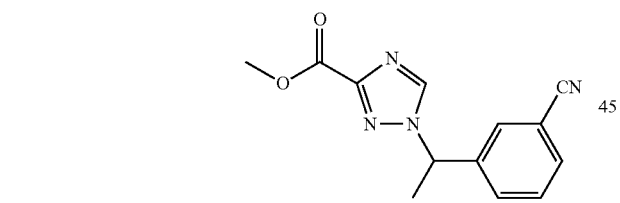

Methyl 1-[1-(3-cyanophenyl)ethyl]-1,2,4-triazole-3-carboxylate To a solution of the product from the previous step (0.9 g, 5 mmol, 1 eq) in DMF (15 mL) was added methyl 1H-1,2,4-triazole-3-carboxylate (414.41 mg, 3.26 mmol, 0.6 eq) and K₂CO₃ (1.50 g, 10.87 mmol, 2 eq), and the mixture was stirred at 25° C. for 16 h. To the mixture was added H₂O (15 mL) and the mixture was extracted with EtOAc (15 mL×3). The combined organic layers were washed with brine (20 mL×3), dried over Na₂SO₄, and concentrated under reduced pressure to give a residue which was purified by prep-HPLC (column: Phenomenex luna C18 150 mm×25 mm×10 μm; mobile phase: [H₂O (0.1% TFA)-CH₃CN];B %: 18%-48%, 10 min). The eluent was concentrated and lyophilized to afford the title compound (0.16 g, 562 μmol, 10% yield) as a colorless oil.

MS(ES+)C₁₃H₁₂N₄O₂ requires:256, found 257 [M+H]⁺.

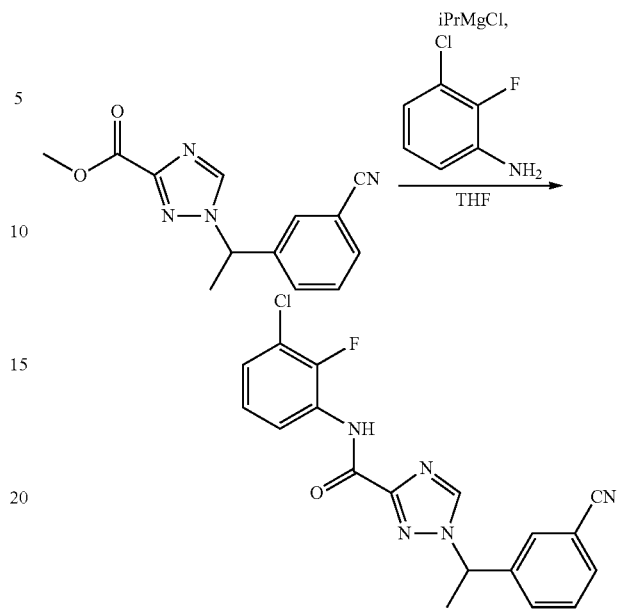

N-(3-Chloro-2-fluorophenyl)-1-[1-(3-cyanophenyl)ethyl]-1,2,4-triazole-3-carboxamide To a solution of the product from the previous step (0.08 g, 312 μmol, 1 eq) in THF (1 mL) was added iPrMgCl (2 M, 312.18 uL, 2 eq) at 25° C. To the mixture was added 3-chloro-2-fluoroaniline (54.53 mg, 374.6 μmol, 1.2 eq), and the reaction was stirred at 25° C. for 16 h. The mixture was poured into H₂O (5 mL) and extracted with CH₂Cl₂ (5 mL×3). The combined organic layers were dried over Na₂SO₄ and concentrated under reduced pressure to give a residue which was purified by prep-HPLC (column: Phenomenex luna C18 150 mm×25 mm×10 μm; mobile phase: [H₂O (0.1% TFA)-CH₃CN];B %: 43%-73%,10 min). The eluent was concentrated and lyophilized to afford the title compound (40 mg, 108 μmol, 34% yield) as a yellow solid.

MS(ES+)C₁₈H₁₃N₅OClF requires:369, found 370 [M+H]⁺.

¹H NMR (400 MHz, CDCl₃) δ=9.15 (s, 1H), 8.45-8.27 (m, 1H), 8.12 (s, 1H), 7.66-7.39 (m, 4H), 7.15-6.99 (m, 2H), 5.65-5.60 (m, 1H), 1.96 (d, J=7.1 Hz, 3H).

Examples 56a and 56b

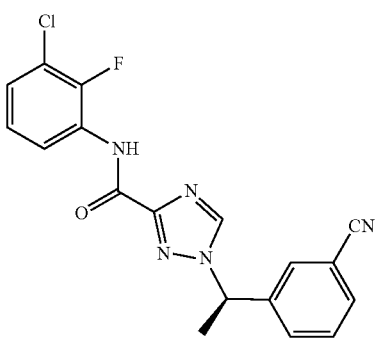 [SMILES: C[C@H](c1cccc(C#N)c1)n1cnc(C(=O)Nc2cccc(Cl)c2F)n1]

153

(R)—N-(3-chloro-2-fluorophenyl)-1-(1-(3-cyanophenyl)ethyl)-1H-1,2,4-triazole-3-carboxamide and

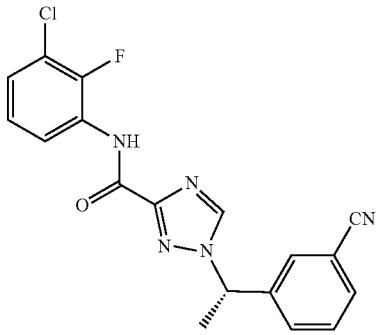 [SMILES: C[C@@H](c1cccc(C#N)c1)n1cnc(C(=O)Nc2cccc(Cl)c2F)n1]

(S)—N-(3-chloro-2-fluorophenyl)-1-(1-(3-cyanophenyl)ethyl)-1H-1,2,4-triazole-3-carboxamide

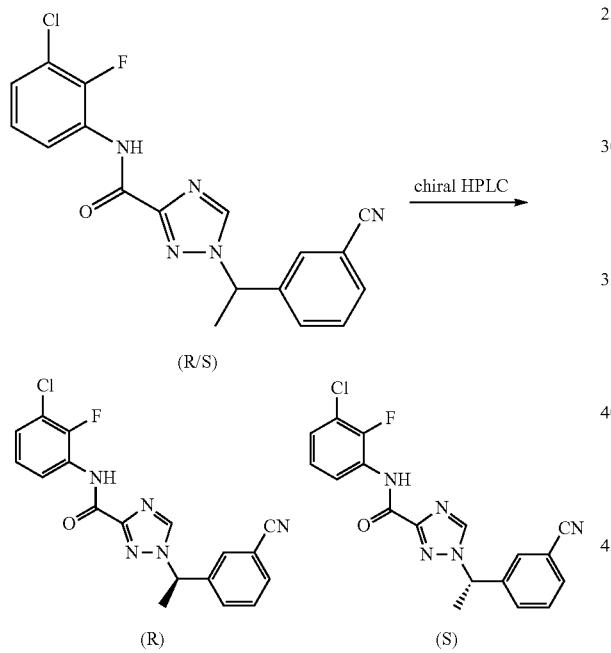

(R)—N-(3-chloro-2-fluorophenyl)-1-(1-(3-cyanophenyl) ethyl)-1H-1,2,4-triazole-3-carboxamide and (S)—N-(3-chloro-2-fluorophenyl)-1-(1-(3-cyanophenyl)ethyl)-1H-1,2,4-triazole-3-carboxamide The Example 56 material was separated by SFC (column: Regis WHELK-O® 1, 250 mm*30 mm*5 μm; mobile phase: [0.1% NH$_4$OH— MeOH]; B %: 60%-60%,4.1 min) to afford to afford two enantiomers of undetermined absolute stereochemistry.

Example 56a: white solid (10.3 mg, 27.85 umol, 34% yield, 100% purity).

MS(ES+)C$_{18}$H$_{13}$N$_5$OClF requires:369, found 370 [M+H]$^+$.

$^1$H NMR (400 MHz, CDCl$_3$) δ=9.15 (s, 1H), 8.46-8.30 (m, 1H), 8.11 (s, 1H), 7.65-7.38 (m, 4H), 7.15-7.00 (m, 2H), 5.62 (q, J=7.1 Hz, 1H), 1.96 (d, J=7.1 Hz, 3H).

Example 56b: white solid (8.8 mg, 23.56 umol, 29% yield, 99% purity).

154

MS(ES+)C$_{18}$H$_{13}$N$_5$OClF requires:369, found 370 [M+H]$^+$.

$^1$H NMR (400 MHz, CDCl$_3$) δ=9.15 (s, 1H), 8.48-8.28 (m, 1H), 8.11 (s, 1H), 7.68-7.38 (m, 4H), 7.12-7.02 (m, 2H), 5.62 (q, J=7.1 Hz, 1H), 1.96 (d, J=7.1 Hz, 3H).

Example 57

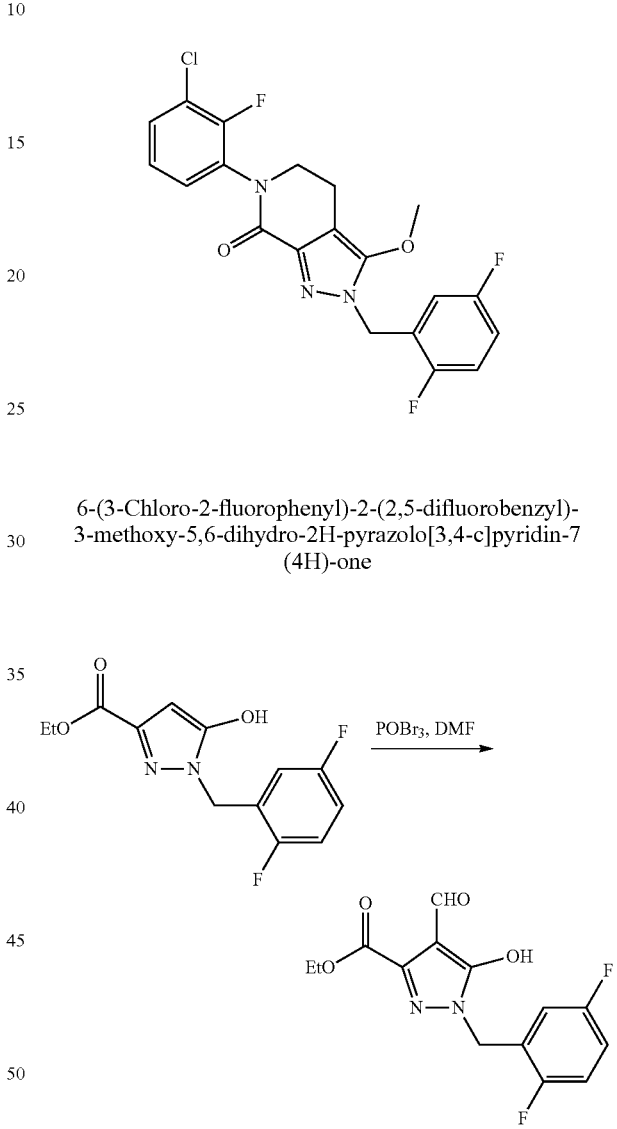

6-(3-Chloro-2-fluorophenyl)-2-(2,5-difluorobenzyl)-3-methoxy-5,6-dihydro-2H-pyrazolo[3,4-c]pyridin-7(4H)-one Ethyl 1-(2,5-difluorobenzyl)-4-formyl-5-hydroxy-1H-pyrazole-3-carboxylate To a solution of Intermediate B (3 g, 9.4 mmol, 1 eq, HCl) in CH$_2$Cl$_2$ (30 mL) was added DMF (1.38 g, 18.8 mmol, 1.45 mL, 2 eq) and POBr$_3$ (5.40 g, 18.8 mmol, 1.91 mL, 2 eq). The mixture was stirred at 90° C. for 16 h. The reaction mixture was diluted with H$_2$O (400 mL) and extracted with EtOAc (400 mL). The combined organic layers were concentrated under reduced pressure to give a residue and then purified by column chromatography (SiO$_2$, petroleum ether/EtOAc=2/1 to 1/1) to afford the title compound (250 mg, 741 μmol, 8% yield) as a yellow solid.

MS (ES$^+$) C$_{14}$H$_{12}$F$_2$N$_2$O$_4$ requires: 310 found: 311 [M+H]$^+$.

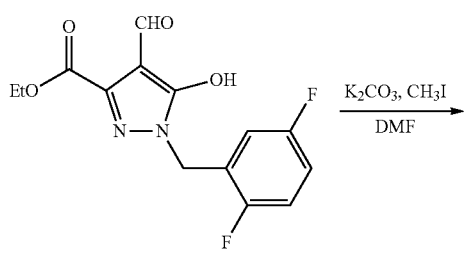

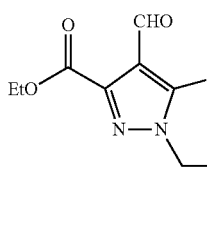

Ethyl 1-(2,5-difluorobenzyl)-4-formyl-5-methoxy-1H-pyrazole-3-carboxylate

To a solution of the product from the previous step (200 mg, 645 μmol, 1 eq) in DMF (5 mL) was added K₂CO₃ (267.3 mg, 1.93 mmol, 3 eq) and MeI (183.0 mg, 1.29 mmol, 80.26 uL, 2 eq). The mixture was stirred at 25° C. for 16 h. H₂O (50 mL) was added, and the mixture was stirred for 5 min. The mixture was then extracted with EtOAc (50 mL×2). The combined organic layers were washed with brine (50 mL×2), dried over Na₂SO₄, concentrated under reduced pressure, and purified by silica gel chromatography (Eluent of 0-20% EtOAc /petroleum ether gradient) to afford the title compound (100 mg, 296.04 μmol, 46% yield) as colorless oil.MS (ES⁺) C₁₅H₁₄F₂N₂O₄ requires: 324 found: 325 [M+H]⁺.

¹H NMR (400 MHz, CDCl₃) δ=10.08 (s, 1H), 7.12-6.94 (m, 2H), 6.91-6.81 (m, 1H), 5.30 (s, 2H), 4.54-4.38 (m, 2H), 4.00 (s, 3H), 1.43 (t, J=7.2 Hz, 3H).

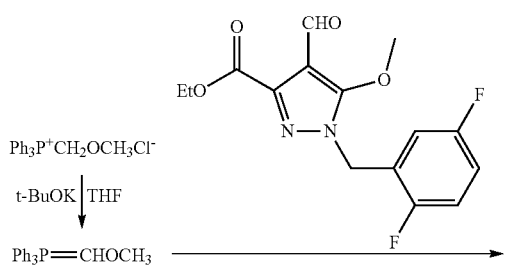

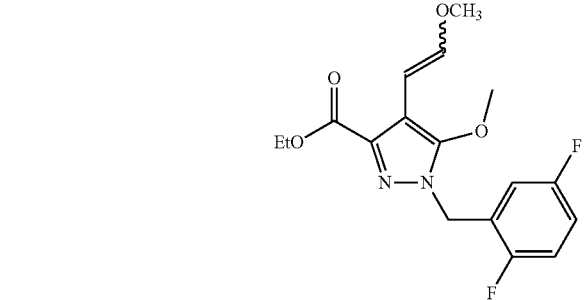

Ethyl 1-(2,5-difluorobenzyl)-5-methoxy-4-(2-methoxyvinyl)-1H-pyrazole-3-carboxylate To a solution of t-BuOK (1 M, 402 uL, 1.5 eq) in THF (1 mL) was added (methoxymethyl)triphenylphosphonium chloride (137.8 mg, 401.98 μmol, 1.5 eq) at 0° C. under N₂, and the mixture was stirred at 0° C. for 10 min. A solution of the product from the previous step (86.9 mg, 267.99 μmol, 1 eq) in THF (1 mL) was then added at 0° C., and the mixture was stirred at 25° C. for 16 h. The mixture was quenched by slow addition of saturated NH₄Cl solution (10 mL) and stirred for 5 min. The mixture was extracted with EtOAc (10 mL×2). The combined organic layers were washed with brine (10 mL×2), dried over Na₂SO₄, concentrated under reduced pressure, and purified by prep-TLC (SiO₂, petroleum ether:EtOAc=5:1) to afford the title compound (50 mg, 97.92 μmol, 37% yield) as yellow oil.

MS (ES⁺) C₁₇H₁₈F₂N₂O₄ requires: 352 found: 353 [M+H]⁺.

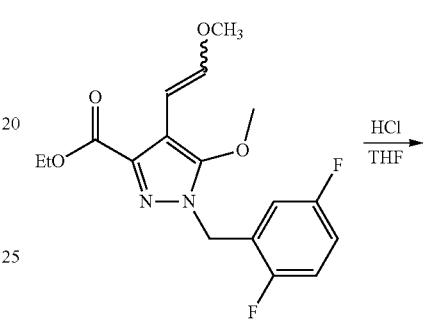

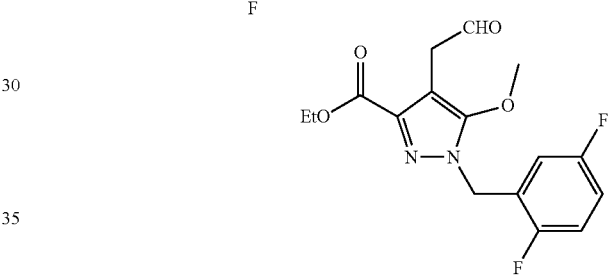

Ethyl 1-(2,5-difluorobenzyl)-5-methoxy-4-(2-oxoethyl)-1H-pyrazole-3-carboxylate To a solution of the product from the previous step (50 mg, 141.91 μmol, 1 eq) in THF (2 mL) was added HCl (6 M, 236.5 uL, 10 eq). The mixture was stirred at 25° C. for 4 h. The mixture was poured into H₂O (10 mL) and the pH was brought to 7 with saturated NaHCO₃. The mixture was extracted with EtOAc (10 mL×2). The combined organic layers were washed with brine (10 mL×2), dried over Na₂SO₄, concentrated under reduced pressure, and purified by prep-TLC (SiO₂, petroleum ether: EtOAc=5:1) to afford the title compound (42 mg, 115.46 μmol, 81% yield, 93% purity) as a white solid.

MS (ES⁺) C₁₆H₁₆F₂N₂O₄ requires: 338 found: 339 [M+H]⁺.

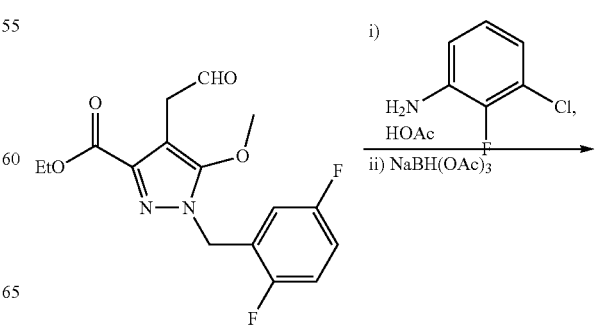

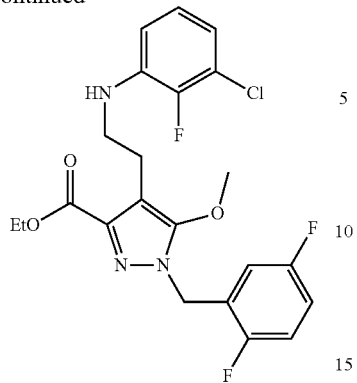

Ethyl 4-(2-((3-chloro-2-fluorophenyl)amino)ethyl)-1-(2,5-difluorobenzyl)-5-methoxy-1H-pyrazole-3-carboxylate To a solution of the product from the previous step (42 mg, 124 μmol, 1 eq) and 3-chloro-2-fluoroaniline (27.1 mg, 186.22 μmol, 37 uL, 1.5 eq) in CH$_2$Cl$_2$ (2 mL) was added HOAc (7.4 mg, 124.15 μmol, 7.1 uL, 1 eq). After addition, the mixture was stirred at 30° C. for 10 min. and then NaBH(OAc)$_3$ (126.3 mg, 595.9 μmol, 4.8 eq) was added at 30° C. The resulting mixture was stirred at 30° C. for 16 h. The reaction mixture was quenched by slow addition of saturated NaHCO$_3$ solution (10 mL), then extracted with EtOAc (10 mL×2). The combined organic layers were washed with brine (10 mL), dried over Na$_2$SO$_4$, concentrated under reduced pressure, and purified by prep-TLC (SiO$_2$, petroleum ether: EtOAc=5:1) to afford the title compound (28 mg, 58.05 μmol, 47% yield) as yellow oil.

MS (ES$^+$) C$_{22}$H$_{21}$ClF$_2$N$_3$O$_3$ requires: 467 found: 468 [M+H]$^+$.

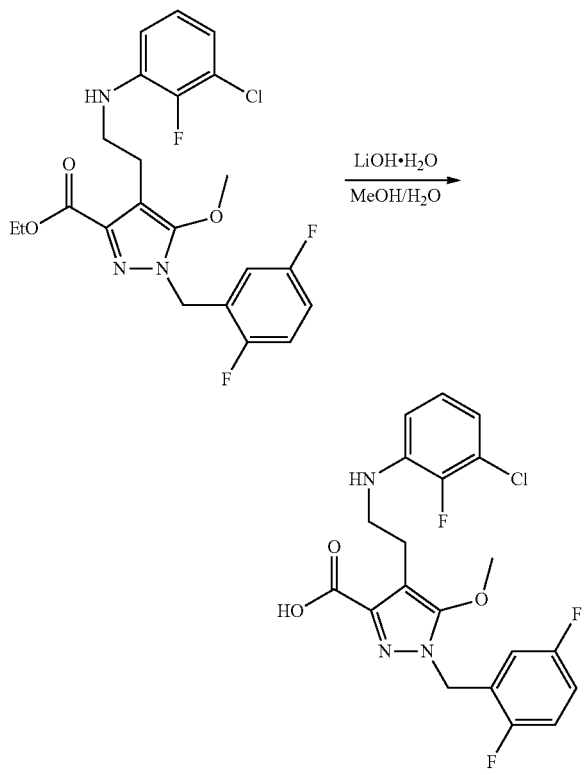

4-(2-((3-Chloro-2-fluorophenyl)amino)ethyl)-1-(2,5-difluorobenzyl)-5-methoxy-1H-pyrazole-3-carboxylic acid To a solution of the product from the previous step (28 mg, 59.85 μmol, 1 eq) in MeOH (1 mL) and H$_2$O (0.5 mL) was added LiOH·H$_2$O (12.6 mg, 299.23 μmol, 5 eq). The mixture was stirred at 50° C. for 2 h. The mixture was poured dropwise into H$_2$O (5 mL) and the pH was brought to 7 with HCl (1M). The mixture was then extracted with EtOAc (5 mL×2). The combined organic layers were washed with brine (5 mL×2), dried over Na$_2$SO$_4$, and concentrated under reduced pressure to afford the title compound (30 mg, crude) as a yellow oil.

MS (ES$^+$) C$_{20}$H$_{17}$ClF$_3$N$_3$O$_3$ requires: 439 found: 440 [M+H]$^+$.

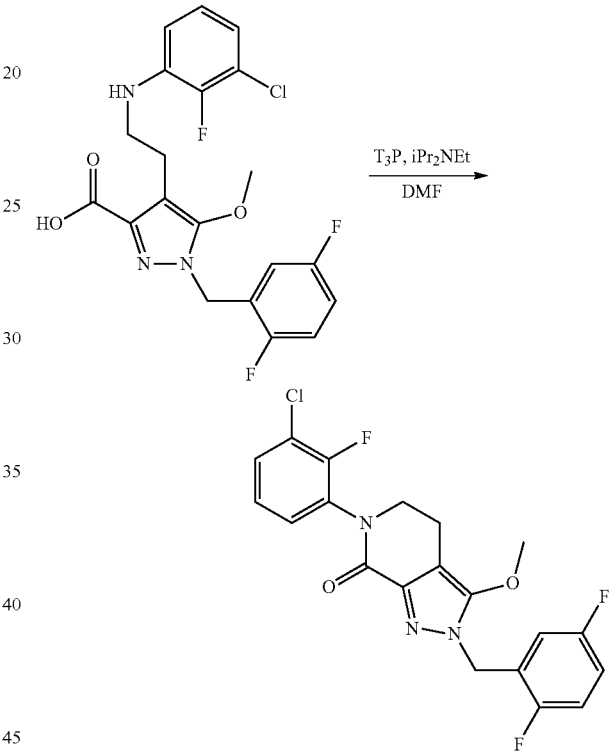

6-(3-Chloro-2-fluorophenyl)-2-(2,5-difluorobenzyl)-3-methoxy-2,4,5,6-tetrahydro-7H-pyrazolo[3,4-c]pyridin-7-one To a solution of the product from the previous step (23.5 mg, 53.57 μmol, 1 eq) in DMF (1 mL) was added T$_3$P (102.3 mg, 321.45 μmol, 95.6 uL, 6 eq) and iPr$_2$NEt (34.62 mg, 267.87 μmol, 46.7 uL, 5 eq) under N$_2$. The mixture was stirred at 25° C. for 16 h. The mixture was poured into H$_2$O (10 mL) and extracted with EtOAc (10 mL×2). The combined organic layers were washed with brine (10 mL×2), dried over Na$_2$SO$_4$, and concentrated under reduced pressure. The residue was purified by prep-TLC (SiO$_2$, petroleum ether: EtOAc=2:1) to afford the title compound (5.1 mg, 12.1 μmol, 22% yield) as a white solid.

MS (ES$^+$) C$_{20}$H$_{15}$ClF$_3$N$_3$O$_2$ requires: 421 found: 422 [M+H]$^+$.

$^1$H NMR (400 MHz, MeOD) 7.52-7.45 (m, 1H), 7.40 (t, J=7.2 Hz, 1H), 7.29-7.22 (m, 1H), 7.19-7.11 (m, 1H), 7.11-7.04 (m, 1H), 6.88 (m, 1H), 5.30 (s, 2H), 4.10 (s, 3H), 3.98 (t, J=6.4 Hz, 2H), 3.18 (t, J=6.4 Hz, 2H).

TABLE 1

RIPK1 inhibitors 20-46 and 51-53.

| Ex. No. | Structure | Name | Analysis | Proc. Ex. No. |
|---|---|---|---|---|
| 20 | 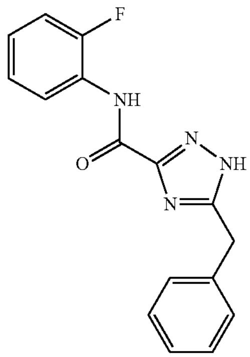 [SMILES: O=C(Nc1ccccc1F)c1n[nH]c(Cc2ccccc2)n1] | 5-benzyl-N-(2-fluorophenyl)-1H-1,2,4-triazole-3-carboxamide | MS (ES+) $C_{16}H_{13}N_4OF$ requires: 296, found: 297 [M + H]$^+$. $^1$H NMR (400 MHz, MeOD) δ: 8.12-8.15 (m, 1H) 7.21-7.37 (m, 8H) 4.23 (s, 2H) | 9 |
| 21 | 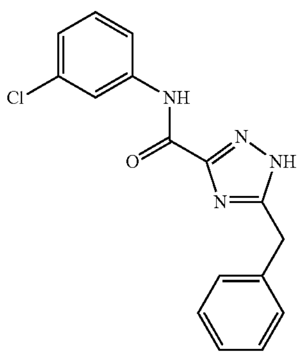 [SMILES: O=C(Nc1cccc(Cl)c1)c1n[nH]c(Cc2ccccc2)n1] | 5-benzyl-N-(3-chlorophenyl)-1H-1,2,4-triazole-3-carboxamide | MS (ES+) $C_{16}H_{13}N_4OCl$ requires: 312, found: 313 [M + H]+. $^1$H NMR (400 MHz, MeOD) δ: 7.94 (s, 1H) 7.61-7.63 (m, 1H) 7.32-7.36 (m, 6H) 7.16-7.17 (m, 1H) 4.22 (s, 2H) | 9 |
| 22 | 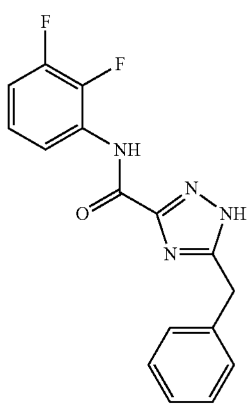 [SMILES: O=C(Nc1cccc(F)c1F)c1n[nH]c(Cc2ccccc2)n1] | 5-benzyl-N-(2,3-difluorophenyl)-1H-1,2,4-triazole-3-carboxamide | MS (ES+) $C_{16}H_{12}N_4OF_2$ requires: 314, found: 315 [M + H]+. $^1$H NMR (400 MHz, MeOD) δ: 7.85-7.89 (m, 1H) 7.33-7.34 (m, 4H) 7.26-7.27 (m, 1H) 7.12-7.17 (m, 2H) 4.22 (s, 2H) | 9 |
| 23 | 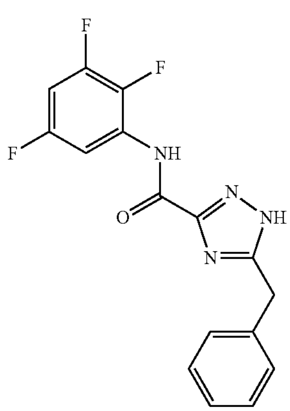 [SMILES: O=C(Nc1cc(F)cc(F)c1F)c1n[nH]c(Cc2ccccc2)n1] | 5-benzyl-N-(2,3,5-trifluorophenyl)-1H-1,2,4-triazole-3-carboxamide | MS (ES+) $C_{16}H_{11}N_4OF_3$ requires: 332, found: 333 [M + H]+. $^1$H NMR (400 MHz, MeOD) δ: 7.84-7.86 (m, 1H) 7.27-7.32 (m, 5H) 6.99-7.01 (m, 1H) 4.23 (s, 2H) | 9 |

TABLE 1-continued

RIPK1 inhibitors 20-46 and 51-53.

| Ex. No. | Structure | Name | Analysis | Proc. Ex. No. |
|---|---|---|---|---|
| 24 | 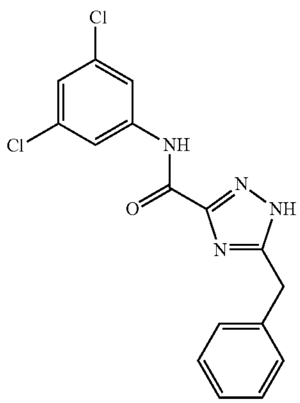 [SMILES: O=C(Nc1cc(Cl)cc(Cl)c1)c1n[nH]c(Cc2ccccc2)n1] | 5-benzyl-N-(3,5-dichlorophenyl)-1H-1,2,4-triazole-3-carboxamide | MS (ES+) $C_{16}H_{12}N_4OCl_2$ requires: 346, found: 347 [M + H]+. $^1$H NMR (400 MHz, MeOD) δ: 7.84 (s, 2H) 7.27-7.35 (m, 6H) 4.22 (s, 2H) | 9 |
| 25 | 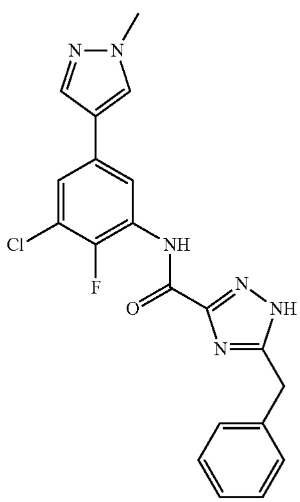 [SMILES: Cn1cc(-c2cc(Cl)c(F)c(NC(=O)c3n[nH]c(Cc4ccccc4)n3)c2)cn1] | 5-benzyl-N-(3-chloro-2-fluoro-5-(1-methyl-1H-pyrazol-4-yl)phenyl)-1H-1,2,4-triazole-3-carboxamide | MS (ES+) $C_{20}H_{16}ClFN_6O$ requires: 410, found: 411 [M + H]+. $^1$H NMR (400 MHz, MeOD) δ: 14.26 (br, 1H) 9.77 (br, 1H) 8.09 (s, 1H) 7.90 (br, 1H) 7.80 (s, 1H) 7.57 (s, 1H) 7.25-7.34 (m, 5H) 4.18 (s, 2H) 3.87 (s, 3H) | 11 |
| 26 | 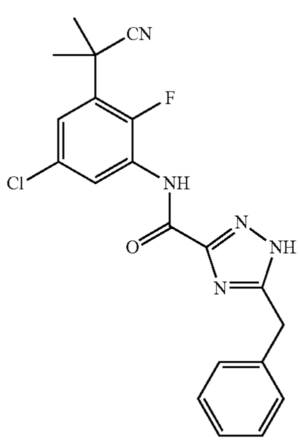 [SMILES: CC(C)(C#N)c1cc(Cl)cc(NC(=O)c2n[nH]c(Cc3ccccc3)n2)c1F] | 5-benzyl-N-(3-chloro-5-(2-cyanopropan-2-yl)-2-fluorophenyl)-1H-1,2,4-triazole-3-carboxamide | MS (ES+) $C_{20}H_{17}N_5OClF$ requires: 397, found: 398 [M + H]+. $^1$H NMR (400 MHz, MeOD) δ: 8.66 (s, 1H) 8.22-8.23 (m, 1H) 7.50-7.52 (m, 1H) 7.36-7.52 (m, 5H) 5.55 (s, 2H) 1.76 (s, 6H) | 9 |

TABLE 1-continued

RIPK1 inhibitors 20-46 and 51-53.

| Ex. No. | Structure | Name | Analysis | Proc. Ex. No. |
|---|---|---|---|---|
| 27 | 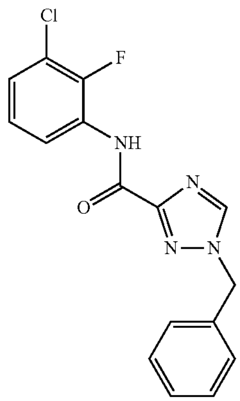 [SMILES: O=C(Nc1cccc(Cl)c1F)c1ncn(Cc2ccccc2)n1] | 1-benzyl-N-(3-chloro-2-fluorophenyl)-1H-1,2,4-triazole-3-carboxamide | MS (ES+) $C_{16}H_{12}N_4OClF$ requires: 330, found: 331 [M + H]+. $^1$H NMR (400 MHz, MeOD) δ: 10.21 (s, 1H) 8.92 (s, 1H) 7.66-7.68 (m, 1H) 7.35-7.46 (m, 6H) 7.24-7.25 (m, 1H) 5.54 (s, 2H) | 12 |
| 28 | 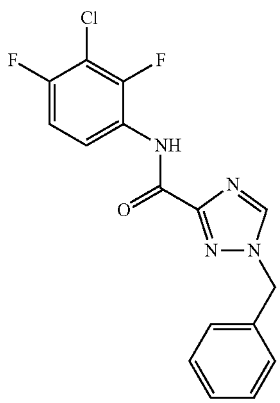 [SMILES: O=C(Nc1ccc(F)c(Cl)c1F)c1ncn(Cc2ccccc2)n1] | 1-benzyl-N-(3-chloro-2,4-difluorophenyl)-1H-1,2,4-triazole-3-carboxamide | MS (ES+) $C_{16}H_{11}N_4ClOF_2$ requires: 348, found: 349 [M + H]+. $^1$H NMR (400 MHz, DMSO-$d_6$) δ: 8.92 (s, 1H) 7.61-7.65 (m, 1H) 7.33-7.42 (m, 6H) 5.54 (s, 2H) | 12 |
| 29 | 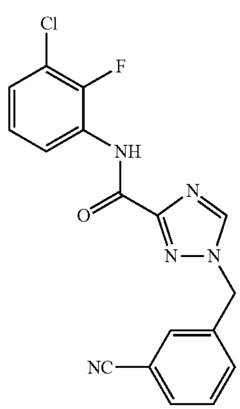 [SMILES: N#Cc1cccc(Cn2cnc(C(=O)Nc3cccc(Cl)c3F)n2)c1] | N-(3-chloro-2-fluorophenyl)-1-(3-cyanobenzyl)-1H-1,2,4-triazole-3-carboxamide | MS (ES+) $C_{17}H_{11}N_5OClF$ requires: 355, found: 356 [M + H]+. $^1$H NMR (400 MHz, DMSO-$d_6$) δ: 10.21 (s, 1H) 8.92 (s, 1H) 7.82-7.87 (m, 2H) 7.61-7.70 (m, 3H) 7.43-7.44 (m, 1H) 7.24-7.26 (m, 1H) 5.61 (s, 2H) | 12 |

TABLE 1-continued

RIPK1 inhibitors 20-46 and 51-53.

| Ex. No. | Structure | Name | Analysis | Proc. Ex. No. |
|---|---|---|---|---|
| 30 | 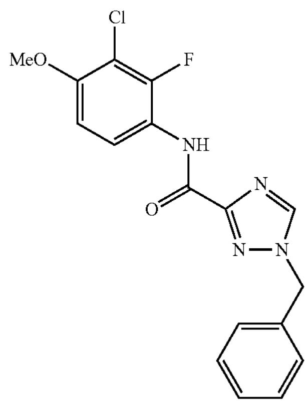 [SMILES: COc1ccc(NC(=O)c2ncn(Cc3ccccc3)n2)c(F)c1Cl] | 1-benzyl-N-(3-chloro-2-fluoro-4-methoxy-phenyl)-1H-1,2,4-triazole-3-carboxamide | MS (ES+) $C_{17}H_{14}N_4O_2ClF$ requires: 360, found: 361 [M + H]+. $^1$H NMR (400 MHz, MeOD) δ: 8.64 (s, 1H) 7.77 (t, J = 10 Hz, 1H) 7.28-7.53 (m, 5H) 6.96 (dd, J = 2, 10 Hz, 1H) 5.32-5.69 (m, 2H) 3.77-4.08 (m, 3H) | 12 |
| 31 | 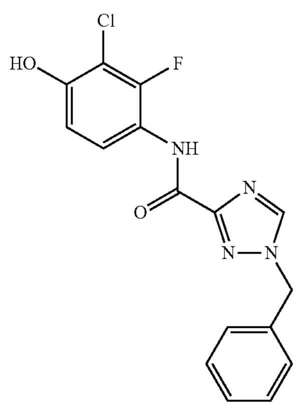 | 1-benzyl-N-(3-chloro-2-fluoro-4-hydroxy-phenyl)-1H-1,2,4-triazole-3-carboxamide | MS (ES+) $C_{16}H_{12}N_4O_2ClF$ requires: 346, found: 347 [M + H]+. $^1$H NMR (400 MHz, DMSO-d$_6$) δ: 10.65 (s, 1H) 10.00 (s, 1H) 8.88 (s, 1H) 7.31-7.40 (m, 6H) 6.82 (dd, J = 2, 10 Hz, 1H) 5.53 (s, 2H) | 12 |
| 32 | 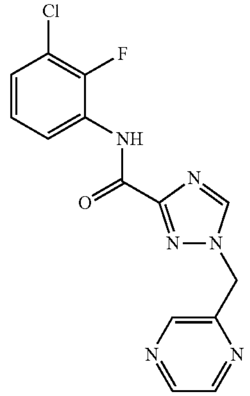 [SMILES: O=C(Nc1cccc(Cl)c1F)c1ncn(Cc2cnccn2)n1] | N-(3-chloro-2-fluoro-phenyl)-1-(pyrazin-2-ylmethyl)-1H-1,2,4-triazole-3-carboxamide | MS (ES+) $C_{14}H_{10}ClFN_6O$ requires: 332, found: 333 [M + H]+. $^1$H NMR (400 MHz, DMSO-d$_6$) δ: 10.23 (s, 1H) 8.94 (s, 1H) 8.78 (s, 1H) 8.64-8.66 (m, 2H) 7.64-7.66 (m, 1H) 7.43-7.47 (m, 1H) 7.24-7.27 (m, 1H) 5.77 (s, 2H) | 12 |

TABLE 1-continued

RIPK1 inhibitors 20-46 and 51-53.

| Ex. No. | Structure | Name | Analysis | Proc. Ex. No. |
|---|---|---|---|---|
| 33 | 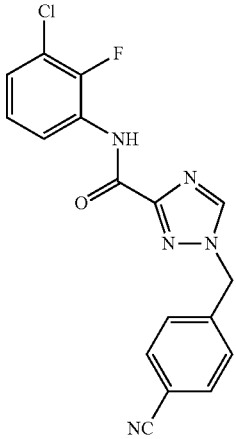 [SMILES: N#Cc1ccc(Cn2cnc(C(=O)Nc3cccc(Cl)c3F)n2)cc1] | N-(3-chloro-2-fluorophenyl)-1-(4-cyanobenzyl)-1H-1,2,4-triazole-3-carboxamide | MS (ES+) $C_{17}H_{11}N_5OClF$ requires: 355, found: 356 [M + H]+. $^1$H NMR (400 MHz, DMSO-$d_6$) δ: 10.23 (s, 1H) 8.93 (s, 1H) 7.87 (d, J = 8.4 Hz, 2H), 7.65-7.67 (m, 1H) 7.43 (d, J = 8.4 Hz, 2H) 7.25-7.27 (m, 1H) 7.23-7.24 (m, 1H), 5.66 (s, 2H) | 12 |
| 34 | 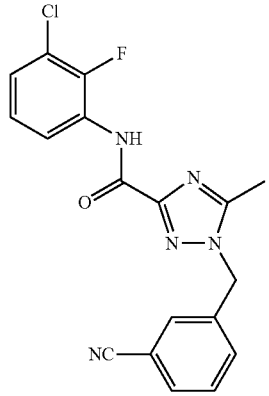 [SMILES: Cc1nc(C(=O)Nc2cccc(Cl)c2F)nn1Cc1cccc(C#N)c1] | N-(3-chloro-2-fluorophenyl)-1-(3-cyanobenzyl)-5-methyl-1H-1,2,4-triazole-3-carboxamide | MS (ES+) $C_{18}H_{13}N_5OClF$ requires: 369, found: 370 [M + H]+. $^1$H NMR (400 MHz, DMSO-$d_6$) δ: 10.17 (s, 1H) 7.86-7.78 (m, 2H) 7.70-7.65 (m, 1H) 7.64-7.58 (m, 2H) 7.44-7.42 (m, 1H) 7.26-7.22 (m, 1H) 5.56 (s, 2H) 2.55 (s, 3H) | 4 |
| 35 | 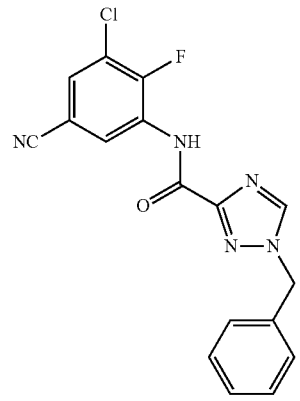 [SMILES: N#Cc1cc(Cl)c(F)c(NC(=O)c2ncn(Cc3ccccc3)n2)c1] | 1-benzyl-N-(3-chloro-5-cyano-2-fluorophenyl)-1H-1,2,4-triazole-3-carboxamide | MS (ES+) $C_{17}H_{11}N_5ClOF$ requires: 355, found: 356 [M + H]+. $^1$H NMR (400 MHz, DMSO-$d_6$) δ: 10.47 (s, 1H) 8.94 (s, 1H) 8.14-8.15 (m, 2H) 7.33-7.42 (m, 5H) 5.55 (s, 2H) | 12 |

TABLE 1-continued

RIPK1 inhibitors 20-46 and 51-53.

| Ex. No. | Structure | Name | Analysis | Proc. Ex. No. |
|---|---|---|---|---|
| 36 | 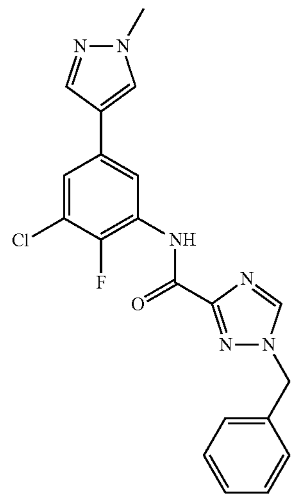 [SMILES: Cn1cc(-c2cc(Cl)c(F)c(NC(=O)c3ncn(Cc4ccccc4)n3)c2)cn1] | 1-benzyl-N-(3-chloro-2-fluoro-5-(1-methyl-1H-pyrazol-4-yl)phenyl)-1H-1,2,4-triazole-3-carboxamide | MS (ES+) $C_{20}H_{16}N_6OClF$ requires: 410, found: 411 [M + H]+. $^1$H NMR (400 MHz, DMSO-$d_6$) δ: 10.25 (s, 1H) 8.92 (s, 1H) 8.19 (s, 1H) 7.88 (s, 1H) 7.75-7.77 (m, 1H) 7.67-7.68 (m, 1H) 7.34-7.40 (m, 5H) 5.54 (s, 2H) 3.85 (s, 3H) | 12 |
| 37 | 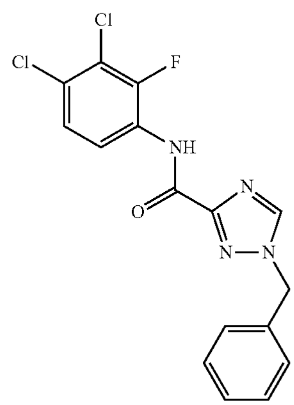 [SMILES: O=C(Nc1ccc(Cl)c(Cl)c1F)c1ncn(Cc2ccccc2)n1] | 1-benzyl-N-(3,4-dichloro-2-fluoro-phenyl)-1H-1,2,4-triazole-3-carboxamide | MS (ES+) $C_{16}H_{11}N_4FCl_2O$ requires: 364, found: 365 [M + H]+. $^1$H NMR (400 MHz, DMSO-$d_6$) δ: 10.28 (s, 1H) 8.92 (s, 1H) 7.70-7.72 (m, 1H) 7.53-7.55 (m, 1H) 7.33-7.39 (m, 5H) 5.54 (s, 2H) | 12 |
| 38 | 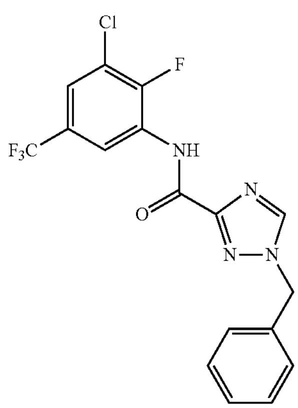 [SMILES: O=C(Nc1cc(C(F)(F)F)cc(Cl)c1F)c1ncn(Cc2ccccc2)n1] | 1-benzyl-N-(3-chloro-2-fluoro-5-(trifluoro-methyl)phenyl)-1H-1,2,4-triazole-3-carboxamide | MS (ES+) $C_{17}H_{11}N_4OClF$ requires: 398, found: 399 [M + H]+. $^1$H NMR (400 MHz, DMSO-$d_6$) δ: 10.43 (s, 1H) 8.95 (s, 1H) 8.11 (d, J = 4.4 Hz, 1H) 7.95 (d, J = 4.4 Hz, 1H) 7.32-7.43 (m, 5H) 5.56 (s, 2H) | 12 |

TABLE 1-continued

RIPK1 inhibitors 20-46 and 51-53.

| Ex. No. | Structure | Name | Analysis | Proc. Ex. No. |
|---|---|---|---|---|
| 39 | 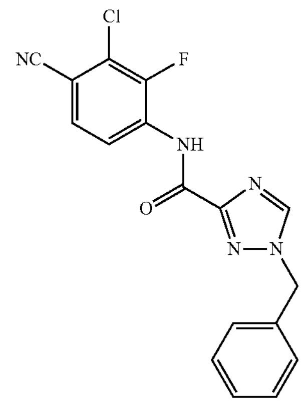 [SMILES: N#Cc1ccc(NC(=O)c2ncn(Cc3ccccc3)n2)c(F)c1Cl] | 1-benzyl-N-(3-chloro-4-cyano-2-fluorophenyl)-1H-1,2,4-triazole-3-carboxamide | MS (ES+) $C_{17}H_{11}N_5ClOF$ requires: 355, found: 356 [M + H]+. $^1$H NMR (400 MHz, DMSO-$d_6$) δ: 10.41 (s, 1H) 8.95 (s, 1H) 7.88-8.01 (m, 1H) 7.85-7.86 (m, 1H) 7.34-7.39 (m, 5H) 5.55 (s, 2H) | 12 |
| 40 | 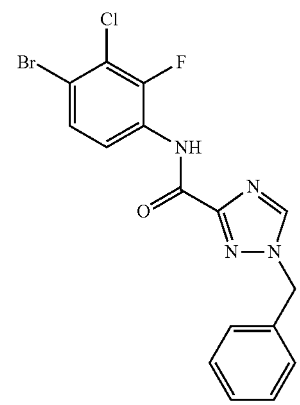 | 1-benzyl-N-(4-bromo-3-chloro-2-fluoro-phenyl)-1H-1,2,4-triazole-3-carboxamide | MS (ES+) $C_{16}H_{11}N_4OClFBr$ requires: 409, found: 410 [M + H]+. $^1$H NMR (400 MHz, DMSO-$d_6$) δ: 10.26 (s, 1H) 8.89 (s, 1H) 7.61-7.70 (m, 2H) 7.34-7.42 (m, 5H) 5.53 (s, 2H) | 12 |
| 41 | 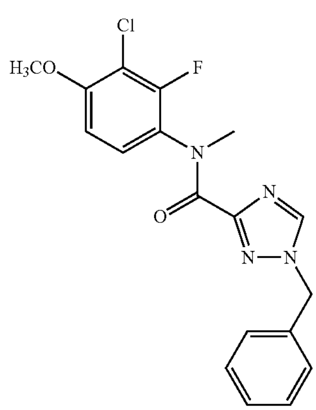 [SMILES: COc1ccc(N(C)C(=O)c2ncn(Cc3ccccc3)n2)c(F)c1Cl] | 1-benzyl-N-(3-chloro-2-fluoro-4-methoxy-phenyl)-N-methyl-1H-1,2,4-triazole-3-carboxamide | MS (ES+) $C_{18}H_{16}N_4O_2ClF$ requires: 374, found: 375 [M + H]+. $^1$H NMR (400 MHz, MeOD) δ: 8.43 (s, 1H) 7.24-7.35 (m, 3H) 7.10 (t, J = 8.7 Hz, 1H) 6.97-7.05 (m, 2H) 6.72 (dd, J = 2, 10 Hz, 1H) 5.24 (s, 2H) 3.88 (s, 3H) 3.38 (s, 3H) | 12 |

TABLE 1-continued

RIPK1 inhibitors 20-46 and 51-53.

| Ex. No. | Structure | Name | Analysis | Proc. Ex. No. |
|---|---|---|---|---|
| 42 | 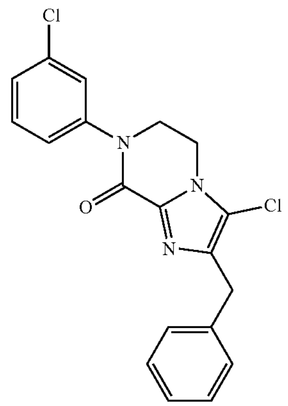 [SMILES: O=C1c2nc(Cc3ccccc3)c(Cl)n2CCN1c1cccc(Cl)c1] | 2-benzyl-3-chloro-7-(3-chlorophenyl)-6,7-dihydroimidazo[1,2-a]pyrazin-8(5H)-one | MS (ES+) $C_{19}H_{15}N_3OCl_2$ requires: 371 found: 372 [M + H]+. $^1$H NMR (400 MHz, DMSO-$d_6$) δ: 7.45-7.51 (m, 2H) 7.37-7.38 (m, 2H) 7.26-7.30 (m, 5H) 4.29-4.32 (m, 2H) 4.18-4.21 (m, 2H) 3.89 (s, 2H) | 16 |
| 43 | 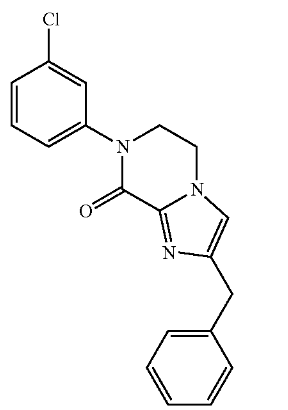 [SMILES: O=C1c2nc(Cc3ccccc3)cn2CCN1c1cccc(Cl)c1] | 2-benzyl-7-(3-chlorophenyl)-6,7-dihydroimidazo[1,2-a]pyrazin-8(5H)-one | MS (ES+) $C_{19}H_{16}N_3OCl$ requires: 337 found: 338 [M + H]+. $^1$H NMR (400 MHz, MeOD) δ: 7.52 (s, 1H) 7.43-7.47 (m, 1H), 7.33-7.39 (m, 2H) 7.25-7.32 (m, 4H) 7.18-7.19 (m, 1H) 7.03 (s, 1H), 4.41-4.44 (m, 2H) 4.20-4.23 (m, 2H) 3.97 (s, 2H) | 15 |
| 44 | 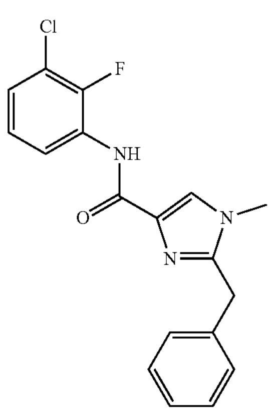 [SMILES: Cn1cc(C(=O)Nc2cccc(Cl)c2F)nc1Cc1ccccc1] | 2-benzyl-N-(3-chloro-2-fluorophenyl)-1-methyl-1H-imidazole-4-carboxamide | MS (ES+) $C_{18}H_{15}N_3OClF$ requires: 343 found: 344 [M + H]+. $^1$H NMR (400 MHz, DMSO-$d_6$) δ: 9.54 (s, 1H) 7.95-7.98 (m, 1H) 7.83 (s, 1H) 7.31-7.35 (m, 3H) 7.19-7.25 (m, 4H) 4.16 (s, 2H) 3.56 (s, 3H) | 13 |

TABLE 1-continued

RIPK1 inhibitors 20-46 and 51-53.

| Ex. No. | Structure | Name | Analysis | Proc. Ex. No. |
|---|---|---|---|---|
| 45 | 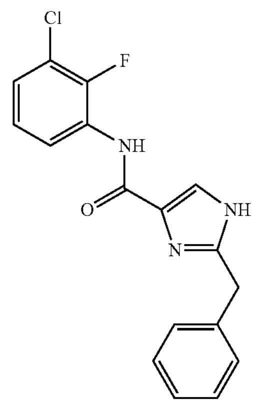 [SMILES: O=C(Nc1cccc(Cl)c1F)c1c[nH]c(Cc2ccccc2)n1] | 2-benzyl-N-(3-chloro-2-fluorophenyl)-1H-imidazole-4-carboxamide | MS (ES+) $C_{17}H_{13}N_3OClF$ requires: 329 found: 330 [M + H]+. $^1$H NMR (400 MHz, DMSO-$d_6$) δ: 7.94 (br, 1H) 7.75 (s, 1H) 7.20-7.31 (m, 8H) 4.04 (s, 2H) | 13 |
| 46 | 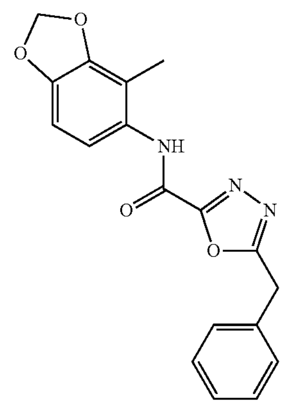 [SMILES: Cc1c(NC(=O)c2nnc(Cc3ccccc3)o2)ccc2c1OCO2] | 5-benzyl-N-(4-methyl-benzo[d][1,3]dioxol-5-yl)-1,3,4-oxadiazole-2-carboxamide | MS (ES+) $C_{18}H_{15}N_3O_4$ requires: 337, found: 338 [M + H]+. $^1$H NMR (400 MHz, DMSO-$d_6$) δ: 10.63 (s, 1H) 7.35-7.42 (m, 4H) 7.32 (m, 1H) 6.78 (s, 2H) 6.04 (s, 2H) 4.40 (s, 2H) 2.05 (s, 3H) | 19 |
| 51 | 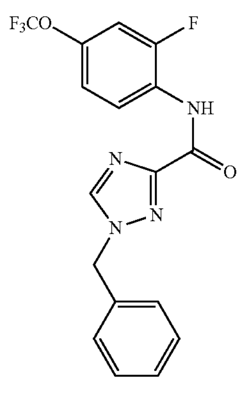 | 1-benzyl-N-(2-fluoro-4-(trifluoromethoxy)-phenyl)-1H-1,2,4-triazole-3-carboxamide | MS (ES+) $C_{17}H_{12}F_4N_4O_2$ requires: 380, found: 381 [M + H]+. $^1$H NMR (600 MHz, DMSO-$d_6$) δ 10.18 (s, 1H), 8.93 (s, 1H), 7.89-7.74 (m, 1H), 7.59-7.48 (m, 1H), 7.44-7.32 (m, 5H), 7.31-7.26 (m, 1H), 5.55 (s, 2H). | 19 |
| 52 | 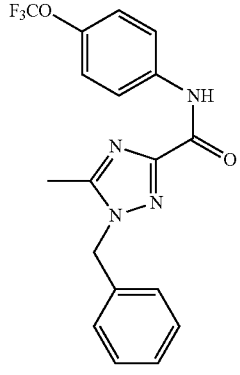 | 1-benzyl-5-methyl-N-(4-(trifluoromethoxy)-phenyl)-1H-1,2,4-triazole-3-carboxamide | MS (ES+) $C_{18}H_{15}F_3N_4O_2$ requires: 376, found: 377 [M + H]+. $^1$H NMR (600 MHz, CDCl$_3$) δ 8.94 (s, 1H), 7.82-7.75 (m, 2H), 7.41-7.35 (m, 3H), 7.26 (s, 4H), 5.41 (s, 2H), 2.47 (s, 3H). | 19 |

TABLE 1-continued

RIPK1 inhibitors 20-46 and 51-53.

| Ex. No. | Structure | Name | Analysis | Proc. Ex. No. |
|---|---|---|---|---|
| 53 | (structure shown) | 1-benzyl-N-(3-methyl-4-(trifluoromethoxy)-phenyl)-1H-1,2,4-triazole-3-carboxamide | MS (ES+) $C_{18}H_{15}F_3N_4O_2$ requires: 376, found: 377 [M + H]+. $^1$H NMR (600 MHz, DMSO-$d_6$) δ 10.50 (s, 1H), 8.91 (s, 1H), 7.84 (s, 1H), 7.77-7.68 (m, 1H), 7.46-7.22 (m, 6H), 5.54 (s, 2H), 2.27 (s, 3H). | 19 |

Example 58

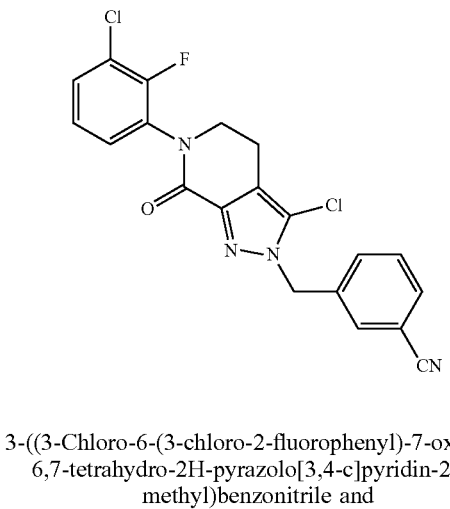

3-((3-Chloro-6-(3-chloro-2-fluorophenyl)-7-oxo-4,5,6,7-tetrahydro-2H-pyrazolo[3,4-c]pyridin-2-yl)methyl)benzonitrile and

Example 59

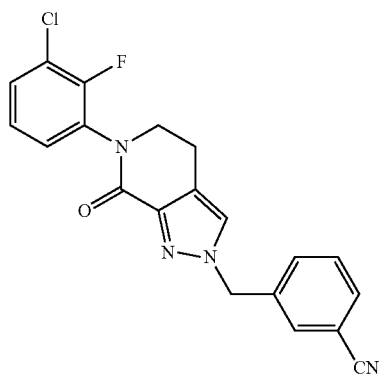 [SMILES: N#Cc1cccc(Cn2cc3c(n2)C(=O)N(c2cccc(Cl)c2F)CC3)c1]

3-((6-(3-chloro-2-fluorophenyl)-7-oxo-4,5,6,7-tetrahydro-2H-pyrazolo[3,4-c]pyridin-2-yl)methyl)benzonitrile 3-((3-Amino-6-(3-chloro-2-fluorophenyl)-7-oxo-4,5,6,7-tetrahydro-2H-pyrazolo[3,4-c]pyridin-2-yl)methyl)benzonitrile To a suspension of Intermediate C (800 mg, 4.4 mmol) in EtOH (8.7 ml, 0.5 M) was added HOAc (374 µl, 6.5 mmol), and the mixture was stirred for 15 minutes. Intermediate D (1162 mg, 4.36 mmol) was then added and the mixture was stirred at 65° C. overnight. The slurry was concentrated slowly under reduced pressure. The resulting solid was azeotroped with $CH_3CN$ to obtain the title compound as a yellow solid. The compound was taken forward to the next step without further purification.

LCMS(ES⁺) $C_{20}H_{15}ClFN_5O$ requires: 395, found 396 [M+H]⁺.

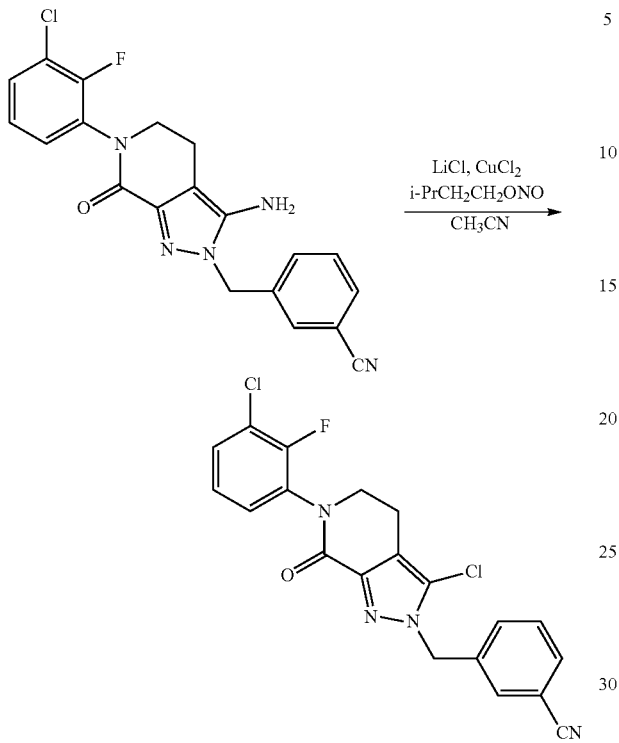

3-((3-Chloro-6-(3-chloro-2-fluorophenyl)-7-oxo-4,5,6,7-tetrahydro-2H-pyrazolo[3,4-c]pyridin-2-yl)methyl)benzonitrile (Example 58).

and 3-((3-Chloro-6-(3-chloro-2-fluorophenyl)-7-oxo-4,5,6,7-tetrahydro-2H-pyrazolo[3,4-c]pyridin-2-yl)methyl)benzonitrile (Example 59).

To a flask containing the dried product from the previous step (1.72 g, 4.4 mmol) was added CuCl₂ (1.17 g, 8.7 mmol) and LiCl (0.37 g, 8.7 mmol) and a stir bar, and the flask was sealed under an N₂ atmosphere. CH₃CN (22 ml, 0.2 M) was added and the entire flask was briefly sonicated under a N₂ balloon for 1 min until all solids were suspended in solvent. The flask was cooled to 0° C. and isopentyl nitrite (1.2 ml, 8.7 mmol) was added dropwise. The reaction was stirred at 0° C. briefly, then stirred at room temperature for 1 h. The brown slurry was cooled to 0° C., then saturated NH₄Cl solution and EtOAc were added. The mixture was stirred at 0° C. for 5 min, H₂O was added, and the layers were separated. The combined organic layers were washed with H₂O×2 and brine. The combined aqueous layers were extracted with EtOAc. The combined organic layers were dried over Na₂SO and concentrated. The residue was purified via silica gel chromatography (20-100% EtOAc in Hexanes).

The first eluting compound was the Example 58 compound (810 mg, 2.0 mmol, 45% yield over 2 steps) as a tan solid.

¹H NMR (300 MHz, CDCl₃) δ 7.65-7.54 (m, 3H), 7.51-7.45 (m, 1H), 7.41-7.27 (m, 2H), 7.20-7.08 (m, 1H), 5.47 (s, 2H), 3.95 (t, J=6.4 Hz, 2H), 2.94 (t, J=6.5 Hz, 2H).

LCMS(ES⁺) $C_{20}H_{13}Cl_2FN_4O$ requires: 414, found 415 [M+H]⁺.

The second eluting compound was the Example 59 compound.

¹H NMR (300 MHz, CDCl₃) δ 7.66-7.44 (m, 4H), 7.39-7.28 (m, 3H), 7.20-7.07 (m, 1H), 5.43 (s, 2H), 4.01-3.88 (m, 2H), 3.09-2.94 (m, 2H).

LCMS(ES⁺) $C_{20}H_{14}ClFN_4O$ requires: 380, found 381 [M+H]⁺.

Example 60

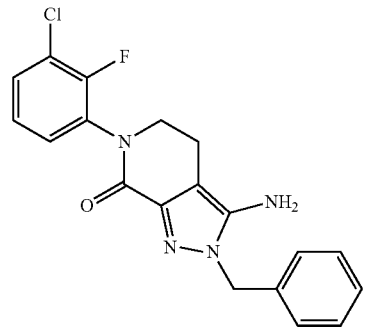

3-amino-2-benzyl-6-(3-chloro-2-fluorophenyl)-2,4,5,6-tetrahydro-7H-pyrazolo[3,4-c]pyridin-7-one

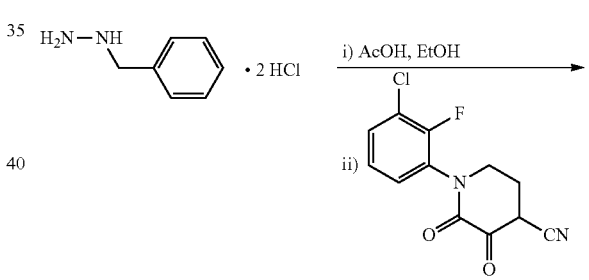

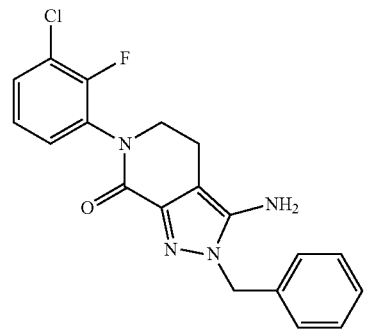 [SMILES: Nc1c2c(nn1Cc1ccccc1)C(=O)N(c1cccc(Cl)c1F)CC2]

To a solution of benzylhydrazine dihydrochloride (173 mg, 0.89 mmol) in EtOH (1770 μl) was added HOAc (144 μl, 1.77 mmol) and stirred for 30 min. Intermediate D (236 mg, 0.89 mmol) was then added, and the reaction was stirred at 65° C. overnight. The reaction was then concentrated to give the title compound (328 mg, 0.885 mmol).

LCMS(ES⁺) $C_{19}H_{16}ClFN_4O$ requires: 370, found 371 [M+H]⁺.

Example 61

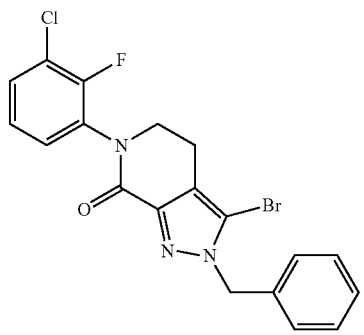 [SMILES: O=C1c2nn(Cc3ccccc3)c(Br)c2CCN1c1cccc(Cl)c1F]

2-benzyl-3-bromo-6-(3-chloro-2-fluorophenyl)-2,4,5,6-tetrahydro-7H-pyrazolo[3,4-c]pyridin-7-one

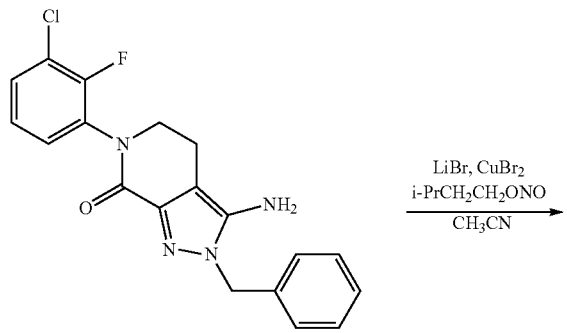

A mixture of LiBr (14.1 mg, 0.162 mmol), $CuBr_2$ (36.1 mg, 0.162 mmol) and the Example 60 material (40 mg, 0.108 mmol) in $CH_3CN$ (539 µl) under $N_2$ atm was cooled to 0° C. Isopentyl nitrite (21.8 µl, 0.16 mmol) was then added, and the mixture was stirred at 0° C. for 15 min. The reaction was warmed to room temperature and stirred for 1 h. $H_2O$ and EtOAc were added, and the mixture was stirred for 5 min, and the layers were separated. The aqueous phase was extracted with EtOAc×3. The combined organic layers were washed with brine, dried over $Na_2SO_4$, and concentrated under reduced pressure. The residue was purified via silica gel chromatography (0-100% EtOAc in Hexanes) to give the title compound (20 mg, 0.046 mmol, 43% yield) as a tan solid.

$^1$H NMR (500 MHz, $CDCl_3$) δ 7.39-7.27 (m, 7H), 7.17-7.09 (m, 1H), 5.48 (s, 2H), 3.96-3.89 (m, 2H), 2.93-2.84 (m, 2H).

LCMS(ES$^+$) $C_{19}H_{14}BrClFN_3O$ requires: 433, found 434 [M+H]$^+$.

The following compounds were prepared using methods similar to that used for Example 58, above.

TABLE 2

Examples 62-69.

| Ex. No | Structure | Name | $^1$H NMR | Analysis |
|---|---|---|---|---|
| 62 | (Cl, F-phenyl substituted pyrazolo[3,4-c]pyridin-7-one with pyrazin-2-ylmethyl and 3-Cl) | 3-chloro-6-(3-chloro-2-fluorophenyl)-2-(pyrazin-2-ylmethyl)-2,4,5,6-tetrahydro-7H-pyrazolo[3,4-c]pyridin-7-one | δ 8.76-8.33 (m, 2H), 7.41-7.28 (m, 1H), 7.19-7.07 (m, 1H), 5.64 (s, 2H), 3.96 (t, J = 6.5 Hz, 2H), 2.97 (t, J = 6.5 Hz, 2H). | $C_{17}H_{12}Cl_2FN_5O$ requires: 391, found 392 [M + H]$^+$ |

TABLE 2-continued

Examples 62-69.

| Ex. No | Structure | Name | ¹H NMR | Analysis |
|---|---|---|---|---|
| 63 | 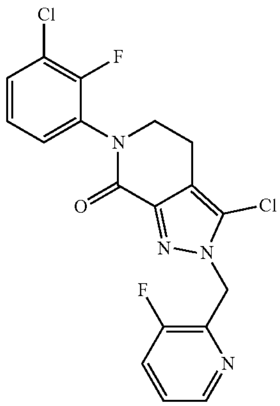 [SMILES: O=C1c2nn(Cc3ncccc3F)c(Cl)c2CCN1c1cccc(Cl)c1F] | 3-chloro-6-(3-chloro-2-fluorophenyl)-2-((3-fluoropyridin-2-yl)methyl)-2,4,5,6-tetrahydro-7H-pyrazolo[3,4-c]pyridin-7-one | δ 8.41-8.33 (m, 1H), 7.47-7.26 (m, 4H), 7.17-7.05 (m, 1H), 5.70-5.63 (m, 2H), 4.02-3.88 (m, 2H), 3.01-2.91 (m, 2H). | $C_{18}H_{12}Cl_2F_2N_4O$ requires: 408, found 409 $[M + H]^+$ |
| 64 | 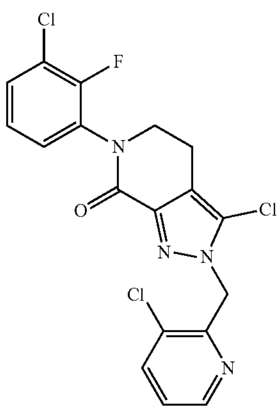 [SMILES: O=C1c2nn(Cc3ncccc3Cl)c(Cl)c2CCN1c1cccc(Cl)c1F] | 3-chloro-6-(3-chloro-2-fluorophenyl)-2-((3-chloropyridin-2-yl)methyl)-2,4,5,6-tetrahydro-7H-pyrazolo[3,4-c]pyridin-7-one | δ 8.44-8.39 (m, 1H), 7.74-7.68 (m, 1H), 7.39-7.32 (m, 1H), 7.32-7.27 (m, 1H), 7.24-7.18 (m, 1H), 7.16-7.08 (m, 1H), 5.72 (s, 2H), 3.97 (t, J = 6.5 Hz, 2H), 2.99 (t, J = 6.5 Hz, 2H). | $C_{18}H_{12}Cl_3FN_4O$ requires: 424, found 425 $[M + H]^+$ |
| 65 | 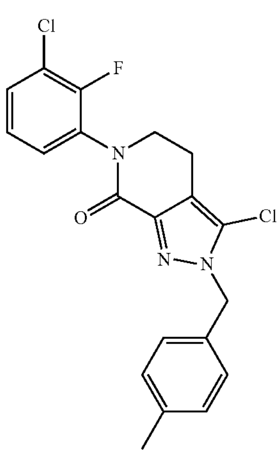 [SMILES: Cc1ccc(Cn2nc3c(c2Cl)CCN(c2cccc(Cl)c2F)C3=O)cc1] | 3-chloro-6-(3-chloro-2-fluorophenyl)-2-(4-methylbenzyl)-2,4,5,6-tetrahydro-7H-pyrazolo[3,4-c]pyridin-7-one | δ 7.39-7.28 (m, 2H), 7.25-7.10 (m, 5H), 5.40 (s, 2H), 3.96-3.86 (m, 2H), 2.89 (t, J = 6.5 Hz, 2H), 2.33 (s, 3H). | |

TABLE 2-continued

Examples 62-69.

| Ex. No | Structure | Name | ¹H NMR | Analysis |
|---|---|---|---|---|
| 66 | 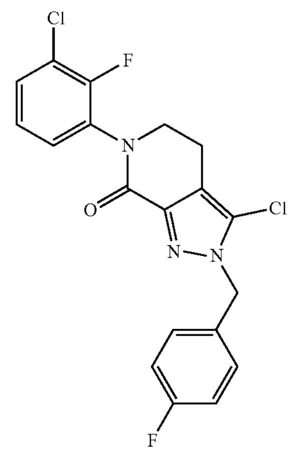 [SMILES: O=C1c2nn(Cc3ccc(F)cc3)c(Cl)c2CCN1c1cccc(Cl)c1F] | 3-chloro-6-(3-chloro-2-fluorophenyl)-2-(4-fluorobenzyl)-2,4,5,6-tetrahydro-7H-pyrazolo[3,4-c]pyridin-7-one | δ 7.39-7.27 (m, 4H), 7.18-7.09 (m, 1H), 7.07-6.99 (m, 2H), 5.41 (s, 2H), 3.95-3.89 (m, 2H), 2.94-2.85 (m, 2H). | $C_{19}H_{13}Cl_2F_2N_3O$ requires: 407, found 408 $[M + H]^+$ |
| 67 | 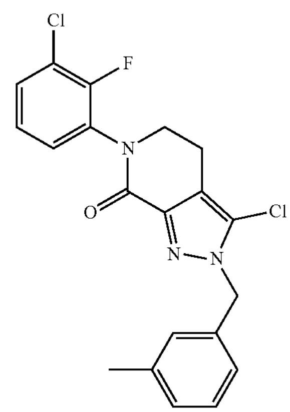 [SMILES: Cc1cccc(Cn2nc3c(c2Cl)CCN(c2cccc(Cl)c2F)C3=O)c1] | 3-chloro-6-(3-chloro-2-fluorophenyl)-2-(3-methylbenzyl)-2,4,5,6-tetrahydro-7H-pyrazolo[3,4-c]pyridin-7-one | δ 7.39-7.27 (m, 2H), 7.24-7.20 (m, 1H), 7.18-7.08 (m, 4H), 5.40 (s, 2H), 3.97-3.87 (m, 2H), 2.97-2.82 (m, 2H), 2.37-2.31 (m, 3H). | $C_{20}H_{16}Cl_2FN_3O$ requires: 403, found 404 $[M + H]^+$ |
| 68 | 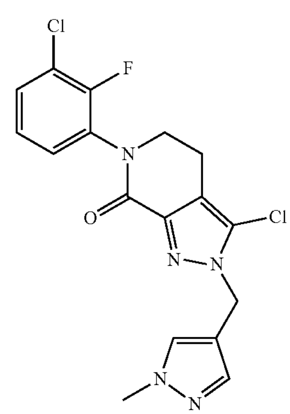 [SMILES: Cn1cc(Cn2nc3c(c2Cl)CCN(c2cccc(Cl)c2F)C3=O)cn1] | 3-chloro-6-(3-chloro-2-fluorophenyl)-2-((1-methyl-1H-pyrazol-4-yl)methyl)-2,4,5,6-tetrahydro-7H-pyrazolo[3,4-c]pyridin-7-one | δ 7.64-7.46 (m, 2H), 7.41-7.27 (m, 2H), 7.18-7.06 (m, 1H), 5.32 (s, 2H), 3.96-3.83 (m, 5H), 2.97-2.82 (m, 2H). | $C_{17}H_{14}Cl_2FN_5O$ requires: 393, found 394 $[M + H]^+$ |

TABLE 2-continued

Examples 62-69.

| Ex. No | Structure | Name | ¹H NMR | Analysis |
|---|---|---|---|---|
| 69 | 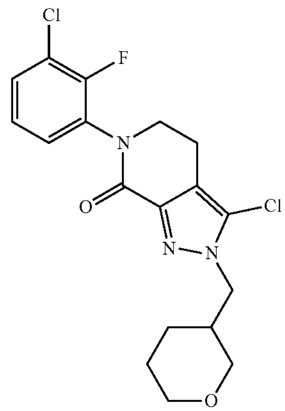 [SMILES: O=C1c2nn(CC3CCCOC3)c(Cl)c2CCN1c1cccc(Cl)c1F] | 3-chloro-6-(3-chloro-2-fluorophenyl)-2-((tetrahydro-2H-pyran-3-yl)methyl)-2,4,5,6-tetrahydro-7H-pyrazolo[3,4-c]pyridin-7-one | δ 7.39-7.27 (m, 2H), 7.16-7.09 (m, 1H), 4.16 (d, J = 7.3 Hz, 2H), 3.98-3.88 (m, 2H), 3.85-3.74 (m, 2H), 3.55-3.45 (m, 1H), 3.37-3.27 (m, 1H), 2.98-2.84 (m, 2H), 2.45-2.25 (m, 1H), 1.85-1.55 (m, 3H), 1.42-1.30 (m, 1H). | $C_{18}H_{18}Cl_2FN_3O_2$ requires: 397, found 398 $[M + H]^+$ |

Example 70

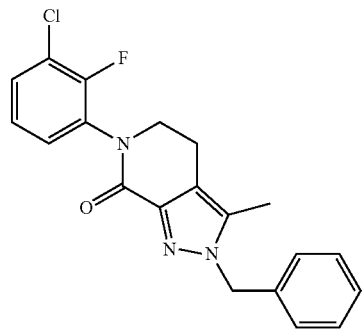 [SMILES: Cc1c2c(nn1Cc1ccccc1)C(=O)N(c1cccc(Cl)c1F)CC2]

2-benzyl-6-(3-chloro-2-fluorophenyl)-3-methyl-2,4,5,6-tetrahydro-7H-pyrazolo[3,4-c]pyridin-7-one

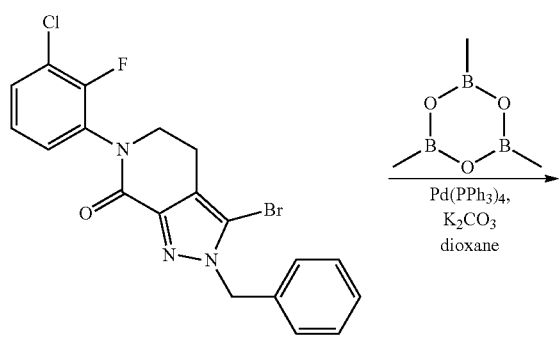

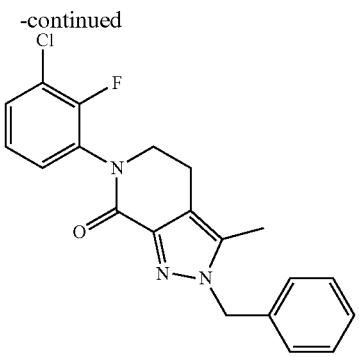

A solution of the Example 61 material (20 mg, 0.046 mmol), K₂CO₃ (12.7 mg, 0.092 mmol) and Pd(PPh₃)4 (5.3 mg, 4.60 μmol) in 1,4-dioxane (230 μl) was degassed with N₂ for 1 min. 2,4,6-trimethyl-1,3,5,2,4,6-trioxatriborinane (8.66 mg, 0.069 mmol) was added, and the reaction mixture was heated at 100° C. for 16 h. The reaction was concentrated, and the residue was purified by mass-triggered preparative HPLC (Mobile phase: A=0.1% TFA/H₂O, B=0.1% TFA/CH₃CN; Gradient: B=10-90%; 12 min; Column: C18) to give the title compound (3.3 mg, 8.92 μmol, 19% yield) as an off-white solid.

¹H NMR (300 MHz, CDCl₃) δ 7.40-7.28 (m, 5H), 7.24-7.07 (m, 3H), 5.40 (s, 2H), 3.91 (t, J=6.3 Hz, 2H), 2.85 (t, J=6.4 Hz, 2H), 2.15 (s, 3H).

LCMS(ES⁺) $C_{20}H_{17}ClFN_3O$ requires: 369, found 370 $[M+H]^+$.

Example 71

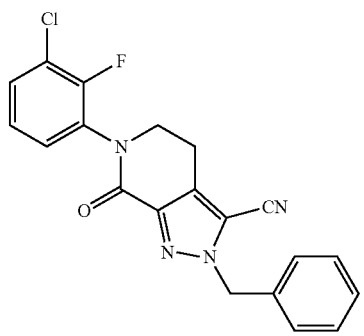 [SMILES: N#Cc1c2c(nn1Cc1ccccc1)C(=O)N(c1cccc(Cl)c1F)CC2]

2-benzyl-6-(3-chloro-2-fluorophenyl)-7-oxo-4,5,6,7-tetrahydro-2H-pyrazolo[3,4-c]pyridine-3-carbonitrile

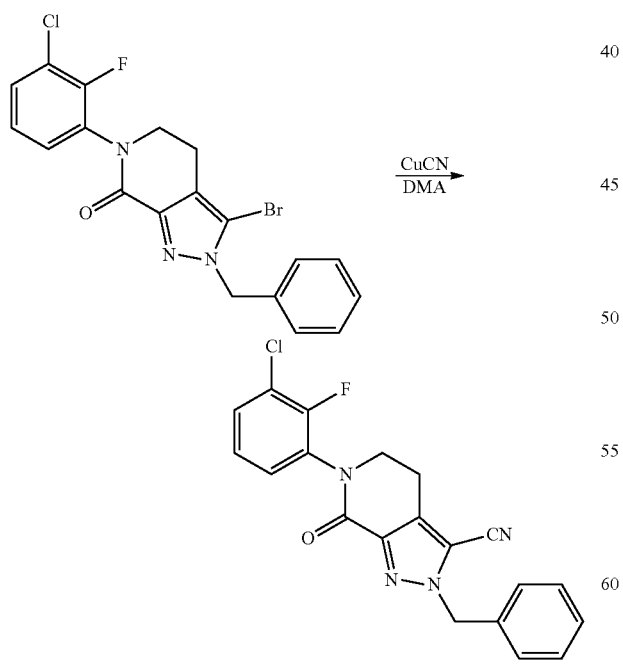

To a solution of the Example 61 material (200 mg, 0.460 mmol) in DMA (920 μl) was added CuCN (61.8 mg, 0.690 mmol), and the resulting mixture was stirred at 150° C. for 20 h. The reaction mixture was allowed to cool to room temperature. The reaction mixture was diluted with EtOAc, 30% NH$_4$OH solution and H$_2$O were added, and the layers were separated. The aqueous phase was extracted with EtOAc. The combined organic layers were washed with brine, dried over Na$_2$SO$_4$, and concentrated under reduced pressure. The residue was purified via silica gel chromatography (0-100% EtOAc in Hexanes) to give the title compound (100 mg, 0.263 mmol, 57% yield) as a tan solid.

$^1$H NMR (500 MHz, CDCl$_3$) δ 7.47-7.43 (m, 2H), 7.41-7.32 (m, 4H), 7.30-7.26 (m, 1H), 7.17-7.12 (m, 1H), 5.55 (s, 2H), 3.95 (t, J=6.6 Hz, 2H), 3.10 (t, J=6.5 Hz, 2H).

LCMS(ES$^+$) C$_{20}$H$_{14}$ClFN$_4$O requires: 380, found 381 [M+H]$^+$.

Example 72

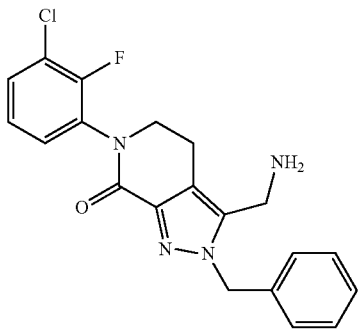 [SMILES: NCc1c2c(nn1Cc1ccccc1)C(=O)N(c1cccc(Cl)c1F)CC2]

3-(aminomethyl)-2-benzyl-6-(3-chloro-2-fluorophenyl)-2,4,5,6-tetrahydro-7H-pyrazolo[3,4-c]pyridin-7-one and

Example 73

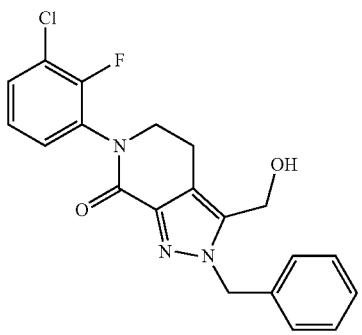 [SMILES: O=C1c2nn(Cc3ccccc3)c(CO)c2CCN1c1cccc(Cl)c1F]

2-benzyl-6-(3-chloro-2-fluorophenyl)-3-(hydroxymethyl)-2,4,5,6-tetrahydro-7H-pyrazolo[3,4-c]pyridin-7-one

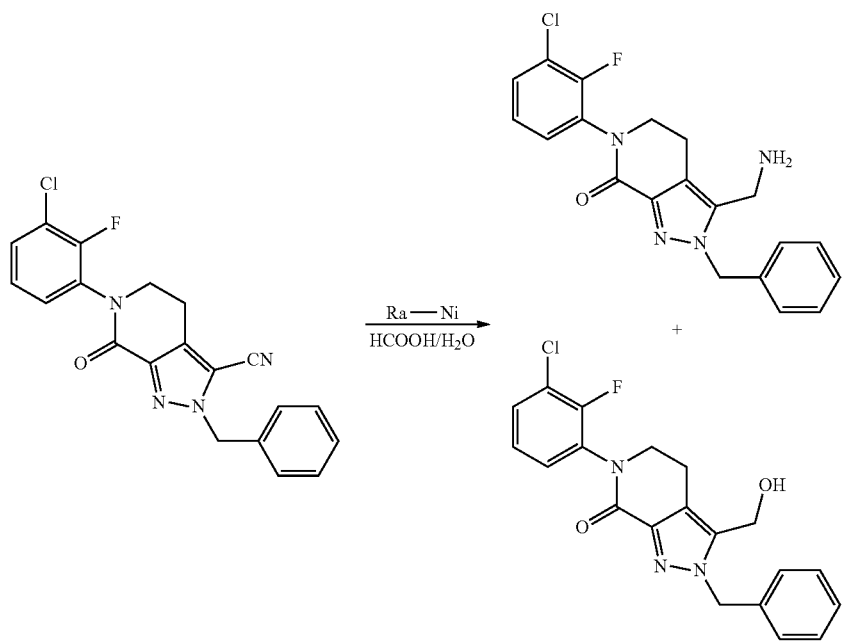

3-(aminomethyl)-2-benzyl-6-(3-chloro-2-fluorophenyl)-2,4,5,6-tetrahydro-7H-pyrazolo[3,4-c]pyridin-7-one (Example 72).
and
2-benzyl-6-(3-chloro-2-fluorophenyl)-3-(hydroxymethyl)-2,4,5,6-tetrahydro-7H-pyrazolo[3,4-c]pyridin-7-one (Example 73).

To a solution of the Example 71 material (10 mg, 0.026 mmol) in formic acid (197 μl) was added Raney Nickel (20 mg, 0.026 mmol) and H$_2$O (66 μl), and the resulting mixture was stirred at 25° C. for 0.25 h. The reaction was then heated at 65° C. for 1 h. The reaction was filterd through CELITE®, and the filter cake was washed with H$_2$O and EtOAc. The layers were separated and the aqueous layers were extracted with EtOAc. The combined organic layers were concentrated. The residue was purified by mass-triggered preparative HPLC (Mobile phase: A=0.1% TFA/H$_2$O, B=0.1% TFA/CH$_3$CN; Gradient: B=10-90%; 20 min; Column: C18).

The first eluting compound was the Example 72 compound (1.1 mg, 2.86 μmol, 11% yield, TFA salt) as a white powder.

$^1$H NMR (500 MHz, DMSO-d$_6$) δ 8.19 (s, 3H), 7.57 (ddd, J=8.3, 6.8, 1.6 Hz, 1H), 7.49 (ddd, J=8.4, 6.8, 1.6 Hz, 1H), 7.42-7.35 (m, 2H), 7.35-7.28 (m, 2H), 7.24-7.18 (m, 2H), 5.56 (s, 2H), 4.21 (s, 2H), 3.96-3.93 (m, 2H), 3.00 (t, J=6.5 Hz, 2H).

LCMS(ES$^+$) C$_{20}$H$_{18}$ClFN$_4$O requires: 384 found 385 [M+H]$^+$.

The second eluting compound was the example 73 compound (1 mg, 2.59 mmol, 10% yield).

$^1$H NMR (500 MHz, DMSO-d$_6$) δ 7.55 (ddd, J=8.3, 6.7, 1.6 Hz, 1H), 7.47 (ddd, J=8.3, 6.9, 1.6 Hz, 1H), 7.39-7.33 (m, 2H), 7.32-7.22 (m, 4H), 6.53 (s, 1H), 5.45 (s, 2H), 4.54-4.50 (m, 2H), 3.91 (t, J=6.4 Hz, 2H), 2.92 (t, J=6.5 Hz, 2H).

LCMS(ES+) C$_{20}$H$_{17}$ClFN$_3$O$_2$ requires: 385, found 386 [M+H]$^+$.

Example 74

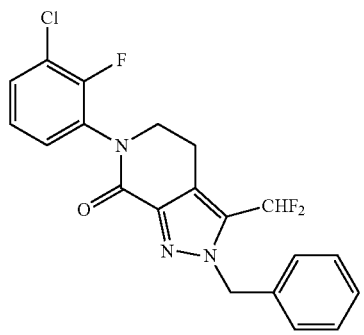 [SMILES: O=C1c2nn(Cc3ccccc3)c(C(F)F)c2CCN1c1cccc(Cl)c1F]

193

2-Benzyl-6-(3-chloro-2-fluorophenyl)-3-(difluoromethyl)-2,4,5,6-tetrahydro-7H-pyrazolo[3,4-c]pyridin-7-one

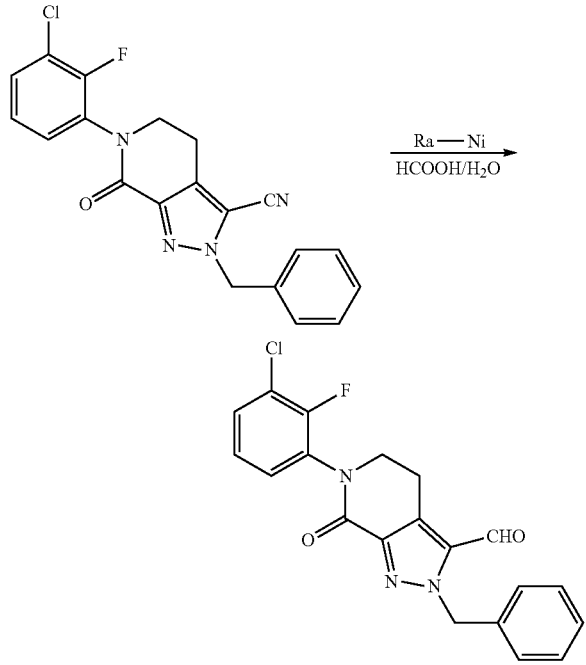

2-Benzyl-6-(3-chloro-2-fluorophenyl)-7-oxo-4,5,6,7-tetrahydro-2H-pyrazolo[3,4-c]pyridine-3-carbaldehyde To a solution of the Example 71 material (90 mg, 0.236 mmol) in HCOOH (1773 μl) and H₂O (591 μl) were added Raney Nickel (90 mg, 0.236 mmol), and the resulting mixture was stirred at 25° C. for 1 h. The reaction was then filtered and washed with EtOAc. The biphasic solution was quenched with saturated NaHCO₃ solution. The layers were separated, and the aqueous layer was extracted with EtOAc. The combined organic layers were washed with brine, dried over Na₂SO₄, and concentrated under reduced pressure. The residue was purified via silica gel chromatography (20-100% EtOAc in Hexanes) to give the title compound (19 mg, 0.050 mmol, 21% yield) as a colorless amorphous material.

LCMS(ES⁺) $C_{20}H_{15}ClFN_3O_2$ requires: 383, found 384 [M+H]⁺.

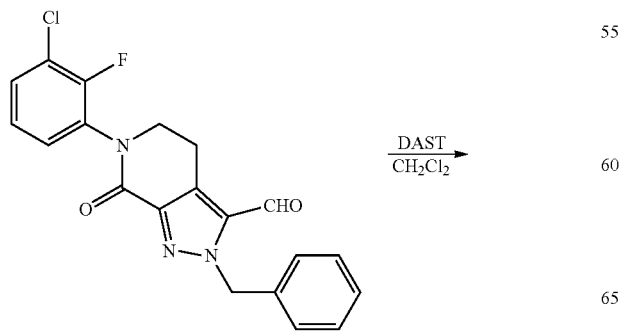

194

-continued

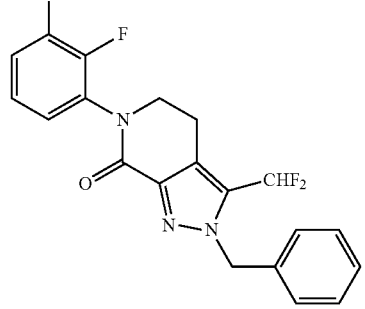

2-Benzyl-6-(3-chloro-2-fluorophenyl)-3-(difluoromethyl)-2,4,5,6-tetrahydro-7H-pyrazolo[3,4-c]pyridin-7-one
To a solution of the product from the previous step (19 mg, 0.050 mmol) in CH₂Cl₂ (495 μl) was added DAST (19.6 μl, 0.149 mmol), and the resulting mixture was stirred at 0° C. for 0.5 h, then let to stir at room temperature for 5 hr. The reaction was quenched with saturated NaHCO₃ solution, and extracted with EtOAc. The combined organic layers were dried over Na₂SO₄ and concentrated. The residue was purified via silica gel chromatography (0-100% EtOAc in Hexanes) to give the title compound (11 mg, 0.027 mmol, 55% yield) as a white solid.

¹H NMR (500 MHz, DMSO-d₆) δ 7.61-7.54 (m, 1H), 7.53-7.46 (m, 2H), 7.40-7.35 (m, 2H), 7.34-7.28 (m, 2H), 7.27-7.22 (m, 2H), 5.56 (s, 2H), 3.95 (t, J=6.6 Hz, 2H), 3.05 (t, J=6.5 Hz, 2H).

LCMS(ES⁺) $C_{20}H_{15}ClF_3N_3O$ requires: 405, found 406 [M+H]⁺.

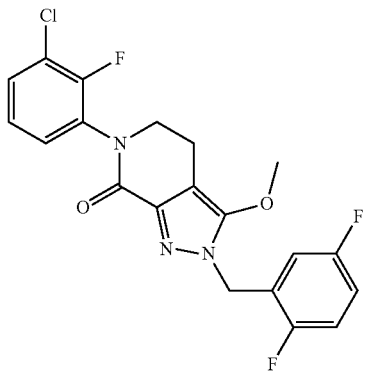 [SMILES: COc1c2c(nn1Cc1cc(F)ccc1F)C(=O)N(c1cccc(Cl)c1F)CC2]

6-(3-Chloro-2-fluorophenyl)-2-(2,5-difluorobenzyl)-3-methoxy-2,4,5,6-tetrahydro-7H-pyrazolo[3,4-c]pyridin-7-one

Example 75

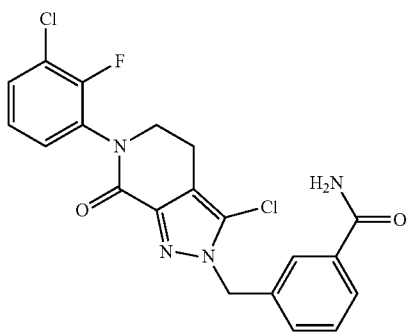 [SMILES: NC(=O)c1cccc(Cn2nc3c(c2Cl)CCN(c2cccc(Cl)c2F)C3=O)c1]

3-((3-chloro-6-(3-chloro-2-fluorophenyl)-7-oxo-4,5,6,7-tetrahydro-2H-pyrazolo[3,4-c]pyridin-2-yl)methyl)benzamide

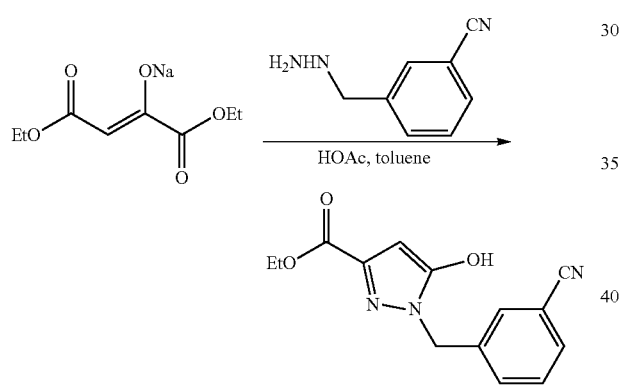

Ethyl 1-(3-cyanobenzyl)-5-hydroxy-1H-pyrazole-3-carboxylate To a solution of HOAc (68.67 g, 1.14 mol, 65.4 mL, 35 eq) in toluene (54 mL) was added sodium (Z)-1,4-diethoxy-1,4-dioxo-but-2-en-2-olate (8.24 g, 39.21 mmol, 1.2 eq) and Intermediate C (6 g, 32.67 mmol, 1 eq, HCl). The mixture was stirred at 110° C. for 16 h, then the resulting solid was removed by filtration and triturated with a mixture of EtOAc and petroleum ether (1:5) to isolate the title compound (6.5 g, 20.85 mmol, 64% yield, 87% purity) as an off-white solid.

LCMS(ES$^+$) $C_{14}H_{13}O_3N_3$ requires:271, found 272 [M+H]$^+$.

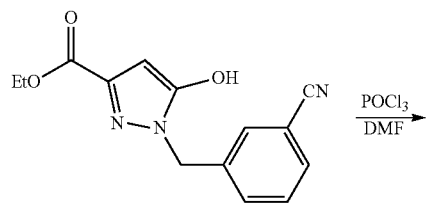

3-((5-chloro-3-(ethoxycarbonyl)-4-formyl-1H-pyrazol-1-yl)methyl)benzoic acid

To a solution of the product from the previous step (4.9 g, 18.06 mmol, 1 eq) in DMF (5.28 g, 72.25 mmol, 5.6 mL, 4 eq) was added POCl$_3$ (24.10 g, 157.15 mmol, 14.6 mL, 8.7 eq) at 25° C. The mixture was stirred at 90° C. for 16 h, then concentrated to dryness on a rotary evaporator. The residual POCl$_3$ was quenched by warm H$_2$O (100 mL). The mixture was poured into H$_2$O (60 mL) and extracted with EtOAc (60 mL×3). The combined organic layers were washed with brine (60 mL×3), dried over Na$_2$SO$_4$, and concentrated under reduced pressure to obtain a residue which was purified by column chromatography (SiO$_2$, petroleum ether/EtOAc=1/1) to afford the title compound (2.2 g, 3.07 mmol, 17% yield, 47% purity) as a yellow solid.

LCMS(ES$^+$) $C_{15}H_{13}O_5N_2Cl$ requires:336, found 359 [M+Na]+.

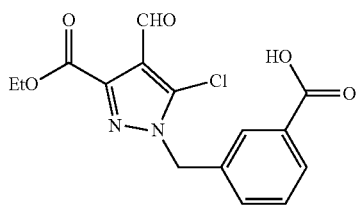

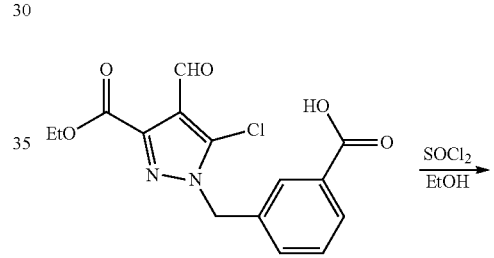

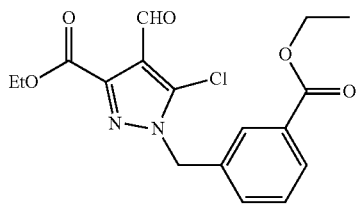

Ethyl 5-chloro-1-(3-(ethoxycarbonyl)benzyl)-4-formyl-1H-pyrazole-3-carboxylate To a solution of the product from the previous step (2.2 g, 3.07 mmol, 1 eq) in EtOH (20 mL) was added SOCl$_2$ (548.0 mg, 4.61 mmol, 334 uL, 1.5 eq). The mixture was stirred at 70° C. for 5 h, then concentrated under reduced pressure. The residue was then purified by column chromatography (SiO$_2$, petroleum ether/EtOAc=5/1) to afford the title compound (0.9 g, 2.47 mmol, 80% yield) as a white solid.

LCMS(ES$^+$) $C_{17}H_{17}O_5N_2Cl$ requires: 364, found 365 [M+H]$^+$.

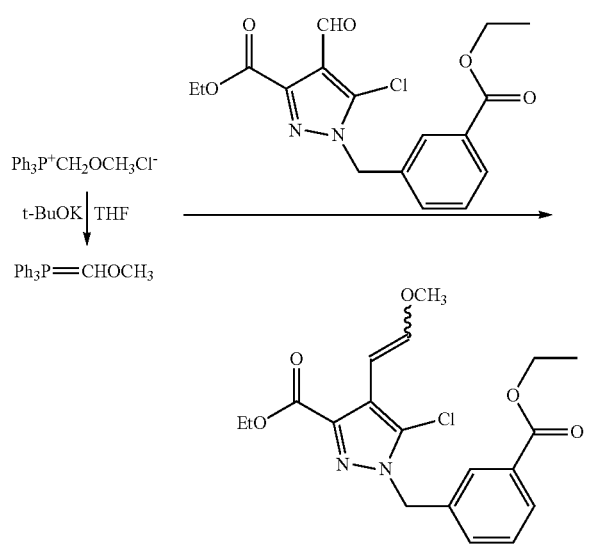

ethyl 5-chloro-1-(3-(ethoxycarbonyl)benzyl)-4-(2-methoxyvinyl)-1H-pyrazole-3-carboxylate To a solution of t-BuOK (1 M, 3.70 mL, 1.5 eq) in THF (3 mL) was added methoxymethyl(triphenyl)phosphonium chloride (1.27 g, 3.70 mmol, 1.5 eq) at 0° C. under $N_2$. The mixture was stirred at 0° C. for 10 min, then a solution of the product from the previous step (900 mg, 2.47 mmol, 1 eq) in THF (2 mL) at 0° C. was added. The mixture was then stirred at 25° C. for 16 h. The mixture was poured into $H_2O$ (10 mL) and extracted with EtOAc (10 mL×3). The combined organic layers were washed with brine (10 mL), dried over $Na_2SO_4$, and concentrated under reduced pressure. The residue was purified by column chromatography ($SiO_2$, petroleum ether/EtOAc=5/1) to afford the title compound (440 mg, 1.05 mmol, 43% yield, 94% purity) as a colourless oil.

LCMS(ES$^+$) $C_{19}H_{21}O_5N_2Cl$ requires:392, found 393 [M+H]$^+$.

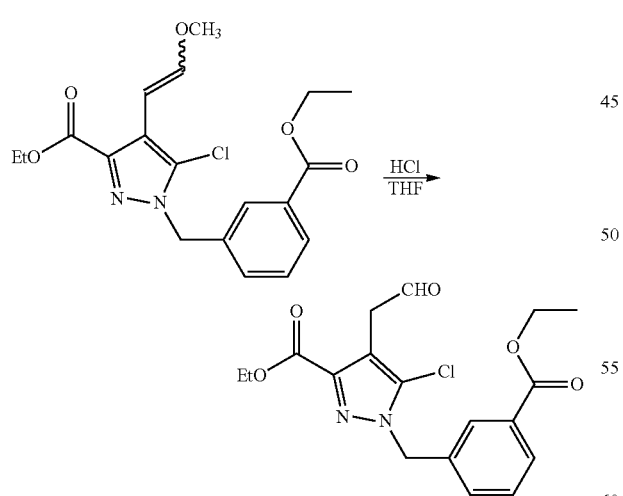

Ethyl 5-chloro-1-(3-(ethoxycarbonyl)benzyl)-4-(2-oxoethyl)-1H-pyrazole-3-carboxylate To a solution of the product from the previous step (430 mg, 1.09 mmol, 1 eq) in THF (3 mL) was added HCl (6 M, 21 mL, 115 eq). The mixture was stirred at 25° C. for 16 h, then poured into $H_2O$ (10 mL) and extracted with EtOAc (10 mL×3). The combined organic layers were dried over $Na_2SO_4$, and concentrated under reduced pressure to afford the title compound (387 mg, 899.04 μmol, 82% yield, 88% purity) as a colourless oil, which was used directly in the next step without further purification.

LCMS(ES$^+$) $C_{18}H_{19}O_5N_2Cl$ requires: 378, found 379 [M+H]$^+$.

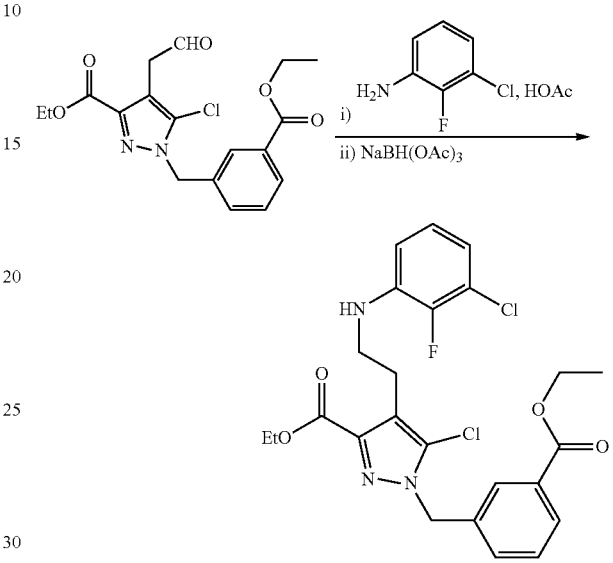

Ethyl 5-chloro-4-(2-((3-chloro-2-fluorophenyl)amino)ethyl)-1-(3-(ethoxycarbonyl)benzyl)-1H-pyrazole-3-carboxylate To a solution of the product from the previous step (350 mg, 813.08 μmol, 1 eq) in 1,2-dichloroethane (5 mL) was added NaBH(OAc)$_3$ (832.3 mg, 3.93 mmol, 4.83 eq), diethoxymethoxyethane (120.5 mg, 813.1 μmol, 135 uL, 1 eq) and AcOH (48.8 mg, 813.08 μmol, 46 uL, 1 eq). The mixture was stirred at 25° C. for 10 min, then 3-chloro-2-fluoroaniline (278.13 mg, 1.91 mmol, 2.35 eq) was added. The mixture was further stirred at 25° C. for 16 h, then poured into $H_2O$ (10 mL) and extracted with EtOAc (10 mL×3). The combined organic layers were dried over $Na_2SO_4$, and concentrated under reduced pressure to afford title compound (160 mg, 314.73 μmol, 39% yield) as a colourless oil, which was used in the next step without further purification.

LCMS(ES$^+$) $C_{24}H_{24}O_4N_3Cl_2F$ requires:507, found 508 [M+H]$^+$.

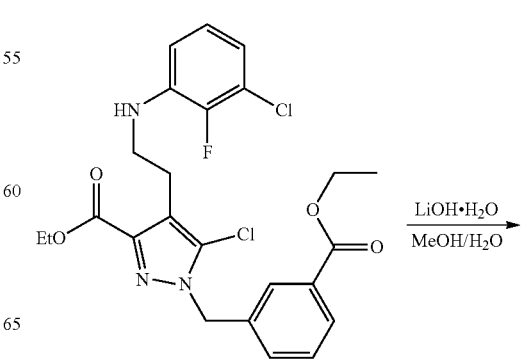

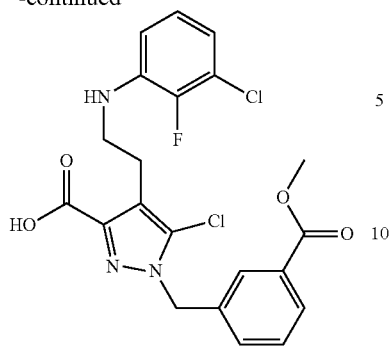

5-Chloro-4-(2-((3-chloro-2-fluorophenyl)amino)ethyl)-1-(3-(methoxycarbonyl)-benzyl)-1H-pyrazole-3-carboxylic acid To a solution of the product from the previous step (265 mg, 521.28 μmol, 1 eq) in H₂O (1 mL) was added a solution of LiOH·H₂O (26.3 mg, 625.53 μmol, 1.2 eq) in MeOH (5 mL) at 25° C. The mixture was stirred at 25° C. for 1 h, then poured into H₂O (10 mL). The pH was brought to 1 and the mixture was then extracted with EtOAc (10 mL×3). The combined organic layers were dried over Na₂SO₄ and concentrated under reduced pressure to afford the title compound (228 mg, 488.97 μmol, 94% yield) as a gray solid, which was used in the following step without further purification.

LCMS(ES+) $C_{21}H_{18}O_4N_3Cl_2F$ requires:465, found 466 [M+H]⁺.

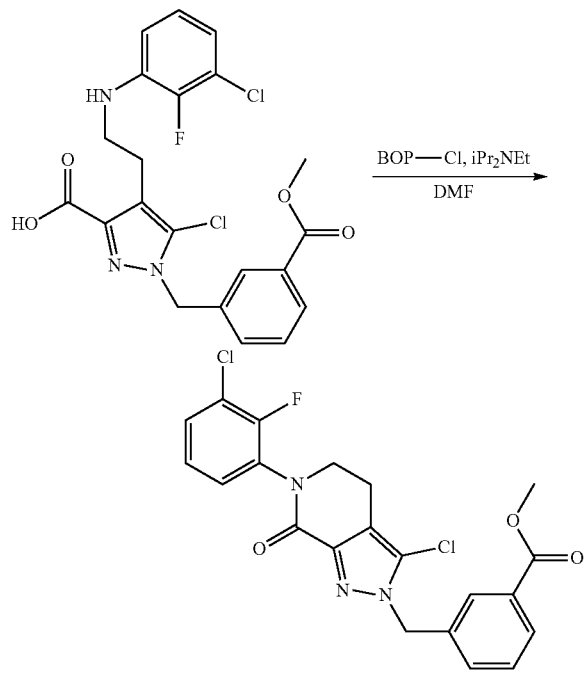

Methyl 3-((3-chloro-6-(3-chloro-2-fluorophenyl)-7-oxo-4,5,6,7-tetrahydro-2H-pyrazolo[3,4-c]pyridin-2-yl)methyl)benzoate To a solution of the product from the previous step (228 mg, 488.97 μmol, 1 eq) in CH₂Cl₂ (10 mL) was added BOP-Cl (186.7 mg, 733.45 μmol, 1.5 eq) and iPr₂NEt (189.6 mg, 1.47 mmol, 255 uL, 3 eq). The mixture was stirred at 25° C. for 4 h, then poured into H₂O (10 mL) and extracted with EtOAc (10 mL×3). The combined organic layers were dried over Na₂SO₄ and concentrated under reduced pressure. The residue was purified by column chromatography (SiO₂, petroleum ether/EtOAc=1/1) to afford the title compound (40 mg, 85.66 μmol, 18% yield, 96% purity) as a colourless oil.

¹H NMR (400 MHz, CDCl₃) δ=8.10-7.94 (m, 2H), 7.54-7.53 (m, 1H), 7.47-7.41 (m, 1H), 7.37 (dt, J=1.5, 7.4 Hz, 1H), 7.30 (dt, J=1.5, 7.4 Hz, 1H), 7.17-7.11 (m, 1H), 5.49 (s, 2H), 3.93 (s, 3H), 2.93 (t, J=6.4 Hz, 2H), 1.86 (m, 2H).

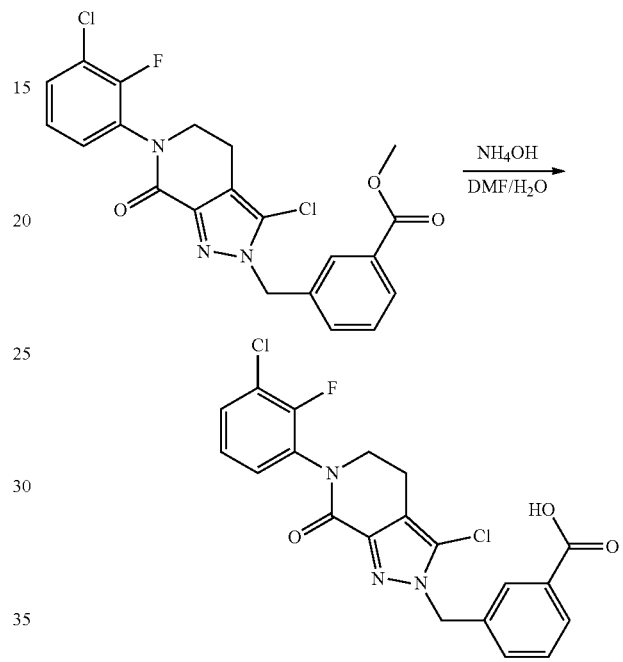

3-((3-Chloro-6-(3-chloro-2-fluorophenyl)-7-oxo-4,5,6,7-tetrahydro-2H-pyrazolo[3,4-c]pyridin-2-yl)methyl)benzoic acid To a mixture of the product from the previous step (20.69 mg, 46.16 μmol, 1 eq) in DMF (0.5 mL) and MeOH (0.5 mL) was added NH₄OH (455 mg, 4.15 mmol, 0.5 mL, 32% purity, 90 eq). The mixture was stirred at 80° C. for 14 h, then poured into H₂O (10 mL) and extracted with EtOAc (10 mL×3). The combined organic layers were dried over Na₂SO₄ and concentrated under reduced pressure to afford the title compound (21 mg, crude) as a colourless oil, which was used in the following step without further purification.

LCMS(ES⁺) $C_{20}H_{14}Cl_2FN_3O_3$ requires: 433, found 434 [M+H]⁺.

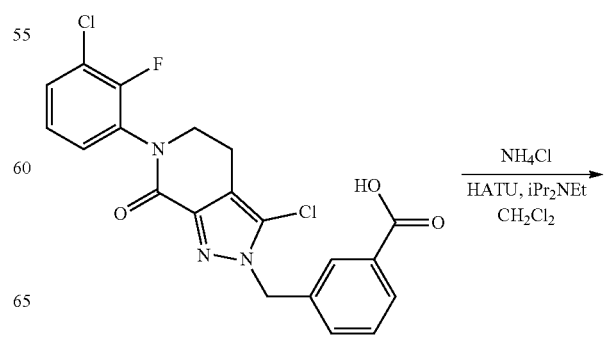

-continued

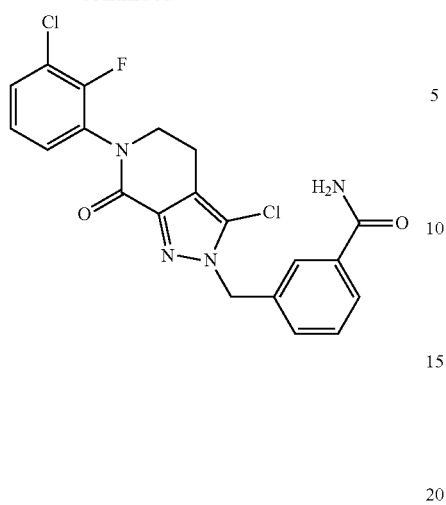

3-((3-Chloro-6-(3-chloro-2-fluorophenyl)-7-oxo-4,5,6,7-tetrahydro-2H-pyrazolo[3,4-c]pyridin-2-yl)methyl)benzamide To a solution of the product from the previous step (20 mg, 46.06 μmol, 1 eq) in DMF (0.5 mL) was added HATU (26.3 mg, 69.09 μmol, 1.5 eq), iPr$_2$NEt (17.86 mg, 138.17 μmol, 24 uL, 3 eq) and NH$_4$Cl (3.7 mg, 69.09 μmol, 1.5 eq). The mixture was stirred at 25° C. for 4 h, then poured into H$_2$O (10 mL) and extracted with EtOAc (10 mL×3). The combined organic layers were dried over Na$_2$SO$_4$, and concentrated under reduced pressure. The residue was purified by prep-HPLC (column: Phenomenex luna C18 150 mm×25 mm×10 μm; mobile phase: [H$_2$O (0.1% TFA)-CH$_3$CN];B %: 38%-58%,10 min) to afford the title compound (2.3 mg, 5.31 μmol, 12% yield, 100% purity) as a white solid.

LCMS(ES$^+$) C$_{20}$H$_{15}$Cl$_2$FN$_4$O$_2$ requires: 432, found 433 [M+H]$^+$.

$^1$H NMR (400 MHz, CDCl$_3$) δ=8.01-7.75 (m, 2H), 7.52 (m, 1H), 7.49-7.41 (m, 1H), 7.39-7.36 (m, 1H), 7.33-7.28 (m, 1H), 7.17-7.10 (m, 1H), 6.71-6.52 (m, 1H), 6.36-6.20 (m, 1H), 5.46 (s, 2H), 3.95 (t, J=6.4 Hz, 2H), 2.94 (t, J=6.4 Hz, 2H).

Example 76

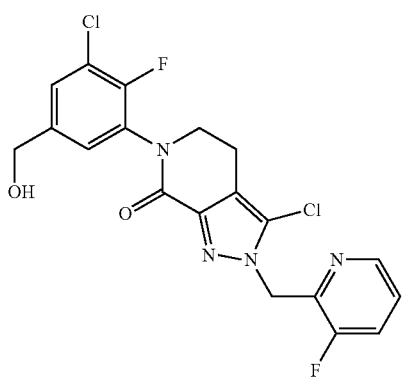 [SMILES: O=C1c2nn(Cc3ncccc3F)c(Cl)c2CCN1c1cc(CO)cc(Cl)c1F]

3-chloro-6-(3-chloro-2-fluoro-5-(hydroxymethyl)phenyl)-2-((3-fluoropyridin-2-yl)methyl)-2,4,5,6-tetrahydro-7H-pyrazolo[3,4-c]pyridin-7-one and Example 77

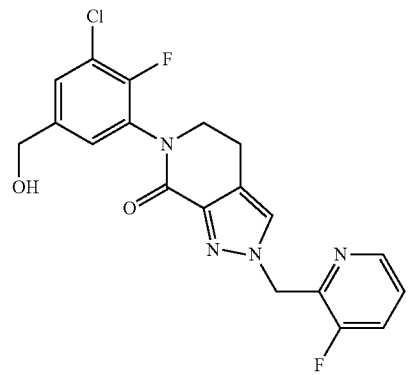 [SMILES: O=C1c2nn(Cc3ncccc3F)cc2CCN1c1cc(CO)cc(Cl)c1F]

6-(3-chloro-2-fluoro-5-(hydroxymethyl)phenyl)-2-((3-fluoropyridin-2-yl)methyl)-2,4,5,6-tetrahydro-7H-pyrazolo[3,4-c]pyridin-7-one

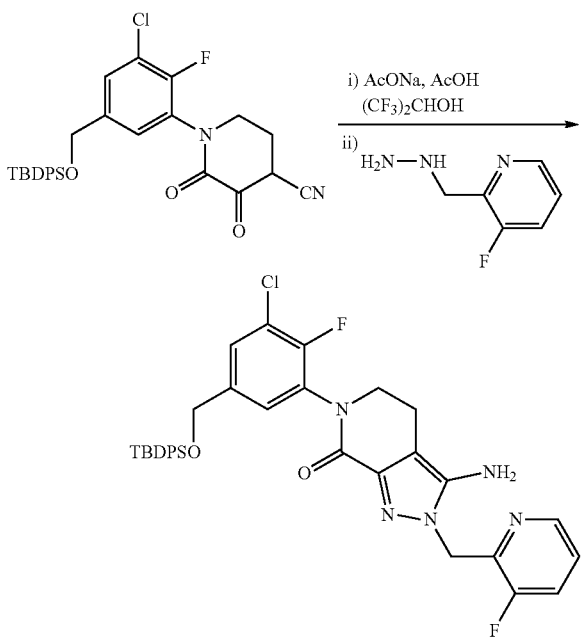

3-Amino-6-(5-(((tert-butyldiphenylsilyl)oxy)methyl)-3-chloro-2-fluorophenyl)-2-((3-fluoropyridin-2-yl)methyl)-2,4,5,6-tetrahydro-7H-pyrazolo[3,4-c]pyridin-7-one To a slurry of Intermediate F (700 mg, 1.1 mmol, 1 eq) in hexafluoroisopropanol (10 mL) was added AcOH (94 mg, 1.6 mmol, 90 uL, 1.5 eq) and AcONa (128 mg, 1.6 mmol, 1.5 eq). The mixture was stirred at 25° C. for 15 minutes, then (3-fluoro-2-pyridyl)methylhydrazine (186 mg, 1.1 mmol, 1 eq, HCl salt) was added. The mixture was further stirred at 60° C. for 16 h, then poured into H$_2$O (20 mL) and extracted with EtOAc (20 mL×3). The combined organic layers were washed with brine (50 mL×3), dried over Na₂SO₄, and concentrated under reduced pressure to afford the title compound (770 mg, 1.2 mmol) as a brown oil.

LCMS(ES⁺) $C_{35}H_{34}N_5O_2F_2ClSi$ requires: 657, found 658 [M+H]⁺.

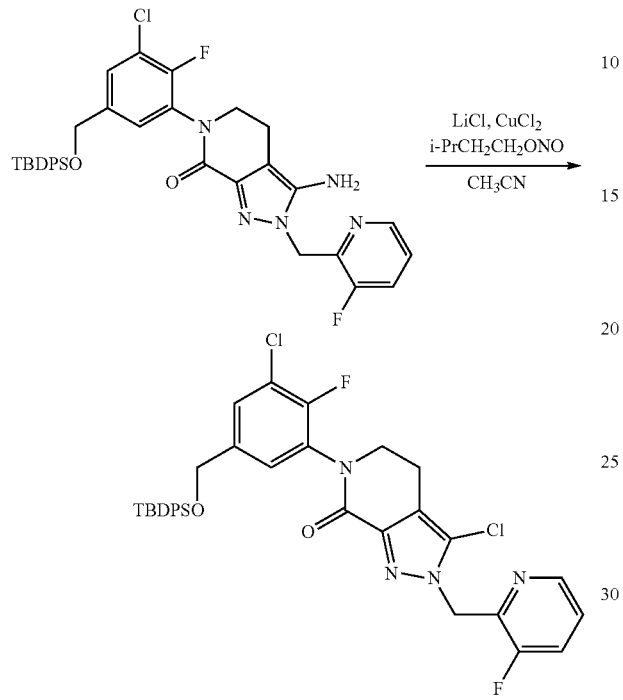

6-(5-(((tert-Butyldiphenylsilyl)oxy)methyl)-3-chloro-2-fluorophenyl)-3-chloro-2-((3-fluoropyridin-2-yl)methyl)-2,4,5,6-tetrahydro-7H-pyrazolo[3,4-c]pyridin-7-one To a solution of the product from the previous step (770 mg, 1.2 mmol, 1 eq) in CH₃CN (10 mL) was added CuCl₂ (315 mg, 2.3 mmol, 2 eq), LiCl (99 mg, 2.3 mmol, 48 uL, 2 eq) and isopentyl nitrite (274 mg, 2.3 mmol, 315 µL, 2 eq) at 0° C. The mixture was stirred at 0° C. for 2.5 h, then poured into H₂O (100 mL) and extracted with EtOAc (100 mL×3). The combined organic layers were washed with brine (10 mL×3), dried over Na₂SO₄, and concentrated under reduced pressure to afford the title compound (770 mg, 1.1 mmol) as a brown oil.

LCMS(ES⁺) $C_{35}H_{32}N_4O_2Cl_2F_2Si$ requires: 676, found 677 [M+H]⁺.

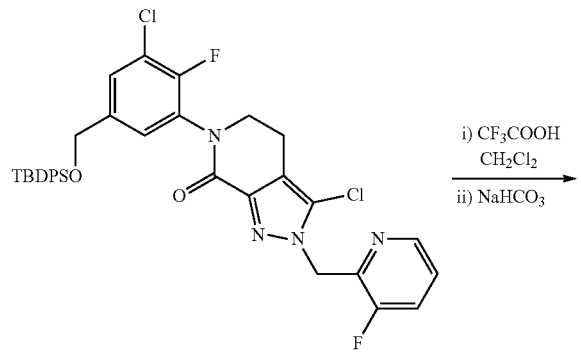

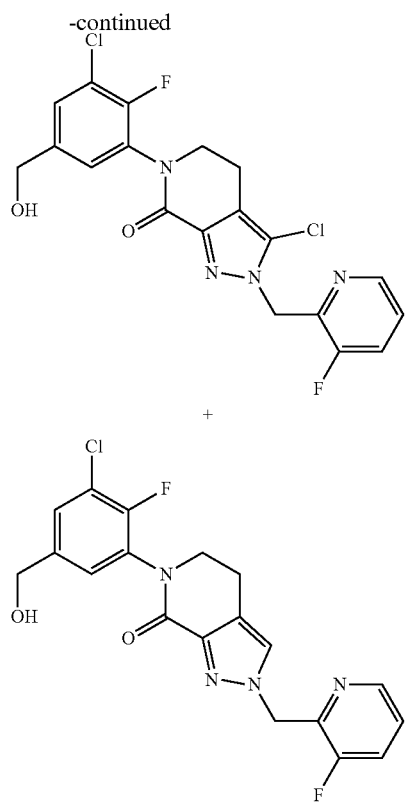

3-Chloro-6-(3-chloro-2-fluoro-5-(hydroxymethyl)phenyl)-2-((3-fluoropyridin-2-yl)methyl)-2,4,5,6-tetrahydro-7H-pyrazolo[3,4-c]pyridin-7-one (Example 76).

and 6-(3-Chloro-2-fluoro-5-(hydroxymethyl)phenyl)-2-((3-fluoropyridin-2-yl)methyl)-2,4,5,6-tetrahydro-7H-pyrazolo[3,4-c]pyridin-7-one (Example 77).

To a solution of the product from the previous step (770 mg, 1.1 mmol, 1 eq) in CH₂Cl₂ (4 mL) was added TFA (5.2 g, 45 mmol, 3.4 mL, 40 eq). The mixture was stirred at 25° C. for 16 h, then concentrated under reduced pressure to obtain a residue. To the obtained residue in THF (4 mL) was added a solution of NaHCO₃ (955 mg, 11 mmol, 442 uL, 10 eq) in H₂O (4 mL). The mixture was stirred at 25° C. for 2 h, then poured into H₂O (20 mL) and extracted with CH₂Cl₂ (20 mL×3), dried over Na₂SO₄, and concentrated under reduced pressure to obtain a residue which was purified by prep-HPLC (column: Phenomenex luna C18 150 mm×40 mm×15 mm; mobile phase: [H₂O (0.1% TFA)-CH₃CN];B %: 31%-61%,10 min).

Example 76: white solid, 44 mg (95 mmol, 8% yield).

¹H NMR (400 MHz, DMSO-d₆) δ=8.42-8.37 (m, 1H), 7.85-7.78 (m, 1H), 7.53-7.46 (m, 2H), 7.42-7.37 (m, 1H), 5.71-5.66 (m, 2H), 5.44 (t, J=5.6 Hz, 1H), 4.53-4.47 (m, 2H), 4.00 (t, J=5.6 Hz, 2H), 2.91 (t, J=5.6 Hz, 2H).

LCMS(ES⁺) $C_{19}H_{14}N_4O_2Cl_2F_2$ requires: 438, found 439 [M+H]⁺.

Example 77: brown solid, 27 mg (65 mmol, 6% yield).

¹H NMR (400 MHz, DMSO-d₆) δ=8.45-8.39 (m, 1H), 7.88-7.84 (m, 1H), 7.83-7.76 (m, 1H), 7.54-7.43 (m, 2H), 7.39-7.34 (m, 1H), 5.63-5.58 (m, 2H), 5.52-5.26 (m, 1H), 4.49 (s, 2H), 3.89 (t, J=6.4 Hz, 2H), 2.93 (t, J=6.4 Hz, 2H).

LCMS(ES⁺) $C_{19}H_{15}N_4O_2F_2Cl$ requires:404, found 405 [M+H]⁺.

Example 78

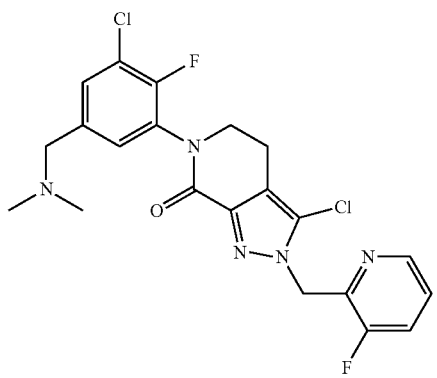 [SMILES: CN(C)Cc1cc(Cl)c(F)c(N2CCc3c(nn(Cc4ncccc4F)c3Cl)C2=O)c1]

3-chloro-6-(3-chloro-5-((dimethylamino)methyl)-2-fluorophenyl)-2-((3-fluoropyridin-2-yl)methyl)-2,4,5,6-tetrahydro-7H-pyrazolo[3,4-c]pyridin-7-one

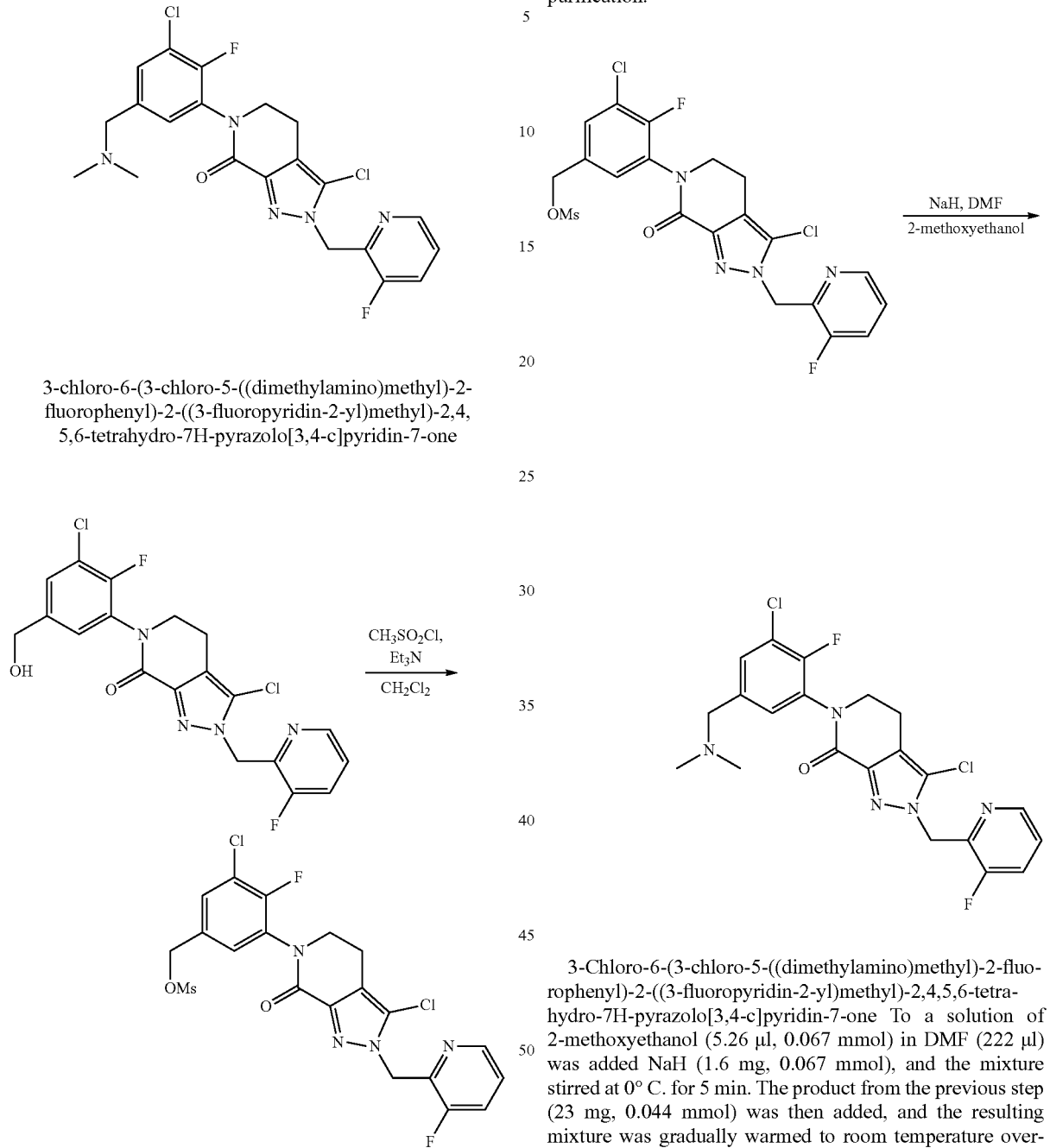

3-Chloro-5-(3-chloro-2-((3-fluoropyridin-2-yl)methyl)-7-oxo-2,4,5,7-tetrahydro-6H-pyrazolo[3,4-c]pyridin-6-yl)-4-fluorobenzyl methanesulfonate To a solution of the Example 76 material (39 mg, 0.089 mmol) in CH$_2$Cl$_2$ (444 µl) was added Et$_3$N (18.6 µl, 0.133 mmol) and methanesulfonyl chloride (10.4 µl, 0.133 mmol), and the resulting mixture was stirred at 0° C. for 0.5 h. The reaction was quenched by addition of saturated NaHCO$_3$ solution. The layers were separated, and the aqeous layer was extracted with CH$_2$Cl$_2$, and the combined organic layers were filtered, dried, and concentrated to give the title compound (45.9 mg, 0.089 mmol) as a brown oil. LCMS(ES$^+$) C$_{20}$H$_{16}$Cl$_2$F$_2$N$_4$O$_4$S requires: 516, found 517 [M+H]$^+$. The compound was taken on to the next step without further purification.

3-Chloro-6-(3-chloro-5-((dimethylamino)methyl)-2-fluorophenyl)-2-((3-fluoropyridin-2-yl)methyl)-2,4,5,6-tetrahydro-7H-pyrazolo[3,4-c]pyridin-7-one To a solution of 2-methoxyethanol (5.26 µl, 0.067 mmol) in DMF (222 µl) was added NaH (1.6 mg, 0.067 mmol), and the mixture stirred at 0° C. for 5 min. The product from the previous step (23 mg, 0.044 mmol) was then added, and the resulting mixture was gradually warmed to room temperature overnight. The reaction was then heated at 60° C. for 18 h. The residue was purified by mass-triggered preparative HPLC (Mobile phase: A=0.1% TFA/H$_2$O, B=0.1% TFA/MeCN; Gradient: B=10-90%; 12 min; Column: C18) to give the title compound (1.1 mg, 2.34 µmol, 5.3% yield, TFA salt) as a tan solid.

$^1$H NMR (300 MHz, DMSO-d$_6$) δ 9.82 (s, 1H), 8.42-8.35 (m, 1H), 7.88-7.70 (m, 2H), 7.65-7.57 (m, 1H), 7.54-7.45 (m, 1H), 5.72-5.65 (m, 2H), 4.32-4.25 (m, 2H), 4.00 (t, J=6.5 Hz, 2H), 2.93 (t, J=6.5 Hz, 2H), 2.76 (s, 6H).

LCMS(ES$^+$) C$_{21}$H$_{19}$Cl$_2$F$_2$N$_5$O requires: 465, found 466 [M+H]$^+$.

Example 79

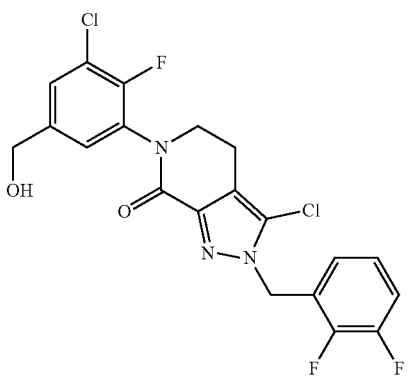

3-chloro-6-(3-chloro-2-fluoro-5-(hydroxymethyl)
phenyl)-2-(2,3-difluorobenzyl)-2,4,5,6-tetrahydro-
7H-pyrazolo[3,4-c]pyridin-7-one

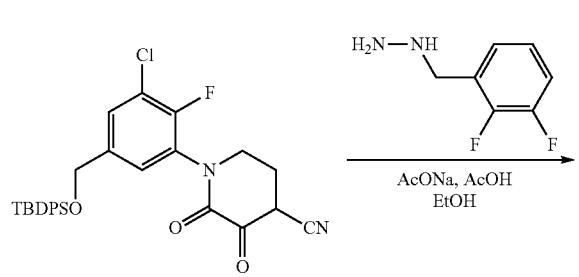

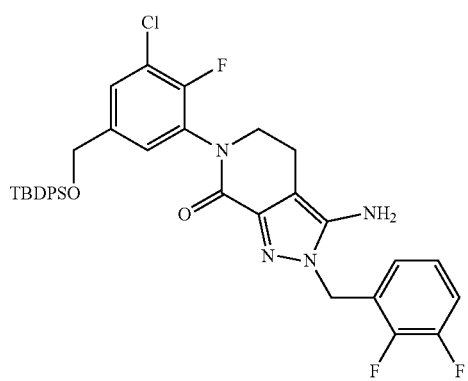

3-Amino-6-(5-(((tert-butyldiphenylsilyl)oxy)methyl)-3-chloro-2-fluorophenyl)-2-(2,3-difluorobenzyl)-2,4,5,6-tetrahydro-7H-pyrazolo[3,4-c]pyridin-7-one To a solution of Intermediate F (530 mg, 0.99 mmol) in EtOH (1.7 mL) was added AcONa (122 mg, 1.5 mmol), AcOH (85 μl, 1.5 mmol), and Intermediate A (193 mg, 0.99 mmol) and the resulting mixture was stirred at 60° C. for 20 h. The reaction was then concentrated under reduced pressure. The residue was adsorbed onto silica gel and purified via flash chromatography (0-60% iPrOH/EtOAc (1:4) in Hexanes) to give the title compound (224 mg, 0.33 mmol, 34% yield) as an off-white powder.

$^1$H NMR (500 MHz, DMSO-$d_6$) δ 7.66-7.61 (m, 4H), 7.52-7.31 (m, 9H), 7.22-7.14 (m, 1H), 6.82-6.76 (m, 1H), 5.57 (s, 2H), 5.34 (s, 2H), 4.76 (s, 2H), 3.82 (t, J=6.5 Hz, 2H), 2.73 (t, J=6.4 Hz, 2H), 1.04 (s, 9H).

LCMS(ES$^+$) $C_{36}H_{34}ClF_3N_4O_2Si$ requires: 674, found 675 [M+H]$^+$.

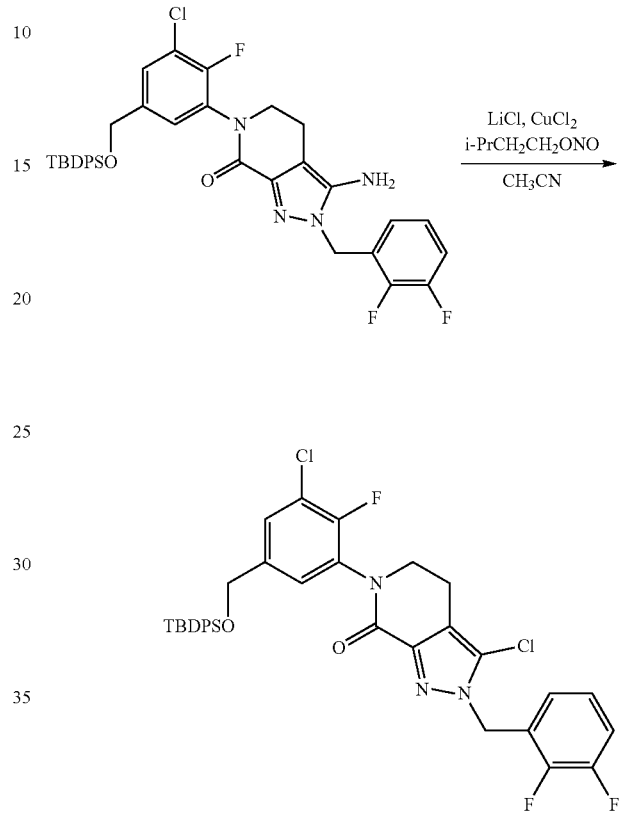

6-(5-(((tert-Butyldiphenylsilyl)oxy)methyl)-3-chloro-2-fluorophenyl)-3-chloro-2-(2,3-difluorobenzyl)-2,4,5,6-tetrahydro-7H-pyrazolo[3,4-c]pyridin-7-one To a suspension of the product from the previous step (224 mg, 0.33 mmol), CuCl$_2$ (67 mg, 0.50 mmol), and LiCl (21 mg, 0.50 mmol) was added CH$_3$CN (1.7 mL). The reaction was degassed by sonification under N$_2$ for 1 minute. Isoamyl nitrite (67 μl, 0.50 mmol) was then added, and the reaction was stirred at room temperature overnight. The reaction was then heated to 60° C. for 0.5 h. The reaction was cooled to room temperature. To the reaction was added 4 mL of saturated NH$_4$Cl solution, EtOAc, and H$_2$O, and the resulting mixture was stirred for 5 minutes. The layers were then separated, and the aqueous phase was extracted with EtOAc. The combined organic layers were washed with brine, dried over Na$_2$SO$_4$, and concentrated under reduced pressure. The residue was purified via silica gel chromatography (0-30% EtOAc in hexanes) to give the title compound (190 mg, 0.27 mmol, 82% yield) as a yellow oil.

$^1$H NMR (300 MHz, DMSO-$d_6$) δ 7.69-7.59 (m, 4H), 7.54-7.35 (m, 9H), 7.31-7.17 (m, 1H), 7.12-7.01 (m, 1H), 5.58 (s, 2H), 4.77 (s, 2H), 3.92 (t, J=6.5 Hz, 2H), 2.88 (t, J=6.5 Hz, 2H), 1.04 (s, 9H).

LCMS(ES$^+$) $C_{36}H_{32}Cl_2F_3N_3O_2Si$ requires: 693, found 694 [M+H]$^+$.

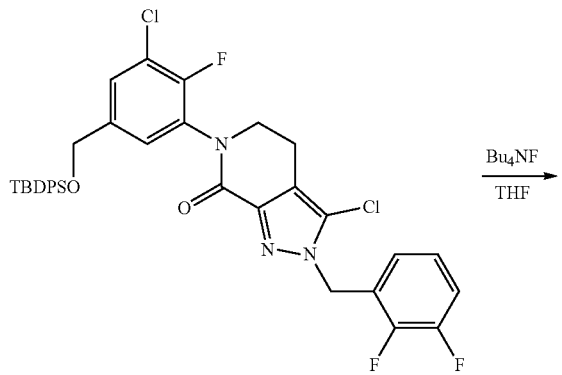

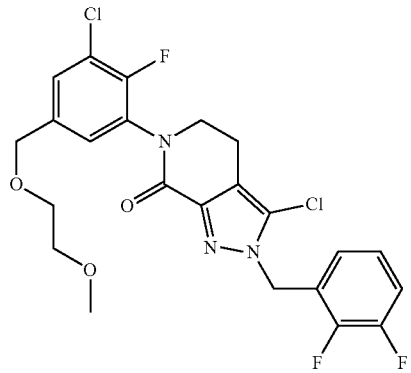 [SMILES: COCCOCc1cc(Cl)c(F)c(N2CCc3c(nn(Cc4cccc(F)c4F)c3Cl)C2=O)c1]

Example 80

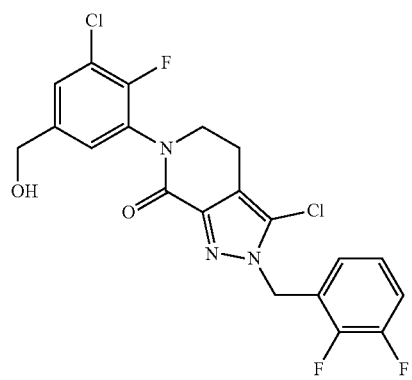

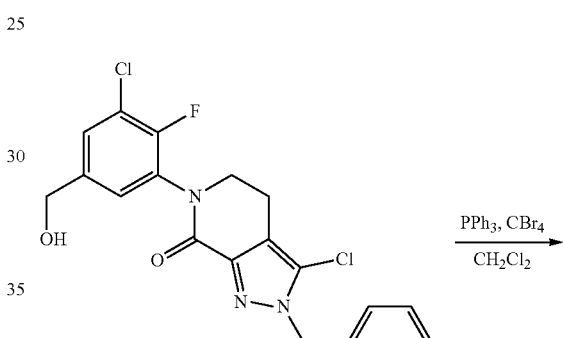

3-chloro-6-(3-chloro-2-fluoro-5-((2-methoxyethoxy)methyl)phenyl)-2-(2,3-difluorobenzyl)-2,4,5,6-tetrahydro-7H-pyrazolo[3,4-c]pyridin-7-one

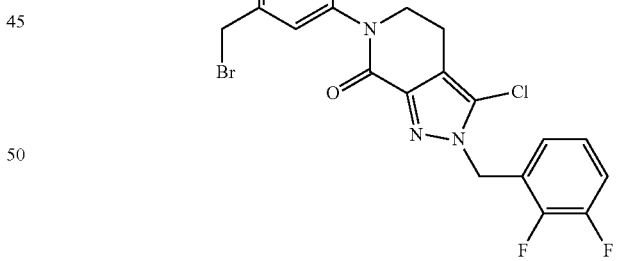

3-Chloro-6-(3-chloro-2-fluoro-5-(hydroxymethyl)phenyl)-2-(2,3-difluorobenzyl)-2,4,5,6-tetrahydro-7H-pyrazolo[3,4-c]pyridin-7-one To a solution of the product from the previous step (190 mg, 0.27 mmol) in THF (1.4 mL) was added Bu₄NF (547 µl, 0.55 mmol) and the resulting mixture was stirred at 25° C. for 2 h. The reaction mixture was diluted with EtOAc, saturated NaHCO₃ solution was added, and the layers were separated. The aqueous phase was extracted with EtOAc. The combined organic layers were washed with brine, dried over Na₂SO₄, and concentrated under reduced pressure. The residue was purified via silica gel chromatography (40-100% EtOAc in hexanes) to give the title compound (60 mg, 0.13 mmol, 48% yield) as a white solid.

$^1$H NMR (500 MHz, DMSO-d₆) δ 7.50-7.42 (m, 2H), 7.41-7.36 (m, 1H), 7.29-7.21 (m, 1H), 7.10-7.03 (m, 1H), 5.59 (s, 2H), 5.44 (t, J=5.7 Hz, 1H), 4.50 (d, J=5.8 Hz, 2H), 3.97-3.93 (m, 2H), 2.90 (t, J=6.5 Hz, 2H).

LCMS(ES⁺) $C_{20}H_{14}Cl_2F_3N_3O_2$ requires: 455, found 456 [M+H]⁺.

6-(5-(Bromomethyl)-3-chloro-2-fluorophenyl)-3-chloro-2-(2,3-difluorobenzyl)-2,4,5,6-tetrahydro-7H-pyrazolo[3,4-c]pyridin-7-one (Intermediate I) To a solution of the Example 79 material (40 mg, 0.09 mmol) in CH₂Cl₂ (438 µl) was added CBr₄ (44 mg, 0.13 mmol) and PPh₃ (35 mg, 0.13 mmol) and the resulting mixture was stirred at 25° C. for 1 h. The reaction was then filtered and concentrated. The residue was purified via silica gel chromatography (0-100% EtOAc in hexanes) to give the title compound (42 mg, 0.08 mmol, 92% yield) as a colorless oil.

LCMS(ES⁺) $C_{20}H_{13}BrCl_2F_3N_3O$ requires: 516, found 517 [M+H]⁺.

211

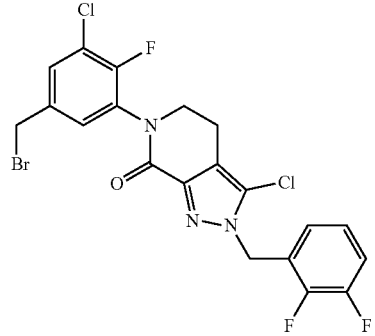

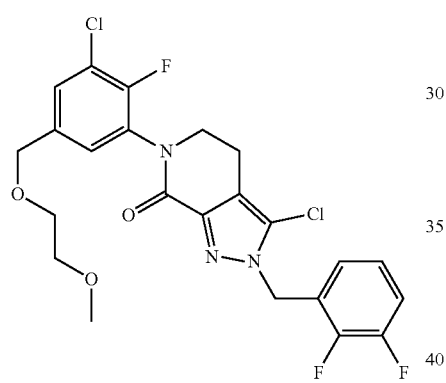

3-Chloro-6-(3-chloro-2-fluoro-5-((2-methoxyethoxy)methyl)phenyl)-2-(2,3-difluorobenzyl)-2,4,5,6-tetrahydro-7H-pyrazolo[3,4-c]pyridin-7-one To a solution of 2-methoxyethanol (6.2 mg, 0.08 mmol) in THF (405 µl) was added NaH (3.2 mg, 0.08 mmol) and resulting mixture was stirred at 0° C. for 0.25 h. A solution of Intermediate I (42 mg, 0.08 mmol) in THF (405 µl) was then added dropwise, and the resulting mixture was stirred at 0° C. for 0.5 h. The reaction was quenched by addition of saturated NH$_4$Cl solution. H$_2$O and EtOAc were then added, and the layers were separated. The aqueous phase was extracted with EtOAc. The combined organic layers were washed with brine, dried over Na$_2$SO$_4$, and concentrated under reduced pressure. The residue was purified via silica gel chromatography (30-100% EtOAc in hexanes) to give the title compound (23 mg, 0.05 mmol, 55% yield) as a colorless amorphous material.

$^1$H NMR (500 MHz, DMSO-d$_6$) δ 7.53-7.38 (m, 3H), 7.28-7.20 (m, 1H), 7.10-7.03 (m, 1H), 5.59 (s, 2H), 4.49 (s, 2H), 3.98-3.92 (m, 2H), 3.61-3.56 (m, 2H), 3.52-3.46 (m, 2H), 3.25 (s, 3H), 2.92-2.86 (m, 2H).

LCMS(ES$^+$) C$_{23}$H$_{20}$Cl$_2$F$_3$N$_3$O$_3$ requires: 513, found 514 [M+H]$^+$.

212

Example 81

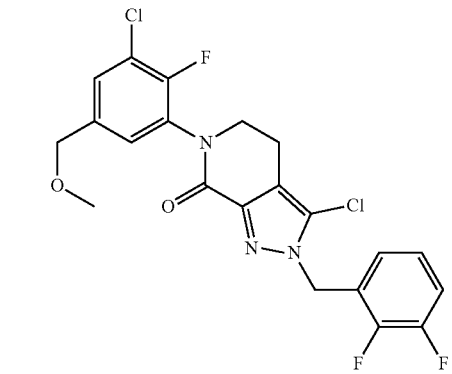 [SMILES: COCc1cc(Cl)c(F)c(N2CCc3c(nn(Cc4cccc(F)c4F)c3Cl)C2=O)c1]

3-chloro-6-(3-chloro-2-fluoro-5-(methoxymethyl)phenyl)-2-(2,3-difluorobenzyl)-2,4,5,6-tetrahydro-7H-pyrazolo[3,4-c]pyridin-7-one

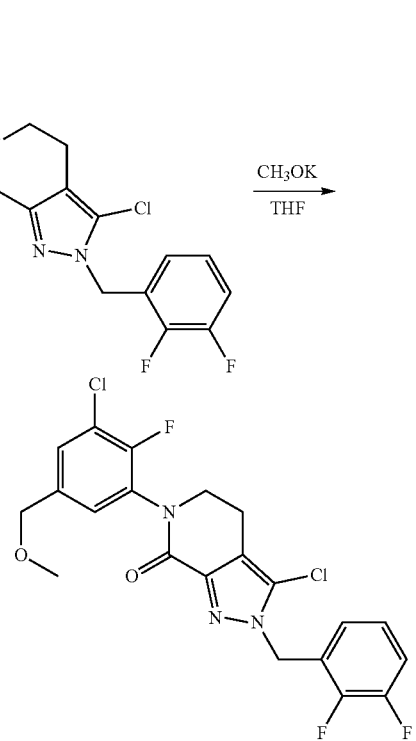

To a cooled 0° C. solution of Intermediate I (40 mg, 0.077 mmol) in THF (385 µl) was added MeOK (8.11 mg, 0.116 mmol). The resulting mixture was stirred at 0° C. for 1 h. Saturated NH$_4$Cl solution and EtOAc were added, and the layers were separated. The aqueous phase was extracted with EtOAc. The combined organic layers were dried over Na$_2$SO$_4$ and concentrated under reduced pressure. The residue was purified by mass-triggered preparative HPLC (Mobile phase: A=0.1% TFA/H$_2$O, B=0.1% TFA/CH$_3$CN; Gradient: B=40-80%; 20 min; Column: C18) to give the title compound (4 mg, 8.51 µmol, 11% yield) as a tan solid.

¹H NMR (300 MHz, DMSO-d₆) δ 7.51-7.36 (m, 1H), 7.27-7.13 (m, 1H), 6.89 (ddt, J=7.9, 6.4, 1.6 Hz, 1H), 6.68 (dd, J=7.8, 2.0 Hz, 1H), 6.56 (dd, J=6.2, 1.8 Hz, 1H), 5.52 (s, 2H), 4.26 (s, 2H), 3.30-3.22 (m, 5H), 2.95-2.84 (m, 2H).

LCMS(ES⁺) $C_{21}H_{16}Cl_2F_3N_3O_2$ requires: 469, found 470 [M+H]⁺.

Example 82

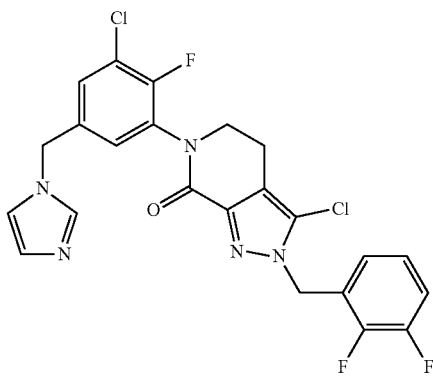 [SMILES: O=C1c2nn(Cc3cccc(F)c3F)c(Cl)c2CCN1c1cc(Cn2ccnc2)cc(Cl)c1F]

6-(5-((1H-imidazol-1-yl)methyl)-3-chloro-2-fluoro-phenyl)-3-chloro-2-(2,3-difluorobenzyl)-2,4,5,6-tetrahydro-7H-pyrazolo[3,4-c]pyridin-7-one To a solution of Intermediate I (40 mg, 0.077 mmol) in CH₃CN (385 μl) was added imidazole (15.74 mg, 0.231 mmol), and the resulting mixture was stirred at 25° C. for 20 h. The volatiles were removed under reduced pressure. The residue was purified by mass-triggered preparative HPLC (Mobile phase: A=0.1% TFA/H₂O, B=0.1% TFA/CH₃CN; Gradient: B=10-90%; 12 min; Column: C18) to afford the title compound (12 mg, 0.024 mmol, 31% yield) as a brown amorphous material.

¹H NMR (300 MHz, DMSO-d₆) δ 9.27-9.20 (m, 1H), 7.88-7.79 (m, 1H), 7.78-7.68 (m, 2H), 7.65-7.56 (m, 1H), 7.53-7.38 (m, 1H), 7.31-7.18 (m, 1H), 7.13-7.01 (m, 1H), 5.59 (s, 2H), 5.44 (s, 2H), 3.96 (t, J=6.4 Hz, 2H), 2.90 (t, J=6.5 Hz, 2H).

LCMS(ES⁺) $C_{23}H_{16}Cl_2F_3N_5O$ requires: 505, found 506 [M+H]⁺.

Example 83

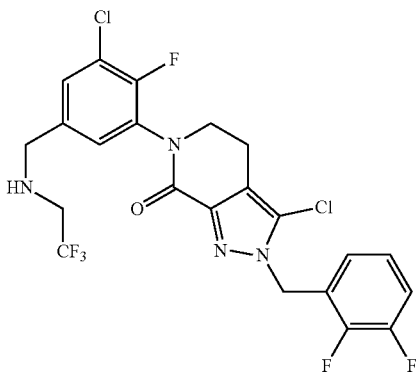 [SMILES: O=C1c2nn(Cc3cccc(F)c3F)c(Cl)c2CCN1c1cc(CNCC(F)(F)F)cc(Cl)c1F]

3-chloro-6-(3-chloro-2-fluoro-5-(((2,2,2-trifluoro-ethyl)amino)methyl)phenyl)-2-(2,3-difluorobenzyl)-2,4,5,6-tetrahydro-7H-pyrazolo[3,4-c]pyridin-7-one

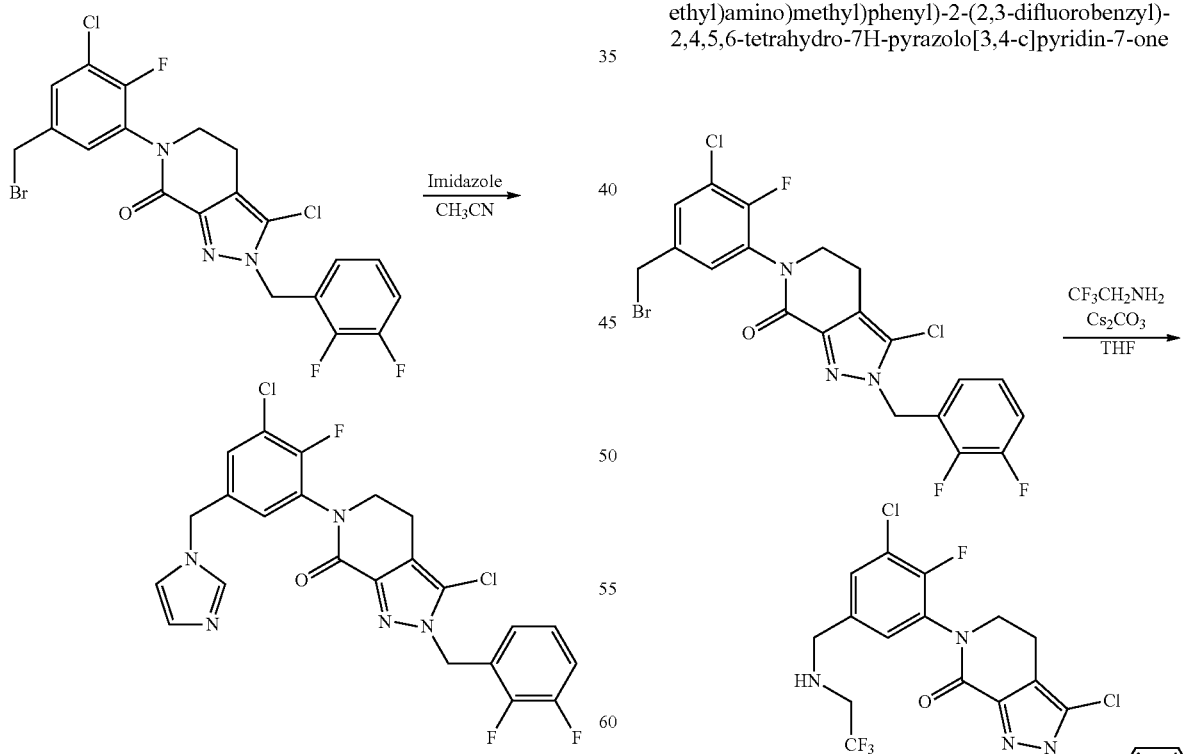

To a solution of Intermediate I (40 mg, 0.077 mmol) in THF (385 μl) was added 2,2,2-trifluoroethanamine hydrochloride (20.9 mg, 0.154 mmol) and Cs$_2$CO$_3$ (62.8 mg, 0.193 mmol), and the resulting mixture was stirred at 25° C. for 20 h. Et$_3$N (21.48 μl, 0.154 mmol) was then added, and the mixture was stirred for 24 h. The reaction mixture was filtered, H$_2$O was added, and the aqueous layer was extracted with EtOAc. The combined organic layers were concentrated. The residue was purified by mass-triggered preparative HPLC (Mobile phase: A=0.1% TFA/H$_2$O, B=0.1% TFA/CH$_3$CN; Gradient: B=40-80%; 12 min; Column: C18) to give the title compound (5 mg, 9.31 μmol, 12% yield) as a white solid.

$^1$H NMR (500 MHz, DMSO-d$_6$) δ 7.62-7.56 (m, 1H), 7.50-7.41 (m, 2H), 7.29-7.21 (m, 1H), 7.10-7.03 (m, 1H), 5.59 (s, 2H), 4.03-3.76 (m, 5H), 3.53-3.42 (m, 2H), 2.90 (t, J=6.5 Hz, 2H).

LCMS(ES$^+$) C$_{22}$H$_{16}$Cl$_2$F$_6$N$_4$O requires: 536, found 537 [M+H]$^+$.

Example 84

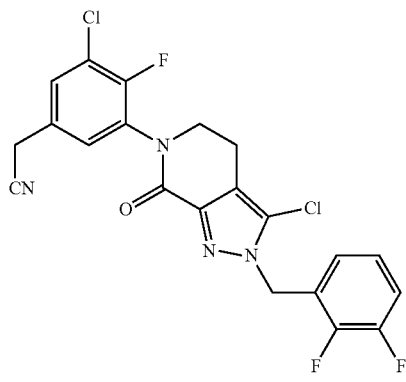

2-(3-chloro-5-(3-chloro-2-(2,3-difluorobenzyl)-7-oxo-2,4,5,7-tetrahydro-6H-pyrazolo[3,4-c]pyridin-6-yl)-4-fluorophenyl)acetonitrile

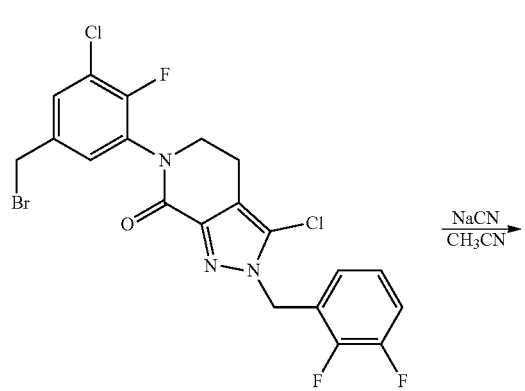

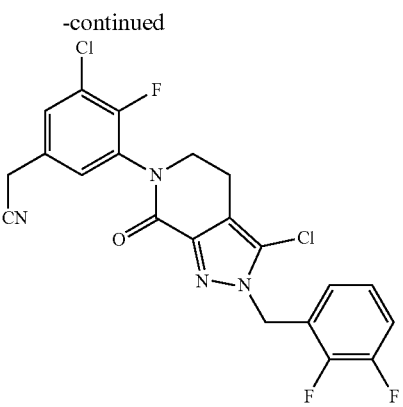

To a solution of Intermediate I (40 mg, 0.077 mmol) in CH$_3$CN (385 μl) was added NaCN (5.66 mg, 0.116 mmol), and the resulting mixture was stirred at 25° C. for 20 h. The reaction mixture was diluted with EtOAc, saturated NaHCO$_3$ solution was added, and the layers were separated. The aqueous phase was extracted with EtOAc. The combined organic layers were washed with brine, dried over Na$_2$SO$_4$, and concentrated under reduced pressure. The residue was purified by mass-triggered preparative HPLC (Mobile phase: A=0.1% TFA/H$_2$O, B=0.1% TFA/CH$_3$CN; Gradient: B=10-90%; 12 min; Column: C18) to give the title compound (10 mg, 0.021 mmol, 28% yield) as an off-white solid.

$^1$H NMR (300 MHz, DMSO-d$_6$) δ 7.63-7.54 (m, 1H), 7.53-7.38 (m, 2H), 7.31-7.18 (m, 1H), 7.12-7.00 (m, 1H), 5.59 (s, 2H), 4.08 (s, 2H), 3.96 (t, J=6.5 Hz, 2H), 2.90 (t, J=6.5 Hz, 2H).

LCMS(ES$^+$) C$_{21}$H$_{13}$Cl$_2$F$_3$N$_4$O requires: 464, found 465 [M+H]$^+$.

Example 85

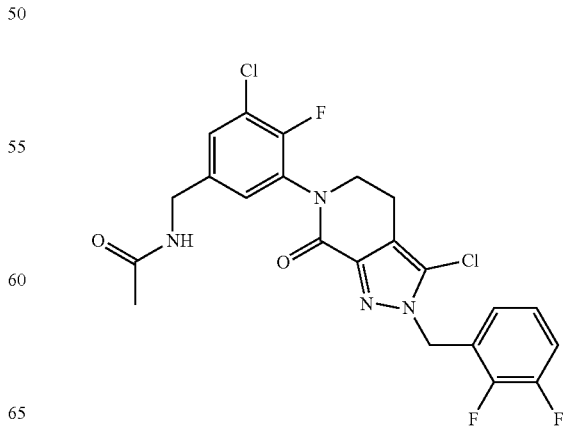

217

N-(3-chloro-5-(3-chloro-2-(2,3-difluorobenzyl)-7-oxo-2,4,5,7-tetrahydro-6H-pyrazolo[3,4-c]pyridin-6-yl)-4-fluorobenzyl)acetamide

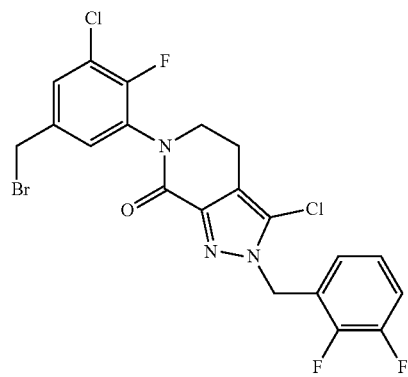

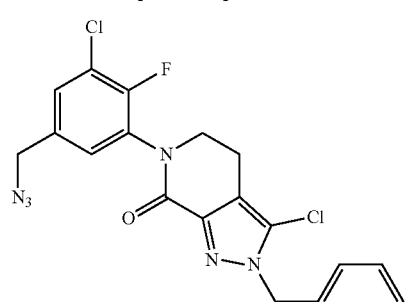

6-(5-(Azidomethyl)-3-chloro-2-fluorophenyl)-3-chloro-2-(2,3-difluorobenzyl)-2,4,5,6-tetrahydro-7H-pyrazolo[3,4-c]pyridin-7-one To a solution of Intermediate I (35 mg, 0.067 mmol) in THF (337 µl) was added NaN₃ (17.5 mg, 0.270 mmol), and the resulting mixture was stirred at 25° C. for 20 h. The reaction mixture was diluted with EtOAc, H₂O was added, and the layers were separated. The aqueous phase was extracted with EtOAc, and the combined organic layers were dried over Na₂SO₄ and concentrated under reduced pressure to give the title compound (32.4 mg, 0.067 mmol) as a yellow oil. The product was taken on to the next step without further purification.

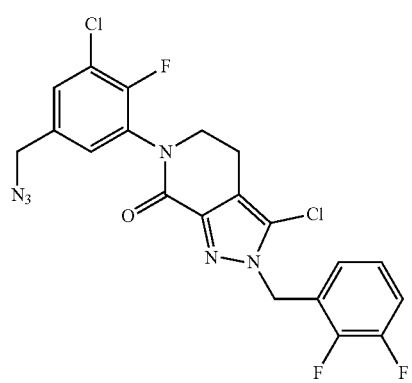

218

-continued

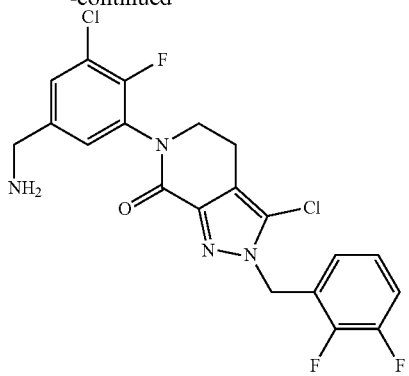

6-(5-(Aminomethyl)-3-chloro-2-fluorophenyl)-3-chloro-2-(2,3-difluorobenzyl)-2,4,5,6-tetrahydro-7H-pyrazolo[3,4-c]pyridin-7-one The produt from the previous step was dissolved in THF (337 µl). H₂O (1.2 µl, 0.067 mmol) and PPh₃ on resin (3 mmol/g, 100 mg) were added and the resulting mixture was stirred at 25° C. for 20 h. The reaction mixture was filtered though CELITE® and concentrated under reduced pressure to obtain the title compound (17 mg, 0.037 mmol, 55% yield over 2 steps) as a yellow oil.

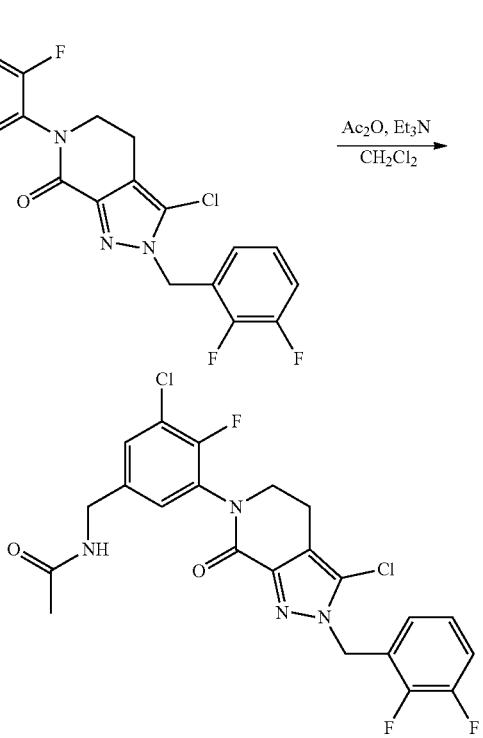

N-(3-Chloro-5-(3-chloro-2-(2,3-difluorobenzyl)-7-oxo-2,4,5,7-tetrahydro-6H-pyrazolo[3,4-c]pyridin-6-yl)-4-fluorobenzyl)acetamide To a solution of the product from the previous step (17 mg, 0.037 mmol) in CH₂Cl₂ (187 µl) was added Et₃N (7.8 µl, 0.056 mmol) and Ac₂O (4.23 µl, 0.045 mmol), and the resulting mixture was stirred at 0° C. for 1 h. The reaction mixture was concentrated under reduced pressure and the residue was purified by mass-triggered preparative HPLC (Mobile phase: A=0.1% TFA/H₂O, B=0.1% TFA/MeCN; Gradient: B=10-90%; 12 min; Column: C18) to give the title compound (1 mg, 2.01 µmol, 5% yield) as a tan solid.

$^1$H NMR (500 MHz, DMSO-d$_6$) δ 8.41 (t, J=6.0 Hz, 1H), 7.49-7.38 (m, 2H), 7.35-7.30 (m, 1H), 7.28-7.20 (m, 1H), 7.09-7.03 (m, 1H), 5.58 (s, 2H), 4.25 (d, J=6.0 Hz, 2H), 3.93 (t, J=6.5 Hz, 2H), 2.89 (t, J=6.5 Hz, 2H), 1.88 (s, 3H).

LCMS(ES$^+$) C$_{22}$H$_{17}$Cl$_2$F$_3$N$_4$O$_2$ requires: 497, found 498 [M+H]$^+$.

Example 86

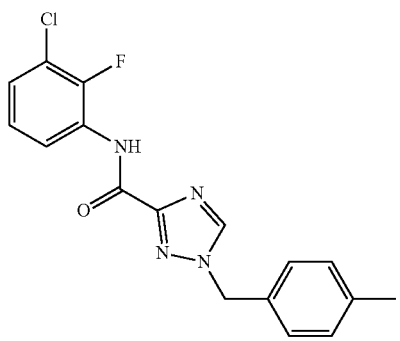 [SMILES: Cc1ccc(Cn2cnc(C(=O)Nc3cccc(Cl)c3F)n2)cc1]

N-(3-chloro-2-fluorophenyl)-1-(4-methylbenzyl)-1H-1,2,4-triazole-3-carboxamide

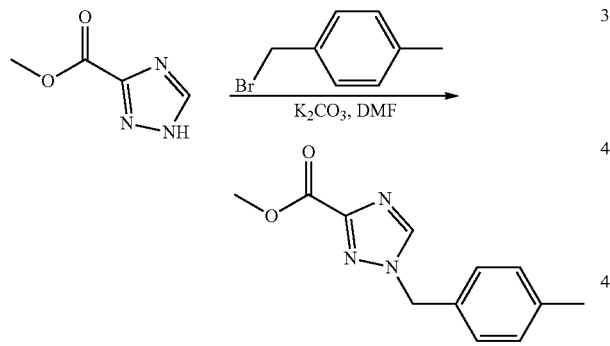

Methyl 1-(4-methylbenzyl)-1H-1,2,4-triazole-3-carboxylate To a solution of methyl 1H-1,2,4-triazole-3-carboxylate (200 mg, 1.57 mmol, 1 eq) in DMF (5 mL) was added K$_2$CO$_3$ (434.95 mg, 3.15 mmol, 2 eq) followed by 1-(bromomethyl)-4-methylbenzene (349.44 mg, 1.89 mmol, 1.2 eq) under an N$_2$ atmosphere (15 Psi). The mixture was stirred at 20° C. for 16 h. The reaction mixture was diluted with H$_2$O (10 mL) and extracted with EtOAc (15 mL×3). The combined organic layers were washed with brine (20 mL×3), dried over MgSO$_4$, and concentrated under reduced pressure to afford a residue that was purified by prep-TLC (petroleum ether: EtOAc=2:1). The fractions were combined and concentrated under reduced pressure to afford the title compound (154 mg, 546 µmol, 35% yield) as a white solid.

MS(ES+)C$_{12}$H$_{13}$N$_3$O$_2$ requires:231, found 232 [M+H]$^+$.

$^1$H NMR (400 MHz, CDCl$_3$) δ=7.99 (s, 1H), 7.31-7.27 (m, 2H), 7.12-7.06 (m, 2H), 5.76 (s, 2H), 3.99 (s, 3H), 2.32 (s, 3H).

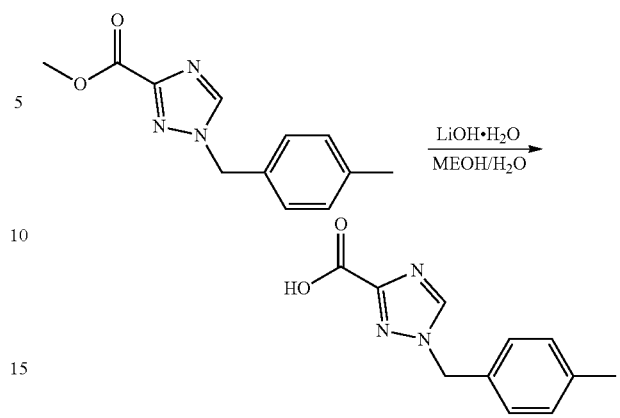

1-(4-Methylbenzyl)-1H-1,2,4-triazole-3-carboxylic acid To a solution of the product from the previous step (154 mg, 546 µmol, 1 eq) in MeOH (4 mL) was added a solution of LiOH·H$_2$O (27.5 mg, 655.3 µmol, 1.2 eq) in H$_2$O (1 mL). The mixture was stirred at 20° C. for 2 h. The reaction mixture was concentrated under reduced pressure to afford the title compound (150 mg, crude) as a white solid.

MS(ES+)C$_{11}$H$_{11}$N$_3$O$_2$ requires:217, found 218 [M+H]$^+$.

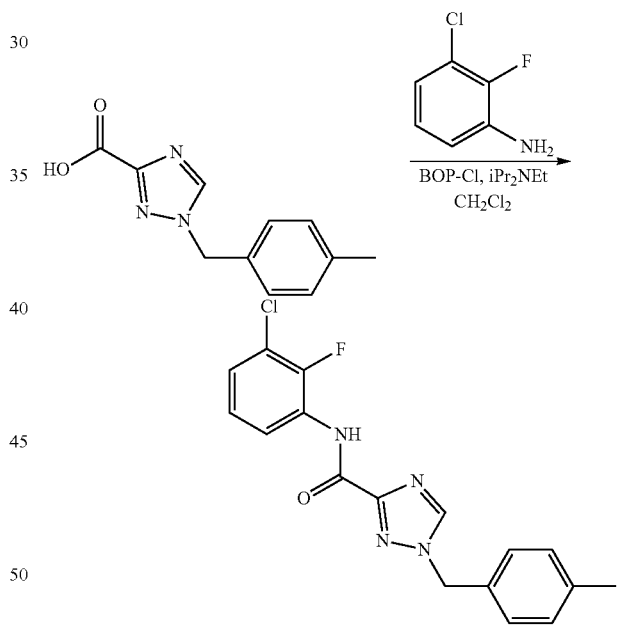

N-(3-chloro-2-fluorophenyl)-1-(4-methylbenzyl)-1H-1,2,4-triazole-3-carboxamide A mixture of the product from the previous step (150 mg, 691 µmol, 1 eq), 3-chloro-2-fluoroaniline (120.6 mg, 828.64 µmol, 1.2 eq), BOP-Cl (263.7 mg, 1.04 mmol, 1.5 eq) and iPr$_2$NEt (267.7 mg, 2.07 mmol, 360 uL, 3 eq) in CH$_2$Cl$_2$ (10 mL) was stirred at 80° C. for 2 h. The mixture was concentrated under reduced pressure to afford a residue which was purified by prep-HPLC (column: Waters Xbridge C18 150 mm×50 mm×10 µm; mobile phase: [H$_2$O (10 mM NH$_4$HCO$_3$)—CH$_3$CN]; B %: 43%-73%, 11.5 min) and lyophilized to afford the title compound (35 mg, 96 µmol, 14% yield) as a white solid.

MS (ES+) C$_{17}$H$_{14}$ON$_4$ClF requires: 344 and 346, found: 345 and 347 [M+H]$^+$.

$^1$H NMR (400 MHz, CDCl$_3$) δ=9.20 (s, 1 H), 8.54-8.39 (m, 1 H), 8.04 (s, 1 H), 7.30-7.27 (m, 4 H), 7.19-7.09 (m, 2 H), 5.40 (s, 2 H), 2.37 (s, 3 H).

Example 87

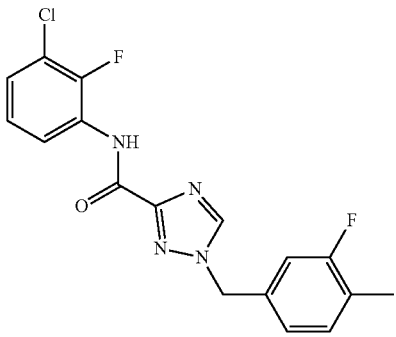

N-(3-chloro-2-fluorophenyl)-1-(3-fluoro-4-methyl-benzyl)-1H-1,2,4-triazole-3-carboxamide

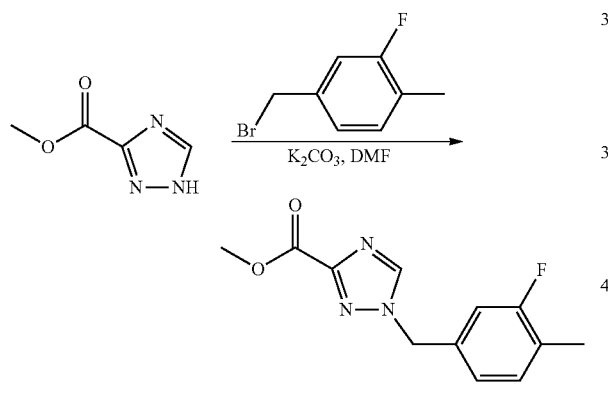

Methyl 1-(3-fluoro-4-methylbenzyl)-1H-1,2,4-triazole-3-carboxylate To a solution of methyl 1H-1,2,4-triazole-3-carboxylate (200 mg, 1.57 mmol, 1 eq) in DMF (5 mL) was added K$_2$CO$_3$ (435.0 mg, 3.15 mmol, 2 eq) followed by 4-(bromomethyl)-2-fluoro-1-methylbenzene (383.42 mg, 1.89 mmol, 1.2 eq) under an N$_2$ atmosphere (15 Psi). The mixture was stirred at 20° C. for 16 h. The reaction mixture was diluted with H$_2$O (10 mL) and extracted with EtOAc (15 mL×3). The combined organic layers were washed with brine (20 mL×3), dried over MgSO$_4$, and concentrated under reduced pressure to afford a residue. The residue was purified by prep-TLC (petroleum ether:EtOAc=2:1) to afford the title compound (167 mg, 502.5 μmol, 32% yield, 75% purity) as a white solid.

MS(ES+)C$_{12}$H$_{12}$N$_3$O$_2$F requires: 249, found 250 [M+H]$^+$.

$^1$H NMR (400 MHz, CDCl$_3$) δ=8.00 (s, 1H), 7.17-7.10 (m, 1H), 7.01-6.93 (m, 2H), 5.74 (s, 2H), 3.99 (s, 3H), 2.32 (s, 3H).

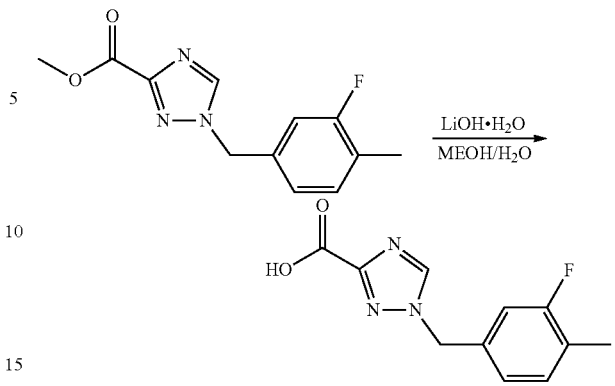

1-(3-Fluoro-4-methylbenzyl)-1H-1,2,4-triazole-3-carboxylic acid To a solution of the product from the previous step (167 mg, 532.5 μmol, 1 eq) in MeOH (4 mL) was added a solution of LiOH·H$_2$O (26.8 mg, 638.99 μmol, 1.2 eq) in H$_2$O (1 mL). The mixture was stirred at 20° C. for 2 h. The reaction was concentrated under reduced pressure to afford the title compound (180 mg, crude) as a white solid.

MS(ES+)C$_{11}$H$_{10}$N$_3$O$_2$F requires:235, found 236 [M+H]$^+$.

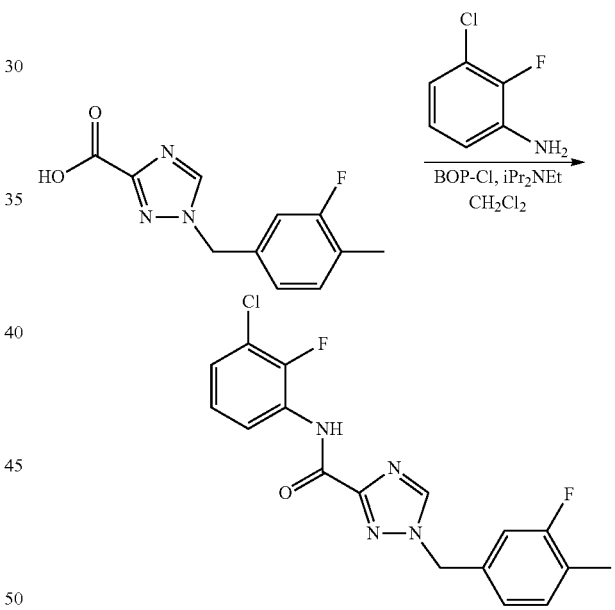

N-(3-chloro-2-fluorophenyl)-1-(3-fluoro-4-methylbenzyl)-1H-1,2,4-triazole-3-carboxamide A mixture of the product from the previous step (180 mg, 765.3 μmol, 1 eq), 3-chloro-2-fluoroaniline (133.7 mg, 918.3 μmol, 1.2 eq), BOP-Cl (292.2 mg, 1.15 mmol, 1.5 eq) and iPr$_2$NEt (296.7 mg, 2.30 mmol, 399.9 uL, 3 eq) in CH$_2$Cl$_2$ (10 mL) was stirred at 80° C. for 2 h. The mixture was concentrated under reduced pressure to afford a residue. The residue was purified by prep-HPLC (column: Waters Xbridge C18 150 mm×50 mm×10 μm; mobile phase: [H$_2$O (10 mM NH$_4$HCO$_3$)—CH$_3$CN]; B %: 40%-70%,11.5 min) and lyophilized to afford the title compound (11.4 mg, 30.48 μmol, 4% yield, 97% purity) as a white solid.

MS (ES+) C$_{17}$H$_{13}$ON$_4$ClF$_2$ requires: 362 and 364, found: 363 and 365 [M+H]$^+$.

¹H NMR (400 MHz, CDCl₃) δ=9.21 (s, 1 H), 8.55-8.40 (m, 1 H), 8.10 (s, 1 H), 7.35-7.30 (m, 1 H), 7.20-7.09 (m, 2 H), 7.00-6.90 (m, 2 H), 5.39 (s, 2 H), 2.29 (s, 3 H).

Example 88

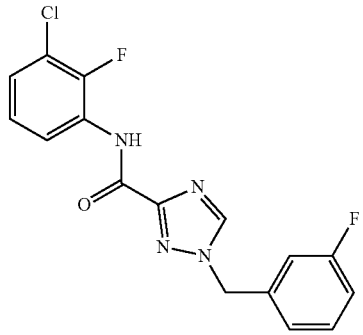 [SMILES: O=C(Nc1cccc(Cl)c1F)c1ncn(Cc2cccc(F)c2)n1]

N-(3-chloro-2-fluorophenyl)-1-(3-fluorobenzyl)-1H-1,2,4-triazole-3-carboxamide

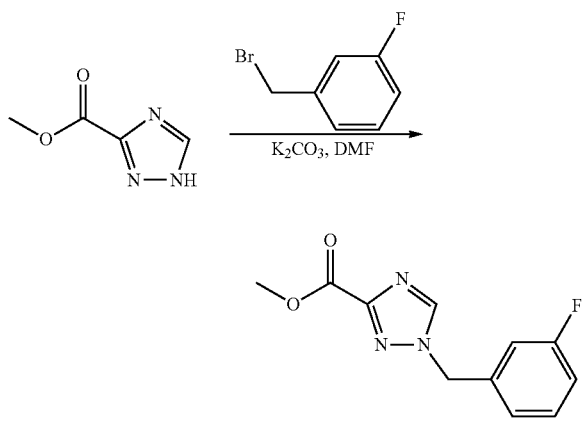

Methyl 1-(3-fluorobenzyl)-1H-1,2,4-triazole-3-carboxylate To a solution of methyl 1H-1,2,4-triazole-3-carboxylate (1 g, 7.87 mmol, 1 eq) in DMF (20 mL) was added K₂CO₃ (2.17 g, 15.7 mmol, 2 eq) and 1-(bromomethyl)-3-fluorobenzene (1.78 g, 9.44 mmol, 1.16 mL, 1.2 eq) at 25° C., and the mixture was stirred at 25° C. for 16 h. To the reaction was added H₂O (20 mL), and the mixture was extracted with EtOAc (20 mL×3). The combined organic layers were washed with brine (20 mL×3), dried over Na₂SO₄, and concentrated under reduced pressure to give a residue which was purified by prep-TLC (SiO₂, petroleum ether/EtOAc=1:1) to afford the title compound (0.9 g, 3.83 mmol, 49% yield) and methyl 1-(3-fluorobenzyl)-1H-1,2,4-triazole-5-carboxylate (0.09 g, 383 μmol, 5% yield) as a white solid.

MS(ES+) C₁₁H₁₀O₂N₃F requires: 235, found 236 [M+H]⁺.

¹H NMR (400 MHz, CDCl₃) δ=8.16 (s, 1H), 7.41-7.36 (m, 1H), 7.12-7.07 (m, 2H), 7.03-7.00 (m. 1H), 5.44 (s, 2H), 4.03 (s, 3H).

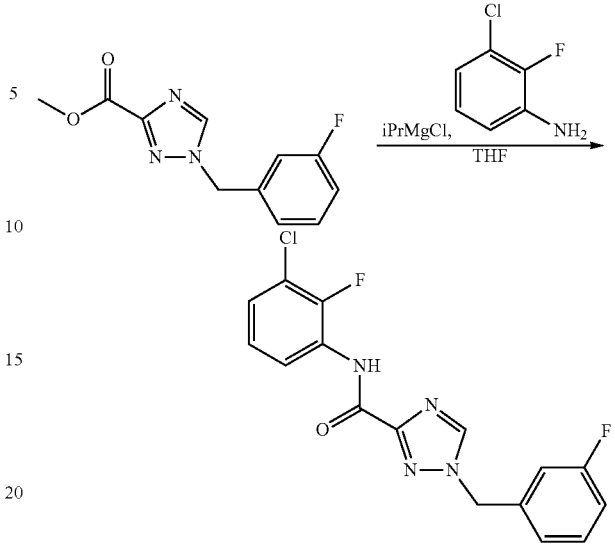

N-(3-Chloro-2-fluorophenyl)-1-(3-fluorobenzyl)-1H-1,2,4-triazole-3-carboxamide

To a solution of 3-chloro-2-fluoroaniline (83.54 mg, 574.0 μmol, 1.5 eq) in THF (5 mL) was added iPrMgCl (1 M, 765.26 uL, 2 eq), and the mixture was stirred at 25° C. for 10 mins. To the mixture was added the product from the previous step (90 mg, 383 μmol, 1 eq), and the mixture was stirred at 25° C. for 16 h. To the reaction was added H₂O (5 mL), and the mixture was extracted with EtOAc (5 mL×3). The combined organic layers were washed with brine (5 mL×3), dried over Na₂SO₄, and concentrated under reduced pressure to give a residue which was purified by prep-HPLC (column: Phenomenex luna C18 150 mm×25 mm×10 μm; mobile phase: [H₂O (0.1% TFA)-CH₃CN];B %: 60%-80%, 10 min). The eluent was concentrated and lyophilized to afford the title compound (31.9 mg, 89.50 μmol, 23% yield) as a white solid.

MS(ES+)C₁₆H₁₁ON₄ClF₂ requires: 348, found 349 [M+H]⁺.

¹H NMR (400 MHz, CDCl₃) δ=10.24 (s, 1H), 8.93 (s, 1H), 7.69-7.65 (m. 1H), 7.49-7.43 (m, 2H), 7.28-7.18 (m, 4H), 5.57 (s, 2H).

Example 89

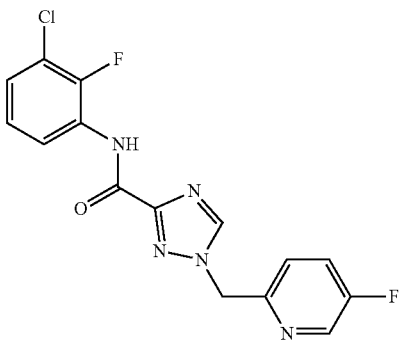 [SMILES: O=C(Nc1cccc(Cl)c1F)c1ncn(Cc2ccc(F)cn2)n1]

N-(3-chloro-2-fluorophenyl)-1-((5-fluoropyridin-2-yl)methyl)-1H-1,2,4-triazole-3-carboxamide

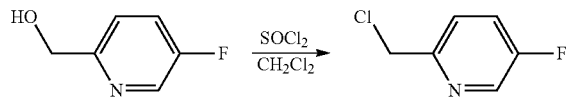

2-(Chloromethyl)-5-fluoropyridine To a solution of (5-fluoro-2-pyridyl)-methanol (500 mg, 3.93 mmol, 1 eq) in CH$_2$Cl$_2$ (10 mL) was added SOCl$_2$ (935.92 mg, 7.87 mmol, 570.68 uL, 2 eq) at 0° C. under an N$_2$ atmosphere (15 Psi). The reaction was stirred at 20° C. for 2 h. The reaction mixture was concentrated under reduced pressure to afford the title compound (710 mg, 3.71 mmol, 94% yield, 95% purity, HCl) as a brown solid.

$^1$H NMR (400 MHz, CDCl$_3$) δ=8.70-8.50 (m, 1H), 8.20-7.95 (m, 2H), 5.13 (s, 2H).

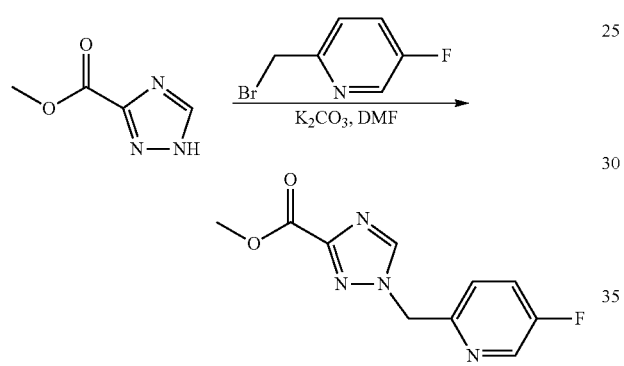

Methyl 1-[(5-fluoro-2-pyridyl)methyl]-1,2,4-triazole-3-carboxylate To a solution of methyl 1H-1,2,4-triazole-3-carboxylate (200 mg, 1.57 mmol, 1 eq) in DMF (5 mL) was added K$_2$CO$_3$ (652.4 mg, 4.72 mmol, 3 eq) followed by the product from the previous step (343.7 mg, 1.89 mmol, 1.20 eq, HCl). The mixture was stirred at 20° C. for 16 h. The mixture was diluted with H$_2$O (10 mL) and extracted with EtOAc (10 mL×2). The combined organic layers were concentrated. The residue was purified by prep-TLC (petroleum ether:EtOAc=0:1) and concentrated under reduced pressure to afford the title compound (130 mg, 440.3 μmol, 28% yield, 80% purity) as a white solid.

MS(ES+)C$_{10}$H$_9$N$_4$O$_2$F requires:236, found 237 [M+H]$^+$.

$^1$H NMR (400 MHz, CDCl$_3$) δ=8.36 (d, J=2.8 Hz, 1H), 8.31 (s, 1H), 7.39-7.32 (m, 1H) 7.30-7.24 (m, 1H), 5.46 (s, 2H), 3.92 (s. 3H).

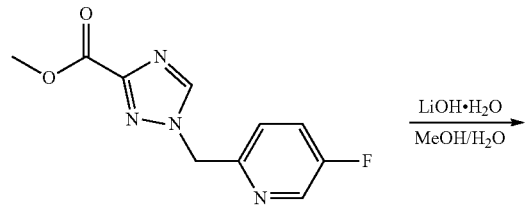

1-((5-Fluoropyridin-2-yl)methyl)-1H-1,2,4-triazole-3-carboxylic acid To a solution of the product from the previous step (130 mg, 440.30 μmol, 1 eq) in H$_2$O (1 mL) and MeOH (4 mL) was added LiOH·H$_2$O (22.17 mg, 528.36 μmol, 1.2 eq). The mixture was stirred at 25° C. for 2 h. The mixture was concentrated to afford the title compound (123 mg, crude) as a white solid.

MS(ES+)C$_9$H$_7$N$_4$O$_2$F requires:222, found 223 [M+H]$^+$.

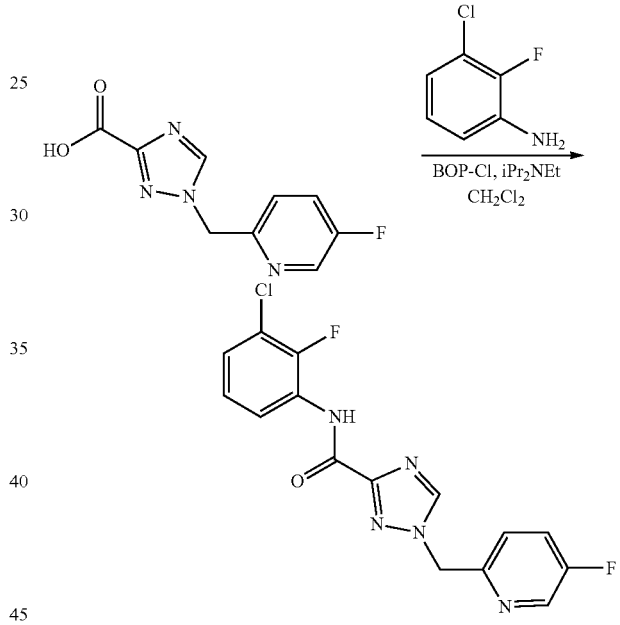

N-(3-Chloro-2-fluorophenyl)-1-((5-fluoropyridin-2-yl)methyl)-1H-1,2,4-triazole-3-carboxamide To a solution of the product from the previous step (123 mg, 553.6 μmol, 1 eq) in CH$_2$Cl$_2$ (6 mL) was added 3-chloro-2-fluoroaniline (96.7 mg, 664.3 μmol, 1.2 eq), BOP-Cl (211.4 mg, 830.4 μmol, 1.5 eq) and iPr$_2$NEt (214.7 mg, 1.66 mmol, 289 uL, 3 eq). The mixture was stirred at 40° C. for 2 h. The mixture was diluted with H$_2$O (10 mL) and extracted with CH$_2$Cl$_2$ (10 mL×2). The combined organic layers were concentrated under reduced pressure and triturated with MeOH (10 mL). The filter cake was collected to afford the title compound (12.8 mg, 36.2 μmol, 6.6% yield, 99% purity) as a white solid.

MS(ES+)C$_{15}$H$_{10}$N$_5$OClF$_2$ requires:349 and 351, found 350 and 352 [M+H]$^+$.

$^1$H NMR (400 MHz, DMSO-d$_6$) δ=10.27 (s, 1H), 8.93 (s, 1H), 8.56 (d, J=2.9 Hz, 1H), 7.86-7.76 (m, 1H), 7.70-7.61 (m, 1H), 7.57-7.51 (m, 1H), 7.50-7.42 (m, 1H), 7.29-7.21 (m, 1H), 5.68 (s, 2H).

Example 90

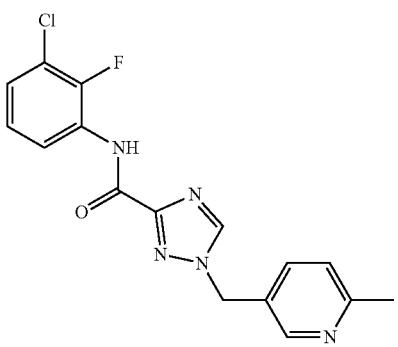 [SMILES: Cc1ccc(Cn2cnc(C(=O)Nc3cccc(Cl)c3F)n2)cn1]

N-(3-chloro-2-fluorophenyl)-1-(((6-methylpyridin-3-yl)methyl)-1H-1,2,4-triazole-3-carboxamide

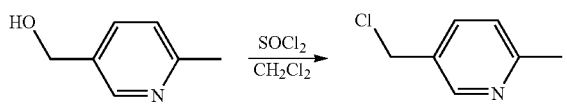

5-(Chloromethyl)-2-methylpyridine To a solution of (6-methylpyridin-3-yl)methanol (500 mg, 4.06 mmol, 1 eq) in CH$_2$Cl$_2$ (10 mL) was added SOCl$_2$ (966.0 mg, 8.12 mmol, 589.1 uL, 2 eq) at 0° C. under an N$_2$ atmosphere (15 Psi). The mixture was stirred at 20° C. for 2 h. The reaction mixture was concentrated under reduced pressure to afford the title compound (700 mg, 3.85 mmol, 95% yield, 98% purity, HCl salt).

$^1$H NMR (400 MHz, CDCl$_3$) δ=8.84 (d, J=2.0 Hz, 1H), 8.35 (dd, J$_1$=8.0 Hz, J$_2$=2.0 Hz, 1H), 7.70 (d, J=8.0 Hz, 1H), 4.77 (s, 2H), 2.96 (s, 3H).

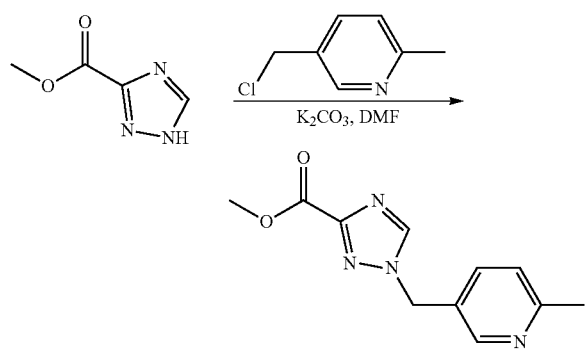

Methyl 1-((6-methylpyridin-3-yl)methyl)-1H-1,2,4-triazole-3-carboxylate To a solution of methyl 1H-1,2,4-triazole-3-carboxylate (200 mg, 1.57 mmol, 1 eq) in DMF (5 mL) was added K$_2$CO$_3$ (652.4 mg, 4.72 mmol, 3 eq) followed by the product from the previous step (353.9 mg, 1.89 mmol, 1.2 eq, HCl). The mixture was stirred at 20° C. for 16 h. The mixture was diluted with H$_2$O (10 mL) and extracted with EtOAc (10 mL×2). The combined organic layers were concentrated to a yellow oil which was purified by prep-TLC (petroleum ether:EtOAc=0:1) to afford the title compound (70 mg, 256.2 μmol, 16% yield, 85% purity) as a white solid.

$^1$H NMR (400 MHz, CDCl$_3$) δ=8.45 (d, J=2.1 Hz, 1H), 8.08 (s, 1H), 7.47 (dd, J$_1$=8.0 Hz, J$_2$=2.4 Hz, 1H), 7.12 (d, J=8.1 Hz, 1H), 5.34 (s, 2H), 3.93 (s, 3H), 2.50 (s, 3H).

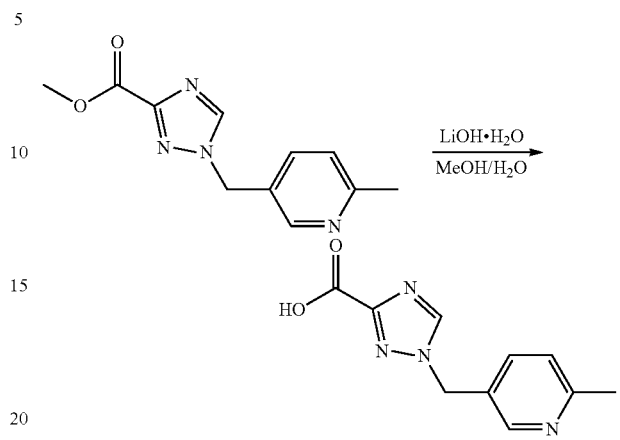

1-((6-methylpyridin-3-yl)methyl)-1H-1,2,4-triazole-3-carboxylic acid To a solution of the product from the previous step (70 mg, 256.20 μmol, 1 eq) in MeOH (2 mL) and H$_2$O (0.5 mL) was added LiOH·H$_2$O (12.9 mg, 307.4 μmol, 1.2 eq). The mixture was stirred at 25° C. for 2 h. The mixture was concentrated under reduced pressure to afford the title compound (66 mg, crude) as a white solid.

MS(ES+)C$_{10}$H$_{10}$N$_4$O$_2$ requires: 218, found 219 [M+H]$^+$.

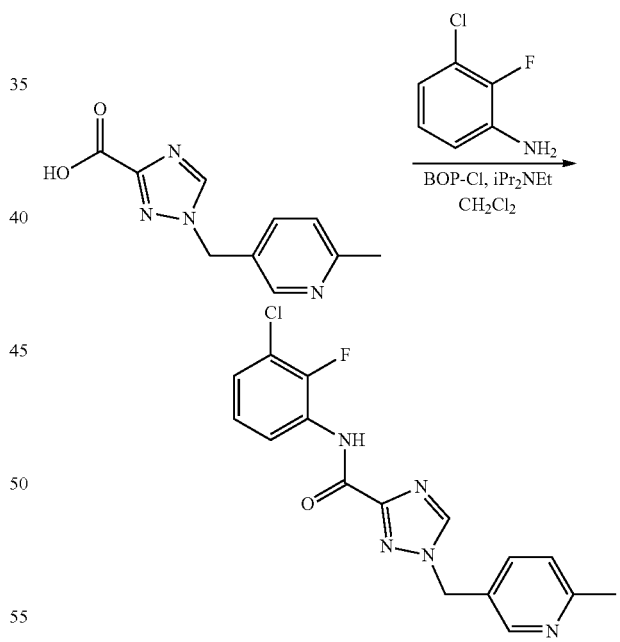

N-(3-chloro-2-fluorophenyl)-1-((6-methylpyridin-3-yl)methyl)-1H-1,2,4-triazole-3-carboxamide To a solution of the product from the previous step (66 mg, 302.5 μmol, 1 eq) in CH$_2$Cl$_2$ (6 mL) was added 3-chloro-2-fluoroaniline (52.8 mg, 363.0 μmol, 1.2 eq), BOP-Cl (115.5 mg, 453.7 μmol, 1.5 eq) and iPr$_2$NEt (117.3 mg, 907.4 μmol, 158.1 uL, 3 eq). The mixture was stirred at 40° C. for 2 h. The mixture was diluted with H$_2$O (10 mL) and extracted with CH$_2$Cl$_2$ (10 mL×2). The combined organic layers were concentrated under reduced pressure to give a residue, which was purified by column chromatography on silica gel (CH$_2$Cl$_2$: MeOH=10:1) to the title compound (2.8 mg, 7.77 µmol, 3% yield, 96% purity) as a white solid.

MS(ES+)C$_{16}$H$_{13}$N$_5$OClF requires:345 and 347, found 346 and 348 [M+H]$^+$.

$^1$H NMR (400 MHz, CDCl$_3$) δ=9.12 (s, 1H), 8.47 (d, J=1.8 Hz, 1H), 8.42-8.34 (m, 1H), 8.07 (s, 1H), 7.53 (dd, J$_1$=7.9 Hz, J$_2$=2.3 Hz, 1H), 7.15-7.02 (m, 3H), 5.35 (s, 2H), 2.51 (s, 3H).

Example 91

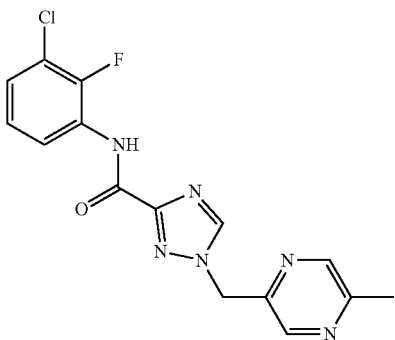 [SMILES: Cc1cnc(Cn2cnc(C(=O)Nc3cccc(Cl)c3F)n2)cn1]

N-(3-chloro-2-fluorophenyl)-1-((5-methylpyrazin-2-yl)methyl)-1H-1,2,4-triazole-3-carboxamide

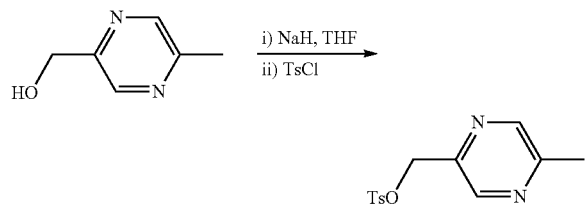

(5-Methylpyrazin-2-yl)methyl 4-methylbenzenesulfonate To a solution of (5-methylpyrazin-2-yl)methanol (1.2 g, 9.67 mmol, 1 eq) in THF (1 mL) was added NaH (773.25 mg, 19.33 mmol, 60% purity, 2 eq) at 0° C., and the mixture was stirred for 30 mins. To the mixture was added a solution of TsCl (2.21 g, 11.60 mmol, 1.2 eq) in THF. The mixture was stirred at 20° C. for 16 h. The mixture was concentrated under reduced pressure to afford the title compound (3 g, 8.73 mmol, 90% yield, 81% purity) as a black oil.

MS(ES+)C$_{13}$H$_{14}$N$_2$O$_3$S requires:278, found 279 [M+H]$^+$.

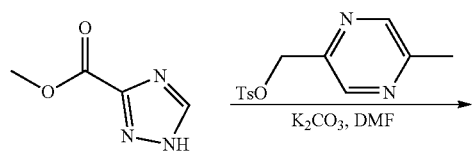

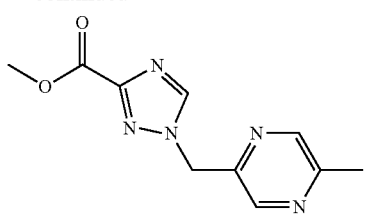

Methyl 1-[(5-methylpyrazin-2-yl)methyl]-1,2,4-triazole-3-carboxylate To a solution of the product from the previous step (3 g, 8.73 mmol, 1 eq) in DMF (2 mL) was added K$_2$CO$_3$ (2.41 g, 17.46 mmol, 2 eq) and methyl 1H-1,2,4-triazole-3-carboxylate (1.33 g, 10.48 mmol, 1.2 eq). The mixture was stirred at 20° C. for 16 h. The mixture was filtered, concentrated under reduced pressure and purified by column chromatography (SiO$_2$, petroleum ether/EtOAc=0/1 to 0/1) to afford the title compound (0.238 g, 989.9 µmol, 11% yield, 97% purity) as a yellow oil.

MS(ES+)C$_{10}$H$_{11}$N$_5$O$_2$ requires:233, found 234 [M+H]$^+$.

$^1$H NMR (400 MHz, CDCl$_3$) δ=8.55 (s, 1H), 8.43 (s, 1H), 8.38 (s, 1H), 5.53 (s, 2H), 3.99 (s, 3H), 2.59 (s, 3H).

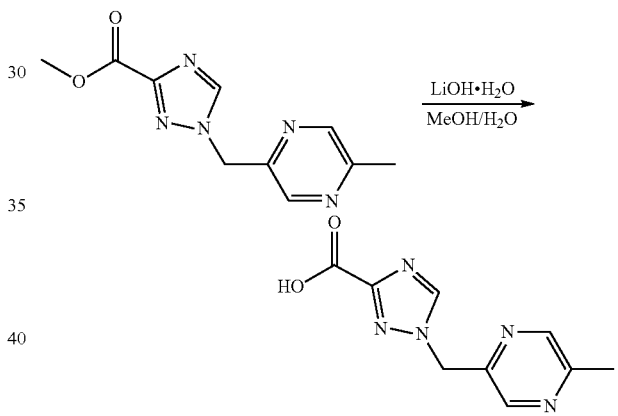

1-[(5-Methylpyrazin-2-yl)methyl]-1,2,4-triazole-3-carboxylic acid To a solution of the product from the previous step (0.18 g, 771.8 µmol, 1 eq) in THF (1.5 mL) and H$_2$O (0.5 mL) was added LiOH·H$_2$O (48.58 mg, 1.16 mmol, 1.5 eq), the mixture was stirred at 20° C. for 16 h. To the mixture was added HCl (1 N) to bring the pH to 6, and the mixture was concentrated under reduced pressure to afford the title compound (0.13 g, 581.2 µmol) as a brown solid.

MS(ES+)C$_9$H$_9$N$_5$O$_2$ requires:219, found 220 [M+H]$^+$.

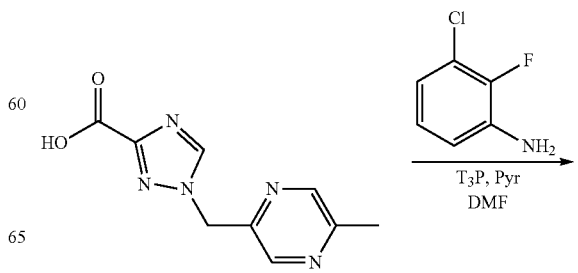

-continued

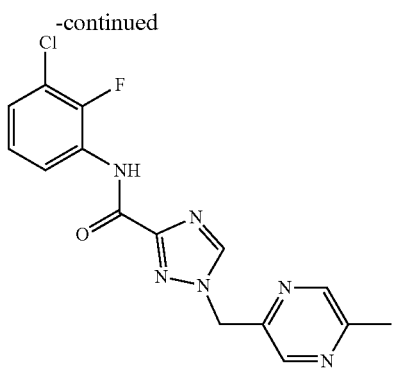

N-(3-Chloro-2-fluorophenyl)-1-[(5-methylpyrazin-2-yl)methyl]-1,2,4-triazole-3-carboxamide To a solution of 3-chloro-2-fluoroaniline (86.3 mg, 593.1 µmol, 1 eq) in DMF (2 mL) was added T₃P (566.1 mg, 889.6 µmol, 529.1 uL, 50% purity, 1.5 eq) pyridine (93.8 mg, 1.2 mmol, 95.7 uL, 2 eq), and the product from the previous step (0.13 g, 593.1 µmol, 1 eq). The mixture was stirred at 40° C. for 16 h. To the mixture was added H₂O (5 mL) and extracted with EtOAc (5 mL×3). The combined organic layers were washed with brine (5 mL×3), dried over Na₂SO₄, and concentrated under reduced pressure to give a residue which was purified by prep-HPLC (column: Phenomenex luna C18 150 mm×25 mm×10 µm; mobile phase: [H₂O (0.1% TFA)-CH₃CN];B %: 28%-58%,10 min). The eluent was concentrated and lyophilized to afford the title compound (81 mg, 233.6 µmol, 39% yield) as a yellow solid.

MS(ES+)$C_{15}H_{12}N_6OFCl$ requires:346, found 347 [M+H]⁺.

¹H NMR (400 MHz, CDCl₃) δ=9.20 (br s, 1H), 8.59 (s, 1H), 8.48-8.41 (m, 2H), 8.38 (s, 1H), 7.21-7.07 (m, 2H), 5.55 (s, 2H), 2.59 (s, 3H).

Example 92

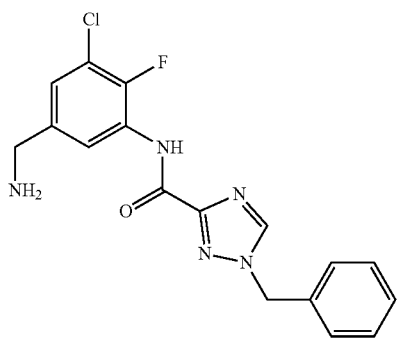

N-(5-(aminomethyl)-3-chloro-2-fluorophenyl)-1-benzyl-1H-1,2,4-triazole-3-carboxamide

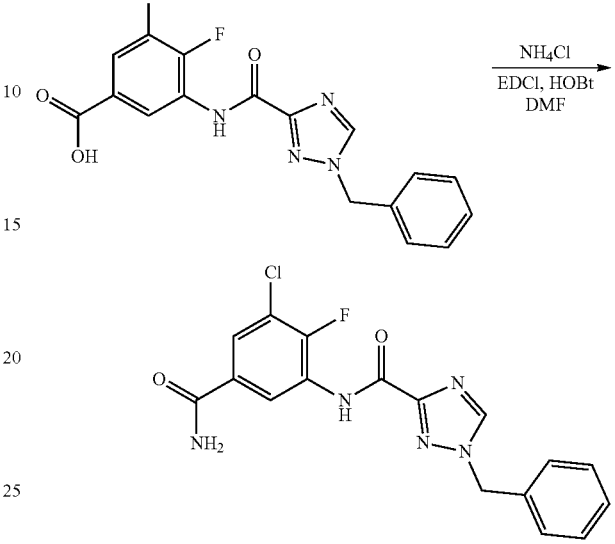

1-Benzyl-N-(5-carbamoyl-3-chloro-2-fluorophenyl)-1H-1,2,4-triazole-3-carboxamide To a solution of Intermediate H (100 mg, 266.84 µmol, 1 eq) in DMF (2 mL) was added NH₄Cl (17.13 mg, 320.2 µmol, 1.2 eq), EDCI (76.73 mg, 400.26 µmol, 1.5 eq), and HOBt (54.08 mg, 400.26 µmol, 1.5 eq). The mixture was stirred at 40° C. for 16 h. The mixture was diluted with H₂O (5 mL) and extracted with EtOAc (5 mL×3). The combined organic layers were washed with brine (5 mL×2), dried over Na₂SO₄, and concentrated under reduced pressure. The residue was purified by prep-HPLC (column: Waters Xbridge 150 mm×25 mm×5 µm; mobile phase: [H₂O (0.05% NH₄OH v/v)-CH₃CN];B %: 23%-53%,10 min). The eluent was concentrated and then lyophilized, to obtain the title compound (37 mg, 97.9 µmol, 37% yield) as a white solid.

MS(ES+) $C_{17}H_{13}N_5O_2FCl$ requires:373, found 374 [M+H]⁺.

¹H NMR (400 MHz, DMSO-d₆) δ=8.94 (s, 1H), 8.14 (dd, J=6.8, 2.0 Hz, 1H), 8.11 (s, 1H), 7.96 (dd, J=6.4, 2.4 Hz, 1H), 7.43-7.33 (m, 5H), 7.58 (s, 1H), 5.55 (s, 2H), 3.30 (s, 1H).

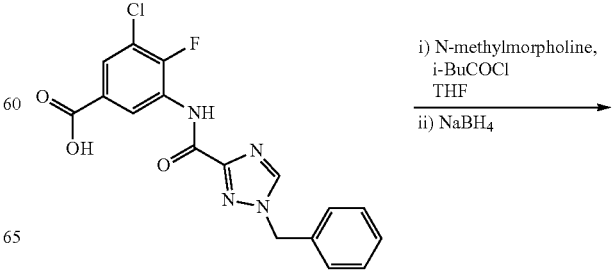

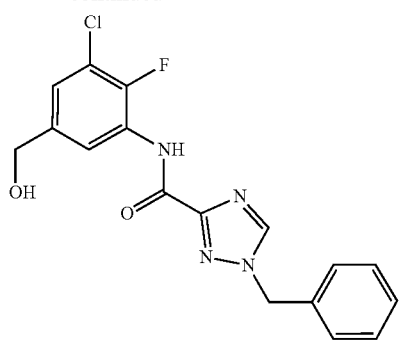 [SMILES: NCc1cc(Cl)c(F)c(NC(=O)c2ncn(Cc3ccccc3)n2)c1]

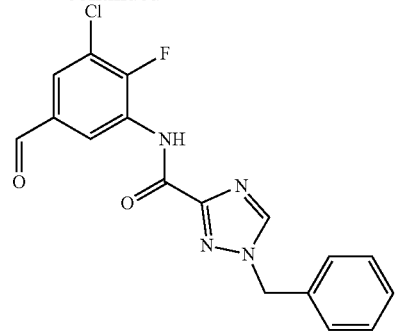

1-Benzyl-N-(3-chloro-2-fluoro-5-formylphenyl)-1H-1,2,4-triazole-3-carboxamide

To a solution the product from the previous step (140 mg, 388 μmol, 1 eq) in CH$_2$Cl$_2$ (2 mL) was added DMP (Dess-Martin Periodinane, 197.5 mg, 465.67 μmol, 144.17 uL, 1.2 eq). The mixture was stirred at 25° C. for 5 h. To the mixture was added H$_2$O (4 mL) and EtOAc (4 mL), and the reaction was filtered and extracted with EtOAc (6 mL×3). The combined organic layers were washed with brine (5 mL×2), dried over Na$_2$SO$_4$, and concentrated under reduced pressure to yield the title compound (139 mg, 387 μmol) which was used for the next step directly.

MS(ES+) C$_{17}$H$_{12}$N$_4$O$_2$FCl requires: 358, found 359 [M+H]$^+$.

$^1$H NMR (400 MHz, DMSO-d$_6$) δ=10.41 (s, 1H), 9.98 (s, 1H), 8.95 (s, 1H), 8.29-8.22 (m, 1H), 7.42-7.25 (m, 6H), 5.55 (s, 2H).

1-Benzyl-N-(3-chloro-2-fluoro-5-(hydroxymethyl)phenyl)-1H-1,2,4-triazole-3-carboxamide To a solution of the product from the previous step (200 mg, 534 μmol, 1 eq) in THF (3 mL) was added N-methylmorpholine (67.5 mg, 667.1 μmol, 73 uL, 1.25 eq) and isobutyl chloroformate (91.11 mg, 667.11 μmol, 87.61 uL, 1.25 eq) at 0° C. The reaction was stirred at 25° C. for 1.5 h. The reaction mixture was filtered and the filtrate was added into a solution of NaBH$_4$ (40.4 mg, 1.07 mmol, 2 eq) in H$_2$O (6 mL), and the reaction mixture was stirred at 25° C. for 16 h. To the mixture was added H$_2$O (10 mL), and aqueous HCl solution was added to bring the pH to 8. The mixture was then extracted with EtOAc (20 mL×3). The combined organic layers were washed with brine (10 mL×2), dried over Na$_2$SO$_4$, and concentrated under reduced pressure. The residue was purified by prep-HPLC (column: Waters Xbridge 150 mm×25 mm×5 μm; mobile phase: [H$_2$O (0.05% NH$_4$OH v/v)-CH$_3$CN];B %: 27%-57%,10 min), and the eluent was concentrated and then lyophilized to obtain the title compound (170 mg, crude) as a yellow solid.

MS(ES+) C$_{17}$H$_{14}$N$_4$O$_2$FCl requires: 360, found 361 [M+H]$^+$.

$^1$H NMR (400 MHz, DMSO-d$_6$) δ=8.92 (s, 1H), 7.65-7.62 (m, 1H), 7.43-7.36 (m, 6H), 5.55 (s, 2H), 5.41 (t, J=6 Hz, 1H), 4.48 (d, J=6 Hz, 2H).

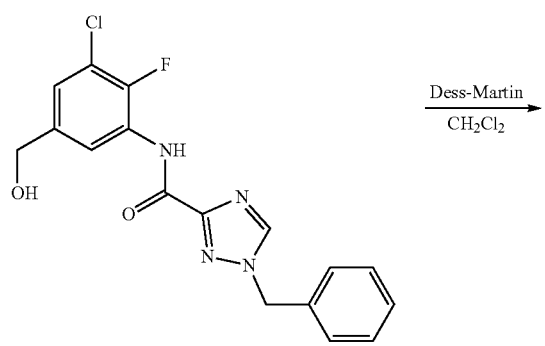

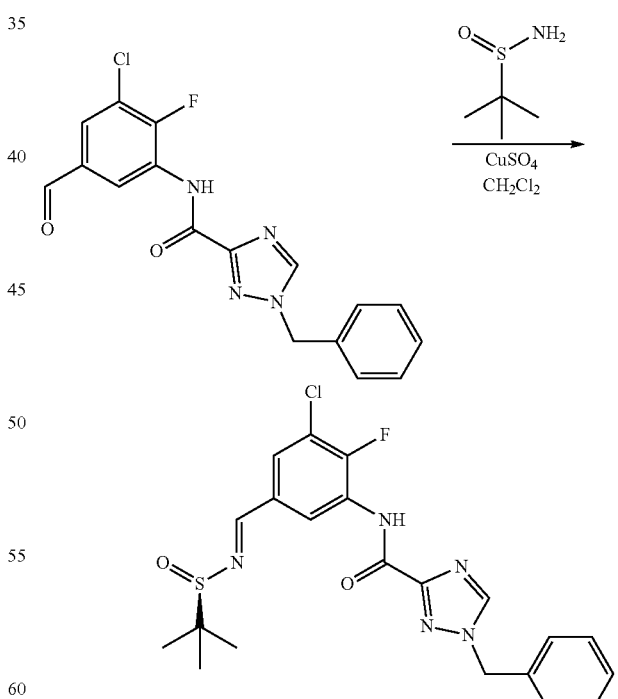

(R,E)-1-benzyl-N-(5-(((tert-butylsulfinyl)imino)methyl)-3-chloro-2-fluorophenyl)-1H-1,2,4-triazole-3-carboxamide To a solution of 2-methylpropane-2-sulfinamide (9.21 mg, 76.0 μmol, 1 eq) in CH$_2$Cl$_2$ (1 mL) was added CuSO$_4$ (26.7 mg, 167.3 μmol, 2.2 eq) and the product from the previous step (30 mg, 84 µmol, 1.1 eq). The mixture was stirred at 25° C. for 48 h. The mixture was filtered and concentrated under reduced pressure to yield the title compound (11 mg, 24 µmol, 31% yield) as a white solid.

MS(ES+) $C_{21}H_{21}N_5O_2FClS$ requires: 461, found 462 [M+H]⁺.

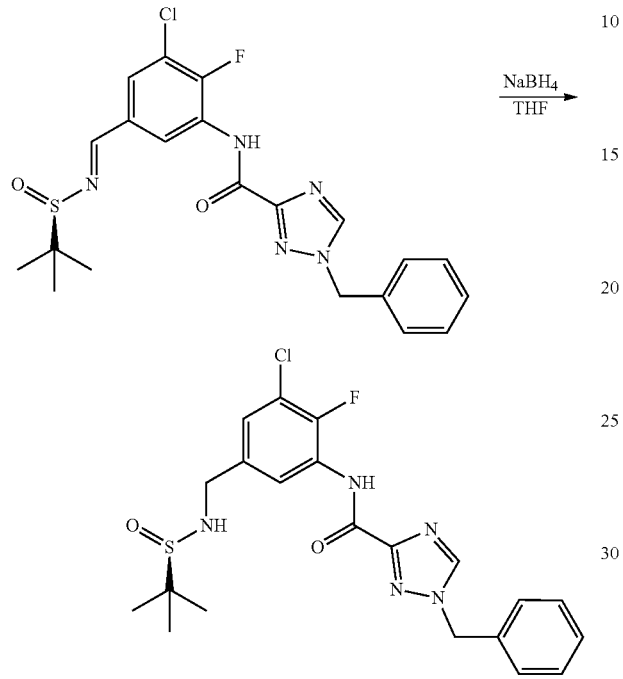

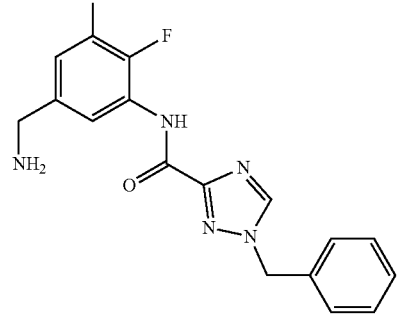

(R)-1-benzyl-N-(5-(((tert-butylsulfinyl)amino)methyl)-3-chloro-2-fluorophenyl)-1H-1,2,4-triazole-3-carboxamide To a solution of the product from the previous step (11 mg, 24 µmol, 1 eq) in THF (0.5 mL) was added a solution of NaBH₄ (3.6 mg, 95.3 µmol, 4 eq) in THF (0.5 mL) under N₂ at −48° C. The mixture was stirred under N₂ at −48° C. for 2 h. To the mixture was added H₂O (5 mL), and the aqueous layer was extracted with EtOAc (5 mL×3). The combined organic layers were washed with brine (5 mL), dried over Na₂SO₄, and concentrated under reduced pressure the title compound (6 mg, 13 µmol, 54% yield) as a green oil, which was used for the next step directly.

MS(ES+) $C_{21}H_{23}N_5O_2FClS$ requires: 463, found 464 [M+H]⁺.

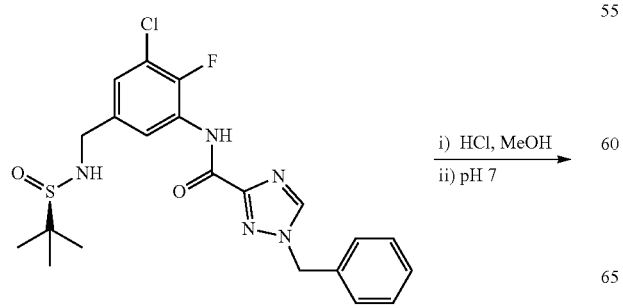

N-[5-(Aminomethyl)-3-chloro-2-fluorophenyl]-1-benzyl-1,2,4-triazole-3-carboxamide To a solution of the product from the previous step (6 mg, 13 µmol, 1 eq) in MeOH (1 mL) was added HCl (102 mg, 1.04 mmol, 0.1 mL, 80.04 eq) and the reaction was stirred at 25° C. for 16 h. Aqueous NaOH was added to bring the pH to 7. The mixture was concentrated under reduced pressure and the residue was purified by prep-HPLC (column: Waters Xbridge 150 mm×25 mm×5 µm; mobile phase: [H₂O (10 mM NH₄HCO₃)—CH₃CN];B %: 18%-48%,10 min). The eluent was concentrated and then lyophilized to yield the title compound (1.9 mg, 5.18 µmol, 40% yield) as a white solid.

MS(ES+) $C_{17}H_{15}N_5OFCl$ requires: 359, found 360 [M+H]⁺.

¹H NMR (400 MHz, DMSO-d₆) δ=8.94 (s, 1H), 7.80-7.78 (m, 1H), 7.58-7.55 (m, 1H), 7.46-7.35 (m, 6H), 5.55 (s, 2H), 4.00 (s, 2H), 3.30 (s, 2H).

Example 93

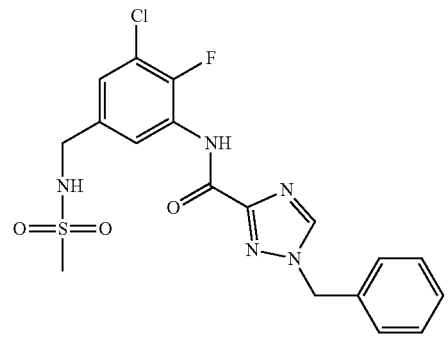 [SMILES: CS(=O)(=O)NCc1cc(Cl)c(F)c(NC(=O)c2ncn(Cc3ccccc3)n2)c1]

237

1-Benzyl-N-(3-chloro-2-fluoro-5-(methylsulfona-midomethyl)phenyl)-1H-1,2,4-triazole-3-carboxamide

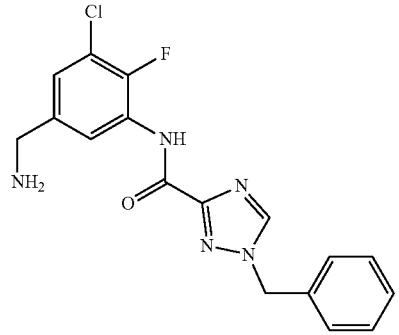 [SMILES: O=C(Nc1cc(CO)cc(Cl)c1F)c1ncn(Cc2ccccc2)n1]

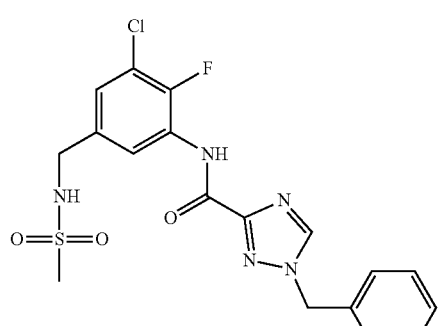

To a solution of N-[5-(aminomethyl)-3-chloro-2-fluorophenyl]-1-benzyl-1,2,4-triazole-3-carboxamide (Example 92, 0.1 g, 277.94 μmol, 1 eq) in CH$_2$Cl$_2$ (2 mL) was added Et$_3$N (84.37 mg, 833.83 μmol, 116.06 uL, 3 eq) and methanesulfonyl chloride (63.68 mg, 555.89 μmol, 43.03 uL, 2 eq) at 0° C. The mixture was warmed and stirred at 25° C. for 2 h. The mixture was diluted with H$_2$O (2 mL) and extracted with CH$_2$Cl$_2$ (5 mL×3). The combined organic layers were washed with brine (5 mL×3), dried over Na$_2$SO$_4$, and concentrated under reduced pressure. The residue was purified by prep-TLC (SiO$_2$, 100% EtOAc) to afford the title compound (28.1 mg, 58.40 μmol, 21% yield) as a white solid.

MS(ES+) C$_{18}$H$_{17}$N$_5$O$_3$FClS requires: 437, found 438 [M+H]$^+$.

$^1$H NMR (400 MHz, CDCl$_3$) δ=9.12 (s, 1H), 8.40 (dd, J=1.8, 6.5 Hz, 1H), 8.01 (s, 1H), 7.39-7.31 (m, 3H), 7.30-7.23 (m, 2H), 7.14 (dd, J=1.9, 6.5 Hz, 1H), 5.37 (s, 2H), 5.11 (t, J=6.3 Hz, 1H), 4.28 (d, J=6.2 Hz, 2H), 2.92 (s, 3H).

238

Example 94

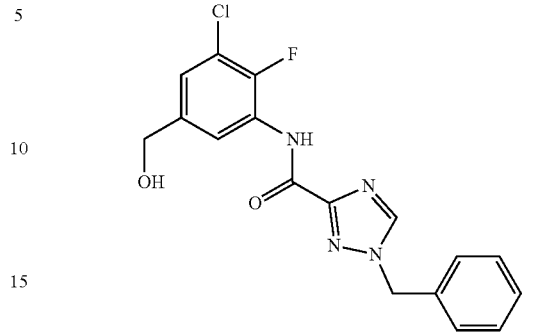

1-Benzyl-N-(3-chloro-2-fluoro-5-(hydroxymethyl)phenyl)-1H-1,2,4-triazole-3-carboxamide

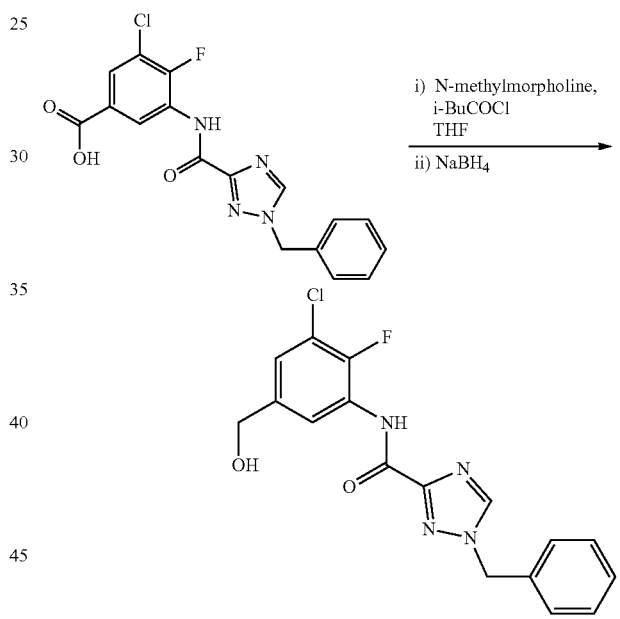

1-Benzyl-N-(3-chloro-2-fluoro-5-(hydroxymethyl)phenyl)-1H-1,2,4-triazole-3-carboxamide To a solution of Intermediate H (2 g, 5.34 mmol, 1 eq) in THF (20 mL) was added N-methylmorpholine (674.78 mg, 6.67 mmol, 733.45 uL, 1.25 eq) and isobutyl chloroformate (911.13 mg, 6.67 mmol, 876.09 uL, 1.25 eq) at 0° C., and the mixture was warmed to room temperature and stirred for 1.5 h. The reaction mixture was filtered, the filtrate was added into a solution of NaBH$_4$ (403.79 mg, 10.67 mmol, 2 eq) in H$_2$O (30 mL), and the mixture was stirred at 25° C. for 16 h. HCl (10 mL) was added to bring the pH to 2. The mixture was extracted with EtOAc (15 mL×3). The combined organic layers were washed with brine (15 mL×3), dried over Na$_2$SO$_4$, and concentrated under reduced pressure to afford the title compound (0.789 g, 2.19 mmol, 41% yield) as a colorless liquid.

MS(ES+)C$_{17}$H$_{14}$ClFN$_4$O$_2$ requires:360, found 361 [M+H]$^+$.

Example 95

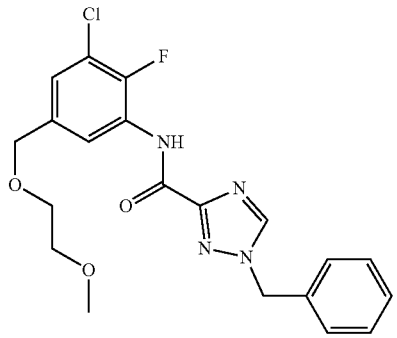 [SMILES: COCCOCc1cc(Cl)c(F)c(NC(=O)c2ncn(Cc3ccccc3)n2)c1]

1-Benzyl-N-(3-chloro-2-fluoro-5-(2-methoxyethoxy) methyl)phenyl)-1H-1,2,4-triazole-3-carboxamide

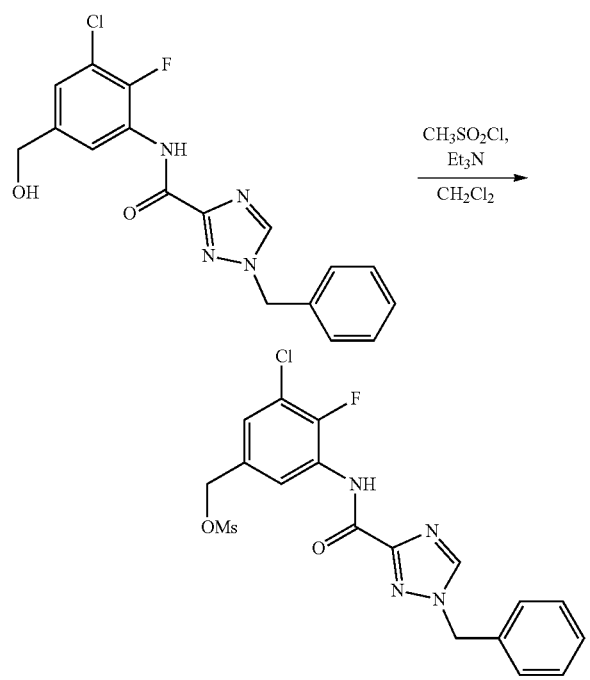

3-(1-Benzyl-1H-1,2,4-triazole-3-carboxamido)-5-chloro-4-fluorobenzyl methanesulfonate (Intermediate J) To a solution of the Example 94 material (0.789 g, 2.19 mmol, 1 eq) in CH$_2$Cl$_2$ (5 mL) was added Et$_3$N (663.90 mg, 6.56 mmol, 913.20 uL, 3 eq) and methanesulfonyl chloride (501.04 mg, 4.37 mmol, 338.54 uL, 2 eq), and the mixture was stirred at 20° C. for 1 h. The mixture was diluted with H$_2$O (10 mL) and extracted with CH$_2$Cl$_2$ (10 mL×3). The combined organic layers were washed with brine (10 mL×3), dried over Na$_2$SO$_4$, and concentrated under reduced pressure to afford the title compound (1.14 g, 1.71 mmol, 78% yield) as colorless oil.

MS(ES+)C$_{18}$H$_{16}$ClFN$_4$O$_4$S requires:438, found 439 [M+H]$^+$.

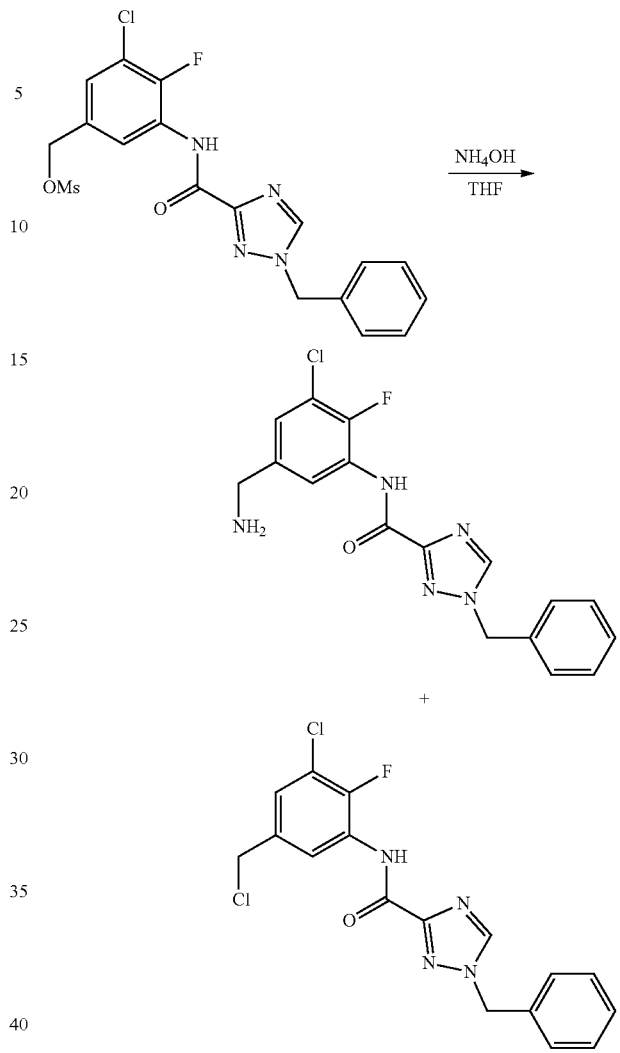

N-(5-(aminomethyl)-3-chloro-2-fluorophenyl)-1-benzyl-1H-1,2,4-triazole-3-carboxamide and 1-benzyl-N-(3-chloro-5-(chloromethyl)-2-fluorophenyl)-1H-1,2,4-triazole-3-carboxamide To a solution of the product from the previous step (0.5 g, 1 mmol, 1 eq) in THF (3 mL) was added NH$_3$·H$_2$O (465.83 mg, 7.98 mmol, 511.90 uL, 60% w/v, 7 eq), and the mixture was stirred at 50° C. for 5 h. The mixture was concentrated under reduced pressure to give a residue which was purified by column chromatography (SiO$_2$, petroleum ether/EtOAc=10/1 to 1/1).

N-(5-(aminomethyl)-3-chloro-2-fluorophenyl)-1-benzyl-1H-1,2,4-triazole-3-carboxamide White solid, 30 mg, 79 μmol, 6.9% yield.

MS(ES+)C$_{17}$H$_{15}$ClFN$_5$O requires:359, found 360 [M+H]$^+$.

1-Benzyl-N-(3-chloro-5-(chloromethyl)-2-fluorophenyl)-1H-1,2,4-triazole-3-carboxamide Yellow oil, 100 mg, 277.94 μmol, 24% yield.

MS(ES+)C$_{17}$H$_{13}$Cl$_2$FN$_4$O requires: 378, found 379 [M+H]$^+$.

Example 96

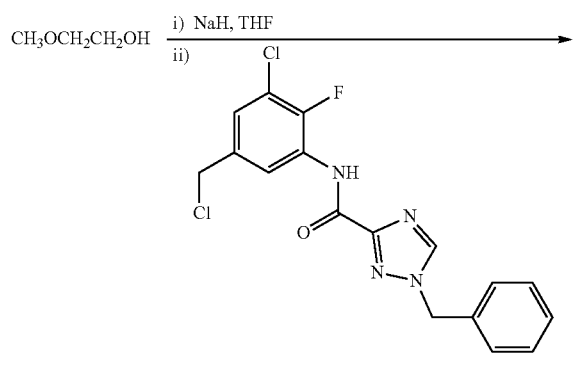
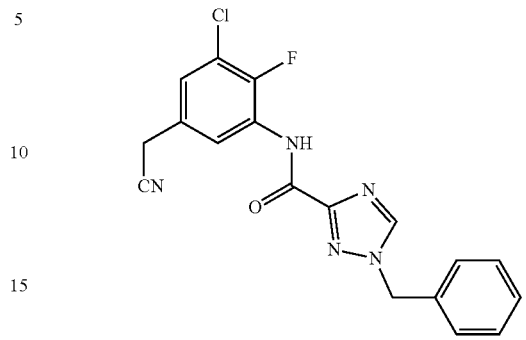

1-Benzyl-N-(3-chloro-5-(cyanomethyl)-2-fluorophenyl)-1H-1,2,4-triazole-3-carboxamide

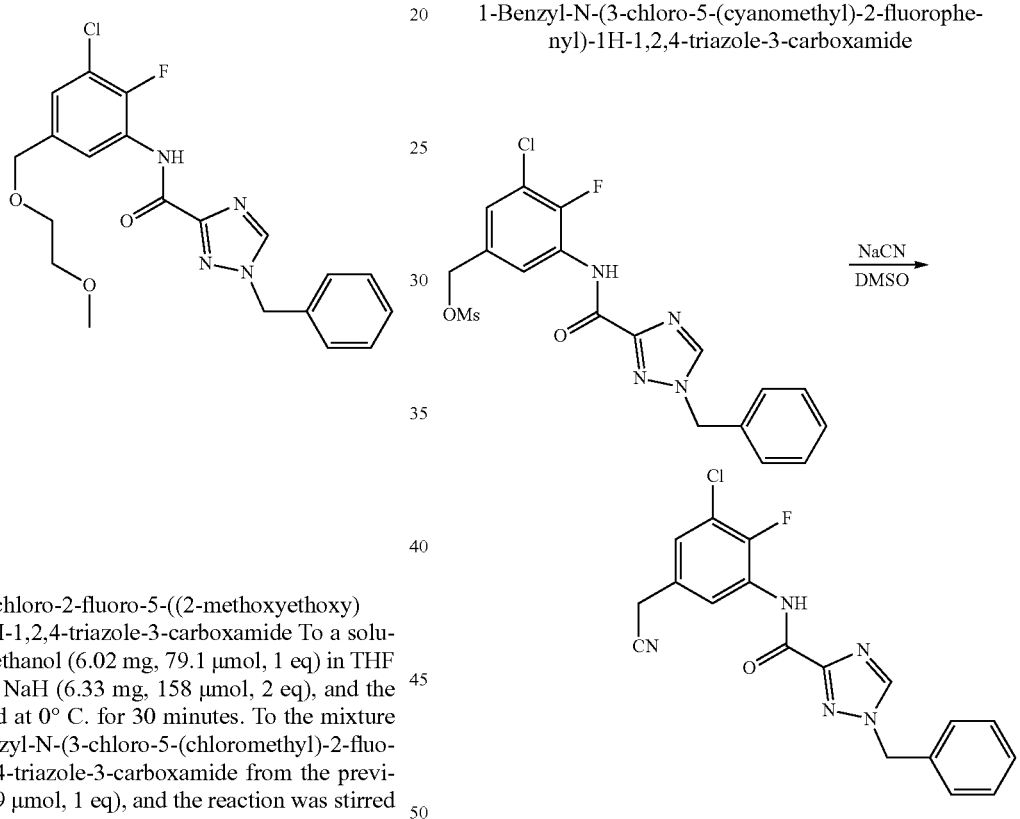

1-Benzyl-N-(3-chloro-2-fluoro-5-((2-methoxyethoxy)methyl)phenyl)-1H-1,2,4-triazole-3-carboxamide To a solution of 2-methoxyethanol (6.02 mg, 79.1 μmol, 1 eq) in THF (2 mL) was added NaH (6.33 mg, 158 μmol, 2 eq), and the mixture was stirred at 0° C. for 30 minutes. To the mixture was added 1-benzyl-N-(3-chloro-5-(chloromethyl)-2-fluorophenyl)-1H-1,2,4-triazole-3-carboxamide from the previous step (0.03 g, 79 μmol, 1 eq), and the reaction was stirred at 20° C. for 16 h. The mixture was diluted with H$_2$O (2 mL) and extracted with CH$_2$Cl$_2$ (5 mL×3). The combined organic layers were washed with brine (5 mL×3), dried over Na$_2$SO$_4$, and concentrated under reduced pressure to give a residue which was purified by prep-HPLC (column: Phenomenex Synergi C18 150 mm×25 mm×10 μm; mobile phase: [H$_2$O (0.1% TFA)-CH$_3$CN];B %: 43%-73%,10 min). The eluent was concentrated and lyophilized to afford the title compound (4.6 mg, 10.87 μmol, 14% yield) as a white solid.

MS(ES+)C$_{20}$H$_{20}$N$_4$O$_3$FCl requires:418, found 419 [M+H]$^+$.

$^1$H NMR (400 MHz, CDCl$_3$) δ=9.11 (br s, 1H), 8.33 (dd, J=2.0, 6.6 Hz, 1H), 8.00 (s, 1H), 7.40-7.30 (m, 3H), 7.30-7.23 (m, 2H), 7.15 (dd, J=2.0, 6.8 Hz, 1H), 5.37 (s, 2H), 4.48 (s, 2H), 3.62-3.55 (m, 2H), 3.55-3.49 (m, 2H), 3.34 (s, 3H).

1-Benzyl-N-(3-chloro-5-(cyanomethyl)-2-fluorophenyl)-1H-1,2,4-triazole-3-carboxamide To a solution of Intermediate J (0.1 g, 228 μmol, 1 eq) in DMSO (2 mL) was added NaCN (22.33 mg, 455.7 μmol, 2 eq), and the mixture was stirred at 50° C. for 1 h. The reaction was diluted with H$_2$O (2 mL) and extracted with CH$_2$Cl$_2$ (5 mL×3). The combined organic layers were washed with brine (5 mL×3), dried over Na$_2$SO$_4$, and concentrated under reduced pressure. The residue was purified by prep-HPLC (column: Phenomenex Luna C18 150 mm×25 mm×10 μm; mobile phase: [H$_2$O (0.1% TFA)-CH$_3$CN]; B %: 40%-70%, 10 min), and the eluent was concentrated and lyophilized to afford the title compound (17.3 mg, 45.8 μmol, 20.1% yield) as a white solid.

MS(ES+) C$_{18}$H$_{13}$N$_5$OFCl requires: 369, found 370 [M+H]$^+$.

$^1$H NMR (400 MHz, CDCl$_3$) δ=9.26 (s, 1H), 8.46 (dd, J=1.8, 6.2 Hz, 1H), 8.11 (s, 1H), 7.48-7.40 (m, 3H), 7.40-7.32 (m, 2H), 7.25 (dd, J=1.9, 6.3 Hz, 1H), 5.47 (s, 2H), 3.79 (s, 2H).

Example 97

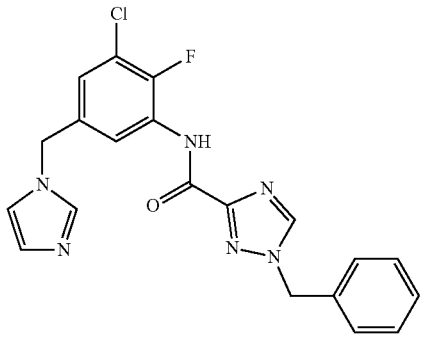 [SMILES: O=C(Nc1cc(Cn2ccnc2)cc(Cl)c1F)c1ncn(Cc2ccccc2)n1]

N-(5-((1H-imidazol-1-yl)methyl)-3-chloro-2-fluorophenyl)-1-benzyl-1H-1,2,4-triazole-3-carboxamide

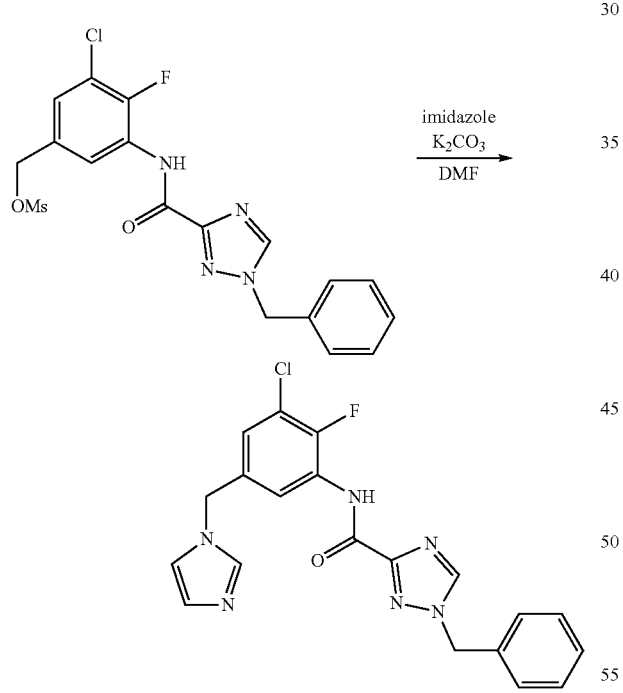

To a solution of imidazole (18.6 mg, 273.4 μmol, 1.2 eq) in DMF (1 mL) was added Intermediate J (0.1 g, 228 μmol, 1 eq) and K$_2$CO$_3$ (63.0 mg, 455.7 μmol, 2 eq), and the mixture was stirred at 50° C. for 1 h. The mixture was diluted with H$_2$O (2 mL) and extracted with CH$_2$Cl$_2$ (5 mL×3). The combined organic layers were washed with brine (5 mL×3), dried over Na$_2$SO$_4$, and concentrated under reduced pressure to give a residue which was purified by prep-HPLC (column: Phenomenex Luna C18 150 mm×25 mm×10 μm; mobile phase: [H$_2$O (0.1% TFA)-CH$_3$CN];B %: 18%-48%, 10 min). The eluent was concentrated and lyophilized to afford the title compound (8 mg, 19.28 μmol, 8% yield) as a white solid.

MS(ES+) C$_{20}$H$_{16}$N$_6$OFCl requires: 410, found 411 [M+H]$^+$.

$^1$H NMR (400 MHz, CDCl$_3$) δ=9.28 (d, J=2.5 Hz, 1H), 8.96 (s, 1H), 8.59-8.47 (m, 1H), 8.16 (s, 1H), 7.47-7.38 (m, 4H), 7.37-7.31 (m, 2H), 7.18 (s, 1H), 7.09 (dd, J=2.0, 6.3 Hz, 1H), 5.46 (s, 2H), 5.36 (s, 2H).

Example 98

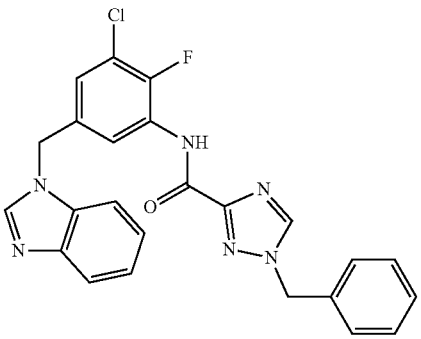 [SMILES: O=C(Nc1cc(Cn2cnc3ccccc32)cc(Cl)c1F)c1ncn(Cc2ccccc2)n1]

N-(5-((1H-benzo[d]imidazol-1-yl)methyl)-3-chloro-2-fluorophenyl)-1-benzyl-1H-1,2,4-triazole-3-carboxamide To a solution of benzimidazole (32.3 mg, 273.4 μmol, 1.2 eq) in DMF (1 mL) was added Intermediate J (0.1 g, 227.86 μmol, 1 eq) and K$_2$CO$_3$ (62.99 mg, 455.7 μmol, 2 eq), and the mixture was stirred at 45° C. for 16 h. The mixture was diluted with H$_2$O (2 mL) and extracted with CH$_2$Cl$_2$ (5 mL×3). The combined organic layers were washed with brine (5 mL×3), dried over Na₂SO₄, and concentrated under reduced pressure to give a residue which was purified by prep-HPLC (column: Phenomenex Luna C18 150 mm×25 mm×10 μm; mobile phase: [H₂O (0.1% TFA)-CH₃CN]; B %: 24%-54%,10 min). The eluent was concentrated and lyophilized to afford the title compound (9.5 mg, 21 μmol, 9% yield) as a white solid.

MS(ES+) $C_{24}H_{18}N_6OFCl$ requires: 460, found 461 [M+H]⁺.

¹H NMR (400 MHz, CDCl₃) δ=9.16 (s, 1H), 8.50 (d, J=6.2 Hz, 1H), 8.00 (s, 1H), 7.92 (s, 1H), 7.81-7.72 (m, 1H), 7.41-7.31 (m, 3H), 7.30-7.17 (m, 5H), 6.80-6.72 (m, 1H), 5.37 (s, 2H), 5.28 (s, 2H).

Example 99

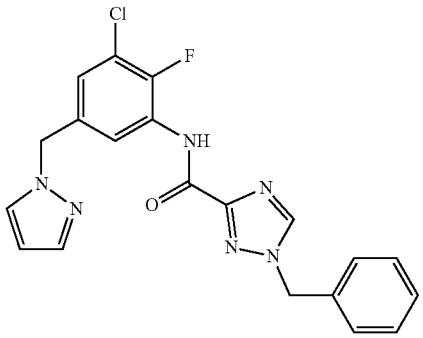 [SMILES: O=C(Nc1cc(Cn2cccn2)cc(Cl)c1F)c1ncn(Cc2ccccc2)n1]

N-(5-((1H-pyrazol-1-yl)methyl)-3-chloro-2-fluorophenyl)-1-benzyl-1H-1,2,4-triazole-3-carboxamide

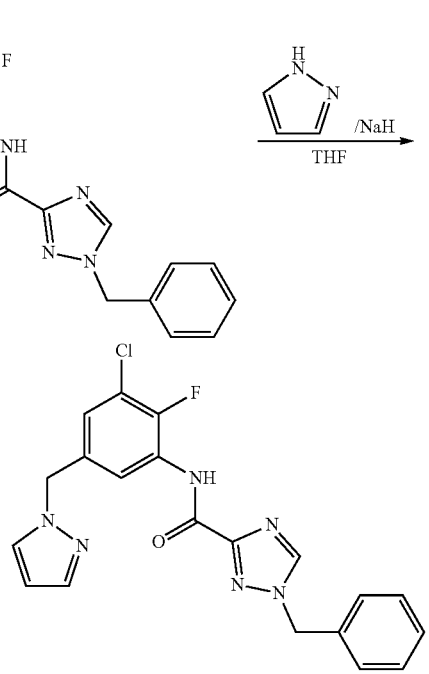

To a solution of pyrazole (18.6 mg, 273.43 μmol, 1.2 eq) in THF (2 mL) was added NaH (18.23 mg, 455.7 μmol, 2 eq), and the mixture was stirred at 0° C. for 30 min. To the mixture was added Intermediate J (0.1 g, 228 μmol, 1 eq), and the mixture was stirred at 20° C. for 16 h. The mixture was diluted with H₂O (2 mL) and extracted with CH₂Cl₂ (5 mL×3). The combined organic layers were washed with brine (5 mL×3), dried over Na₂SO₄, and concentrated under reduced pressure to give a residue which was purified by prep-HPLC (column: Phenomenex Luna C18 150 mm×25 mm×10 μm; mobile phase: [H₂O (0.1% TFA)-CH₃CN];B %: 40%-70%, 10 min). The eluent was concentrated and lyophilized to afford the title compound (18.5 mg, 45.0 μmol, 20% yield) as a white solid.

MS(ES+)$C_{20}H_{16}N_6OFCl$ requires:410, found 411 [M+H]⁺.

¹H NMR (400 MHz, CDCl₃) δ=9.20 (s, 1H), 8.40 (dd, J=1.9, 6.4 Hz, 1H), 8.07 (s, 1H), 7.57 (d, J=1.5 Hz, 1H), 7.48 (d, J=2.3 Hz, 1H), 7.45-7.37 (m, 3H), 7.37-7.30 (m, 2H), 6.95 (dd, J=2.1, 6.5 Hz, 1H), 6.32 (t, J=2.1 Hz, 1H), 5.44 (s, 2H), 5.32 (s, 2H).

Example 100

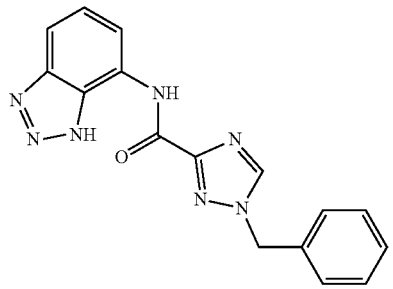 [SMILES: O=C(Nc1cccc2nn[nH]c12)c1ncn(Cc2ccccc2)n1]

N-(1H-benzo[d][1,2,3]triazol-7-yl)-1-benzyl-1H-1,2,4-triazole-3-carboxamide

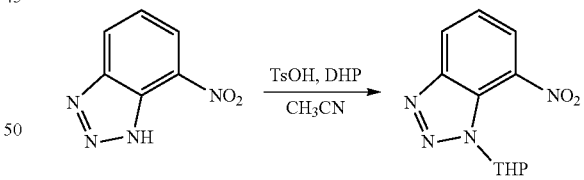

7-Nitro-1-(tetrahydro-2H-pyran-2-yl)-1H-benzo[d][1,2,3]triazole To a solution of 7-nitro-1H-benzo[d][1,2,3]triazole (600 mg, 3.66 mmol, 1 eq) and 3,4-dihydro-2H-pyran (616.4 mg, 7.33 mmol, 670 uL, 2.00 eq) in CH₃CN (10 mL) was added TsOH monohydrate (34.8 mg, 183.0 μmol, 0.05 eq). The reaction mixture was stirred at 85° C. for 2 h. The mixture was concentrated under reduced pressure and then purified by prep-TLC (petroleum ether: EtOAc=5/1) to afford the title compound (270 mg, 1.04 mmol, 29% yield) as a yellow oil.

MS (ES⁺): $C_{11}H_{12}N_4O_3$ requires: 248, found: 165 [M-84+H]⁺.

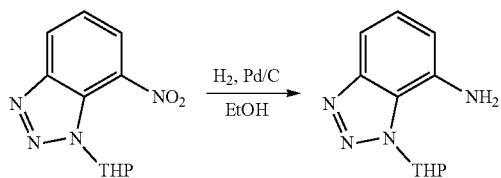

1-(Tetrahydro-2H-pyran-2-yl)-1H-benzo[d][1,2,3]triazol-7-amine To a solution of the product from the previous step (270 mg, 1.09 mmol, 1 eq) in EtOH (5 mL) was added Pd/C (50 mg, 10% purity), and the mixture was stirred at 25° C. under $H_2$ (15 Psi) for 2 h. The mixture was filtered and concentrated under reduced pressure to afford the title compound (150 mg, crude) as a yellow oil.

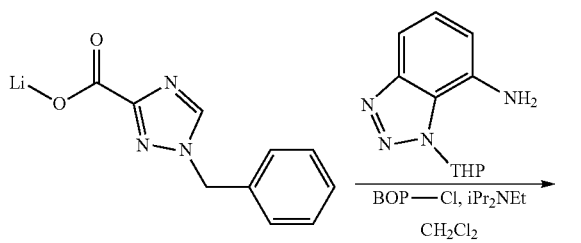

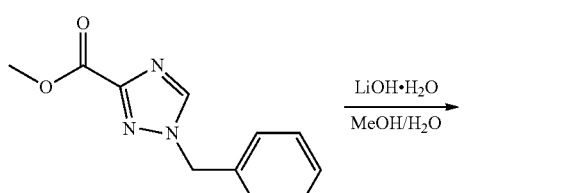

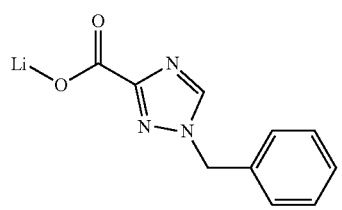

Lithium 1-benzyl-1H-1,2,4-triazole-3-carboxylate To a solution of Intermediate G (1.4 g, 6.4 mmol, 1 eq) in MeOH (25.2 mL) was added a solution of LiOH·$H_2O$ (324.52 mg, 7.73 mmol, 1.2 eq) in $H_2O$ (8.1 mL), and the mixture was stirred at 25° C. for 2 h. The mixture was concentrated under reduced pressure to afford the title compound (1.9 g, crude) as a white solid, which was taken to the next step immediately.

MS(ES+) $C_{10}H_8O_2N_3Li$ requires:203, found 204 $[M+H]^+$.

$^1$H NMR (400 MHz, DMSO-$d_6$) δ=8.57 (s, 1H), 7.39-7.28 (m, 5H), 5.17 (s, 2H).

1-Benzyl-N-(1-(tetrahydro-2H-pyran-2-yl)-1H-benzo[d][1,2,3]triazol-7-yl)-1H-1,2,4-triazole-3-carboxamide To a solution of the product from the previous step (100 mg, 478.17 μmol, 1 eq) and the product from the previous step (100 mg, 458.18 μmol, 9.58e-1 eq) in $CH_2Cl_2$ (2 mL) was added BOP-Cl (182.59 mg, 717.26 μmol, 1.5 eq) and $iPr_2NEt$ (185.50 mg, 1.44 mmol, 250 uL, 3 eq). The mixture was stirred at 25° C. for 14 h. The mixture was diluted with $CH_2Cl_2$ (10 mL) and $H_2O$ (10 mL). The aqueous layer was extracted with $CH_2Cl_2$ (10 mL×3). The combined organic layers were washed with $H_2O$ (10 mL), dried over $Na_2SO_4$, and concentrated under reduced pressure to afford the title compound (180 mg, crude) as a yellow oil.

MS (ES+): $C_{21}H_{21}N_7O_2$ requires: 403, found: 404 $[M+H]^+$.

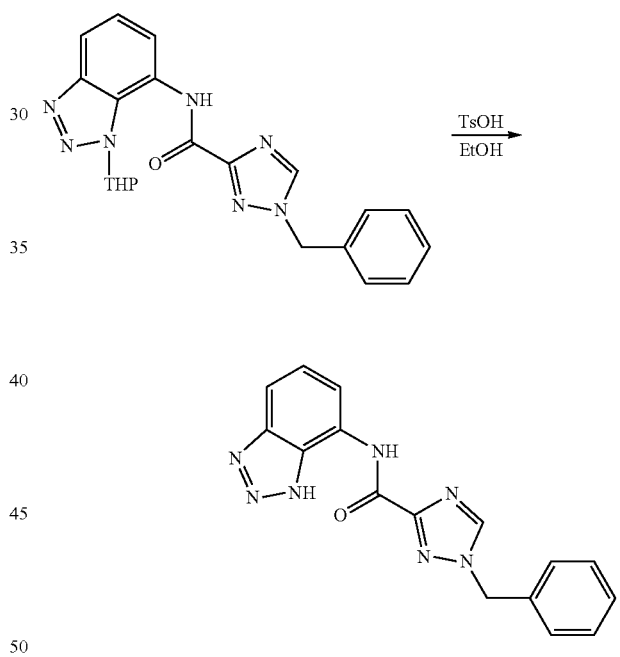

N-(1H-Benzo[d][1,2,3]triazol-7-yl)-1-benzyl-1H-1,2,4-triazole-3-carboxamide

To a solution of the product from the previous step (90 mg, 223.08 μmol, 1 eq) in EtOH (2 mL) was added TsOH (77 mg, 447.15 μmol, 2 eq), and the mixture was stirred at 60° C. for 1 h. The mixture was cooled to 25° C., then filtered, and the filter cake was washed with EtOH (10 mL). The filter cake was collected and dried under reduced pressure to afford the title compound (16.9 mg, 51.34 μmol, 23% yield) as a white solid.

MS (ES+): $C_{16}H_{13}N_7O_2$ requires: 319, found: 320 $[M+H]^+$.

$^1$H NMR (400 MHz, DMSO-$d_6$) 15.55 (s, 1H), 10.67 (s, 1H), 8.92 (s, 1H), 8.46 (s, 1H), 8.05-7.68 (m, 2H), 7.53-7.24 (m, 5H), 5.54 (s, 2H).

TABLE 3

Examples 101-103

| Ex. No. | Structure | Name | Analysis | Proc. Ex. No. |
|---|---|---|---|---|
| 101 | 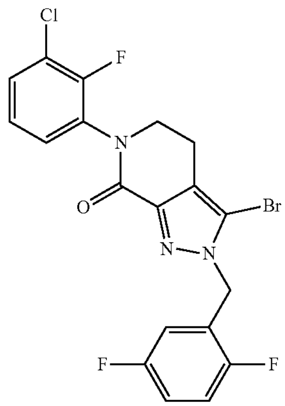 [SMILES: O=C1c2nn(Cc3cc(F)ccc3F)c(Br)c2CCN1c1cccc(Cl)c1F] | 3-Bromo-6-(3-chloro-2-fluoro-phenyl)-2-(2,5-difluorobenzyl)-2,4,5,6-tetrahydro-7H-pyrazolo[3,4-c]-pyridin-7-one | $^1$H NMR (400 MHz, CDCl$_3$) 7.4-7.5 (m, 1H), 7.32-7.37 (m, 1H) 7.14-7.2 (m, 1H), 7.05-7.12 (m, 1H), 6.97-7.04 (m, 1H), 5.54 (s. 2H), 3.94-4.0 (m, 2H), 2.9-2.96 (m, 2H). MS (ES$^+$): C$_{19}$H$_{12}$BrClF$_3$N$_3$O requires: 469, found: 470 [M + H]$^+$. | 50 |
| 102 | 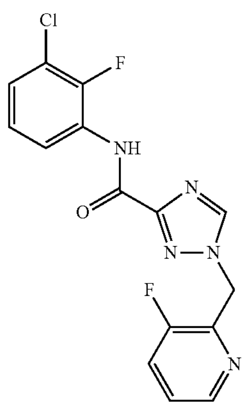 [SMILES: O=C(Nc1cccc(Cl)c1F)c1ncn(Cc2ncccc2F)n1] | N-(3-chloro-2-fluorophenyl)-1-((3-fluoropyridin-2-yl)methyl)-1H-1,2,4-triazole-3-carboxamide | MS (ES+): C$_{15}$H$_{10}$ClF$_2$N$_5$O requires: 349.05, found: 350 [M + H]$^+$ | 91 |
| 103 | 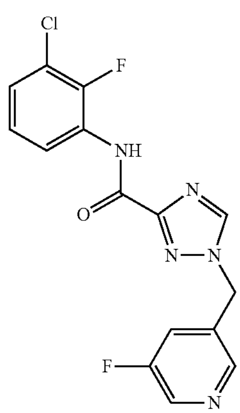 [SMILES: O=C(Nc1cccc(Cl)c1F)c1ncn(Cc2cncc(F)c2)n1] | N-(3-chloro-2-fluorophenyl)-1-((5-fluoropyridin-3-yl)methyl)-1H-1,2,4-triazole-3-carboxamide | MS (ES+): C$_{15}$H$_{10}$ClF$_2$N$_5$O requires: 349.05, found: 350 [M + H]$^+$ | 89 |

The following compounds can generally be made using the methods described above. It is expected that these compounds when made will have activity similar to those that have been made in the examples disclosed herein.

| Structure | Name | Exact Mass, amu |
|---|---|---|
| 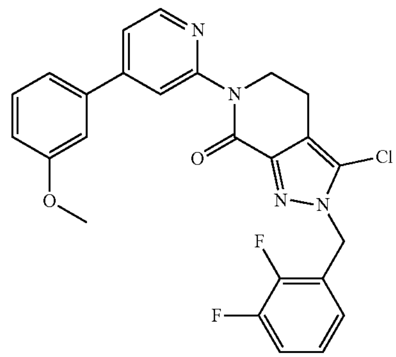 [SMILES: COc1cccc(-c2ccnc(N3CCc4c(nn(Cc5cccc(F)c5F)c4Cl)C3=O)c2)c1] | 3-Chloro-2-(2,3-difluorobenzyl)-6-(4-(3-methoxyphenyl)pyridin-2-yl)-2,4,5,6-tetrahydro-7H-pyrazolo[3,4-c]pyridin-7-one | 480.12 |
| 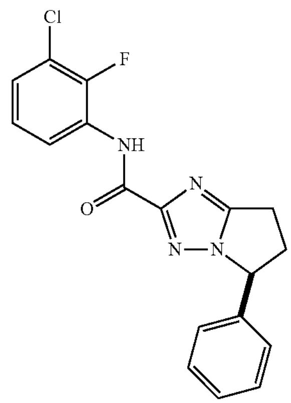 [SMILES: O=C(Nc1cccc(Cl)c1F)c1nc2n(n1)[C@H](c1ccccc1)CC2] | (S)-N-(3-chloro-2-fluorophenyl)-5-phenyl-6,7-dihydro-5H-pyrrolo[1,2-b][1,2,4]triazole-2-carboxamide | 356.08 |
| 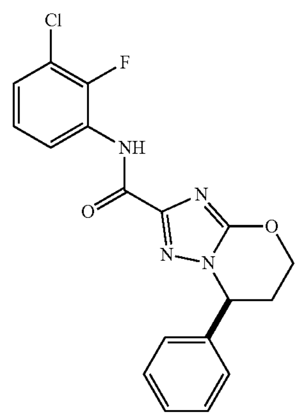 [SMILES: O=C(Nc1cccc(Cl)c1F)c1nc2n(n1)[C@H](c1ccccc1)CCO2] | (S)-N-(3-chloro-2-fluorophenyl)-7-phenyl-6,7-dihydro-5H-[1,2,4]-triazolo[5,1-b][1,3]oxazine-2-carboxamide | 372.08 |
| 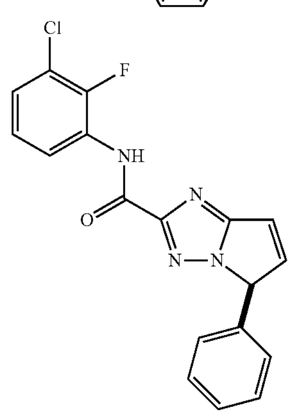 | (S)-N-(3-chloro-2-fluorophenyl)-5-phenyl-5H-pyrrolo[1,2-b][1,2,4]-triazole-2-carboxamide | 354.07 |

The activity of the compounds in Examples 1-57 as RIPK1 inhibitors is illustrated in the following assays.

Biological Activity Assays

ADP-Glo Kinase Assay

In order to measure RIPK1 activity the ADP-Glo kinase assay (Promega, Catalog #V7002) was used to measure the conversion of ATP to ADP. This enzymatic assay was performed in a 384-well white, Optiplate (Perkin Elmer, Catalog #6007299) with assay buffer consisting of 50 mM HEPES pH 7.5 (Gibco, Catalog #15630-080), 50 mM NaCl (Teknova, Catalog #S0252), 30 mM $MgCl_2$ (Ambion, Catalog #AM9530G), 1 mM DTT (Santa Cruz Biotechnology, Catalog #sc-29089), 0.05% BSA (Sigma, Catalog #A3059-50G) and 0.02% CHAPS (Sigma, Catalog #C5070-5G). Stock solutions of the test compounds were prepared in 100% DMSO (Sigma, Catalog #D2650) and serially diluted 1:3 using 100% DMSO. Compounds were additionally diluted 1:40 in assay buffer, and 2 μL/well were transferred to the assay plate. 4 μL/well (final concentration of 5 nM) of RIPK1 protein (SignalChem, Catalog #R07-11G-05) diluted in assay buffer and added to the assay plate followed by a 10 minute preincutation at room temperature. 4 μL/well of ATP (Promega, Catalog #V7002) (final concentration of 50 μM) diluted in assay buffer were then added to the assay plate followed by a 6 hr reaction time. Final concentrations of RIPK1 and ATP refer to a 10 μL volume. Luminescence was measured using a BioTek Synergy™ NEO plate reader. $IC_{50}$ values were calculated using a four-parameter logistic curve fit using Genedata Screener software.

Human U937 Cellular Necroptosis Assay

The human monocytic cell line U937 (CRL-1593.2) may be purchased from ATCC. The cells are routinely maintained in RPMI-1640 Medium (Gibco, Catalog #11875-093) supplemented with 10% heat inactivated fetal bovine serum (Gibco, Catalog #16140-071), 100 units/mL penicillin and 100 μg/mL streptomycin (Gibco, Catalog #15140-122), in a humidified incubator (37° C., 5% $CO_2$). For the assay, cells are resuspended in RPMI-1640 phenol red free Media (Gibco, Catalog #11835-030) supplemented with 10% fetal bovine serum (Sigma, Catalog #F2442), 100 units/mL penicillin and 100 ug/mL streptomycin. Cells are stimulated with 25 ng/mL human TNFalpha (Cell Sciences, Catalog #CSI15659B) and 25 μM z-VAD-FMK (R&D Systems, Catalog #FMK001) followed by seeding 5000 cells per well in a volume of 40 μL to a white, CulturPlate-384 (Perkin Elmer, Catalog #6007680). Stock solutions of the test compounds are prepared in 100% DMSO (Sigma, Catalog #D2650) and serially diluted 1:3 using 100% DMSO. Compounds are additionally diluted 1:40 in assay medium, and 10 μL/well was transferred to the plate. Following the compound addition, the plate is incubated at 37° C. and 5% $CO_2$ for 22 hr. After 22 hr, viability is assessed with the addition of 20 μL of Cell Titer-Glo 2.0 (Promega, Catalog #G9243). The tissue culture plate is shaken on an orbital shaker at 300 RPM for 15 minutes at room temperature in the dark. Luminescence is measured using a PerkinElmer Envision™ plate reader. $IC_{50}$ values are calculated using a four-parameter logistic curve fit using Genedata Screener software. Compounds disclosed herein are expected to have activity in this assay.

TABLE 4

ADP-Glo Kinase RIPK1 activity

| Ex. # | RIPK1 IC50, nM |
|---|---|
| 1 | 13.13 |
| 2 | 17.39 |
| 3 | 111.1 |
| 4 | 110.2 |
| 5 | 14536 |
| 6 | 920 |
| 7 | 12148 |
| 8 | 31226 |
| 9 | 244.8833333 |
| 10 | 701.7 |
| 11 | 4059 |
| 12 | 18.61 |
| 13 | 41.89666667 |
| 14 | 6962 |
| 15 | 3147 |
| 16 | 122.8 |
| 17 | 17053 |
| 18 | 18687 |
| 19 | 1008 |
| 20 | 521 |
| 21 | 854 |
| 22 | 1572 |
| 23 | 2255 |
| 24 | 3363 |
| 25 | 4353 |
| 26 | 12126 |
| 27 | 30.63333333 |
| 28 | 40.3 |
| 29 | 34.07 |
| 30 | 110 |
| 31 | 159.5 |
| 32 | 257.4 |
| 33 | 389.45 |
| 34 | 472.2 |
| 35 | 702.85 |
| 36 | 803.55 |
| 37 | 1096 |
| 38 | 1295 |
| 39 | 1411 |
| 40 | 1648 |
| 41 | 9252.5 |
| 42 | 318 |
| 43 | 13662 |
| 44 | >33000 |
| 45 | 48626 |
| 46 | |
| 47 | 48.43 |
| 48 | 2471 |
| 49 | 3675 |
| 50 | 18.59 |
| 51 | 807 |
| 52 | 4624 |
| 53 | 4913 |
| 54 | 131.1025 |
| 55 | 1368 |
| 55a | 24570 |
| 55b | 1619 |
| 56 | 1410 |
| 56a | 179.6 |
| 56b | 14422.5 |
| 57 | 22 |
| 75 | 296.8 |
| 86 | 564.1 |
| 87 | 32.17 |
| 88 | 36.28 |
| 89 | 1598 |
| 90 | 1456 |
| 100 | 685 |
| 101 | 17.3525 |
| 102 | 194.8 |
| 103 | 83.91 |

TABLE 5

| Ex. No. | U937 Avg Ic50 (nM) Avg |
|---|---|
| 1 | 34.213 |
| 2 | 71.155 |
| 3 | 189.4 |
| 4 | 1430.5 |
| 9 | 6300 |
| 10 | 9217.5 |
| 11 | >10000 |
| 12 | 656.7 |
| 13 | 1274.7 |
| 19 | >10000 |
| 20 | 6230 |
| 21 | >10000 |
| 22 | >10000 |
| 23 | >10000 |
| 24 | >10000 |
| 25 | 10000 |
| 27 | 851.18 |
| 28 | 1471.3 |
| 29 | 355.98 |
| 30 | 1494 |
| 31 | 1702 |
| 32 | 1916.5 |
| 33 | 5424 |
| 35 | 7293 |
| 36 | 10000 |
| 47 | 24.845 |
| 50 | 42.534 |
| 51 | 8243 |
| 52 | >10000 |
| 54 | 128 |
| 55 | >10000 |
| 55a | >10000 |
| 55b | 6393 |
| 56 | 1513.5 |
| 56a | 1376 |
| 56b | >10000 |
| 57 | 115 |
| 58 | 95.878 |
| 59 | 810.6 |
| 60 | 1257 |
| 61 | 44.58 |
| 62 | 53.715 |
| 63 | 64.135 |
| 64 | 130.2 |
| 65 | 207.35 |
| 66 | 291.22 |
| 67 | 444.4 |
| 68 | 1338 |
| 69 | 563 |
| 70 | 233.35 |
| 71 | 255.8 |
| 72 | 6113 |
| 73 | 348 |
| 74 | 42 |
| 75 | 1162 |
| 76 | 917 |
| 77 | 593.63 |
| 78 | >10000 |
| 79 | 346 |
| 80 | 958 |
| 81 | >10000 |
| 82 | 863 |
| 83 | 1234 |
| 84 | 142 |
| 85 | 1036 |
| 86 | 2083.5 |
| 87 | 4303 |
| 88 | 872.28 |
| 89 | 5583.5 |
| 90 | 2600 |
| 91 | 2555 |
| 92 | 1645.5 |
| 93 | 1504 |
| 94 | 797.3 |
| 95 | 529.05 |
| 96 | 347.4 |
| 97 | 1177.5 |
| 98 | 3865 |
| 99 | 2538 |
| 100 | 4141 |
| 101 | 16.21 |
| 102 | 1257.5 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula I

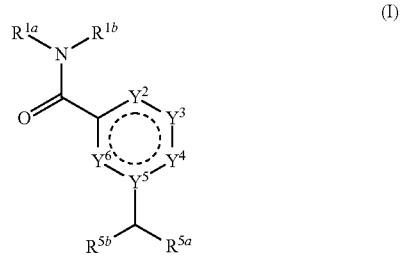

or a salt thereof, wherein:

$Y^2$ is $CR^2$;

$Y^3$ a bond;

$Y^4$ $CR^4$;

$Y^5$ is N;

$Y^6$ is N;

$R^{1a}$ is phenyl, which is optionally substituted with one or more $R^7$;

$R^{1b}$ and $R^2$, together with the intervening atoms, combine to form an unsubstituted 6-membered heterocycloalkyl;

$R^3$ is chosen from hydrogen and alkyl;

$R^4$ is chosen from hydrogen and halo;

$R^5$ hydrogen;

$R^{5b}$ is chosen from phenyl and pyridyl, either of which is optionally substituted with one or more $R^{10}$;

each $R^7$ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or two or more R⁷, together with the intervening atoms, can form a heterocycloalkyl or heteroaryl; and each R¹⁰ is independently chosen from alkyl, haloalkyl, amino, aminoalkyl, aminocarbonyl, alkoxy, haloalkoxy, cyano, halo, and hydroxy.

2. The compound as recited in claim 1, or a salt thereof, wherein each R⁷ is independently chosen from halo, cyano, and hydroxy.

3. The compound as recited in claim 2, or a salt thereof, wherein each R⁷ is independently chosen from F and Cl.

4. The compound as recited in claim 1, or a salt thereof, wherein R¹ᵃ is

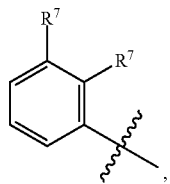

and each R⁷ is the same or different.

5. The compound as recited in claim 1, or a salt thereof, wherein R⁵ᵇ is phenyl optionally substituted with one or more R¹⁰.

6. The compound as recited in claim 5, or a salt thereof, wherein each R¹⁰ is independently chosen from halo and cyano.

7. The compound as recited in claim 5, or a salt thereof, wherein R⁵ᵇ is chosen from

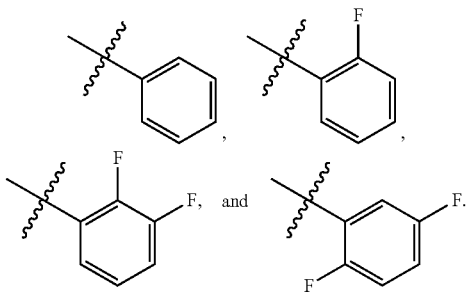

8. A compound of structural Formula VI:

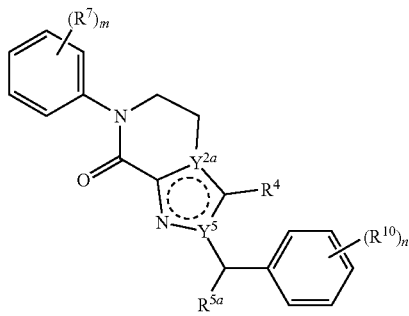

(VI)

or a salt thereof, wherein:

Y²ᵇ is C;

Y⁵ is N;

R⁴ is chosen from hydrogen, and halo;

R⁵ᵃ hydrogen;

each R⁷ is independently chosen from halo, cyano, hydroxy, alkyl, alkoxy, haloalkyl, hydroxyalkyl, cyanoalkyl, alkoxyalkyl, alkoxyalkoxyalkyl, aminoalkyl, acylaminoalkyl, (haloalkyl)aminoalkyl, alkylsulfonylaminoalkyl, arylalkyl, heteroarylalkyl, haloalkoxy, heteroaryl optionally substituted with alkyl, and heterocycloalkyl optionally substituted with alkyl, or two or more R⁷, together with the intervening atoms, can form a heterocycloalkyl or heteroaryl;

each R¹⁰ is independently chosen from alkyl, haloalkyl, amino, aminoalkyl, aminocarbonyl, alkoxy, haloalkoxy, cyano, halo, and hydroxy;

m is chosen from 0, 1, and 2; and n is chosen from 0, 1, 2, and 3.

9. A compound chosen from:

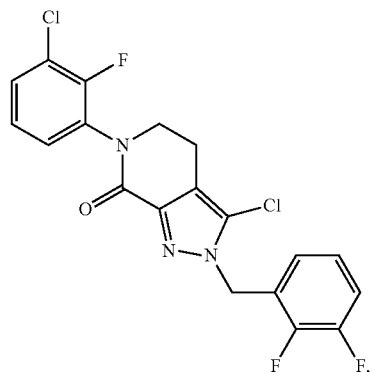

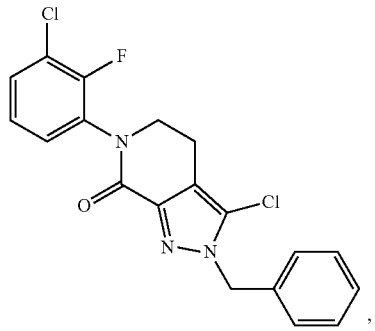

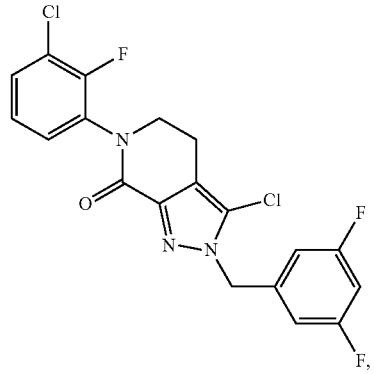

259
-continued
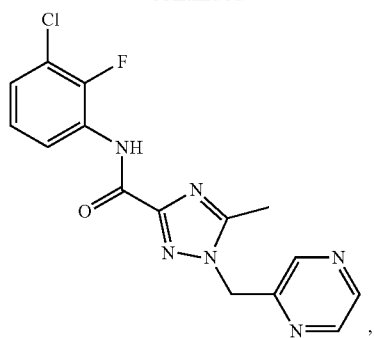
,
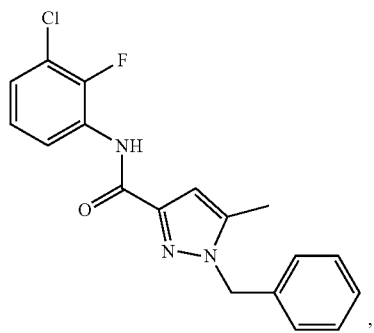
,
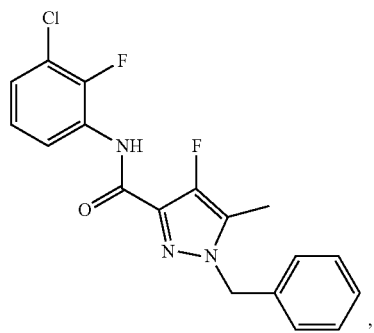
,
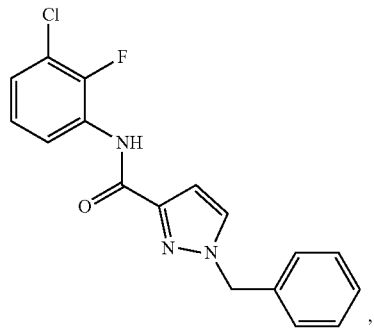
,
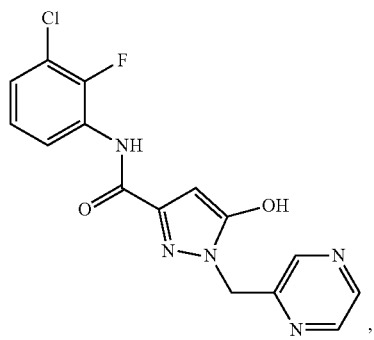
,
260
-continued
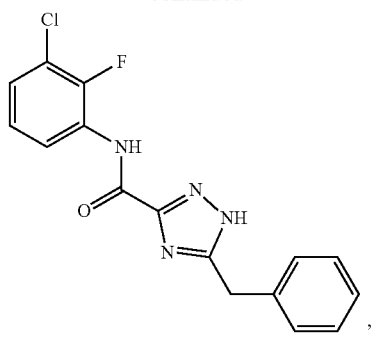
,
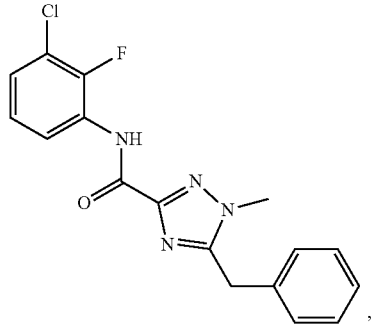
,
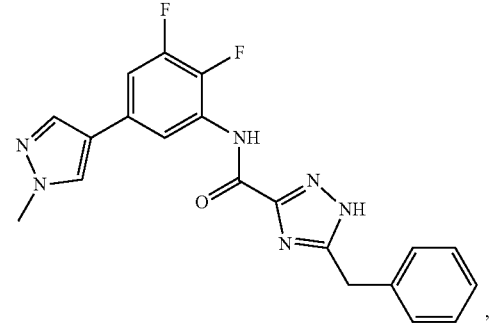
,
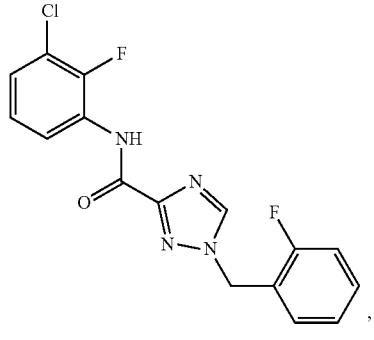
,
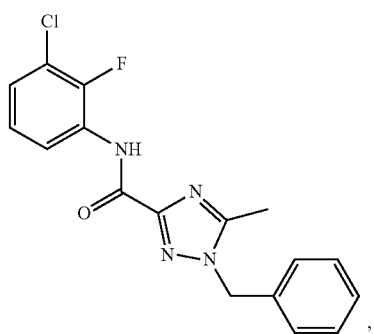
, -continued
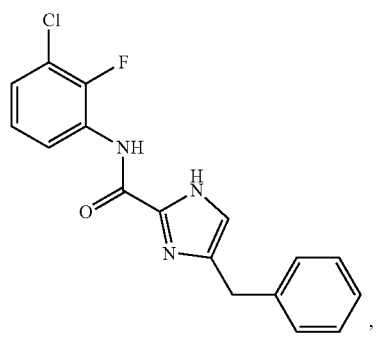
,
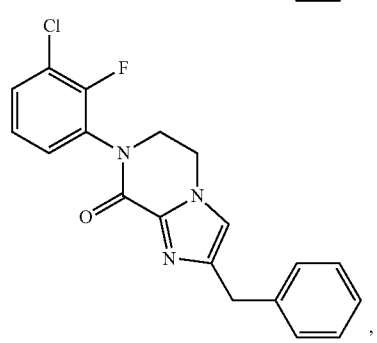
,
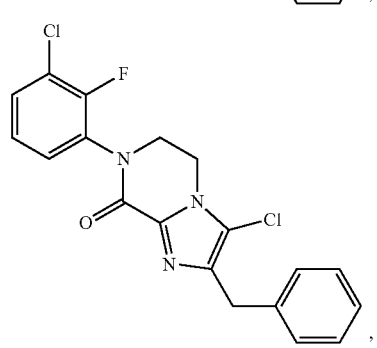
,
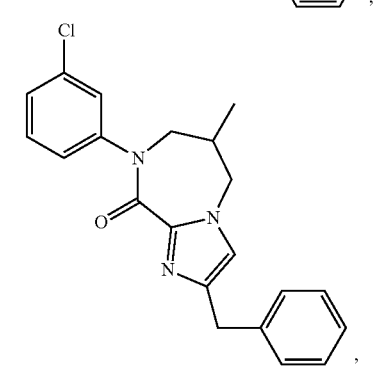
,
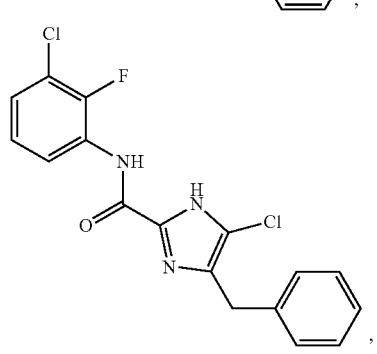
,
-continued
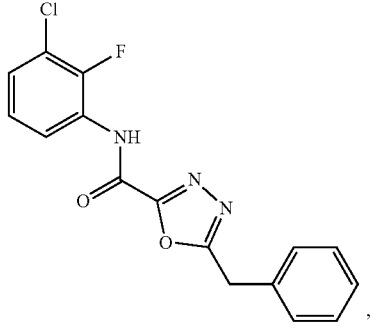
,
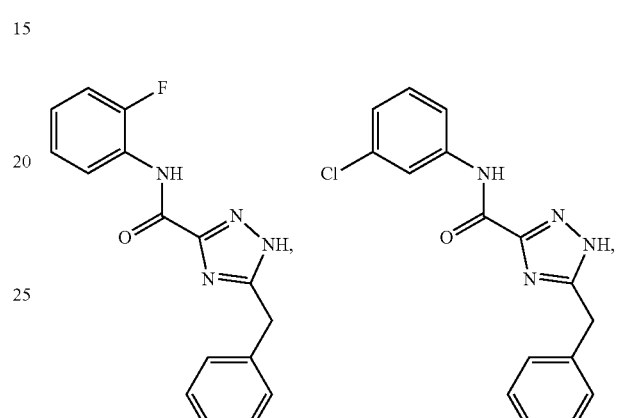
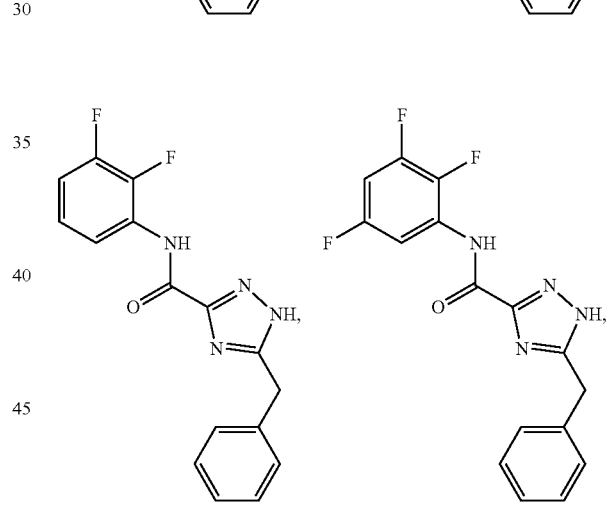
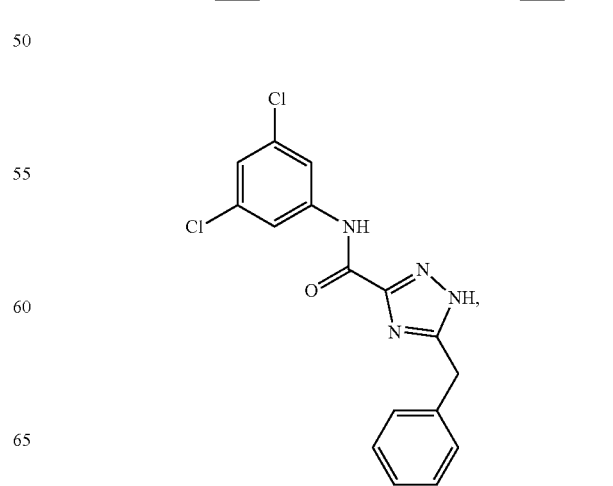

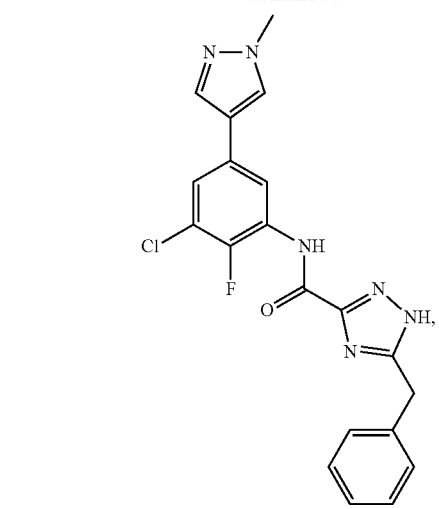
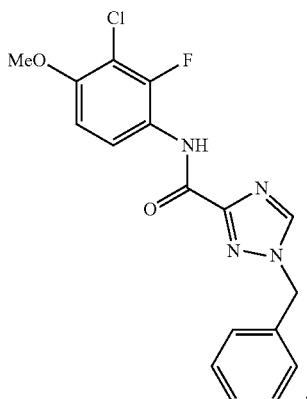
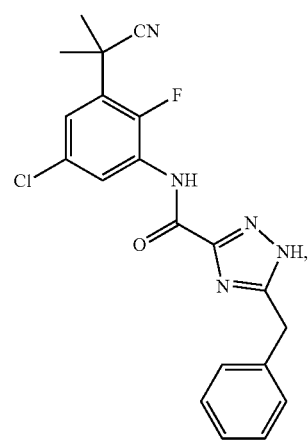
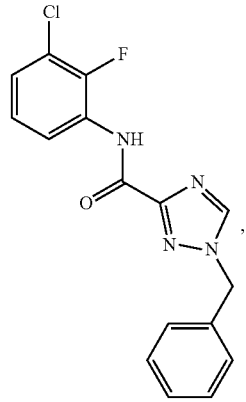
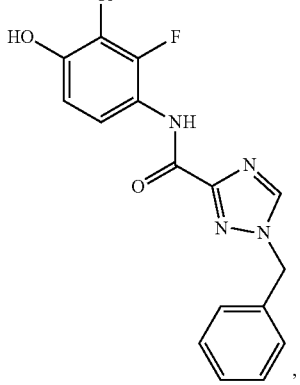
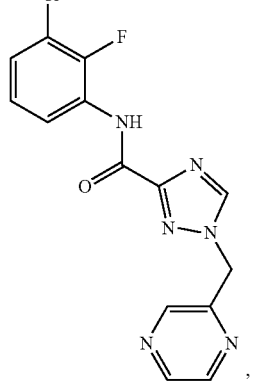
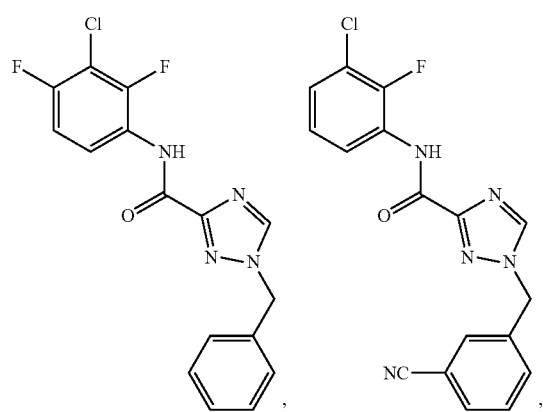
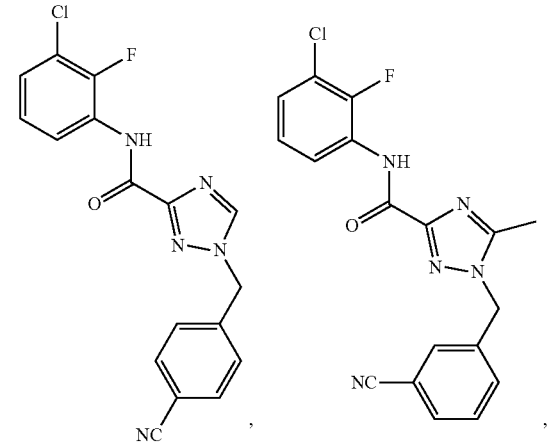
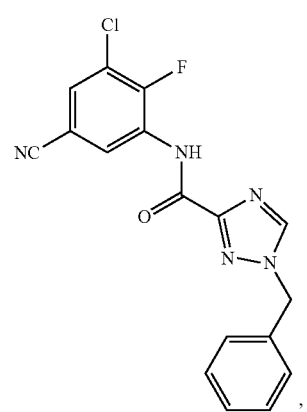

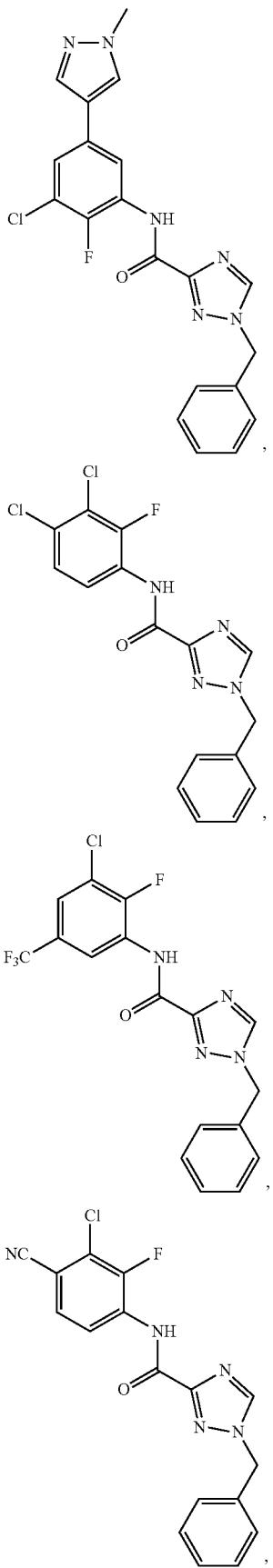
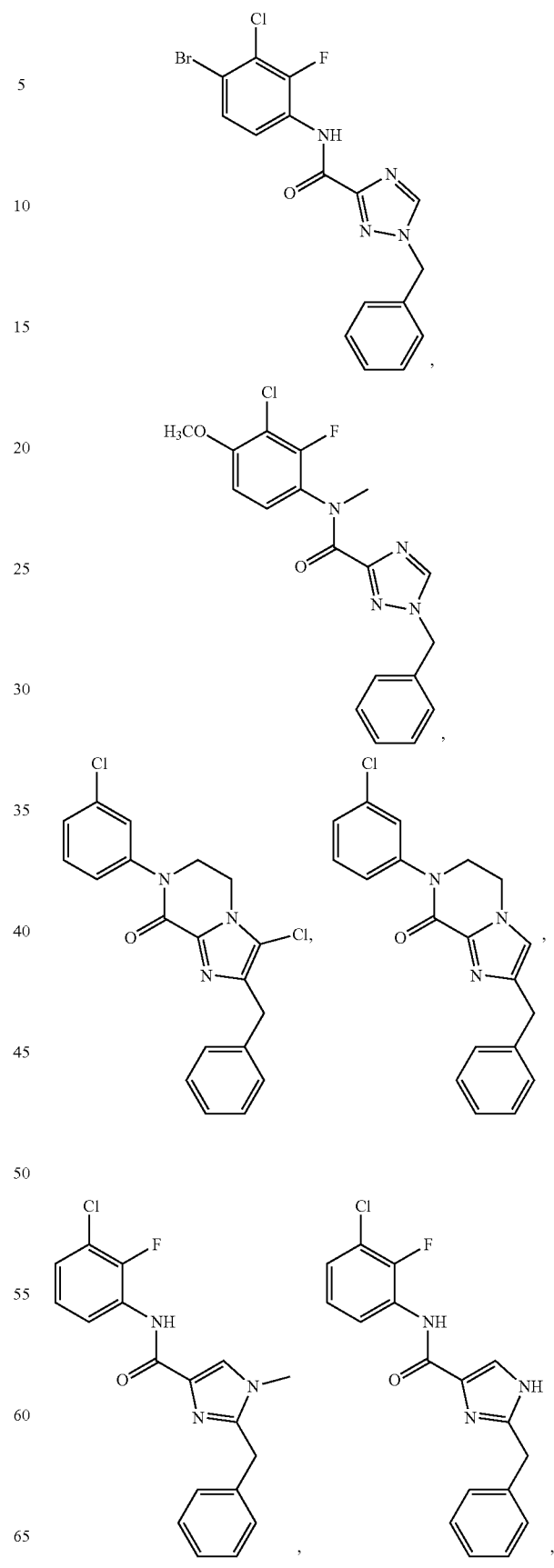

267
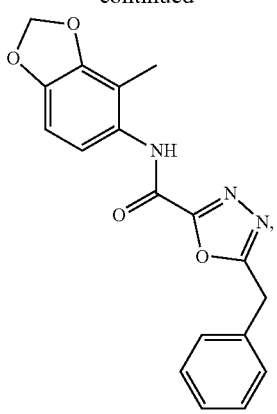
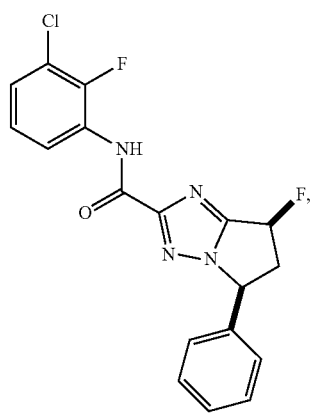
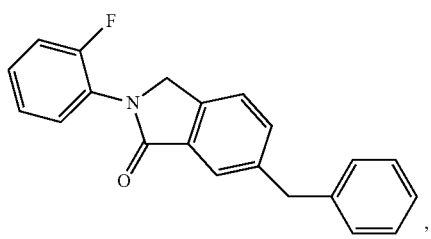
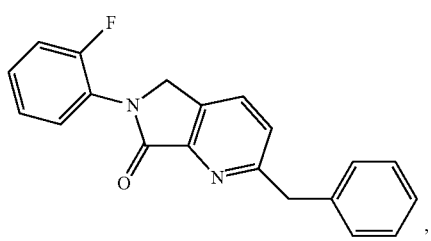
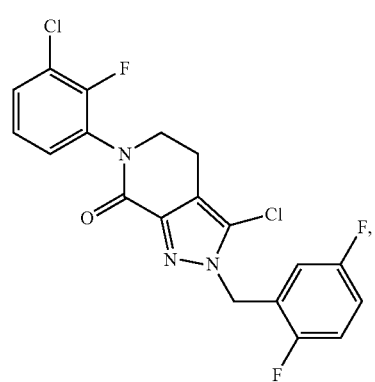
268
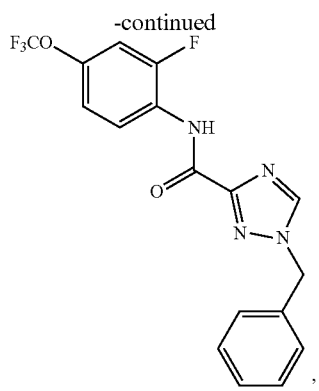
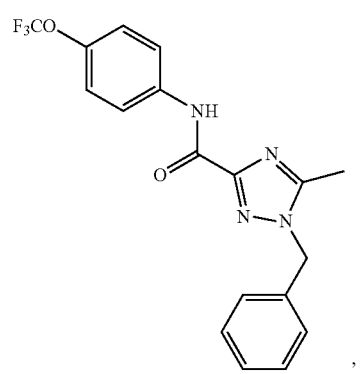
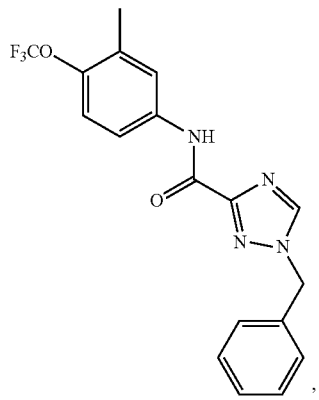
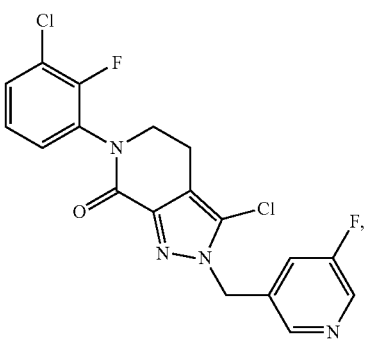

269
-continued
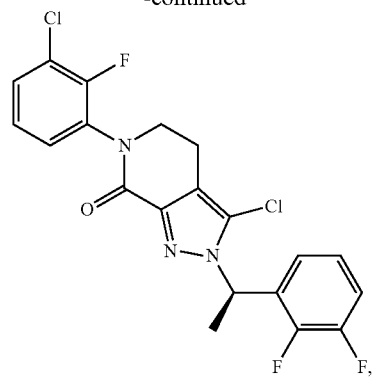
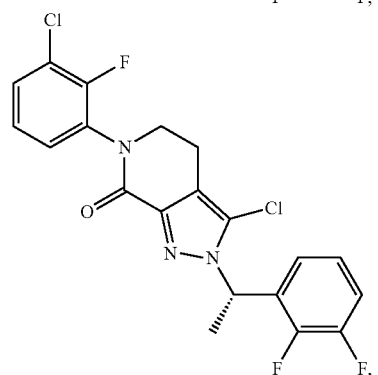
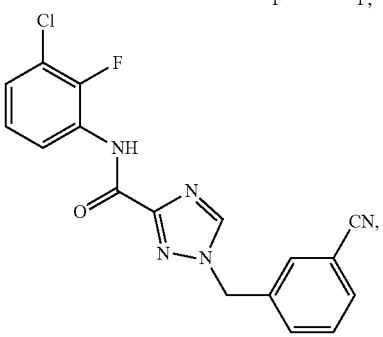
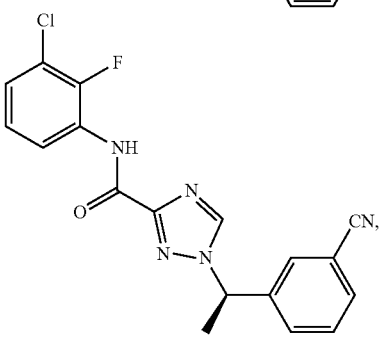
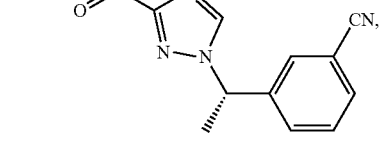
270
-continued
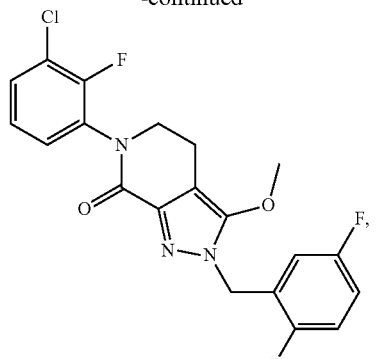
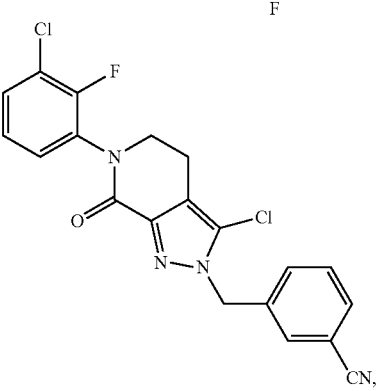
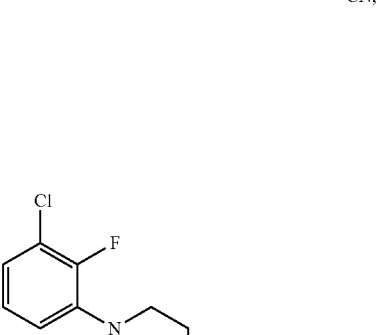
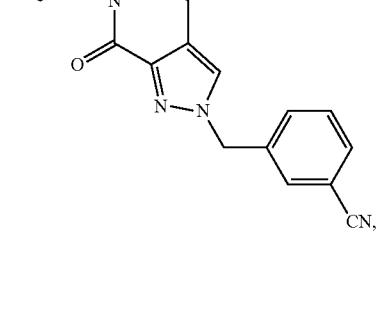
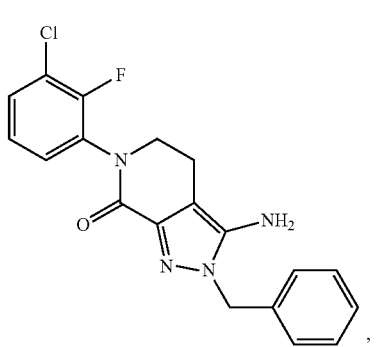

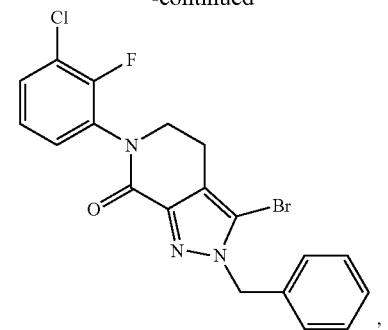
,
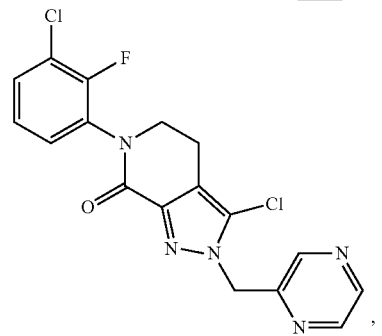
,
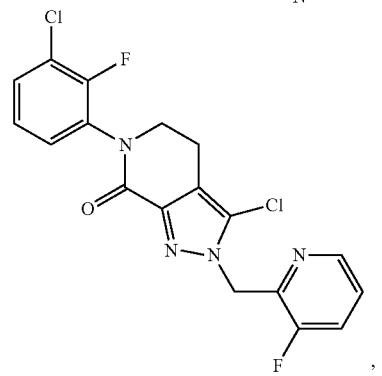
,
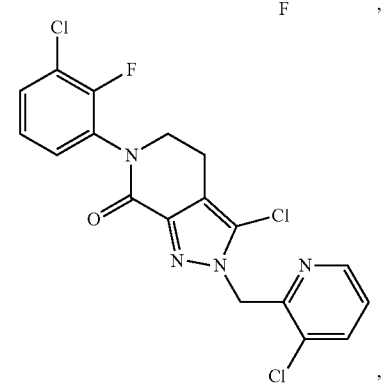
,
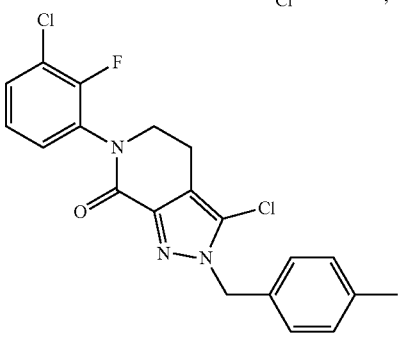
,
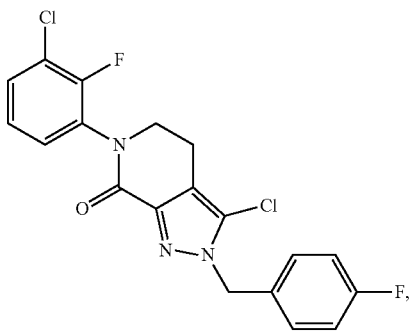
,
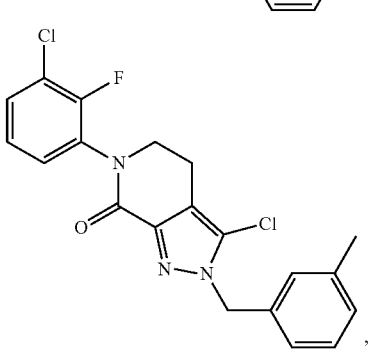
,
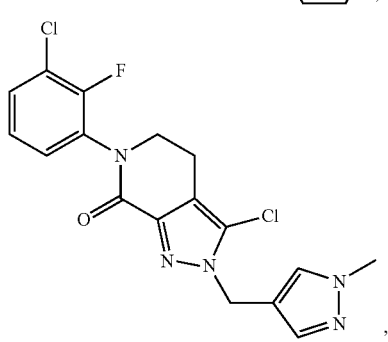
,
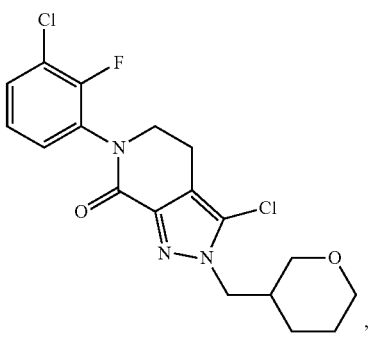
,
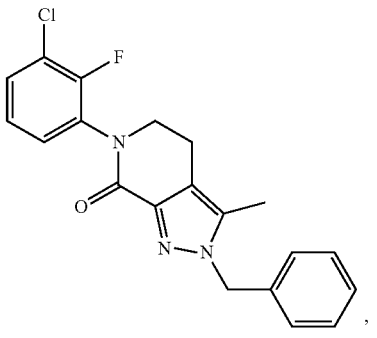
, 273
-continued
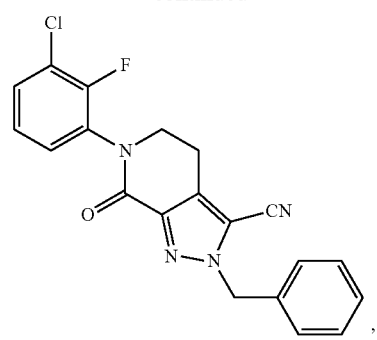
,
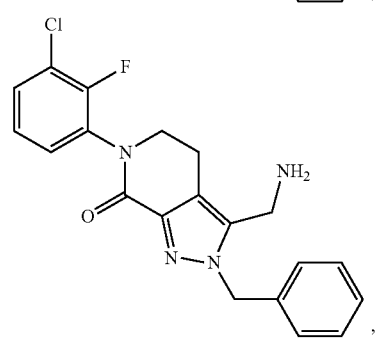
,
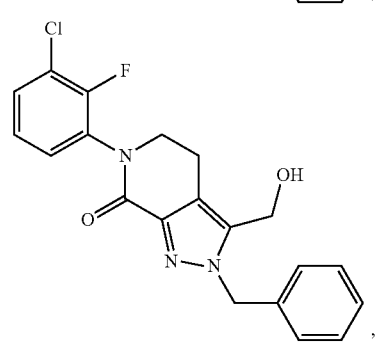
,
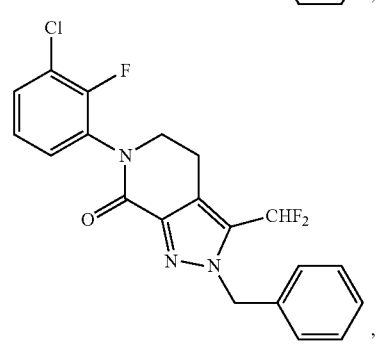
,
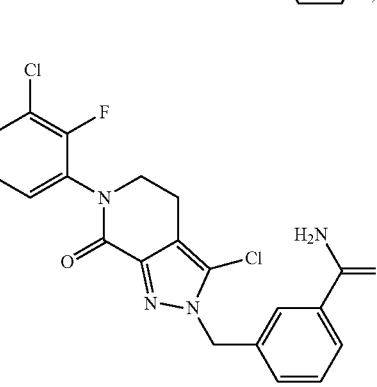
,
274
-continued
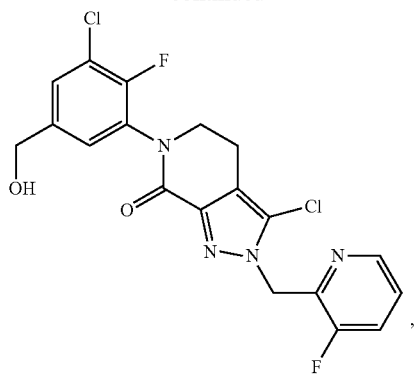
,
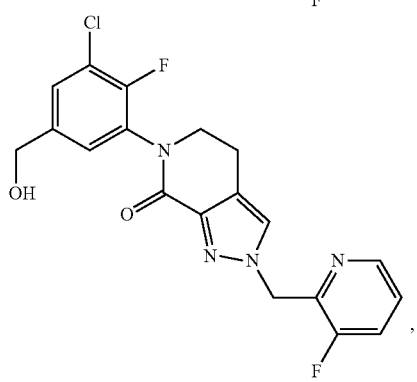
,
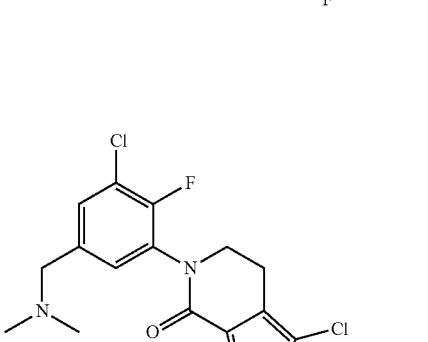
,
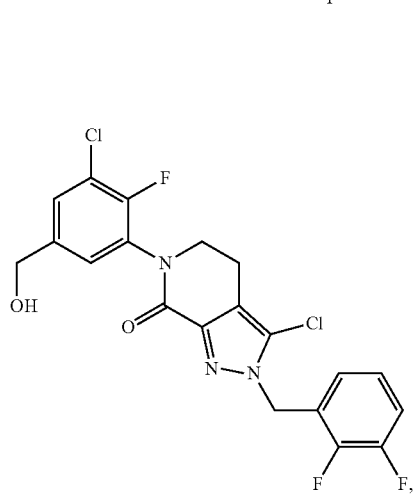
, 275
-continued
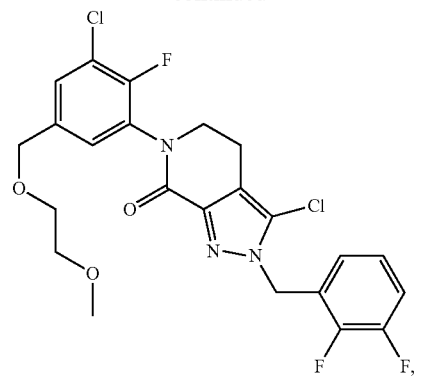
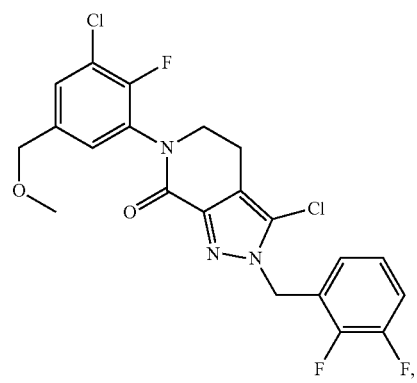
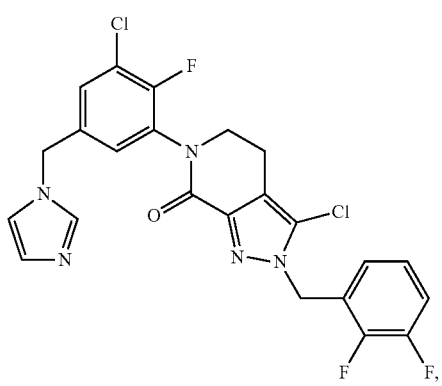
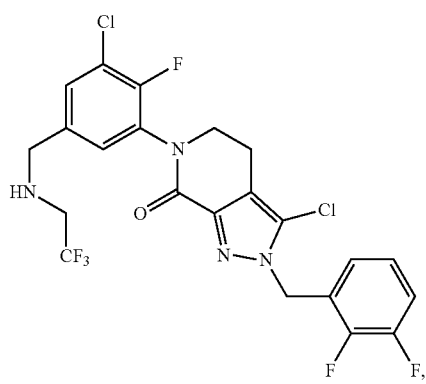
276
-continued
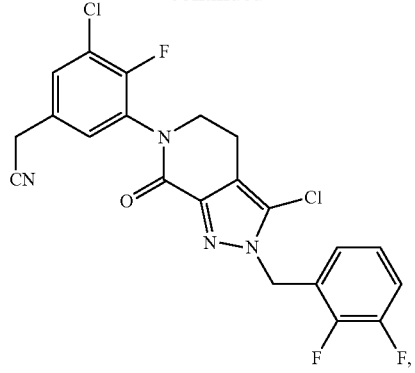
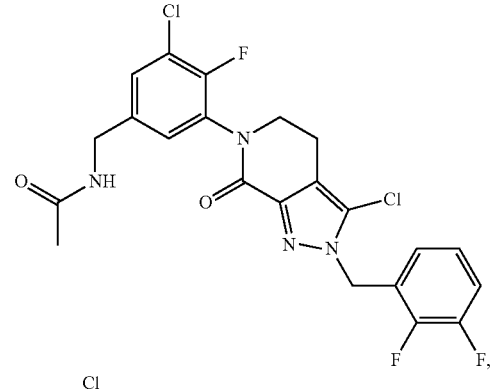
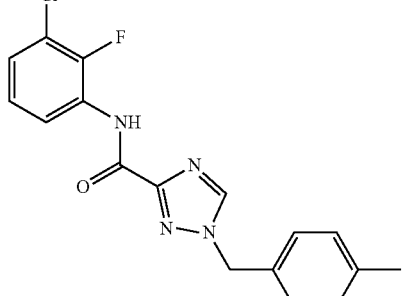
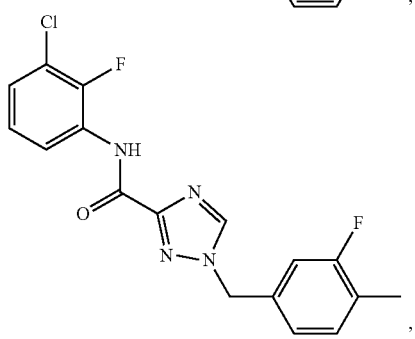
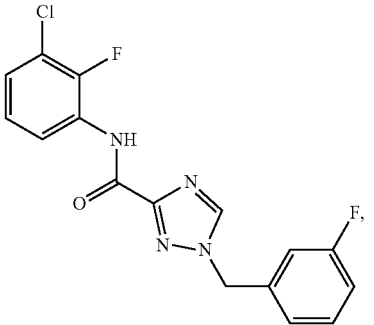

277
-continued
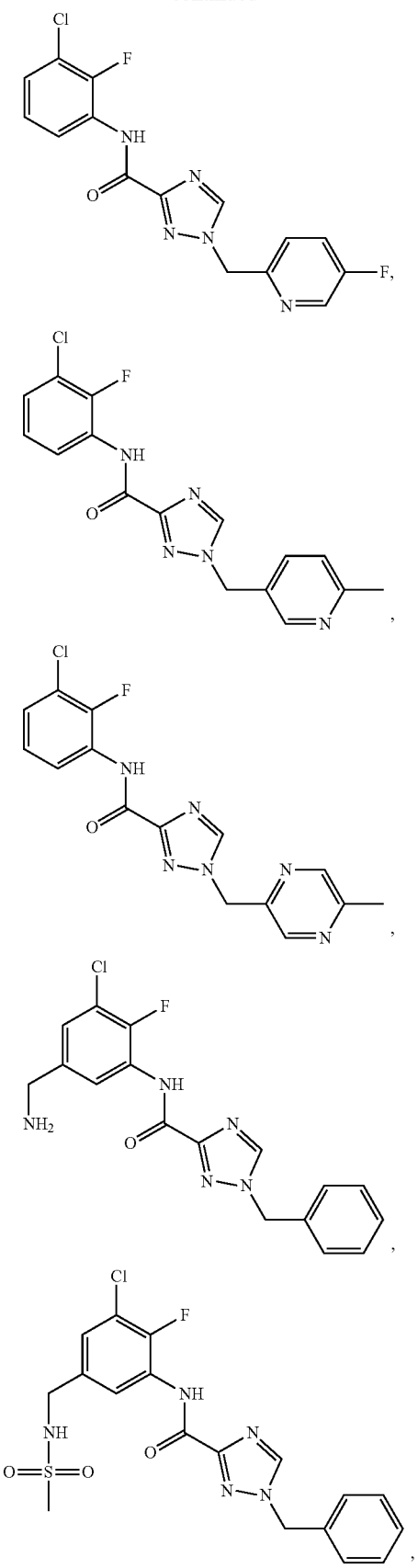
278
-continued
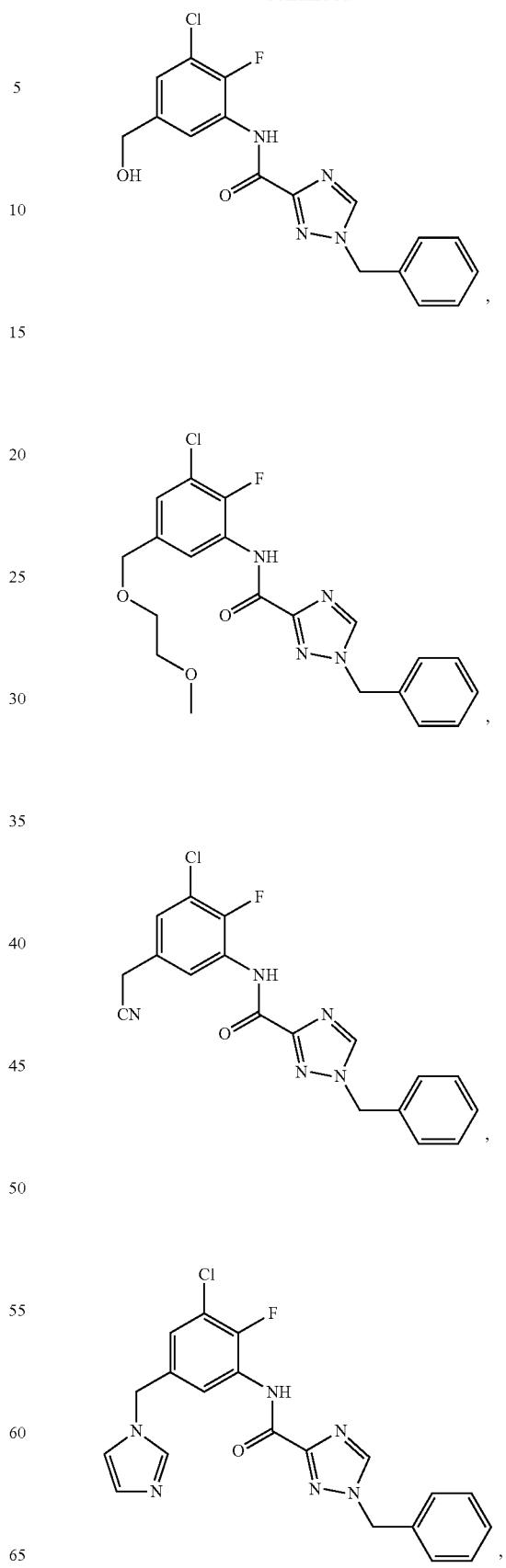

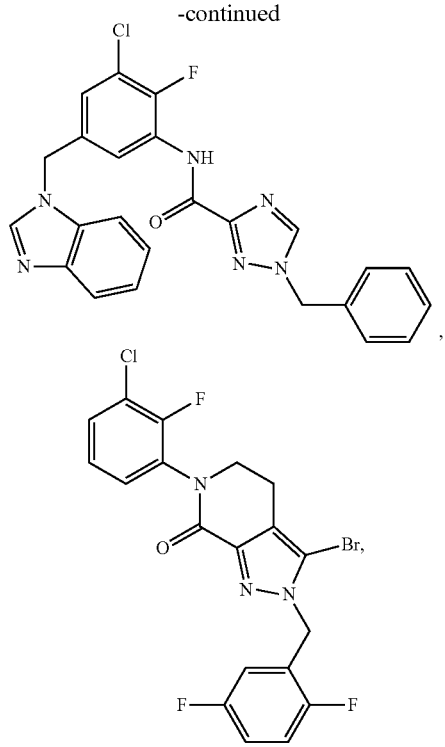
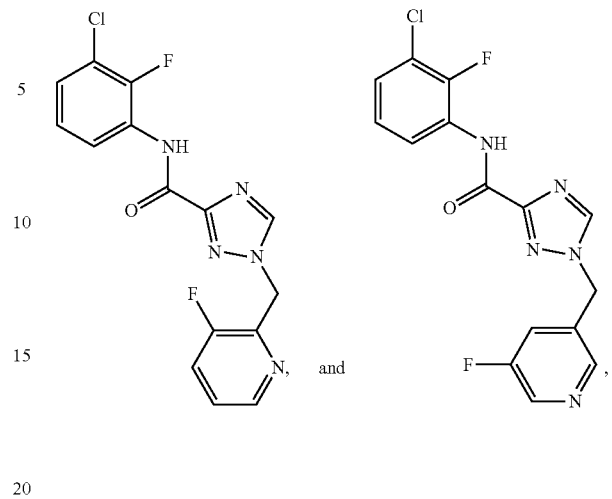
10. A pharmaceutical composition comprising a compound as recited in claim 1, or a salt thereof, together with a pharmaceutically acceptable carrier.
* * * * *

UNITED STATES PATENT AND TRADEMARK OFFICE
CERTIFICATE OF CORRECTION

PATENT NO. : 11,718,612 B2
APPLICATION NO. : 17/014184
DATED : August 8, 2023
INVENTOR(S) : Lewis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 107 days.

Signed and Sealed this
Twelfth Day of November, 2024

Katherine Kelly Vidal
*Director of the United States Patent and Trademark Office*